United States Patent
Sudo et al.

(10) Patent No.: US 11,519,927 B2
(45) Date of Patent: Dec. 6, 2022

(54) LUNG CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Hiroko Sudo, Kamakura (JP); Hitoshi Nobumasa, Kamakura (JP); Satoko Kozono, Kamakura (JP); Satoshi Kondou, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 60 days.

(21) Appl. No.: 16/800,755

(22) Filed: Feb. 25, 2020

(65) Prior Publication Data

US 2020/0182897 A1   Jun. 11, 2020

Related U.S. Application Data

(62) Division of application No. 15/319,695, filed as application No. PCT/JP2015/067533 on Jun. 18, 2015, now Pat. No. 10,620,228.

(30) Foreign Application Priority Data

Jun. 18, 2014 (JP) ................... 2014-125561

(51) Int. Cl.
| | |
|---|---|
| *C12Q 1/68* | (2018.01) |
| *C12P 19/34* | (2006.01) |
| *G01N 37/00* | (2006.01) |
| *C12N 15/09* | (2006.01) |
| *C12M 1/00* | (2006.01) |

(52) U.S. Cl.
CPC ............. *G01N 37/00* (2013.01); *C12M 1/00* (2013.01); *C12N 15/09* (2013.01); *C12Q 1/68* (2013.01); *C12Q 2600/118* (2013.01); *C12Q 2600/158* (2013.01); *C12Q 2600/178* (2013.01)

(58) Field of Classification Search
CPC ................ C12Q 1/68; C12Q 2600/158; C12Q 2600/178; C12Q 1/6837; C12Q 1/6886
See application file for complete search history.

(56) References Cited

U.S. PATENT DOCUMENTS

| | | |
|---|---|---|
| 2001/0053519 A1 | 12/2001 | Fodor et al. |
| 2011/0053158 A1 | 3/2011 | Mambo et al. |
| 2012/0108462 A1 | 5/2012 | Keller et al. |
| 2015/0080243 A1 | 3/2015 | Whitney |
| 2015/0337332 A1 | 11/2015 | Ruohoa-Baker et al. |
| 2017/0121779 A1 | 5/2017 | Kondou et al. |
| 2017/0130278 A1 | 5/2017 | Sudo et al. |
| 2017/0166975 A1 | 6/2017 | Kondou et al. |

FOREIGN PATENT DOCUMENTS

| | | |
|---|---|---|
| CN | 103173448 A | 6/2013 |
| EP | 3156500 A1 | 4/2017 |
| JP | 2011-505143 A | 2/2011 |
| JP | 2013-502931 A | 1/2013 |
| WO | WO 2009/070653 A1 | 6/2009 |
| WO | WO 2010/139810 A1 | 12/2010 |
| WO | WO 2011/025919 A1 | 3/2011 |
| WO | WO 2011/076144 A1 | 6/2011 |
| WO | WO 2011/146937 A1 | 11/2011 |
| WO | WO 2014/013258 A1 | 1/2014 |
| WO | WO 2014/192907 A1 | 12/2014 |
| WO | WO 2015/115923 A2 | 8/2015 |
| WO | WO 2015/190542 A1 | 12/2015 |
| WO | WO 2015/190584 A1 | 12/2015 |
| WO | WO 2015/194610 A1 | 12/2015 |
| WO | WO 2015/194615 A1 | 12/2015 |

OTHER PUBLICATIONS

Qiagen Product Description "miScript™ miRNA PCR Array (384-well, 384HC) Human miRBase Profiler HC Plate 3" document 1073798, Aug. 2012, from https://b2b.qiagen.com/~/media/genetable/mi/hs/34/mihs-3403z (Year: 2012).*

Dissertation of Xin Wang, "Microrna: Profiling and Functional Implications in Cancer and Metabolism" from University of Houston, Dec. 2012, available online at https://uh-ir.tdl.org/bitstream/handle/10657/540/Diss_XinWang_20121.pdf?sequence=1 &isAllowed=y (Year: 2012).*

American Cancer Society, "Lung Cancer (Non-Small Cell)", 2013, total 77 pages, pp. 2-7 and 37-56.

Bai et al., "MiR-296-3p regulates cell growth and multi-drug resistance of human glioblastoma by targeting ether-á-go-go (EAG1)," European Journal of Cancer, vol. 49, No. 3, 2013 (available online Sep. 18, 2012), pp. 710-724.

Chen et al., "Identification of ten serum microRNAs from a genome-wide serum microRNA expression profile as novel noninvasive biomarkers for nonsmall cell lung cancer diagnosis", International Journal Cancer, vol. 130, May 9, 2011, pp. 1620-1628.

(Continued)

Primary Examiner — Stephen T Kapushoc

(74) Attorney, Agent, or Firm — Birch, Stewart, Kolasch & Birch, LLP

(57) ABSTRACT

It is intended to provide a kit or a device for the detection of lung cancer and a method for detecting lung cancer. The present invention provides a kit or a device for the detection of lung cancer, comprising a nucleic acid capable of specifically binding to a miRNA in a sample from a subject, and a method for detecting lung cancer, comprising measuring the miRNA in vitro.

6 Claims, 4 Drawing Sheets

Specification includes a Sequence Listing.

(56) References Cited

OTHER PUBLICATIONS

Cheung et al., "Natural variation in human gene expression assessed in lymphoblastoid cells", Nature Genetics, vol. 33, Mar. 2003, pp. 422-425.
Cobb et al., "Sepsis gene expression profiling: Murine splenic compared with hepatic responses determined by using complementary DNA microarrays", Critical Care Medicine, vol. 30, No. 12, 2002, pp. 2711-2721.
Eto et al., "Prospect of microRNA toward laboratory medicine Gastrointestinal Cancer and microRNA", Clinical Chemistry, 2014, vol. 43, pp. 99-105.
GenBank Locus NR_ 106826, "Homo sapiens micro RNA 6768 (MIR6768), micro RNA", (Apr. 3, 2014) from /www.ncbi.nlm.nih.gov, printed pp. 1-3.
Hoshikawa et al., "Hypoxia induces different genes in the lungs of rats compared with mice", Physiological Genomics, vol. 12, 2003, pp. 209-219.
International Search Report, issued in PCT/JP2015/067533, dated Sep. 15, 2015.
Keller et al., "Stable serum miRNA profiles as potential tool for non-invasive lung cancer diagnosis", RNA Biology, May 1, 2011, vol. 8, No. 3, pp. 506-516, Supplemental Content.
Kozomara et al., "miRBase: annotating high confidence microRNAs using deep sequencing data", Nucleic Acids Research, Nov. 25, 2013, vol. 42, Database issue, pp. D68-D73.
MiScript™ miRNA PCR Array (384-well, 384HC) Human miRBase Profiler HC Plate 5, Qiagen, 2012, 10 pages, from https://b2b.qiagen.com/-/media/genetable/mi/hs/34/mihs-3403z.
Okamura et al., "Diagnostic value of CEA and CYFRA 21-1 tumor markers in primary lung cancer", Lung Cancer, 2013, vol. 80, pp. 45-49.
Partial Supplementary European Search Report, dated Dec. 14, 2017, for European Application No. 15809623.0.
Sobin et al., "TNM Classification of Malignant Tumours, the 7th edition", International Union Against Cancer, 2010, pp. 129-134.
Takizawa et al., "miRNA Profiling in Serum Samples Using DNA Chip 3D-Gene®", BIO Clinica, Jun. 10, 2014, vol. 29, No. 6, pp. 588-589.
Written Opinion of the International Searching Authority, issued in PCT/JP2015/067533, dated Sep. 15, 2015.
Yanaihara et al., "Unique microRNA molecular profiles in lung cancer diagnosis and prognosis," Cancer Cell, vol. 9, No. 3, Mar. 13, 2006, pp. 189-198.
Jin et al., "Circulating microRNA: a novel potential biomarker for early diagnosis of Intracranial Aneurysm Rupture a case control study," Journal of Translational Medicine (2013), vol. 11, No. 296, pp. 1-9.
Office Action dated Aug. 23, 2021, in Republic of Korea Patent Application No. 10-2017-7000867.
Shen et al., "Applications of MicroRNAs in the Diagnosis and Prognosis of Lung Cancer," Expert Opin. Med. Diagn. (2012), vol. 6, No. 3, pp. 197-207.
Office Action dated Jun. 7, 2022, in Japanese Patent Application No. 2019-527064.
Enard et al., "Intra- and Interspecific Variation in Primate Gene Expression Patterns," Science, vol. 296, No. 340, Apr. 12, 2002, pp. 339-343.
Foss et al., "miR-1254 and miR-574-5p Serum-Based microRNA Biomarkers for Early-Stage Non-small Cell Lung Cancer", Journal of Thoracic Oncology, Mar. 2011, vol. 6, No. 3, pp. 482-488.
International Search Report, issued in PCT/JP2018/024834, dated Oct. 2, 2018.
Leidinger et al., "What makes a blood cell based miRNA expression pattern disease specific?—A miRNome analysis of blood cell subsets in lung cancer patients and healthy controls", Oncotarget, Sep. 19, 2014, vol. 5, No. 19, pp. 9484-9497.
Ondracek et al., "Global MicroRNA Expression Profiling identifies Unique MicroRNA Pattern of Radioresistant Glioblastoma Cells", Anticancer Research 37, pp. 1099-1104, 2017.
Persson et al., "Identification of New MicroRNAs in Paired Normal and Tumor Breast Tissue Suggests a Dual Role for the ERBB2/Her2 Gene", Cancer Research 71(1), pp. 78-86, 2011.
Rani et al., "Global analysis of serum microRNAs as potential biomarkers for lung adenocarcinoma", Cancer Biology & Therapy, 2013, vol. 14, Issue 12, pp. 1104-1112.
Roth et al., "Low Levels of Cell-Free Circulating miR-361-3p and miR-625* as Blood-Based Markers for Discriminating Malignant from Benign Lung Tumors", PLoS ONE, Jun. 2012, vol. 7, Issue 6, e38248, pp. 1-10.
Schmidt et al., "Liquid Profiling in Lung Cancer—Quantification of Extracellular miRNAs in Bronchial Lavage", Adv Exp Med Biol., 2016, vol. 924, pp. 33-37.
Supplementary Partial European Search Report issued in Application No. 18823484.3 dated Mar. 12, 2021.
Tai et al., "Blood-borne miRNA profile-based diagnostic classifier for lung adenocarcinoma", Scientific Reports, Aug. 10, 2016, 6: 31389, total 9 pages.
U.S. Office Action for U.S. Appl. No. 16/626,781, dated Apr. 15, 2021.
U.S. Office Action for U.S. Appl. No. 16/626,781, dated Feb. 18, 2022.
U.S. Office Action for U.S. Appl. No. 16/626,781, dated Jun. 17, 2022.
U.S. Office Action for U.S. Appl. No. 16/626,781, dated May 25, 2022.
U.S. Office Action for U.S. Appl. No. 16/626,781, dated Sep. 14, 2021.
Written Opinion of the International Searching Authority, issued in PCT/JP2018/024834, dated Oct. 2, 2018.

* cited by examiner

LUNG CANCER DETECTION KIT OR DEVICE, AND DETECTION METHOD

CROSS-REFERENCE TO RELATED APPLICATIONS

This application is a Divisional of application Ser. No. 15/319,695, filed on Dec. 16, 2016, which is the National Phase under 35 U.S.C. § 371 of International Application No. PCT/JP2015/067533, filed on Jun. 18, 2015, and claims the benefit under 35 U.S.C. § 119(a) to Patent Application No. 2014-125561, filed in Japan on Jun. 18, 2014, all of which are hereby expressly incorporated by reference into the present application.

TECHNICAL FIELD

The present invention relates to a kit or a device for the detection of lung cancer, comprising a nucleic acid capable of specifically binding to a particular miRNA, which is used for examining the presence or absence of lung cancer in a subject, and a method for detecting lung cancer, comprising measuring an expression level of the miRNA using the nucleic acid.

BACKGROUND ART

The lungs have important functions of supplying oxygen into the body through respiration and eliminating carbon dioxide. Air taken up from the mouth or the nose passes through the trachea and the bronchus, then separately enters the left lung and the right lung, and spreads throughout the lung through the thinner bronchial tubes. Eventually, oxygen is taken up into blood in the alveoli while carbon dioxide is eliminated (Non Patent Literature 1).

According to the 2012 cancer type-specific statistics in Japan disclosed by the Center for Cancer Control and Information Services, National Cancer Center, the number of individuals affected by lung cancer was 107,241 people. Namely, it is estimated that one out of 10 males and one out of 22 females experience lung cancer. The number of incidences of this cancer among other cancer types takes the 3rd in place. Men are twice as likely as women to develop lung cancer. The number of lung cancer deaths in men and women together climbs to 71,518 people and takes the 1st in place among other cancer types. The estimated number of American individuals affected by lung cancer climbed to 224,210 people in 2014, among which approximately 159,260 people reportedly died (Non Patent Literature 1).

Lung cancer has multiple histological types. Small-cell lung cancer occupies approximately 15%, while the remaining histological types are called non-small cell lung cancer. The non-small cell lung cancer is further broadly classified into three subtypes; adenocarcinoma, squamous cell carcinoma, and large-cell carcinoma. These histological types differ largely in the site of origin, the manner and rate of progression, symptoms, etc., and therefore differ in treatment methods.

The stages of lung cancer progression are classified into stages 0 to 4 according to the degrees of tumor spread (T0, Tis, and T1 to T4), lymph node metastasis (N0 to N3), and distant metastasis (M0 and M1). Particularly, as for the tumor spread, T1 denotes tumor of 3 cm or less in greatest diameter; T2 denotes tumor of more than 3 cm but 7 cm or less across; T3 denotes tumor of more than 7 cm across or found to have invaded adjacent sites; and T4 denotes tumor that has invaded adjacent sites more widely regardless of its size.

The survival rate of lung cancer differs depending on the stages of progression. According to the report of Non Patent Literature 1, the 5-year relative survival rate of non-small cell lung cancer is 45 to 49% for stage 1, 30 to 31% for stage 2, 5 to 14% for stage 3, and 1% for stage 4. Thus, the detection and treatment of lung cancer at an early stage makes a significant contribution to improvement in the survival rate.

The treatment of lung cancer is mainly performed by surgical resection, radiotherapy, and anticancer drug treatment. Particularly, in early lung cancer, surgery is applicable and the cancer is likely to be completely cured (Non Patent Literature 1). For early lung cancer, there are some therapeutic options, and for example, treatment that places less burden on patients, such as thoracoscopic surgery, stereotactic body radiotherapy (SBRT), photo dynamic therapy, laser treatment, and brachytherapy, which delivers radiation from within the body, can also be applied to such lung cancer (Non Patent Literature 1).

As described in Non Patent Literature 1, diagnostic tests of lung cancer are medical history check and physical examination as well as chest X-ray examination which is most commonly conducted. When there are findings that suspects lung cancer by the chest X-ray examination, more precise diagnostic imaging such as CT, MRI, or PET is carried out. Alternatively, as tests using samples, sputum cytology, pleural fluid analysis, or pathological examination which involves inserting a needle into a lesion and collecting cells or tissues, which are then examined under a microscope is carried out. Furthermore, CEA and CYFRA21-1 are known as tumor markers for the detection of lung cancer.

As shown in Patent Literatures 1 and 2, there are reports, albeit at a research stage, on the detection of lung cancer using the expression levels of microRNAs (miRNAs) or combinations of the expression levels of miRNAs and the expression levels of additional protein markers in biological samples including blood.

Patent Literature 1 discloses a method for detecting lung cancer or other lung diseases using miR-19b (miR-19b-3p) and the like in serum.

Patent Literature 2 discloses a method for detecting lung cancer using miR-1268 and miR-1228 in serum or plasma.

Patent Literature 3 discloses a method for detecting lung cancer using miR-1307 and the like in blood cells.

CITATION LIST

Patent Literature

Patent Literature 1: JP Patent Publication (Kohyo) No. 2013-502931 A (2013)
Patent Literature 2: International Publication No. WO 2011/146937
Patent Literature 3: U.S. patent application Ser. No. 13/376,281

Non Patent Literature

Non Patent Literature 1: American Cancer Society, "Lung Cancer (Non-Small Cell)", 2013, p. 2 to 7 and 37 to 56
Non Patent Literature 2: Sobin, L. et al., "TNM Classification of Malignant Tumours, the 7th edition", 2010, p. 129-134

Non Patent Literature 3: Okamura, K. et al, Lung Cancer, 2013, Vol. 80 (1), p. 45-9

SUMMARY OF INVENTION

Technical Problem

An object of the present invention is to find a novel tumor marker for lung cancer and to provide a method that can effectively detect lung cancer using a nucleic acid capable of specifically binding to the marker. Chest X-ray examination is being commonly practiced as a test of lung cancer. Nonetheless, the number of lung cancer deaths is increasing yearly and takes the first place by cancer type. For these reasons, it is not always true that the X-ray examination works as a deterrent for lung cancer. Although CT and MRI are capable of detecting lung cancer with high performance, these tests are not suitable for widespread use as 1st tests because of the necessity of their special apparatuses and expensive examination cost.

For example, CEA and CYFRA21-1 are known as tumor markers in blood for the detection of lung cancer (Non Patent Literature 3). The usefulness thereof, however, has not yet been established. The lung cancer guidebook provided by the American Cancer Society makes no mention about these markers (Non Patent Literature 1). According to the report of Non Patent Literature 3, these tumor markers in blood have general lung cancer detection sensitivity of 69% (CEA) and 43% (CYFRA21-1). The tumor markers such as CEA and CYFRA21-1 may elevate for reasons other than lung cancer and therefore allegedly fail to determine the presence or absence of lung cancer. The false diagnosis of other cancers as lung cancer wastes appropriate therapeutic opportunity or places unnecessary economical and physical burdens on patients due to the application of wrong medicine.

As described below, there are reports, albeit at a research stage, on the determination of lung cancer using the expression levels of microRNAs (miRNAs) in biological samples including blood, none of which, however, have yet been brought into practical use.

Patent Literature 1 discloses a method for detecting lung cancer or other lung diseases using miR-19b (miR-19b-3p) and the like in serum. However, the number of samples from healthy subjects used as negative controls was as small as a dozen. Therefore, the universality of the marker for the difference among subjects is not insured. Thus, this method has low reliability as a method for detecting lung cancer.

Patent Literature 2 discloses a method for detecting lung cancer using miR-1268 and miR-1228 in serum or plasma. These markers, however, were validated in only 3 mesothelioma cases as a cancer other than lung cancer. Thus, the possibility that these markers have a high rate of false positives and detect cancers other than lung cancer cannot be excluded.

Patent Literature 3 discloses a method for detecting lung cancer using miR-1307 and the like in blood cells. However, a marker obtained using one case group was not validated in another independent case group. Thus, this method has low reliability as a method for testing lung cancer.

As mentioned above, the existing tumor markers exhibit low performance in the detection of lung cancer, or neither performance nor detection methods are specifically shown as to the markers at a research stage. Therefore, use of these markers might lead to carrying out needless extra examination due to the false detection of healthy subjects as being lung cancer patients, or might waste therapeutic opportunity because of overlooking lung cancer patients. In addition, the measurement of several dozens to several hundreds of miRNAs increases examination cost and is therefore difficult to use in large-scale screening such as medical checkup. Furthermore, the collection of lung tissues for measuring the tumor markers is highly invasive to patients and is not favorable. Hence, there is a demand for a highly accurate lung cancer marker that is detectable from blood, which can be collected with limited invasiveness, and is capable of correctly determining a lung cancer patient as a lung cancer patient and a healthy subject as a healthy subject. Particularly, the early detection of lung cancer can increase the applicability of surgery and drastically improve the survival rates. For early lung cancer, there are multiple therapeutic options. There is a possibility that treatment that places less burden on patients, such as thoracoscopic surgery or stereotactic body radiotherapy, can also be applied to such lung cancer. Therefore, a highly sensitive lung cancer marker that can detect lung cancer even at an early stage of progression is desired.

Solution to Problem

The present inventors have conducted diligent studies to attain the object and consequently completed the present invention by finding multiple genes usable as markers for the detection of lung cancer from blood, which can be collected with limited invasiveness, and finding that lung cancer can be significantly detected by using a nucleic acid capable of specifically binding to any of these markers.

SUMMARY OF INVENTION

Specifically, the present invention has the following features:

(1) A kit for the detection of lung cancer, comprising a nucleic acid capable of specifically binding to at least one or more polynucleotide(s) selected from the group consisting of lung cancer markers miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR- 7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

(2) The kit according to (1), wherein miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR-663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR-371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-187-5p, miR-614 is hsa-miR-614, miR-1225-5p is hsa-miR-1225-5p, miR-451a is hsa-miR-451a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125, 127 to 130, 132 to 134, and 561 to 578, (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other lung cancer markers miR-19b-3p, miR-1228-5p, and miR-1307-3p.

(5) The kit according to (4), wherein miR-19b-3p is hsa-miR-19b-3p, miR-1228-5p is hsa-miR-1228-5p, and miR-1307-3p is hsa-miR-1307-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126, 131, and 579, (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other lung cancer markers miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

(8) The kit according to (7), wherein miR-4271 is hsa-miR-4271, miR-642b-3p is hsa-miR-642b-3p, miR-6075 is hsa-miR-6075, miR-6125 is hsa-miR-6125, miR-887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 135 to 174, (m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 135 to 174 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from the group consisting of all of the lung cancer markers according to (1) or (2).

(11) A device for the detection of lung cancer, comprising a nucleic acid capable of specifically binding to at least one or more polynucleotide(s) selected from the group consisting of lung cancer markers miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

(12) The device according to (11), wherein miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR- 663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR-371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-187-5p, miR-614 is hsa-miR-614, miR-1225-5p is hsa-miR-1225-5p, miR-451a is hsa-miR-4511a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

(13) The device according to (11) or (12), wherein the nucleic acid is a polynucleotide selected from the group consisting of the following polynucleotides (a) to (e):

(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125, 127 to 130, 132 to 134, and 561 to 578, (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s) selected from the group consisting of other lung cancer markers miR-19b-3p, miR-1228-5p, and miR-1307-3p.

(15) The device according to (14), wherein miR-19b-3p is hsa-miR-19b-3p, miR-1228-5p is hsa-miR-1228-5p, and miR-1307-3p is hsa-miR-1307-3p.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126, 131, and 579, (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other lung cancer markers miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

(18) The device according to (17), wherein miR-4271 is hsa-miR-4271, miR-642b-3p is hsa-miR-642b-3p, miR-6075 is hsa-miR-6075, miR-6125 is hsa-miR-6125, miR-887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

(19) The device according to (17) or (18), wherein the nucleic acid is a polynucleotide selected from the group consisting of the following polynucleotides (k) to (o):
(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 135 to 174,
(m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 135 to 174 or a nucleotide sequence derived from the nucleotide sequence by the replacement of u with t, and
(o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the lung cancer markers according to (11) or (12).

(23) A method for detecting lung cancer, comprising measuring an expression level of a target nucleic acid in a sample from a subject using a kit according to any one of (1) to (10) or a device according to any one of (11) to (22), and evaluating in vitro whether or not the subject has lung cancer using both of the measured expression level and a control expression level in a sample from a healthy subject measured in the same way.

(24) The method according to (23), wherein the subject is a human.

(25) The method according to (23) or (24), wherein the sample is blood, serum, or plasma.

Definition of Terms

The terms used herein are defined as follows.
Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein is used for a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. Herein, the term "polynucleotide" is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but each single-stranded DNA such as a plus strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID NO) but "nucleic acids" encoding RNAs having biological functions equivalent to an RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 618, or a nucleotide sequence derived from the nucleotide sequence by the replacement of u with t. The "gene" is not particularly limited by its functional region and can contain, for example, an expression regulatory region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is encapsulated by a lipid bilayer and secreted from a cell. The exosome is derived from a multivesicular endosome and may incorporate biomaterials such as a "gene" (e.g., RNA or DNA) or a protein when released into an extracellular environment. The exosome is known to be contained in a body fluid such as blood, serum, plasma, or lymph.

The term "transcript" used herein refers to an RNA synthesized with the DNA sequence of a gene as a template. RNA polymerase binds to a site called a promoter located upstream of the gene and adds ribonucleotides complementary to the nucleotide sequence of the DNA to the 3' end to synthesize RNA. This RNA contains not only the gene itself but also the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is involved in the suppression of translation of mRNA, and that transcribed as an RNA precursor having a hairpin-like structure, cleaved by a dsRNA-cleaving enzyme which has RNase III cleavage activity, and integrated into a protein complex called RISC, unless otherwise specified. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 618. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship of A:T (U) and G:C base pairs with the full-length sequence of a polynucleotide consisting of a nucleotide sequence defined by any of SEQ ID NOs: 1 to 618 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence that is 100% complementary to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2, or 3 or more nucleotides in a nucleotide sequence represented by any of SEQ ID NOs: 1 to 618 or a nucleotide sequence derived from the nucleotide sequence by the replacement of u with t, or a partial sequence thereof; a variant containing the deletion, substitution, addition, or insertion of 1 or 2 or more nucleotides in a nucleotide sequence of a premature miRNA of a sequence represented by any of SEQ ID NOs: 1 to 618 or a nucleotide sequence derived from the nucleotide sequence by the replacement of u with t, or a partial sequence thereof; a variant that exhibits identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the lung cancer marker miRNAs described above is a synthesized or prepared nucleic acid and specifically includes a "nucleic acid probe" or a "primer". The "nucleic acid" is utilized directly or indirectly for detecting the presence or absence of lung cancer in a subject, for diagnosing the presence or absence of lung cancer, the severity of lung cancer, the presence or absence of amelioration or the degree of amelioration of lung cancer, or the sensitivity of lung cancer for treatment, or for screening for a candidate substance useful in the prevention, amelioration, or treatment of lung cancer. The "nucleic acid" includes a nucleotide, an oligonucleotide, and a polynucleotide capable of specifically recognizing and binding to a transcript represented by any of SEQ ID NOs: 1 to 618 or a synthetic cDNA nucleic acid thereof in vivo, particularly, in a sample such as a body fluid (e.g., blood or urine), in relation to the development of lung cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that actually calculated from data under null hypothesis is observed in a statistical test. Thus, smaller "P" or "P value" means more significant difference between subjects to be compared.

The term "sensitivity" used herein means a value of (the number of true positives)/(the number of true positives+the number of false negatives). High sensitivity allows lung cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being lung cancer patients, leading to reduction in burden on patients and reduction in medical expense.

The term "accuracy" used herein means a value of (the number of true positives+the number of true negatives)/(the total number of cases). The accuracy indicates the ratio of samples that correctly identified in the discriminant results to all samples, and serves as a primary index for evaluating detection performance.

As used herein, the "sample" that is subject to determination, detection, or diagnosis refers to a tissue and a biological material in which the expression of the gene of the present invention varies as lung cancer develops, lung cancer progresses, and therapeutic effects on lung cancer are exerted. Specifically, the "sample" refers to a lung tissue, a peripulmonary vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6768-5p gene" or "hsa-miR-6768-5p" used herein includes the hsa-miR-6768-5p gene (miRBase Accession No. MIMAT0027436) described in SEQ ID NO: 1, a homolog or an ortholog of a different organism species, and the like. The hsa-miR-6768-5p gene can be obtained by a method described in Ladewig E et al., 2012, Genome Res, Vol. 22, p. 1634-1645. Also, "hsa-mir-6768" (miRBase Accession No. MI0022613, SEQ ID NO: 175) having a hairpin-like structure is known as a precursor of "hsa-miR-6768-5p".

The term "hsa-miR-6836-3p gene" or "hsa-miR-6836-3p" used herein includes the hsa-miR-6836-3p gene (miRBase Accession No. MIMAT0027575) described in SEQ ID NO: 2, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 176) having a hairpin-like structure is known as a precursor of "hsa-miR-6836-3p".

The term "hsa-miR-6782-5p gene" or "hsa-miR-6782-5p" used herein includes the hsa-miR-6782-5p gene (miRBase Accession No. MIMAT0027464) described in SEQ ID NO: 3, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 177) having a hairpin-like structure is known as a precursor of "hsa-miR-6782-5p".

The term "hsa-miR-3663-3p gene" or "hsa-miR-3663-3p" used herein includes the hsa-miR-3663-3p gene (miRBase Accession No. MIMAT0018085) described in SEQ ID NO: 4, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 178) having a hairpin-like structure is known as a precursor of "hsa-miR-3663-3p".

The term "hsa-miR-1908-3p gene" or "hsa-miR-1908-3p" used herein includes the hsa-miR-1908-3p gene (miRBase Accession No. MIMAT0026916) described in SEQ ID NO: 5, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI0008329, SEQ ID NO: 179) having a hairpin-like structure is known as a precursor of "hsa-miR-1908-3p".

The term "hsa-miR-6726-5p gene" or "hsa-miR-6726-5p" used herein includes the hsa-miR-6726-5p gene (miRBase Accession No. MIMAT0027353) described in SEQ ID NO: 6, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 180) having a hairpin-like structure is known as a precursor of "hsa-miR-6726-5p".

The term "hsa-miR-4258 gene" or "hsa-miR-4258" used herein includes the hsa-miR-4258 gene (miRBase Accession No. MIMAT0016879) described in SEQ ID NO: 7, a homolog or an ortholog of a different organism species, and the like. The hsa-miR-4258 gene can be obtained by a method described in Goff L A et al., 2009, PLoS One, Vol. 4, e7192. Also, "hsa-mir-4258" (miRBase Accession No. MI0015857, SEQ ID NO: 181) having a hairpin-like structure is known as a precursor of "hsa-miR-4258".

The term "hsa-miR-1343-3p gene" or "hsa-miR-1343-3p" used herein includes the hsa-miR-1343-3p gene (miRBase Accession No. MIMAT0019776) described in SEQ ID NO: 8, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 182) having a hairpin-like structure is known as a precursor of "hsa-miR-1343-3p".

The term "hsa-miR-4516 gene" or "hsa-miR-4516" used herein includes the hsa-miR-4516 gene (miRBase Accession No. MIMAT0019053) described in SEQ ID NO: 9, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 183) having a hairpin-like structure is known as a precursor of "hsa-miR-4516".

The term "hsa-miR-6875-5p gene" or "hsa-miR-6875-5p" used herein includes the hsa-miR-6875-5p gene (miRBase Accession No. MIMAT0027650) described in SEQ ID NO: 10, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 184) having a hairpin-like structure is known as a precursor of "hsa-miR-6875-5p".

The term "hsa-miR-4651 gene" or "hsa-miR-4651" used herein includes the hsa-miR-4651 gene (miRBase Accession No. MIMAT0019715) described in SEQ ID NO: 11, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 185) having a hairpin-like structure is known as a precursor of "hsa-miR-4651".

The term "hsa-miR-6825-5p gene" or "hsa-miR-6825-5p" used herein includes the hsa-miR-6825-5p gene (miRBase Accession No. MIMAT0027550) described in SEQ ID NO: 12, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 186) having a hairpin-like structure is known as a precursor of "hsa-miR-6825-5p".

The term "hsa-miR-6840-3p gene" or "hsa-miR-6840-3p" used herein includes the hsa-miR-6840-3p gene (miRBase Accession No. MIMAT0027583) described in SEQ ID NO: 13, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 187) having a hairpin-like structure is known as a precursor of "hsa-miR-6840-3p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 14, a homolog or an ortholog of a different organism species, and the like. The hsa-miR-6780b-5p gene can be obtained by a method described in Ladewig E et al., 2012, Genome Res, Vol. 22, p. 1634-1645. Also, "hsa-mir-6780b" (miRBase Accession No. MI0022681, SEQ ID NO: 188) having a hairpin-like structure is known as a precursor of "hsa-miR-6780b-5p".

The term "hsa-miR-6749-5p gene" or "hsa-miR-6749-5p" used herein includes the hsa-miR-6749-5p gene (miRBase Accession No. MIMAT0027398) described in SEQ ID NO: 15, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 189) having a hairpin-like structure is known as a precursor of "hsa-miR-6749-5p".

The term "hsa-miR-8063 gene" or "hsa-miR-8063" used herein includes the hsa-miR-8063 gene (miRBase Accession No. MIMAT0030990) described in SEQ ID NO: 16, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 190) having a hairpin-like structure is known as a precursor of "hsa-miR-8063".

The term "hsa-miR-6784-5p gene" or "hsa-miR-6784-5p" used herein includes the hsa-miR-6784-5p gene (miRBase Accession No. MIMAT0027468) described in SEQ ID NO: 17, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 191) having a hairpin-like structure is known as a precursor of "hsa-miR-6784-5p".

The term "hsa-miR-3679-5p gene" or "hsa-miR-3679-5p" used herein includes the hsa-miR-3679-5p gene (miRBase Accession No. MIMAT0018104) described in SEQ ID NO: 18, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 192) having a hairpin-like structure is known as a precursor of "hsa-miR-3679-5p".

The term "hsa-miR-3184-5p gene" or "hsa-miR-3184-5p" used herein includes the hsa-miR-3184-5p gene (miRBase Accession No. MIMAT0015064) described in SEQ ID NO: 19, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 193) having a hairpin-like structure is known as a precursor of "hsa-miR-3184-5p".

The term "hsa-miR-663b gene" or "hsa-miR-663b" used herein includes the hsa-miR-663b gene (miRBase Accession No. MIMAT0005867) described in SEQ ID NO: 20, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 194) having a hairpin-like structure is known as a precursor of "hsa-miR-663b".

The term "hsa-miR-6880-5p gene" or "hsa-miR-6880-5p" used herein includes the hsa-miR-6880-5p gene (miRBase Accession No. MIMAT0027660) described in SEQ ID NO: 21, a homolog or an ortholog of a different organism species, and the like. The hsa-miR-6880-5p gene can be obtained by a method described in Ladewig E et al., 2012, Genome Res, Vol. 22, p. 1634-1645. Also, "hsa-mir-6880" (miRBase Accession No. MI0022727, SEQ ID NO: 195) having a hairpin-like structure is known as a precursor of "hsa-miR-6880-5p".

The term "hsa-miR-1908-5p gene" or "hsa-miR-1908-5p" used herein includes the hsa-miR-1908-5p gene (miRBase Accession No. MIMAT0007881) described in SEQ ID NO: 22, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 179) having a hairpin-like structure is known as a precursor of "hsa-miR-1908-5p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 23, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 196) having a hairpin-like structure is known as a precursor of "hsa-miR-92a-2-5p".

The term "hsa-miR-7975 gene" or "hsa-miR-7975" used herein includes the hsa-miR-7975 gene (miRBase Accession No. MIMAT0031178) described in SEQ ID NO: 24, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 197) having a hairpin-like structure is known as a precursor of "hsa-miR-7975".

The term "hsa-miR-7110-5p gene" or "hsa-miR-7110-5p" used herein includes the hsa-miR-7110-5p gene (miRBase Accession No. MIMAT0028117) described in SEQ ID NO: 25, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 198) having a hairpin-like structure is known as a precursor of "hsa-miR-7110-5p".

The term "hsa-miR-6842-5p gene" or "hsa-miR-6842-5p" used herein includes the hsa-miR-6842-5p gene (miRBase Accession No. MIMAT0027586) described in SEQ ID NO: 26, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 199) having a hairpin-like structure is known as a precursor of "hsa-miR-6842-5p".

The term "hsa-miR-6857-5p gene" or "hsa-miR-6857-5p" used herein includes the hsa-miR-6857-5p gene (miRBase Accession No. MIMAT0027614) described in SEQ ID NO: 27, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 200) having a hairpin-like structure is known as a precursor of "hsa-miR-6857-5p".

The term "hsa-miR-5572 gene" or "hsa-miR-5572" used herein includes the hsa-miR-5572 gene (miRBase Accession No. MIMAT0022260) described in SEQ ID NO: 28, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 201) having a hairpin-like structure is known as a precursor of "hsa-miR-5572".

The term "hsa-miR-3197 gene" or "hsa-miR-3197" used herein includes the hsa-miR-3197 gene (miRBase Accession No. MIMAT0015082) described in SEQ ID NO: 29, a homolog or an ortholog of a different organism species, and the like. The hsa-miR-3197 gene can be obtained by a method described in Stark M S et al., 2010, PLoS One, Vol. 5, e9685. Also, "hsa-mir-3197" (miRBase Accession No. MI0014245, SEQ ID NO: 202) having a hairpin-like structure is known as a precursor of "hsa-miR-3197".

The term "hsa-miR-6131 gene" or "hsa-miR-6131" used herein includes the hsa-miR-6131 gene (miRBase Accession No. MIMAT0024615) described in SEQ ID NO: 30, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. M10021276, SEQ ID NO: 203) having a hairpin-like structure is known as a precursor of "hsa-miR-6131".

The term "hsa-miR-6889-5p gene" or "hsa-miR-6889-5p" used herein includes the hsa-miR-6889-5p gene (miRBase Accession No. MIMAT0027678) described in SEQ ID NO: 31, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 204) having a hairpin-like structure is known as a precursor of "hsa-miR-6889-5p".

The term "hsa-miR-4454 gene" or "hsa-miR-4454" used herein includes the hsa-miR-4454 gene (miRBase Accession No. MIMAT0018976) described in SEQ ID NO: 32, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 205) having a hairpin-like structure is known as a precursor of "hsa-miR-4454".

The term "hsa-miR-1199-5p gene" or "hsa-miR-1199-5p" used herein includes the hsa-miR-1199-5p gene (miRBase Accession No. MIMAT0031119) described in SEQ ID NO: 33, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 206) having a hairpin-like structure is known as a precursor of "hsa-miR-1199-5p".

The term "hsa-miR-1247-3p gene" or "hsa-miR-1247-3p" used herein includes the hsa-miR-1247-3p gene (miRBase Accession No. MIMAT0022721) described in SEQ ID NO: 34, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. M10006382, SEQ ID NO: 207) having a hairpin-like structure is known as a precursor of "hsa-miR-1247-3p".

The term "hsa-miR-6800-5p gene" or "hsa-miR-6800-5p" used herein includes the hsa-miR-6800-5p gene (miRBase Accession No. MIMAT0027500) described in SEQ ID NO: 35, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 208) having a hairpin-like structure is known as a precursor of "hsa-miR-6800-5p".

The term "hsa-miR-6872-3p gene" or "hsa-miR-6872-3p" used herein includes the hsa-miR-6872-3p gene (miRBase Accession No. MIMAT0027645) described in SEQ ID NO: 36, a homolog or an ortholog of a different organism species, and the like. The hsa-miR-6872-3p gene can be obtained by a method described in Ladewig E et al., 2012, Genome Res, Vol. 22, p. 1634-1645. Also, "hsa-mir-6872" (miRBase Accession No. MI0022719, SEQ ID NO: 209) having a hairpin-like structure is known as a precursor of "hsa-miR-6872-3p".

The term "hsa-miR-4649-5p gene" or "hsa-miR-4649-5p" used herein includes the hsa-miR-4649-5p gene (miRBase Accession No. MIMAT0019711) described in SEQ ID NO: 37, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 210) having a hairpin-like structure is known as a precursor of "hsa-miR-4649-5p".

The term "hsa-miR-6791-5p gene" or "hsa-miR-6791-5p" used herein includes the hsa-miR-6791-5p gene (miRBase Accession No. MIMAT0027482) described in SEQ ID NO: 38, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. M10022636, SEQ ID NO: 211) having a hairpin-like structure is known as a precursor of "hsa-miR-6791-5p".

The term "hsa-miR-4433b-3p gene" or "hsa-miR-4433b-3p" used herein includes the hsa-miR-4433b-3p gene (miRBase Accession No. MIMAT0030414) described in SEQ ID NO: 39, a homolog or an ortholog of a different organism species, and the like. The hsa-miR-4433b-3p gene can be obtained by a method described in Ple H et al., 2012, PLoS One, Vol. 7, e50746. Also, "hsa-mir-4433b" (miRBase Accession No. MI0025511, SEQ ID NO: 212) having a hairpin-like structure is known as a precursor of "hsa-miR-4433b-3p".

The term "hsa-miR-3135b gene" or "hsa-miR-3135b" used herein includes the hsa-miR-3135b gene (miRBase Accession No. MIMAT0018985) described in SEQ ID NO: 40, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. M10016809, SEQ ID NO: 213) having a hairpin-like structure is known as a precursor of "hsa-miR-3135b".

The term "hsa-miR-128-2-5p gene" or "hsa-miR-128-2-5p" used herein includes the hsa-miR-128-2-5p gene (miRBase Accession No. MIMAT0031095) described in SEQ ID NO: 41, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. M10000727, SEQ ID NO: 214) having a hairpin-like structure is known as a precursor of "hsa-miR-128-2-5p".

The term "hsa-miR-4675 gene" or "hsa-miR-4675" used herein includes the hsa-miR-4675 gene (miRBase Accession No. MIMAT0019757) described in SEQ ID NO: 42, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 215) having a hairpin-like structure is known as a precursor of "hsa-miR-4675".

The term "hsa-miR-4472 gene" or "hsa-miR-4472" used herein includes the hsa-miR-4472 gene (miRBase Accession No. MIMAT0018999) described in SEQ ID NO: 43, a homolog or an ortholog of a different organism species, and the like. The hsa-miR-4472 gene can be obtained by a method described in Jima D D et al., 2010, Blood, Vol. 116, e118-e127. Also, "hsa-mir-4472-1 and hsa-mir-4472-2" (miRBase Accession Nos. MI0016823 and MI10016824, SEQ ID NOs: 216 and 217) having a hairpin-like structure are known as precursors of "hsa-miR-4472".

The term "hsa-miR-6785-5p gene" or "hsa-miR-6785-5p" used herein includes the hsa-miR-6785-5p gene (miRBase Accession No. MIMAT0027470) described in SEQ ID NO: 44, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 218) having a hairpin-like structure is known as a precursor of "hsa-miR-6785-5p".

The term "hsa-miR-6741-5p gene" or "hsa-miR-6741-5p" used herein includes the hsa-miR-6741-5p gene (miRBase Accession No. MIMAT0027383) described in SEQ ID NO: 45, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. M10022586, SEQ ID NO: 219) having a hairpin-like structure is known as a precursor of "hsa-miR-6741-5p".

The term "hsa-miR-7977 gene" or "hsa-miR-7977" used herein includes the hsa-miR-7977 gene (miRBase Accession No. MIMAT0031180) described in SEQ ID NO: 46, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. M10025753, SEQ ID NO: 220) having a hairpin-like structure is known as a precursor of "hsa-miR-7977".

The term "hsa-miR-3665 gene" or "hsa-miR-3665" used herein includes the hsa-miR-3665 gene (miRBase Accession No. MIMAT0018087) described in SEQ ID NO: 47, a homolog or an ortholog of a different organism species, and the like. The hsa-miR-3665 gene can be obtained by a method described in Xie X et al., 2005, Nature, Vol. 434, p. 338-345. Also, "hsa-mir-3665" (miRBase Accession No. MI0016066, SEQ ID NO: 221) having a hairpin-like structure is known as a precursor of "hsa-miR-3665".

The term "hsa-miR-128-1-5p gene" or "hsa-miR-128-1-5p" used herein includes the hsa-miR-128-1-5p gene (miRBase Accession No. MIMAT0026477) described in SEQ ID NO: 48, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. M10000447, SEQ ID NO: 222) having a hairpin-like structure is known as a precursor of "hsa-miR-128-1-5p".

The term "hsa-miR-4286 gene" or "hsa-miR-4286" used herein includes the hsa-miR-4286 gene (miRBase Accession No. MIMAT0016916) described in SEQ ID NO: 49, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 223) having a hairpin-like structure is known as a precursor of "hsa-miR-4286".

The term "hsa-miR-6765-3p gene" or "hsa-miR-6765-3p" used herein includes the hsa-miR-6765-3p gene (miRBase Accession No. MIMAT0027431) described in SEQ ID NO: 50, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 224) having a hairpin-like structure is known as a precursor of "hsa-miR-6765-3p".

The term "hsa-miR-4632-5p gene" or "hsa-miR-4632-5p" used herein includes the hsa-miR-4632-5p gene (miRBase Accession No. MIMAT0022977) described in SEQ ID NO: 51, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 225) having a hairpin-like structure is known as a precursor of "hsa-miR-4632-5p".

The term "hsa-miR-365a-5p gene" or "hsa-miR-365a-5p" used herein includes the hsa-miR-365a-5p gene (miRBase Accession No. MIMAT0009199) described in SEQ ID NO: 52, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 226) having a hairpin-like structure is known as a precursor of "hsa-miR-365a-5p".

The term "hsa-miR-6088 gene" or "hsa-miR-6088" used herein includes the hsa-miR-6088 gene (miRBase Accession No. MIMAT0023713) described in SEQ ID NO: 53, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 227) having a hairpin-like structure is known as a precursor of "hsa-miR-6088".

The term "hsa-miR-6816-5p gene" or "hsa-miR-6816-5p" used herein includes the hsa-miR-6816-5p gene (miRBase Accession No. MIMAT0027532) described in SEQ ID NO: 54, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 228) having a hairpin-like structure is known as a precursor of "hsa-miR-6816-5p".

The term "hsa-miR-6885-5p gene" or "hsa-miR-6885-5p" used herein includes the hsa-miR-6885-5p gene (miRBase Accession No. MIMAT0027670) described in SEQ ID NO: 55, a homolog or an ortholog of a different organism species, and the like. The hsa-miR-6885-5p gene can be obtained by a method described in Ladewig E et al., 2012, Genome Res, Vol. 22, p. 1634-1645. Also, "hsa-mir-6885" (miRBase Accession No. MI0022732, SEQ ID NO: 229) having a hairpin-like structure is known as a precursor of "hsa-miR-6885-5p".

The term "hsa-miR-7111 gene" or "hsa-miR-711" used herein includes the hsa-miR-711 gene (miRBase Accession No. MIMAT0012734) described in SEQ ID NO: 56, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 230) having a hairpin-like structure is known as a precursor of "hsa-miR-711".

The term "hsa-miR-6765-5p gene" or "hsa-miR-6765-5p" used herein includes the hsa-miR-6765-5p gene (miRBase Accession No. MIMAT0027430) described in SEQ ID NO: 57, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 224) having a hairpin-like structure is known as a precursor of "hsa-miR-6765-5p".

The term "hsa-miR-3180 gene" or "hsa-miR-3180" used herein includes the hsa-miR-3180 gene (miRBase Accession No. MIMAT0018178) described in SEQ ID NO: 58, a homolog or an ortholog of a different organism species, and the like. The hsa-miR-3180 gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 231 and 232) having a hairpin-like structure are known as precursors of "hsa-miR-3180".

The term "hsa-miR-4442 gene" or "hsa-miR-4442" used herein includes the hsa-miR-4442 gene (miRBase Accession No. MIMAT0018960) described in SEQ ID NO: 59, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 233) having a hairpin-like structure is known as a precursor of "hsa-miR-4442".

The term "hsa-miR-4792 gene" or "hsa-miR-4792" used herein includes the hsa-miR-4792 gene (miRBase Accession No. MIMAT0019964) described in SEQ ID NO: 60, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 234) having a hairpin-like structure is known as a precursor of "hsa-miR-4792".

The term "hsa-miR-6721-5p gene" or "hsa-miR-6721-5p" used herein includes the hsa-miR-6721-5p gene (miRBase Accession No. MIMAT0025852) described in SEQ ID NO: 61, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 235) having a hairpin-like structure is known as a precursor of "hsa-miR-6721-5p".

The term "hsa-miR-6798-5p gene" or "hsa-miR-6798-5p" used herein includes the hsa-miR-6798-5p gene (miRBase Accession No. MIMAT0027496) described in SEQ ID NO: 62, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 236) having a hairpin-like structure is known as a precursor of "hsa-miR-6798-5p".

The term "hsa-miR-3162-5p gene" or "hsa-miR-3162-5p" used herein includes the hsa-miR-3162-5p gene (miRBase Accession No. MIMAT0015036) described in SEQ ID NO: 63, a homolog or an ortholog of a different organism species, and the like. The hsa-miR-3162-5p gene can be obtained by a method described in Stark M S et al., 2010, PLoS One, Vol. 5, e9685. Also, "hsa-mir-3162" (miRBase Accession No. MI0014192, SEQ ID NO: 237) having a hairpin-like structure is known as a precursor of "hsa-miR-3162-5p".

The term "hsa-miR-6126 gene" or "hsa-miR-6126" used herein includes the hsa-miR-6126 gene (miRBase Accession No. MIMAT0024599) described in SEQ ID NO: 64, a homolog or an ortholog of a different organism species, and the like. The hsa-miR-6126 gene can be obtained by a method described in Smith J L et al., 2012, J Virol, Vol. 86, p. 5278-5287. Also, "hsa-mir-6126" (miRBase Accession No. MI0021260, SEQ ID NO: 238) having a hairpin-like structure is known as a precursor of "hsa-miR-6126".

The term "hsa-miR-4758-5p gene" or "hsa-miR-4758-5p" used herein includes the hsa-miR-4758-5p gene (miRBase Accession No. MIMAT0019903) described in SEQ ID NO: 65, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 239) having a hairpin-like structure is known as a precursor of "hsa-miR-4758-5p".

The term "hsa-miR-2392 gene" or "hsa-miR-2392" used herein includes the hsa-miR-2392 gene (miRBase Accession No. MIMAT0019043) described in SEQ ID NO: 66, a homolog or an ortholog of a different organism species, and the like. The hsa-miR-2392 gene can be obtained by a method described in Jima D D et al., 2010, Blood, Vol. 116, e118-e127. Also, "hsa-mir-2392" (miRBase Accession No. MI0016870, SEQ ID NO: 240) having a hairpin-like structure is known as a precursor of "hsa-miR-2392".

The term "hsa-miR-486-3p gene" or "hsa-miR-486-3p" used herein includes the hsa-miR-486-3p gene (miRBase Accession No. MIMAT0004762) described in SEQ ID NO: 67, a homolog or an ortholog of a different organism species, and the like. The hsa-miR-486-3p gene can be obtained by a method described in Fu H et al., 2005, FEBS Lett, Vol. 579, p. 3849-3854. Also, "hsa-mir-486 and hsa-mir-486-2" (miRBase Accession Nos. MI0002470 and MI0023622, SEQ ID NOs: 241 and 242) having a hairpin-like structure are known as precursors of "hsa-miR-486-3p".

The term "hsa-miR-6727-5p gene" or "hsa-miR-6727-5p" used herein includes the hsa-miR-6727-5p gene (miRBase Accession No. MIMAT0027355) described in SEQ ID NO: 68, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 243) having a hairpin-like structure is known as a precursor of "hsa-miR-6727-5p".

The term "hsa-miR-4728-5p gene" or "hsa-miR-4728-5p" used herein includes the hsa-miR-4728-5p gene (miRBase Accession No. MIMAT0019849) described in SEQ ID NO: 69, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 244) having a hairpin-like structure is known as a precursor of "hsa-miR-4728-5p".

The term "hsa-miR-6746-5p gene" or "hsa-miR-6746-5p" used herein includes the hsa-miR-6746-5p gene (miRBase Accession No. MIMAT0027392) described in SEQ ID NO: 70, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 245) having a hairpin-like structure is known as a precursor of "hsa-miR-6746-5p".

The term "hsa-miR-4270 gene" or "hsa-miR-4270" used herein includes the hsa-miR-4270 gene (miRBase Accession No. MIMAT0016900) described in SEQ ID NO: 71, a homolog or an ortholog of a different organism species, and the like. The hsa-miR-4270 gene can be obtained by a method described in Goff L A et al., 2009, PLoS One, Vol. 4, e7192. Also, "hsa-mir-4270" (miRBase Accession No. MI0015878, SEQ ID NO: 246) having a hairpin-like structure is known as a precursor of "hsa-miR-4270".

The term "hsa-miR-3940-5p gene" or "hsa-miR-3940-5p" used herein includes the hsa-miR-3940-5p gene (miRBase Accession No. MIMAT0019229) described in SEQ ID NO: 72, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 247) having a hairpin-like structure is known as a precursor of "hsa-miR-3940-5p".

The term "hsa-miR-4725-3p gene" or "hsa-miR-4725-3p" used herein includes the hsa-miR-4725-3p gene (miRBase Accession No. MIMAT0019844) described in SEQ ID NO: 73, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 248) having a hairpin-like structure is known as a precursor of "hsa-miR-4725-3p".

The term "hsa-miR-7108-5p gene" or "hsa-miR-7108-5p" used herein includes the hsa-miR-7108-5p gene (miRBase Accession No. MIMAT0028113) described in SEQ ID NO: 74, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 249) having a hairpin-like structure is known as a precursor of "hsa-miR-7108-5p".

The term "hsa-miR-3656 gene" or "hsa-miR-3656" used herein includes the hsa-miR-3656 gene (miRBase Accession No. MIMAT0018076) described in SEQ ID NO: 75, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 250) having a hairpin-like structure is known as a precursor of "hsa-miR-3656".

The term "hsa-miR-6879-5p gene" or "hsa-miR-6879-5p" used herein includes the hsa-miR-6879-5p gene (miRBase Accession No. MIMAT0027658) described in SEQ ID NO: 76, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 251) having a hairpin-like structure is known as a precursor of "hsa-miR-6879-5p".

The term "hsa-miR-6738-5p gene" or "hsa-miR-6738-5p" used herein includes the hsa-miR-6738-5p gene (miRBase Accession No. MIMAT0027377) described in SEQ ID NO: 77, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 252) having a hairpin-like structure is known as a precursor of "hsa-miR-6738-5p".

The term "hsa-miR-1260a gene" or "hsa-miR-1260a" used herein includes the hsa-miR-1260a gene (miRBase Accession No. MIMAT0005911) described in SEQ ID NO: 78, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. M10006394, SEQ ID NO: 253) having a hairpin-like structure is known as a precursor of "hsa-miR-1260a".

The term "hsa-miR-4446-3p gene" or "hsa-miR-4446-3p" used herein includes the hsa-miR-4446-3p gene (miRBase Accession No. MIMAT0018965) described in SEQ ID NO: 79, a homolog or an ortholog of a different organism species, and the like. The hsa-miR-4446-3p gene can be obtained by a method described in Jima D D et al., 2010, Blood, Vol. 116, e118-e127. Also, "hsa-mir-4446" (miRBase Accession No. MI0016789, SEQ ID NO: 254) having a hairpin-like structure is known as a precursor of "hsa-miR-4446-3p".

The term "hsa-miR-3131 gene" or "hsa-miR-3131" used herein includes the hsa-miR-3131 gene (miRBase Accession No. MIMAT0014996) described in SEQ ID NO: 80, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 255) having a hairpin-like structure is known as a precursor of "hsa-miR-3131".

The term "hsa-miR-4463 gene" or "hsa-miR-4463" used herein includes the hsa-miR-4463 gene (miRBase Accession No. MIMAT0018987) described in SEQ ID NO: 81, a homolog or an ortholog of a different organism species, and the like. The hsa-miR-4463 gene can be obtained by a method described in Jima D D et al., 2010, Blood, Vol. 116, e118-e127. Also, "hsa-mir-4463" (miRBase Accession No. MI0016811, SEQ ID NO: 256) having a hairpin-like structure is known as a precursor of "hsa-miR-4463".

The term "hsa-miR-3185 gene" or "hsa-miR-3185" used herein includes the hsa-miR-3185 gene (miRBase Accession No. MIMAT0015065) described in SEQ ID NO: 82, a homolog or an ortholog of a different organism species, and the like. The hsa-miR-3185 gene can be obtained by a method described in Stark M S et al., 2010, PLoS One, Vol. 5, e9685. Also, "hsa-mir-3185" (miRBase Accession No. MI0014227, SEQ ID NO: 257) having a hairpin-like structure is known as a precursor of "hsa-miR-3185".

The term "hsa-miR-6870-5p gene" or "hsa-miR-6870-5p" used herein includes the hsa-miR-6870-5p gene (miRBase Accession No. MIMAT0027640) described in SEQ ID NO: 83, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 258) having a hairpin-like structure is known as a precursor of "hsa-miR-6870-5p".

The term "hsa-miR-6779-5p gene" or "hsa-miR-6779-5p" used herein includes the hsa-miR-6779-5p gene (miRBase Accession No. MIMAT0027458) described in SEQ ID NO: 84, a homolog or an ortholog of a different organism species, and the like. The hsa-miR-6779-5p gene can be obtained by a method described in Ladewig E et al., 2012, Genome Res, Vol. 22, p. 1634-1645. Also, "hsa-mir-6779" (miRBase Accession No. MI0022624, SEQ ID NO: 259) having a hairpin-like structure is known as a precursor of "hsa-miR-6779-5p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 85, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. M10018003, SEQ ID NO: 260) having a hairpin-like structure is known as a precursor of "hsa-miR-1273g-3p".

The term "hsa-miR-8059 gene" or "hsa-miR-8059" used herein includes the hsa-miR-8059 gene (miRBase Accession No. MIMAT0030986) described in SEQ ID NO: 86, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 261) having a hairpin-like structure is known as a precursor of "hsa-miR-8059".

The term "hsa-miR-4697-5p gene" or "hsa-miR-4697-5p" used herein includes the hsa-miR-4697-5p gene (miRBase Accession No. MIMAT0019791) described in SEQ ID NO: 87, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. M10017330, SEQ ID NO: 262) having a hairpin-like structure is known as a precursor of "hsa-miR-4697-5p".

The term "hsa-miR-4674 gene" or "hsa-miR-4674" used herein includes the hsa-miR-4674 gene (miRBase Accession No. MIMAT0019756) described in SEQ ID NO: 88, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 263) having a hairpin-like structure is known as a precursor of "hsa-miR-4674".

The term "hsa-miR-4433-3p gene" or "hsa-miR-4433-3p" used herein includes the hsa-miR-4433-3p gene (miRBase Accession No. MIMAT0018949) described in SEQ ID NO: 89, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. M10016773, SEQ ID NO: 264) having a hairpin-like structure is known as a precursor of "hsa-miR-4433-3p".

The term "hsa-miR-4257 gene" or "hsa-miR-4257" used herein includes the hsa-miR-4257 gene (miRBase Accession No. MIMAT0016878) described in SEQ ID NO: 90, a homolog or an ortholog of a different organism species, and the like. The hsa-miR-4257 gene can be obtained by a method described in Goff L A et al., 2009, PLoS One, Vol. 4, e7192. Also, "hsa-mir-4257" (miRBase Accession No. M10015856, SEQ ID NO: 265) having a hairpin-like structure is known as a precursor of "hsa-miR-4257".

The term "hsa-miR-1915-5p gene" or "hsa-miR-1915-5p" used herein includes the hsa-miR-1915-5p gene (miRBase Accession No. MIMAT0007891) described in SEQ ID NO: 91, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 266) having a hairpin-like structure is known as a precursor of "hsa-miR-1915-5p".

The term "hsa-miR-4417 gene" or "hsa-miR-4417" used herein includes the hsa-miR-4417 gene (miRBase Accession No. MIMAT0018929) described in SEQ ID NO: 92, a homolog or an ortholog of a different organism species, and the like. The hsa-miR-4417 gene can be obtained by a method described in Jima D D et al., 2010, Blood, Vol. 116, e118-e127. Also, "hsa-mir-4417" (miRBase Accession No. MI0016753, SEQ ID NO: 267) having a hairpin-like structure is known as a precursor of "hsa-miR-4417".

The term "hsa-miR-1343-5p gene" or "hsa-miR-1343-5p" used herein includes the hsa-miR-1343-5p gene (miRBase Accession No. MIMAT0027038) described in SEQ ID NO: 93, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 182) having a hairpin-like structure is known as a precursor of "hsa-miR-1343-5p".

The term "hsa-miR-6781-5p gene" or "hsa-miR-6781-5p" used herein includes the hsa-miR-6781-5p gene (miRBase Accession No. MIMAT0027462) described in SEQ ID NO: 94, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 268) having a hairpin-like structure is known as a precursor of "hsa-miR-6781-5p".

The term "hsa-miR-4695-5p gene" or "hsa-miR-4695-5p" used herein includes the hsa-miR-4695-5p gene (miRBase Accession No. MIMAT0019788) described in SEQ ID NO: 95, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 269) having a hairpin-like structure is known as a precursor of "hsa-miR-4695-5p".

The term "hsa-miR-1237-5p gene" or "hsa-miR-1237-5p" used herein includes the hsa-miR-1237-5p gene (miRBase Accession No. MIMAT0022946) described in SEQ ID NO: 96, a homolog or an ortholog of a different organism species, and the like. The hsa-miR-1237-5p gene can be obtained by a method described in Berezikov E et al., 2007, Mol Cell, Vol. 28, p. 328-336. Also, "hsa-mir-1237" (miRBase Accession No. MI0006327, SEQ ID NO: 270) having a hairpin-like structure is known as a precursor of "hsa-miR-1237-5p".

The term "hsa-miR-6775-5p gene" or "hsa-miR-6775-5p" used herein includes the hsa-miR-6775-5p gene (miRBase Accession No. MIMAT0027450) described in SEQ ID NO: 97, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 271) having a hairpin-like structure is known as a precursor of "hsa-miR-6775-5p".

The term "hsa-miR-7845-5p gene" or "hsa-miR-7845-5p" used herein includes the hsa-miR-7845-5p gene (miRBase Accession No. MIMAT0030420) described in SEQ ID NO: 98, a homolog or an ortholog of a different organism species, and the like. The hsa-miR-7845-5p gene can be obtained by a method described in Ple H et al., 2012, PLoS One, Vol. 7, e50746. Also, "hsa-mir-7845" (miRBase Accession No. MI0025515, SEQ ID NO: 272) having a hairpin-like structure is known as a precursor of "hsa-miR-7845-5p".

The term "hsa-miR-4746-3p gene" or "hsa-miR-4746-3p" used herein includes the hsa-miR-4746-3p gene (miRBase Accession No. MIMAT0019881) described in SEQ ID NO: 99, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 273) having a hairpin-like structure is known as a precursor of "hsa-miR-4746-3p".

The term "hsa-miR-7641 gene" or "hsa-miR-7641" used herein includes the hsa-miR-7641 gene (miRBase Accession No. MIMAT0029782) described in SEQ ID NO: 100, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 274 and 275) having a hairpin-like structure are known as precursors of "hsa-miR-7641".

The term "hsa-miR-7847-3p gene" or "hsa-miR-7847-3p" used herein includes the hsa-miR-7847-3p gene (miRBase Accession No. MIMAT0030422) described in SEQ ID NO: 101, a homolog or an ortholog of a different organism species, and the like. The hsa-miR-7847-3p gene can be obtained by a method described in Ple H et al., 2012, PLoS One, Vol. 7, e50746. Also, "hsa-mir-7847" (miRBase Accession No. MI0025517, SEQ ID NO: 276) having a hairpin-like structure is known as a precursor of "hsa-miR-7847-3p".

The term "hsa-miR-6806-5p gene" or "hsa-miR-6806-5p" used herein includes the hsa-miR-6806-5p gene (miRBase Accession No. MIMAT0027512) described in SEQ ID NO: 102, a homolog or an ortholog of a different organism species, and the like. The hsa-miR-6806-5p gene can be obtained by a method described in Ladewig E et al., 2012, Genome Res, Vol. 22, p. 1634-1645. Also, "hsa-mir-6806" (miRBase Accession No. MI0022651, SEQ ID NO: 277) having a hairpin-like structure is known as a precursor of "hsa-miR-6806-5p".

The term "hsa-miR-4467 gene" or "hsa-miR-4467" used herein includes the hsa-miR-4467 gene (miRBase Accession No. MIMAT0018994) described in SEQ ID NO: 103, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 278) having a hairpin-like structure is known as a precursor of "hsa-miR-4467".

The term "hsa-miR-4726-5p gene" or "hsa-miR-4726-5p" used herein includes the hsa-miR-4726-5p gene (miRBase Accession No. MIMAT0019845) described in SEQ ID NO: 104, a homolog or an ortholog of a different organism species, and the like. The hsa-miR-4726-5p gene can be obtained by a method described in Persson H et al., 2011, Cancer Res, Vol. 71, p. 78-86. Also, "hsa-mir-4726" (miRBase Accession No. MI0017363, SEQ ID NO: 279) having a hairpin-like structure is known as a precursor of "hsa-miR-4726-5p".

The term "hsa-miR-4648 gene" or "hsa-miR-4648" used herein includes the hsa-miR-4648 gene (miRBase Accession No. MIMAT0019710) described in SEQ ID NO: 105, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No.

M10017275, SEQ ID NO: 280) having a hairpin-like structure is known as a precursor of "hsa-miR-4648".

The term "hsa-miR-6089 gene" or "hsa-miR-6089" used herein includes the hsa-miR-6089 gene (miRBase Accession No. MIMAT0023714) described in SEQ ID NO: 106, a homolog or an ortholog of a different organism species, and the like. The hsa-miR-6089 gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. M10020366 and M10023563, SEQ ID NOs: 281 and 282) having a hairpin-like structure are known as precursors of "hsa-miR-6089".

The term "hsa-miR-1260b gene" or "hsa-miR-1260b" used herein includes the hsa-miR-1260b gene (miRBase Accession No. MIMAT0015041) described in SEQ ID NO: 107, a homolog or an ortholog of a different organism species, and the like. The hsa-miR-1260b gene can be obtained by a method described in Stark M S et al., 2010, PLoS One, Vol. 5, e9685. Also, "hsa-mir-1260b" (miRBase Accession No. MI0014197, SEQ ID NO: 283) having a hairpin-like structure is known as a precursor of "hsa-miR-1260b".

The term "hsa-miR-4532 gene" or "hsa-miR-4532" used herein includes the hsa-miR-4532 gene (miRBase Accession No. MIMAT0019071) described in SEQ ID NO: 108, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. M10016899, SEQ ID NO: 284) having a hairpin-like structure is known as a precursor of "hsa-miR-4532".

The term "hsa-miR-5195-3p gene" or "hsa-miR-5195-3p" used herein includes the hsa-miR-5195-3p gene (miRBase Accession No. MIMAT0021127) described in SEQ ID NO: 109, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. M10018174, SEQ ID NO: 285) having a hairpin-like structure is known as a precursor of "hsa-miR-5195-3p".

The term "hsa-miR-3188 gene" or "hsa-miR-3188" used herein includes the hsa-miR-3188 gene (miRBase Accession No. MIMAT0015070) described in SEQ ID NO: 110, a homolog or an ortholog of a different organism species, and the like. The hsa-miR-3188 gene can be obtained by a method described in Stark M S et al., 2010, PLoS One, Vol. 5, e9685. Also, "hsa-mir-3188" (miRBase Accession No. MI0014232, SEQ ID NO: 286) having a hairpin-like structure is known as a precursor of "hsa-miR-3188".

The term "hsa-miR-6848-5p gene" or "hsa-miR-6848-5p" used herein includes the hsa-miR-6848-5p gene (miRBase Accession No. MIMAT0027596) described in SEQ ID NO: 111, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 287) having a hairpin-like structure is known as a precursor of "hsa-miR-6848-5p".

The term "hsa-miR-1233-5p gene" or "hsa-miR-1233-5p" used herein includes the hsa-miR-1233-5p gene (miRBase Accession No. MIMAT0022943) described in SEQ ID NO: 112, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 288 and 289) having a hairpin-like structure are known as precursors of "hsa-miR-1233-5p".

The term "hsa-miR-6717-5p gene" or "hsa-miR-6717-5p" used herein includes the hsa-miR-6717-5p gene (miRBase Accession No. MIMAT0025846) described in SEQ ID NO: 113, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. M10022551, SEQ ID NO: 290) having a hairpin-like structure is known as a precursor of "hsa-miR-6717-5p".

The term "hsa-miR-3195 gene" or "hsa-miR-3195" used herein includes the hsa-miR-3195 gene (miRBase Accession No. MIMAT0015079) described in SEQ ID NO: 114, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 291) having a hairpin-like structure is known as a precursor of "hsa-miR-3195".

The term "hsa-miR-6757-5p gene" or "hsa-miR-6757-5p" used herein includes the hsa-miR-6757-5p gene (miRBase Accession No. MIMAT0027414) described in SEQ ID NO: 115, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 292) having a hairpin-like structure is known as a precursor of "hsa-miR-6757-5p".

The term "hsa-miR-8072 gene" or "hsa-miR-8072" used herein includes the hsa-miR-8072 gene (miRBase Accession No. MIMAT0030999) described in SEQ ID NO: 116, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 293) having a hairpin-like structure is known as a precursor of "hsa-miR-8072".

The term "hsa-miR-4745-5p gene" or "hsa-miR-4745-5p" used herein includes the hsa-miR-4745-5p gene (miRBase Accession No. MIMAT0019878) described in SEQ ID NO: 117, a homolog or an ortholog of a different organism species, and the like. The hsa-miR-4745-5p gene can be obtained by a method described in Persson H et al., 2011, Cancer Res, Vol. 71, p. 78-86. Also, "hsa-mir-4745" (miRBase Accession No. MI0017384, SEQ ID NO: 294) having a hairpin-like structure is known as a precursor of "hsa-miR-4745-5p".

The term "hsa-miR-6511a-5p gene" or "hsa-miR-6511a-5p" used herein includes the hsa-miR-6511a-5p gene (miRBase Accession No. MIMAT0025478) described in SEQ ID NO: 118, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3, and hsa-mir-6511a-4" (miRBase Accession Nos. MI0022223, MI0023564, M10023565, and MI0023566, SEQ ID NOs: 295, 296, 297, and 298) having a hairpin-like structure are known as precursors of "hsa-miR-6511a-5p".

The term "hsa-miR-6776-5p gene" or "hsa-miR-6776-5p" used herein includes the hsa-miR-6776-5p gene (miRBase Accession No. MIMAT0027452) described in SEQ ID NO:

119, a homolog or an ortholog of a different organism species, and the like. The hsa-miR-6776-5p gene can be obtained by a method described in Ladewig E et al., 2012, Genome Res, Vol. 22, p. 1634-1645. Also, "hsa-mir-6776" (miRBase Accession No. MI0022621, SEQ ID NO: 299) having a hairpin-like structure is known as a precursor of "hsa-miR-6776-5p".

The term "hsa-miR-371a-5p gene" or "hsa-miR-371a-5p" used herein includes the hsa-miR-371a-5p gene (miRBase Accession No. MIMAT0004687) described in SEQ ID NO: 120, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 300) having a hairpin-like structure is known as a precursor of "hsa-miR-371a-5p".

The term "hsa-miR-1227-5p gene" or "hsa-miR-1227-5p" used herein includes the hsa-miR-1227-5p gene (miRBase Accession No. MIMAT0022941) described in SEQ ID NO: 121, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 301) having a hairpin-like structure is known as a precursor of "hsa-miR-1227-5p".

The term "hsa-miR-7150 gene" or "hsa-miR-7150" used herein includes the hsa-miR-7150 gene (miRBase Accession No. MIMAT0028211) described in SEQ ID NO: 122, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 302) having a hairpin-like structure is known as a precursor of "hsa-miR-7150".

The term "hsa-miR-1915-3p gene" or "hsa-miR-1915-3p" used herein includes the hsa-miR-1915-3p gene (miRBase Accession No. MIMAT0007892) described in SEQ ID NO: 123, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 266) having a hairpin-like structure is known as a precursor of "hsa-miR-1915-3p".

The term "hsa-miR-187-5p gene" or "hsa-miR-187-5p" used herein includes the hsa-miR-187-5p gene (miRBase Accession No. MIMAT0004561) described in SEQ ID NO: 124, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 303) having a hairpin-like structure is known as a precursor of "hsa-miR-187-5p".

The term "hsa-miR-614 gene" or "hsa-miR-614" used herein includes the hsa-miR-614 gene (miRBase Accession No. MIMAT0003282) described in SEQ ID NO: 125, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 304) having a hairpin-like structure is known as a precursor of "hsa-miR-614".

The term "hsa-miR-19b-3p gene" or "hsa-miR-19b-3p" used herein includes the hsa-miR-19b-3p gene (miRBase Accession No. MIMAT0000074) described in SEQ ID NO: 126, a homolog or an ortholog of a different organism species, and the like. The hsa-miR-19b-3p gene can be obtained by a method described in Lagos-Quintana M et al., 2001, Science, Vol. 294, p. 853-858. Also, "hsa-mir-19b-1 and hsa-mir-19b-2" (miRBase Accession Nos. MI0000074 and MI0000075, SEQ ID NOs: 305 and 306) having a hairpin-like structure are known as precursors of "hsa-miR-19b-3p".

The term "hsa-miR-1225-5p gene" or "hsa-miR-1225-5p" used herein includes the hsa-miR-1225-5p gene (miRBase Accession No. MIMAT0005572) described in SEQ ID NO: 127, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 307) having a hairpin-like structure is known as a precursor of "hsa-miR-1225-5p".

The term "hsa-miR-451a gene" or "hsa-miR-451a" used herein includes the hsa-miR-451a gene (miRBase Accession No. MIMAT0001631) described in SEQ ID NO: 128, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 308) having a hairpin-like structure is known as a precursor of "hsa-miR-451a".

The term "hsa-miR-939-5p gene" or "hsa-miR-939-5p" used herein includes the hsa-miR-939-5p gene (miRBase Accession No. MIMAT0004982) described in SEQ ID NO: 129, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 309) having a hairpin-like structure is known as a precursor of "hsa-miR-939-5p".

The term "hsa-miR-223-3p gene" or "hsa-miR-223-3p" used herein includes the hsa-miR-223-3p gene (miRBase Accession No. MIMAT0000280) described in SEQ ID NO: 130, a homolog or an ortholog of a different organism species, and the like. The hsa-miR-223-3p gene can be obtained by a method described in Lim L P et al., 2003, Science, Vol. 299, p. 1540. Also, "hsa-mir-223" (miRBase Accession No. MI0000300, SEQ ID NO: 310) having a hairpin-like structure is known as a precursor of "hsa-miR-223-3p".

The term "hsa-miR-1228-5p gene" or "hsa-miR-1228-5p" used herein includes the hsa-miR-1228-5p gene (miRBase Accession No. MIMAT0005582) described in SEQ ID NO: 131, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 311) having a hairpin-like structure is known as a precursor of "hsa-miR-1228-5p".

The term "hsa-miR-125a-3p gene" or "hsa-miR-125a-3p" used herein includes the hsa-miR-125a-3p gene (miRBase Accession No. MIMAT0004602) described in SEQ ID NO: 132, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 312) having a hairpin-like structure is known as a precursor of "hsa-miR-125a-3p".

The term "hsa-miR-92b-5p gene" or "hsa-miR-92b-5p" used herein includes the hsa-miR-92b-5p gene (miRBase Accession No. MIMAT0004792) described in SEQ ID NO: 133, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 313) having a hairpin-like structure is known as a precursor of "hsa-miR-92b-5p".

The term "hsa-miR-22-3p gene" or "hsa-miR-22-3p" used herein includes the hsa-miR-22-3p gene (miRBase Accession No. MIMAT0000077) described in SEQ ID NO: 134, a homolog or an ortholog of a different organism species, and the like. The hsa-miR-22-3p gene can be obtained by a method described in Lagos-Quintana M et al., 2001, Science, Vol. 294, p. 853-858. Also, "hsa-mir-22" (miRBase Accession No. MI0000078, SEQ ID NO: 314) having a hairpin-like structure is known as a precursor of "hsa-miR-22-3p".

The term "hsa-miR-4271 gene" or "hsa-miR-4271" used herein includes the hsa-miR-4271 gene (miRBase Accession No. MIMAT0016901) described in SEQ ID NO: 135, a homolog or an ortholog of a different organism species, and the like. The hsa-miR-4271 gene can be obtained by a method described in Goff L A et al., 2009, PLoS One, Vol. 4, e7192. Also, "hsa-mir-4271" (miRBase Accession No. MI0015879, SEQ ID NO: 315) having a hairpin-like structure is known as a precursor of "hsa-miR-4271".

The term "hsa-miR-642b-3p gene" or "hsa-miR-642b-3p" used herein includes the hsa-miR-642b-3p gene (miRBase Accession No. MIMAT0018444) described in SEQ ID NO: 136, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 316) having a hairpin-like structure is known as a precursor of "hsa-miR-642b-3p".

The term "hsa-miR-6075 gene" or "hsa-miR-6075" used herein includes the hsa-miR-6075 gene (miRBase Accession No. MIMAT0023700) described in SEQ ID NO: 137, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 317) having a hairpin-like structure is known as a precursor of "hsa-miR-6075".

The term "hsa-miR-6125 gene" or "hsa-miR-6125" used herein includes the hsa-miR-6125 gene (miRBase Accession No. MIMAT0024598) described in SEQ ID NO: 138, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 318) having a hairpin-like structure is known as a precursor of "hsa-miR-6125".

The term "hsa-miR-887-3p gene" or "hsa-miR-887-3p" used herein includes the hsa-miR-887-3p gene (miRBase Accession No. MIMAT0004951) described in SEQ ID NO: 139, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 319) having a hairpin-like structure is known as a precursor of "hsa-miR-887-3p".

The term "hsa-miR-6851-5p gene" or "hsa-miR-6851-5p" used herein includes the hsa-miR-6851-5p gene (miRBase Accession No. MIMAT0027602) described in SEQ ID NO: 140, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 320) having a hairpin-like structure is known as a precursor of "hsa-miR-6851-5p".

The term "hsa-miR-6763-5p gene" or "hsa-miR-6763-5p" used herein includes the hsa-miR-6763-5p gene (miRBase Accession No. MIMAT0027426) described in SEQ ID NO: 141, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 321) having a hairpin-like structure is known as a precursor of "hsa-miR-6763-5p".

The term "hsa-miR-3928-3p gene" or "hsa-miR-3928-3p" used herein includes the hsa-miR-3928-3p gene (miRBase Accession No. MIMAT0018205) described in SEQ ID NO: 142, a homolog or an ortholog of a different organism species, and the like. The hsa-miR-3928-3p gene can be obtained by a method described in Creighton C J et al., 2010, PLoS One, Vol. 5, e9637. Also, "hsa-mir-3928" (miRBase Accession No. MI0016438, SEQ ID NO: 322) having a hairpin-like structure is known as a precursor of "hsa-miR-3928-3p".

The term "hsa-miR-4443 gene" or "hsa-miR-4443" used herein includes the hsa-miR-4443 gene (miRBase Accession No. MIMAT0018961) described in SEQ ID NO: 143, a homolog or an ortholog of a different organism species, and the like. The hsa-miR-4443 gene can be obtained by a method described in Jima D D et al., 2010, Blood, Vol. 116, e118-e127. Also, "hsa-mir-4443" (miRBase Accession No. MI0016786, SEQ ID NO: 323) having a hairpin-like structure is known as a precursor of "hsa-miR-4443".

The term "hsa-miR-3648 gene" or "hsa-miR-3648" used herein includes the hsa-miR-3648 gene (miRBase Accession No. MIMAT0018068) described in SEQ ID NO: 144, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648" (miRBase Accession No. MI0016048, SEQ ID NO: 324) having a hairpin-like structure is known as a precursor of "hsa-miR-3648".

The term "hsa-miR-149-3p gene" or "hsa-miR-149-3p" used herein includes the hsa-miR-149-3p gene (miRBase Accession No. MIMAT0004609) described in SEQ ID NO: 145, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 325) having a hairpin-like structure is known as a precursor of "hsa-miR-149-3p".

The term "hsa-miR-4689 gene" or "hsa-miR-4689" used herein includes the hsa-miR-4689 gene (miRBase Accession No. MIMAT0019778) described in SEQ ID NO: 146, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 326) having a hairpin-like structure is known as a precursor of "hsa-miR-4689".

The term "hsa-miR-4763-3p gene" or "hsa-miR-4763-3p" used herein includes the hsa-miR-4763-3p gene (miRBase Accession No. MIMAT0019913) described in SEQ ID NO: 147, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. M10017404, SEQ ID NO: 327) having a hairpin-like structure is known as a precursor of "hsa-miR-4763-3p".

The term "hsa-miR-6729-5p gene" or "hsa-miR-6729-5p" used herein includes the hsa-miR-6729-5p gene (miRBase Accession No. MIMAT0027359) described in SEQ ID NO: 148, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 328) having a hairpin-like structure is known as a precursor of "hsa-miR-6729-5p".

The term "hsa-miR-3196 gene" or "hsa-miR-3196" used herein includes the hsa-miR-3196 gene (miRBase Accession No. MIMAT0015080) described in SEQ ID NO: 149, a homolog or an ortholog of a different organism species, and the like. The hsa-miR-3196 gene can be obtained by a method described in Stark M S et al., 2010, PLoS One, Vol. 5, e9685. Also, "hsa-mir-3196" (miRBase Accession No. MI0014241, SEQ ID NO: 329) having a hairpin-like structure is known as a precursor of "hsa-miR-3196".

The term "hsa-miR-8069 gene" or "hsa-miR-8069" used herein includes the hsa-miR-8069 gene (miRBase Accession No. MIMAT0030996) described in SEQ ID NO: 150, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 330) having a hairpin-like structure is known as a precursor of "hsa-miR-8069".

The term "hsa-miR-1268a gene" or "hsa-miR-1268a" used herein includes the hsa-miR-1268a gene (miRBase Accession No. MIMAT0005922) described in SEQ ID NO: 151, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 331) having a hairpin-like structure is known as a precursor of "hsa-miR-1268a".

The term "hsa-miR-4739 gene" or "hsa-miR-4739" used herein includes the hsa-miR-4739 gene (miRBase Accession No. MIMAT0019868) described in SEQ ID NO: 152, a homolog or an ortholog of a different organism species, and the like. The hsa-miR-4739 gene can be obtained by a method described in Persson H et al., 2011, Cancer Res, Vol. 71, p. 78-86. Also, "hsa-mir-4739" (miRBase Accession No. M10017377, SEQ ID NO: 332) having a hairpin-like structure is known as a precursor of "hsa-miR-4739".

The term "hsa-miR-1268b gene" or "hsa-miR-1268b" used herein includes the hsa-miR-1268b gene (miRBase Accession No. MIMAT0018925) described in SEQ ID NO: 153, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 333) having a hairpin-like structure is known as a precursor of "hsa-miR-1268b".

The term "hsa-miR-5698 gene" or "hsa-miR-5698" used herein includes the hsa-miR-5698 gene (miRBase Accession No. MIMAT0022491) described in SEQ ID NO: 154, a homolog or an ortholog of a different organism species, and the like. The hsa-miR-5698 gene can be obtained by a method described in Watahiki A et al., 2011, PLoS One, Vol. 6, e24950. Also, "hsa-mir-5698" (miRBase Accession No. MI0019305, SEQ ID NO: 334) having a hairpin-like structure is known as a precursor of "hsa-miR-5698".

The term "hsa-miR-6752-5p gene" or "hsa-miR-6752-5p" used herein includes the hsa-miR-6752-5p gene (miRBase Accession No. MIMAT0027404) described in SEQ ID NO: 155, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. M10022597, SEQ ID NO: 335) having a hairpin-like structure is known as a precursor of "hsa-miR-6752-5p".

The term "hsa-miR-4507 gene" or "hsa-miR-4507" used herein includes the hsa-miR-4507 gene (miRBase Accession No. MIMAT0019044) described in SEQ ID NO: 156, a homolog or an ortholog of a different organism species, and the like. The hsa-miR-4507 gene can be obtained by a method described in Jima D D et al., 2010, Blood, Vol. 116, e118-e127. Also, "hsa-mir-4507" (miRBase Accession No. MI0016871, SEQ ID NO: 336) having a hairpin-like structure is known as a precursor of "hsa-miR-4507".

The term "hsa-miR-564 gene" or "hsa-miR-564" used herein includes the hsa-miR-564 gene (miRBase Accession No. MIMAT0003228) described in SEQ ID NO: 157, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 337) having a hairpin-like structure is known as a precursor of "hsa-miR-564".

The term "hsa-miR-4497 gene" or "hsa-miR-4497" used herein includes the hsa-miR-4497 gene (miRBase Accession No. MIMAT0019032) described in SEQ ID NO: 158, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 338) having a hairpin-like structure is known as a precursor of "hsa-miR-4497".

The term "hsa-miR-6877-5p gene" or "hsa-miR-6877-5p" used herein includes the hsa-miR-6877-5p gene (miRBase Accession No. MIMAT0027654) described in SEQ ID NO: 159, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI10022724, SEQ ID NO: 339) having a hairpin-like structure is known as a precursor of "hsa-miR-6877-5p".

The term "hsa-miR-6087 gene" or "hsa-miR-6087" used herein includes the hsa-miR-6087 gene (miRBase Accession No. MIMAT0023712) described in SEQ ID NO: 160, a homolog or an ortholog of a different organism species, and the like. The hsa-miR-6087 gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 340) having a hairpin-like structure is known as a precursor of "hsa-miR-6087".

The term "hsa-miR-4731-5p gene" or "hsa-miR-4731-5p" used herein includes the hsa-miR-4731-5p gene (miRBase Accession No. MIMAT0019853) described in SEQ ID NO: 161, a homolog or an ortholog of a different organism species, and the like. The hsa-miR-4731-5p gene can be obtained by a method described in Persson H et al., 2011, Cancer Res, Vol. 71, p. 78-86. Also, "hsa-mir-4731" (miRBase Accession No. MI0017368, SEQ ID NO: 341) having a hairpin-like structure is known as a precursor of "hsa-miR-4731-5p".

The term "hsa-miR-615-5p gene" or "hsa-miR-615-5p" used herein includes the hsa-miR-615-5p gene (miRBase Accession No. MIMAT0004804) described in SEQ ID NO: 162, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 342) having a hairpin-like structure is known as a precursor of "hsa-miR-615-5p".

The term "hsa-miR-760 gene" or "hsa-miR-760" used herein includes the hsa-miR-760 gene (miRBase Accession No. MIMAT0004957) described in SEQ ID NO: 163, a homolog or an ortholog of a different organism species, and the like. The hsa-miR-760 gene can be obtained by a method described in Berezikov E et al., 2006, Genome Res, Vol. 16, p. 1289-1298. Also, "hsa-mir-760" (miRBase Accession No. MI0005567, SEQ ID NO: 343) having a hairpin-like structure is known as a precursor of "hsa-miR-760".

The term "hsa-miR-6891-5p gene" or "hsa-miR-6891-5p" used herein includes the hsa-miR-6891-5p gene (miRBase Accession No. MIMAT0027682) described in SEQ ID NO: 164, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 344) having a hairpin-like structure is known as a precursor of "hsa-miR-6891-5p".

The term "hsa-miR-6887-5p gene" or "hsa-miR-6887-5p" used herein includes the hsa-miR-6887-5p gene (miRBase Accession No. MIMAT0027674) described in SEQ ID NO: 165, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 345) having a hairpin-like structure is known as a precursor of "hsa-miR-6887-5p".

The term "hsa-miR-4525 gene" or "hsa-miR-4525" used herein includes the hsa-miR-4525 gene (miRBase Accession No. MIMAT0019064) described in SEQ ID NO: 166, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 346) having a hairpin-like structure is known as a precursor of "hsa-miR-4525".

The term "hsa-miR-1914-3p gene" or "hsa-miR-1914-3p" used herein includes the hsa-miR-1914-3p gene (miRBase Accession No. MIMAT0007890) described in SEQ ID NO: 167, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 347) having a hairpin-like structure is known as a precursor of "hsa-miR-1914-3p".

The term "hsa-miR-619-5p gene" or "hsa-miR-619-5p" used herein includes the hsa-miR-619-5p gene (miRBase Accession No. MIMAT0026622) described in SEQ ID NO: 168, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 348) having a hairpin-like structure is known as a precursor of "hsa-miR-619-5p".

The term "hsa-miR-5001-5p gene" or "hsa-miR-5001-5p" used herein includes the hsa-miR-5001-5p gene (miRBase Accession No. MIMAT0021021) described in SEQ ID NO: 169, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 349) having a hairpin-like structure is known as a precursor of "hsa-miR-5001-5p".

The term "hsa-miR-6722-3p gene" or "hsa-miR-6722-3p" used herein includes the hsa-miR-6722-3p gene (miRBase Accession No. MIMAT0025854) described in SEQ ID NO: 170, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 350) having a hairpin-like structure is known as a precursor of "hsa-miR-6722-3p".

The term "hsa-miR-3621 gene" or "hsa-miR-3621" used herein includes the hsa-miR-3621 gene (miRBase Accession No. MIMAT0018002) described in SEQ ID NO: 171, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 351) having a hairpin-like structure is known as a precursor of "hsa-miR-3621".

The term "hsa-miR-4298 gene" or "hsa-miR-4298" used herein includes the hsa-miR-4298 gene (miRBase Accession No. MIMAT0016852) described in SEQ ID NO: 172, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 352) having a hairpin-like structure is known as a precursor of "hsa-miR-4298".

The term "hsa-miR-675-5p gene" or "hsa-miR-675-5p" used herein includes the hsa-miR-675-5p gene (miRBase Accession No. MIMAT0004284) described in SEQ ID NO: 173, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 353) having a hairpin-like structure is known as a precursor of "hsa-miR-675-5p".

The term "hsa-miR-4655-5p gene" or "hsa-miR-4655-5p" used herein includes the hsa-miR-4655-5p gene (miRBase Accession No. MIMAT0019721) described in SEQ ID NO: 174, a homolog or an ortholog of a different organism species, and the like. The hsa-miR-4655-5p gene can be obtained by a method described in Persson H et al., 2011, Cancer Res, Vol. 71, p. 78-86. Also, "hsa-mir-4655" (miRBase Accession No. MI0017283, SEQ ID NO: 354) having a hairpin-like structure is known as a precursor of "hsa-miR-4655-5p".

The term "hsa-miR-6073 gene" or "hsa-miR-6073" used herein includes the hsa-miR-6073 gene (miRBase Accession No. MIMAT0023698) described in SEQ ID NO: 561, a homolog or an ortholog of a different organism species, and the like. The hsa-miR-6073 gene can be obtained by a method described in Voellenkle C et al., 2012, RNA, Vol. 18, p. 472-484. Also, "hsa-mir-6073" (miRBase Accession No. MI0020350, SEQ ID NO: 580) having a hairpin-like structure is known as a precursor of "hsa-miR-6073".

The term "hsa-miR-6845-5p gene" or "hsa-miR-6845-5p" used herein includes the hsa-miR-6845-5p gene (miRBase Accession No. MIMAT0027590) described in SEQ ID NO: 562, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 581) having a hairpin-like structure is known as a precursor of "hsa-miR-6845-5p".

The term "hsa-miR-6769b-5p gene" or "hsa-miR-6769b-5p" used herein includes the hsa-miR-6769b-5p gene (miRBase Accession No. MIMAT0027620) described in SEQ ID NO: 563, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 582) having a hairpin-like structure is known as a precursor of "hsa-miR-6769b-5p".

The term "hsa-miR-4665-3p gene" or "hsa-miR-4665-3p" used herein includes the hsa-miR-4665-3p gene (miRBase Accession No. MIMAT0019740) described in SEQ ID NO: 564, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 583) having a hairpin-like structure is known as a precursor of "hsa-miR-4665-3p".

The term "hsa-miR-1913 gene" or "hsa-miR-1913" used herein includes the hsa-miR-1913 gene (miRBase Accession No. MIMAT0007888) described in SEQ ID NO: 565, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 584) having a hairpin-like structure is known as a precursor of "hsa-miR-1913".

The term "hsa-miR-1228-3p gene" or "hsa-miR-1228-3p" used herein includes the hsa-miR-1228-3p gene (miRBase Accession No. MIMAT0005583) described in SEQ ID NO: 566, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 311) having a hairpin-like structure is known as a precursor of "hsa-miR-1228-3p".

The term "hsa-miR-940 gene" or "hsa-miR-940" used herein includes the hsa-miR-940 gene (miRBase Accession No. MIMAT0004983) described in SEQ ID NO: 567, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 585) having a hairpin-like structure is known as a precursor of "hsa-miR-940".

The term "hsa-miR-296-3p gene" or "hsa-miR-296-3p" used herein includes the hsa-miR-296-3p gene (miRBase Accession No. MIMAT0004679) described in SEQ ID NO: 568, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 586) having a hairpin-like structure is known as a precursor of "hsa-miR-296-3p".

The term "hsa-miR-4690-5p gene" or "hsa-miR-4690-5p" used herein includes the hsa-miR-4690-5p gene (miRBase Accession No. MIMAT0019779) described in SEQ ID NO: 569, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 587) having a hairpin-like structure is known as a precursor of "hsa-miR-4690-5p".

The term "hsa-miR-548q gene" or "hsa-miR-548q" used herein includes the hsa-miR-548q gene (miRBase Accession No. MIMAT0011163) described in SEQ ID NO: 570, a homolog or an ortholog of a different organism species, and the like. The hsa-miR-548q gene can be obtained by a method described in Wyman S K et al., 2009, PLoS One., Vol. 4, e5311. Also, "hsa-mir-548q" (miRBase Accession No. MI0010637, SEQ ID NO: 588) having a hairpin-like structure is known as a precursor of "hsa-miR-548q".

The term "hsa-miR-663a gene" or "hsa-miR-663a" used herein includes the hsa-miR-663a gene (miRBase Accession No. MIMAT0003326) described in SEQ ID NO: 571, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 589) having a hairpin-like structure is known as a precursor of "hsa-miR-663a".

The term "hsa-miR-1249 gene" or "hsa-miR-1249" used herein includes the hsa-miR-1249 gene (miRBase Accession No. MIMAT0005901) described in SEQ ID NO: 572, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 590) having a hairpin-like structure is known as a precursor of "hsa-miR-1249".

The term "hsa-miR-1202 gene" or "hsa-miR-1202" used herein includes the hsa-miR-1202 gene (miRBase Accession No. MIMAT0005865) described in SEQ ID NO: 573, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 591) having a hairpin-like structure is known as a precursor of "hsa-miR-1202".

The term "hsa-miR-7113-3p gene" or "hsa-miR-7113-3p" used herein includes the hsa-miR-7113-3p gene (miRBase Accession No. MIMAT0028124) described in SEQ ID NO: 574, a homolog or an ortholog of a different organism species, and the like. The hsa-miR-7113-3p gene can be obtained by a method described in Ladewig E et al., 2012, Genome Res, Vol. 22, p. 1634-1645. Also, "hsa-mir-7113" (miRBase Accession No. MI0022964, SEQ ID NO: 592) having a hairpin-like structure is known as a precursor of "hsa-miR-7113-3p".

The term "hsa-miR-1225-3p gene" or "hsa-miR-1225-3p" used herein includes the hsa-miR-1225-3p gene (miRBase Accession No. MIMAT0005573) described in SEQ ID NO: 575, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 307) having a hairpin-like structure is known as a precursor of "hsa-miR-1225-3p".

The term "hsa-miR-4783-3p gene" or "hsa-miR-4783-3p" used herein includes the hsa-miR-4783-3p gene (miRBase Accession No. MIMAT0019947) described in SEQ ID NO: 576, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 593) having a hairpin-like structure is known as a precursor of "hsa-miR-4783-3p".

The term "hsa-miR-4448 gene" or "hsa-miR-4448" used herein includes the hsa-miR-4448 gene (miRBase Accession No. MIMAT0018967) described in SEQ ID NO: 577, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No. MI0016791, SEQ ID NO: 594) having a hairpin-like structure is known as a precursor of "hsa-miR-4448".

The term "hsa-miR-4534 gene" or "hsa-miR-4534" used herein includes the hsa-miR-4534 gene (miRBase Accession No. MIMAT0019073) described in SEQ ID NO: 578, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 595) having a hairpin-like structure is known as a precursor of "hsa-miR-4534".

The term "hsa-miR-1307-3p gene" or "hsa-miR-1307-3p" used herein includes the hsa-miR-1307-3p gene (miRBase Accession No. MIMAT0005951) described in SEQ ID NO: 579, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 596) having a hairpin-like structure is known as a precursor of "hsa-miR-1307-3p".

A mature miRNA may become a variant due to the sequence cleaved shorter or longer by one to several upstream or downstream nucleotides or nucleotide substitution when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 174 and 561 to 579 as well as a large number of the nucleotide sequence variants and fragments represented by SEQ ID NOs: 355 to 560 and 597 to 618, called isomiRs. These variants can also be obtained as miRNAs having a nucleotide sequence represented by any of SEQ ID NOs: 1 to 174 and 561 to 579. Specifically, among the variants of polynucleotides consisting of the nucleotide sequence represented by any of SEQ ID NOs: 5, 8, 9, 11, 18, 20, 22, 23, 24, 28, 29, 30, 32, 34, 37, 40, 41, 47, 48, 49, 51, 52, 53, 56, 58, 59, 60, 61, 63, 64, 65, 66, 67, 69, 72, 73, 75, 78, 79, 80, 81, 82, 85, 88, 89, 91, 92, 95, 96, 103, 104, 105, 106, 107, 108, 109, 110, 112, 113, 114, 117, 118, 120, 123, 124, 125, 126, 128, 129, 130, 131, 132, 133, 134, 135, 136, 138, 139, 142, 143, 144, 145, 146, 147, 149, 151, 152, 153, 154, 156, 157, 158, 160, 161, 162, 163, 166, 167, 168, 169, 172, 173, 174, 565, 566, 567, 568, 569, 571, 572, 573, 576, 577, 579, or a nucleotide sequence derived from the nucleotide sequence by the replacement of u with t in the nucleotide sequence, examples of the longest variants registered in the miRBase Release 20 include polynucleotides represented by SEQ ID NOs: 355, 357, 359, 361, 363, 365, 367, 369, 371, 373, 375, 377, 379, 381, 383, 385, 387, 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 597, 599, 601, 603, 605, 607, 609, 611, 613, 615 and 617, respectively.

Also, among the variants of polynucleotides consisting of a nucleotide sequence represented by any of SEQ ID NOs: 5, 8, 9, 11, 18, 20, 22, 23, 24, 28, 29, 30, 32, 34, 37, 40, 41, 47, 48, 49, 51, 52, 53, 56, 58, 59, 60, 61, 63, 64, 65, 66, 67, 69, 72, 73, 75, 78, 79, 80, 81, 82, 85, 88, 89, 91, 92, 95, 96, 103, 104, 105, 106, 107, 108, 109, 110, 112, 113, 114, 117, 118, 120, 123, 124, 125, 126, 128, 129, 130, 131, 132, 133, 134, 135, 136, 138, 139, 142, 143, 144, 145, 146, 147, 149, 151, 152, 153, 154, 156, 157, 158, 160, 161, 162, 163, 166, 167, 168, 169, 172, 173, 174, 565, 566, 567, 568, 569, 571, 572, 573, 576, 577, 579 or a nucleotide sequence derived from the nucleotide sequence by the replacement of u with t in the nucleotide sequence, examples of the shortest variants registered in the miRBase Release 20 include polynucleotides having sequences represented by SEQ ID NOs: 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 598, 600, 602, 604, 606, 608, 610, 612, 614, 616 and 618, respectively.

In addition to these variants and fragments, examples thereof include a large number of isomiR polynucleotides of SEQ ID NOs: 1 to 174 and 561 to 579 registered in miRBase. Examples of the polynucleotide comprising a nucleotide sequence represented by any of SEQ ID NOs: 1 to 174 and 561 to 579 include a polynucleotide represented by any of SEQ ID NOs: 175 to 354 and 579 to 596, which are their respective precursors.

The names and miRBase Accession Nos. (registration numbers) of the genes represented by SEQ ID NOs: 1 to 618 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-6768-5p | MIMAT0027436 |
| 2 | hsa-miR-6836-3p | MIMAT0027575 |
| 3 | hsa-miR-6782-5p | MIMAT0027464 |
| 4 | hsa-miR-3663-3p | MIMAT0018085 |
| 5 | hsa-miR-1908-3p | MIMAT0026916 |
| 6 | hsa-miR-6726-5p | MIMAT0027353 |
| 7 | hsa-miR-4258 | MIMAT0016879 |
| 8 | hsa-miR-1343-3p | MIMAT0019776 |
| 9 | hsa-miR-4516 | MIMAT0019053 |
| 10 | hsa-miR-6875-5p | MIMAT0027650 |
| 11 | hsa-miR-4651 | MIMAT0019715 |
| 12 | hsa-miR-6825-5p | MIMAT0027550 |
| 13 | hsa-miR-6840-3p | MIMAT0027583 |
| 14 | hsa-miR-6780b-5p | MIMAT0027572 |
| 15 | hsa-miR-6749-5p | MIMAT0027398 |
| 16 | hsa-miR-8063 | MIMAT0030990 |
| 17 | hsa-miR-6784-5p | MIMAT0027468 |
| 18 | hsa-miR-3679-5p | MIMAT0018104 |
| 19 | hsa-miR-3184-5p | MIMAT0015064 |
| 20 | hsa-miR-663b | MIMAT0005867 |
| 21 | hsa-miR-6880-5p | MIMAT0027660 |
| 22 | hsa-miR-1908-5p | MIMAT0007881 |
| 23 | hsa-miR-92a-2-5p | MIMAT0004508 |
| 24 | hsa-miR-7975 | MIMAT0031178 |
| 25 | hsa-miR-7110-5p | MIMAT0028117 |
| 26 | hsa-miR-6842-5p | MIMAT0027586 |
| 27 | hsa-miR-6857-5p | MIMAT0027614 |
| 28 | hsa-miR-5572 | MIMAT0022260 |
| 29 | hsa-miR-3197 | MIMAT0015082 |
| 30 | hsa-miR-6131 | MIMAT0024615 |
| 31 | hsa-miR-6889-5p | MIMAT0027678 |
| 32 | hsa-miR-4454 | MIMAT0018976 |
| 33 | hsa-miR-1199-5p | MIMAT0031119 |
| 34 | hsa-miR-1247-3p | MIMAT0022721 |
| 35 | hsa-miR-6800-5p | MIMAT0027500 |
| 36 | hsa-miR-6872-3p | MIMAT0027645 |
| 37 | hsa-miR-4649-5p | MIMAT0019711 |
| 38 | hsa-miR-6791-5p | MIMAT0027482 |
| 39 | hsa-miR-4433b-3p | MIMAT0030414 |
| 40 | hsa-miR-3135b | MIMAT0018985 |
| 41 | hsa-miR-128-2-5p | MIMAT0031095 |
| 42 | hsa-miR-4675 | MIMAT0019757 |
| 43 | hsa-miR-4472 | MIMAT0018999 |
| 44 | hsa-miR-6785-5p | MIMAT0027470 |
| 45 | hsa-miR-6741-5p | MIMAT0027383 |
| 46 | hsa-miR-7977 | MIMAT0031180 |
| 47 | hsa-miR-3665 | MIMAT0018087 |
| 48 | hsa-miR-128-1-5p | MIMAT0026477 |
| 49 | hsa-miR-4286 | MIMAT0016916 |
| 50 | hsa-miR-6765-3p | MIMAT0027431 |
| 51 | hsa-miR-4632 | MIMAT0022977 |
| 52 | hsa-miR-365a-5p | MIMAT0009199 |
| 53 | hsa-miR-6088 | MIMAT0023713 |
| 54 | hsa-miR-6816-5p | MIMAT0027532 |
| 55 | hsa-miR-6885-5p | MIMAT0027670 |
| 56 | hsa-miR-711 | MIMAT0012734 |
| 57 | hsa-miR-6765-5p | MIMAT0027430 |
| 58 | hsa-miR-3180 | MIMAT0018178 |
| 59 | hsa-miR-4442 | MIMAT0018960 |
| 60 | hsa-miR-4792 | MIMAT0019964 |
| 61 | hsa-miR-6721-5p | MIMAT0025852 |
| 62 | hsa-miR-6798-5p | MIMAT0027496 |
| 63 | hsa-miR-3162-5p | MIMAT0015036 |
| 64 | hsa-miR-6126 | MIMAT0024599 |
| 65 | hsa-miR-4758-5p | MIMAT0019903 |
| 66 | hsa-miR-2392 | MIMAT0019043 |
| 67 | hsa-miR-486-3p | MIMAT0004762 |
| 68 | hsa-miR-6727-5p | MIMAT0027355 |
| 69 | hsa-miR-4728-5p | MIMAT0019849 |
| 70 | hsa-miR-6746-5p | MIMAT0027392 |
| 71 | hsa-miR-4270 | MIMAT0016900 |
| 72 | hsa-miR-3940-5p | MIMAT0019229 |
| 73 | hsa-miR-4725-3p | MIMAT0019844 |
| 74 | hsa-miR-7108-5p | MIMAT0028113 |
| 75 | hsa-miR-3656 | MIMAT0018076 |
| 76 | hsa-miR-6879-5p | MIMAT0027658 |
| 77 | hsa-miR-6738-5p | MIMAT0027377 |
| 78 | hsa-miR-1260a | MIMAT0005911 |
| 79 | hsa-miR-4446-3p | MIMAT0018965 |
| 80 | hsa-miR-3131 | MIMAT0014996 |
| 81 | hsa-miR-4463 | MIMAT0018987 |
| 82 | hsa-miR-3185 | MIMAT0015065 |
| 83 | hsa-miR-6870-5p | MIMAT0027640 |
| 84 | hsa-miR-6779-5p | MIMAT0027458 |
| 85 | hsa-miR-1273g-3p | MIMAT0022742 |
| 86 | hsa-miR-8059 | MIMAT0030986 |
| 87 | hsa-miR-4697-5p | MIMAT0019791 |
| 88 | hsa-miR-4674 | MIMAT0019756 |
| 89 | hsa-miR-4433-3p | MIMAT0018949 |
| 90 | hsa-miR-4257 | MIMAT0016878 |
| 91 | hsa-miR-1915-5p | MIMAT0007891 |
| 92 | hsa-miR-4417 | MIMAT0018929 |
| 93 | hsa-miR-1343-5p | MIMAT0027038 |
| 94 | hsa-miR-6781-5p | MIMAT0027462 |
| 95 | hsa-miR-4695-5p | MIMAT0019788 |
| 96 | hsa-miR-1237-5p | MIMAT0022946 |
| 97 | hsa-miR-6775-5p | MIMAT0027450 |
| 98 | hsa-miR-7845-5p | MIMAT0030420 |
| 99 | hsa-miR-4746-3p | MIMAT0019881 |
| 100 | hsa-miR-7641 | MIMAT0029782 |
| 101 | hsa-miR-7847-3p | MIMAT0030422 |
| 102 | hsa-miR-6806-5p | MIMAT0027512 |
| 103 | hsa-miR-4467 | MIMAT0018994 |
| 104 | hsa-miR-4726-5p | MIMAT0019845 |
| 105 | hsa-miR-4648 | MIMAT0019710 |
| 106 | hsa-miR-6089 | MIMAT0023714 |
| 107 | hsa-miR-1260b | MIMAT0015041 |
| 108 | hsa-miR-4532 | MIMAT0019071 |
| 109 | hsa-miR-5195-3p | MIMAT0021127 |
| 110 | hsa-miR-3188 | MIMAT0015070 |
| 111 | hsa-miR-6848-5p | MIMAT0027596 |
| 112 | hsa-miR-1233-5p | MIMAT0022943 |
| 113 | hsa-miR-6717-5p | MIMAT0025846 |
| 114 | hsa-miR-3195 | MIMAT0015079 |
| 115 | hsa-miR-6757-5p | MIMAT0027414 |
| 116 | hsa-miR-8072 | MIMAT0030999 |
| 117 | hsa-miR-4745-5p | MIMAT0019878 |
| 118 | hsa-miR-6511a-5p | MIMAT0025478 |
| 119 | hsa-miR-6776-5p | MIMAT0027452 |
| 120 | hsa-miR-371a-5p | MIMAT0004687 |
| 121 | hsa-miR-1227-5p | MIMAT0022941 |
| 122 | hsa-miR-7150 | MIMAT0028211 |
| 123 | hsa-miR-1915-3p | MIMAT0007892 |
| 124 | hsa-miR-187-5p | MIMAT0004561 |
| 125 | hsa-miR-614 | MIMAT0003282 |
| 126 | hsa-miR-19b-3p | MIMAT0000074 |
| 127 | hsa-miR-1225-5p | MIMAT0005572 |
| 128 | hsa-miR-451a | MIMAT0001631 |
| 129 | hsa-miR-939-5p | MIMAT0004982 |
| 130 | hsa-miR-223-3p | MIMAT0000280 |
| 131 | hsa-miR-1228-5p | MIMAT0005582 |
| 132 | hsa-miR-125a-3p | MIMAT0004602 |
| 133 | hsa-miR-92b-5p | MIMAT0004792 |
| 134 | hsa-miR-22-3p | MIMAT0000077 |
| 135 | hsa-miR-4271 | MIMAT0016901 |
| 136 | hsa-miR-642b-3p | MIMAT0018444 |
| 137 | hsa-miR-6075 | MIMAT0023700 |
| 138 | hsa-miR-6125 | MIMAT0024598 |
| 139 | hsa-miR-887-3p | MIMAT0004951 |
| 140 | hsa-miR-6851-5p | MIMAT0027602 |
| 141 | hsa-miR-6763-5p | MIMAT0027426 |
| 142 | hsa-miR-3928-3p | MIMAT0018205 |
| 143 | hsa-miR-4443 | MIMAT0018961 |
| 144 | hsa-miR-3648 | MIMAT0018068 |
| 145 | hsa-miR-149-3p | MIMAT0004609 |
| 146 | hsa-miR-4689 | MIMAT0019778 |
| 147 | hsa-miR-4763-3p | MIMAT0019913 |
| 148 | hsa-miR-6729-5p | MIMAT0027359 |
| 149 | hsa-miR-3196 | MIMAT0015080 |
| 150 | hsa-miR-8069 | MIMAT0030996 |
| 151 | hsa-miR-1268a | MIMAT0005922 |
| 152 | hsa-miR-4739 | MIMAT0019868 |
| 153 | hsa-miR-1268b | MIMAT0018925 |
| 154 | hsa-miR-5698 | MIMAT0022491 |

TABLE 1-continued

| SEQ ID NO: | Gene name | miRBase registration No. |
|---|---|---|
| 155 | hsa-miR-6752-5p | MIMAT0027404 |
| 156 | hsa-miR-4507 | MIMAT0019044 |
| 157 | hsa-miR-564 | MIMAT0003228 |
| 158 | hsa-miR-4497 | MIMAT0019032 |
| 159 | hsa-miR-6877-5p | MIMAT0027654 |
| 160 | hsa-miR-6087 | MIMAT0023712 |
| 161 | hsa-miR-4731-5p | MIMAT0019853 |
| 162 | hsa-miR-615-5p | MIMAT0004804 |
| 163 | hsa-miR-760 | MIMAT0004957 |
| 164 | hsa-miR-6891-5p | MIMAT0027682 |
| 165 | hsa-miR-6887-5p | MIMAT0027674 |
| 166 | hsa-miR-4525 | MIMAT0019064 |
| 167 | hsa-miR-1914-3p | MIMAT0007890 |
| 168 | hsa-miR-619-5p | MIMAT0026622 |
| 169 | hsa-miR-5001-5p | MIMAT0021021 |
| 170 | hsa-miR-6722-3p | MIMAT0025854 |
| 171 | hsa-miR-3621 | MIMAT0018002 |
| 172 | hsa-miR-4298 | MIMAT0016852 |
| 173 | hsa-miR-675-5p | MIMAT0004284 |
| 174 | hsa-miR-4655-5p | MIMAT0019721 |
| 175 | hsa-mir-6768 | MI0022613 |
| 176 | hsa-mir-6836 | MI0022682 |
| 177 | hsa-mir-6782 | MI0022627 |
| 178 | hsa-mir-3663 | MI0016064 |
| 179 | hsa-mir-1908 | MI0008329 |
| 180 | hsa-mir-6726 | MI0022571 |
| 181 | hsa-mir-4258 | MI0015857 |
| 182 | hsa-mir-1343 | MI0017320 |
| 183 | hsa-mir-4516 | MI0016882 |
| 184 | hsa-mir-6875 | MI0022722 |
| 185 | hsa-mir-4651 | MI0017279 |
| 186 | hsa-mir-6825 | MI0022670 |
| 187 | hsa-mir-6840 | MI0022686 |
| 188 | hsa-mir-6780b | MI0022681 |
| 189 | hsa-mir-6749 | MI0022594 |
| 190 | hsa-mir-8063 | MI0025899 |
| 191 | hsa-mir-6784 | MI0022629 |
| 192 | hsa-mir-3679 | MI0016080 |
| 193 | hsa-mir-3184 | MI0014226 |
| 194 | hsa-mir-663b | MI0006336 |
| 195 | hsa-mir-6880 | MI0022727 |
| 196 | hsa-mir-92a-2 | MI0000094 |
| 197 | hsa-mir-7975 | MI0025751 |
| 198 | hsa-mir-7110 | MI0022961 |
| 199 | hsa-mir-6842 | MI0022688 |
| 200 | hsa-mir-6857 | MI0022703 |
| 201 | hsa-mir-5572 | MI0019117 |
| 202 | hsa-mir-3197 | MI0014245 |
| 203 | hsa-mir-6131 | MI0021276 |
| 204 | hsa-mir-6889 | MI0022736 |
| 205 | hsa-mir-4454 | MI0016800 |
| 206 | hsa-mir-1199 | MI0020340 |
| 207 | hsa-mir-1247 | MI0006382 |
| 208 | hsa-mir-6800 | MI0022645 |
| 209 | hsa-mir-6872 | MI0022719 |
| 210 | hsa-mir-4649 | MI0017276 |
| 211 | hsa-mir-6791 | MI0022636 |
| 212 | hsa-mir-4433b | MI0025511 |
| 213 | hsa-mir-3135b | MI0016809 |
| 214 | hsa-mir-128-2 | MI0000727 |
| 215 | hsa-mir-4675 | MI0017306 |
| 216 | hsa-mir-4472-1 | MI0016823 |
| 217 | hsa-mir-4472-2 | MI0016824 |
| 218 | hsa-mir-6785 | MI0022630 |
| 219 | hsa-mir-6741 | MI0022586 |
| 220 | hsa-mir-7977 | MI0025753 |
| 221 | hsa-mir-3665 | MI0016066 |
| 222 | hsa-mir-128-1 | MI0000447 |
| 223 | hsa-mir-4286 | MI0015894 |
| 224 | hsa-mir-6765 | MI0022610 |
| 225 | hsa-mir-4632 | MI0017259 |
| 226 | hsa-mir-365a | MI0000767 |
| 227 | hsa-mir-6088 | MI0020365 |
| 228 | hsa-mir-6816 | MI0022661 |
| 229 | hsa-mir-6885 | MI0022732 |
| 230 | hsa-mir-711 | MI0012488 |
| 231 | hsa-mir-3180-4 | MI0016408 |
| 232 | hsa-mir-3180-5 | MI0016409 |
| 233 | hsa-mir-4442 | MI0016785 |
| 234 | hsa-mir-4792 | MI0017439 |
| 235 | hsa-mir-6721 | MI0022556 |
| 236 | hsa-mir-6798 | MI0022643 |
| 237 | hsa-mir-3162 | MI0014192 |
| 238 | hsa-mir-6126 | MI0021260 |
| 239 | hsa-mir-4758 | MI0017399 |
| 240 | hsa-mir-2392 | MI0016870 |
| 241 | hsa-mir-486 | MI0002470 |
| 242 | hsa-mir-486-2 | MI0023622 |
| 243 | hsa-mir-6727 | MI0022572 |
| 244 | hsa-mir-4728 | MI0017365 |
| 245 | hsa-mir-6746 | MI0022591 |
| 246 | hsa-mir-4270 | MI0015878 |
| 247 | hsa-mir-3940 | MI0016597 |
| 248 | hsa-mir-4725 | MI0017362 |
| 249 | hsa-mir-7108 | MI0022959 |
| 250 | hsa-mir-3656 | MI0016056 |
| 251 | hsa-mir-6879 | MI0022726 |
| 252 | hsa-mir-6738 | MI0022583 |
| 253 | hsa-mir-1260a | MI0006394 |
| 254 | hsa-mir-4446 | MI0016789 |
| 255 | hsa-mir-3131 | MI0014151 |
| 256 | hsa-mir-4463 | MI0016811 |
| 257 | hsa-mir-3185 | MI0014227 |
| 258 | hsa-mir-6870 | MI0022717 |
| 259 | hsa-mir-6779 | MI0022624 |
| 260 | hsa-mir-1273g | MI0018003 |
| 261 | hsa-mir-8059 | MI0025895 |
| 262 | hsa-mir-4697 | MI0017330 |
| 263 | hsa-mir-4674 | MI0017305 |
| 264 | hsa-mir-4433 | MI0016773 |
| 265 | hsa-mir-4257 | MI0015856 |
| 266 | hsa-mir-1915 | MI0008336 |
| 267 | hsa-mir-4417 | MI0016753 |
| 268 | hsa-mir-6781 | MI0022626 |
| 269 | hsa-mir-4695 | MI0017328 |
| 270 | hsa-mir-1237 | MI0006327 |
| 271 | hsa-mir-6775 | MI0022620 |
| 272 | hsa-mir-7845 | MI0025515 |
| 273 | hsa-mir-4746 | MI0017385 |
| 274 | hsa-mir-7641-1 | MI0024975 |
| 275 | hsa-mir-7641-2 | MI0024976 |
| 276 | hsa-mir-7847 | MI0025517 |
| 277 | hsa-mir-6806 | MI0022651 |
| 278 | hsa-mir-4467 | MI0016818 |
| 279 | hsa-mir-4726 | MI0017363 |
| 280 | hsa-mir-4648 | MI0017275 |
| 281 | hsa-mir-6089-1 | MI0020366 |
| 282 | hsa-mir-6089-2 | MI0023563 |
| 283 | hsa-mir-1260b | MI0014197 |
| 284 | hsa-mir-4532 | MI0016899 |
| 285 | hsa-mir-5195 | MI0018174 |
| 286 | hsa-mir-3188 | MI0014232 |
| 287 | hsa-mir-6848 | MI0022694 |
| 288 | hsa-mir-1233-1 | MI0006323 |
| 289 | hsa-mir-1233-2 | MI0015973 |
| 290 | hsa-mir-6717 | MI0022551 |
| 291 | hsa-mir-3195 | MI0014240 |
| 292 | hsa-mir-6757 | MI0022602 |
| 293 | hsa-mir-8072 | MI0025908 |
| 294 | hsa-mir-4745 | MI0017384 |
| 295 | hsa-mir-6511a-1 | MI0022223 |
| 296 | hsa-mir-6511a-2 | MI0023564 |
| 297 | hsa-mir-6511a-3 | MI0023565 |
| 298 | hsa-mir-6511a-4 | MI0023566 |
| 299 | hsa-mir-6776 | MI0022621 |
| 300 | hsa-mir-371a | MI0000779 |
| 301 | hsa-mir-1227 | MI0006316 |
| 302 | hsa-mir-7150 | MI0023610 |
| 303 | hsa-mir-187 | MI0000274 |
| 304 | hsa-mir-614 | MI0003627 |
| 305 | hsa-mir-19b-1 | MI0000074 |
| 306 | hsa-mir-19b-2 | MI0000075 |
| 307 | hsa-mir-1225 | MI0006311 |
| 308 | hsa-mir-451a | MI0001729 |

TABLE 1-continued

| SEQ ID NO: | Gene name | miRBase registration No. |
|---|---|---|
| 309 | hsa-mir-939 | MI0005761 |
| 310 | hsa-mir-223 | MI0000300 |
| 311 | hsa-mir-1228 | MI0006318 |
| 312 | hsa-mir-125a | MI0000469 |
| 313 | hsa-mir-92b | MI0003 560 |
| 314 | hsa-mir-22 | MI0000078 |
| 315 | hsa-mir-4271 | MI0015879 |
| 316 | hsa-mir-642b | MI0016685 |
| 317 | hsa-mir-6075 | MI0020352 |
| 318 | hsa-mir-6125 | MI0021259 |
| 319 | hsa-mir-887 | MI0005562 |
| 320 | hsa-mir-6851 | MI0022697 |
| 321 | hsa-mir-6763 | MI0022608 |
| 322 | hsa-mir-3928 | MI0016438 |
| 323 | hsa-mir-4443 | MI0016786 |
| 324 | hsa-mir-3648 | MI0016048 |
| 325 | hsa-mir-149 | MI0000478 |
| 326 | hsa-mir-4689 | MI0017322 |
| 327 | hsa-mir-4763 | MI0017404 |
| 328 | hsa-mir-6729 | MI0022574 |
| 329 | hsa-mir-3196 | MI0014241 |
| 330 | hsa-mir-8069 | MI0025905 |
| 331 | hsa-mir-1268a | MI0006405 |
| 332 | hsa-mir-4739 | MI0017377 |
| 333 | hsa-mir-1268b | MI0016748 |
| 334 | hsa-mir-5698 | MI0019305 |
| 335 | hsa-mir-6752 | MI0022597 |
| 336 | hsa-mir-4507 | MI0016871 |
| 337 | hsa-mir-564 | MI0003570 |
| 338 | hsa-mir-4497 | MI0016859 |
| 339 | hsa-mir-6877 | MI0022724 |
| 340 | hsa-mir-6087 | MI0020364 |
| 341 | hsa-mir-4731 | MI0017368 |
| 342 | hsa-mir-615 | MI0003628 |
| 343 | hsa-mir-760 | MI0005567 |
| 344 | hsa-mir-6891 | MI0022738 |
| 345 | hsa-mir-6887 | MI0022734 |
| 346 | hsa-mir-4525 | MI0016892 |
| 347 | hsa-mir-1914 | MI0008335 |
| 348 | hsa-mir-619 | MI0003633 |
| 349 | hsa-mir-5001 | MI0017867 |
| 350 | hsa-mir-6722 | MI0022557 |
| 351 | hsa-mir-3621 | MI0016012 |
| 352 | hsa-mir-4298 | MI0015830 |
| 353 | hsa-mir-675 | MI0005416 |
| 354 | hsa-mir-4655 | MI0017283 |
| 355 | isomiR example 1 of SEQ ID NO: 5 | — |
| 356 | isomiR example 2 of SEQ ID NO: 5 | — |
| 357 | isomiR example 1 of SEQ ID NO: 8 | — |
| 358 | isomiR example 2 of SEQ ID NO: 8 | — |
| 359 | isomiR example 1 of SEQ ID NO: 9 | — |
| 360 | isomiR example 2 of SEQ ID NO: 9 | — |
| 361 | isomiR example 1 of SEQ ID NO: 11 | — |
| 362 | isomiR example 2 of SEQ ID NO: 11 | — |
| 363 | isomiR example 1 of SEQ ID NO: 18 | — |
| 364 | isomiR example 2 of SEQ ID NO: 18 | — |
| 365 | isomiR example 1 of SEQ ID NO: 20 | — |
| 366 | isomiR example 2 of SEQ ID NO: 20 | — |
| 367 | isomiR example 1 of SEQ ID NO: 22 | — |
| 368 | isomiR example 2 of SEQ ID NO: 22 | — |
| 369 | isomiR example 1 of SEQ ID NO: 23 | — |
| 370 | isomiR example 2 of SEQ ID NO: 23 | — |
| 371 | isomiR example 1 of SEQ ID NO: 24 | — |
| 372 | isomiR example 2 of SEQ ID NO: 24 | — |
| 373 | isomiR example 1 of SEQ ID NO: 28 | — |
| 374 | isomiR example 2 of SEQ ID NO: 28 | — |
| 375 | isomiR example 1 of SEQ ID NO: 29 | — |
| 376 | isomiR example 2 of SEQ ID NO: 29 | — |
| 377 | isomiR example 1 of SEQ ID NO: 30 | — |
| 378 | isomiR example 2 of SEQ ID NO: 30 | — |
| 379 | isomiR example 1 of SEQ ID NO: 32 | — |
| 380 | isomiR example 2 of SEQ ID NO: 32 | — |
| 381 | isomiR example 1 of SEQ ID NO: 34 | — |
| 382 | isomiR example 2 of SEQ ID NO: 34 | — |
| 383 | isomiR example 1 of SEQ ID NO: 37 | — |
| 384 | isomiR example 2 of SEQ ID NO: 37 | — |
| 385 | isomiR example 1 of SEQ ID NO: 40 | — |
| 386 | isomiR example 2 of SEQ ID NO: 40 | — |
| 387 | isomiR example 1 of SEQ ID NO: 41 | — |
| 388 | isomiR example 2 of SEQ ID NO: 41 | — |
| 389 | isomiR example 1 of SEQ ID NO: 47 | — |
| 390 | isomiR example 2 of SEQ ID NO: 47 | — |
| 391 | isomiR example 1 of SEQ ID NO: 48 | — |
| 392 | isomiR example 2 of SEQ ID NO: 48 | — |
| 393 | isomiR example 1 of SEQ ID NO: 49 | — |
| 394 | isomiR example 2 of SEQ ID NO: 49 | — |
| 395 | isomiR example 1 of SEQ ID NO: 51 | — |
| 396 | isomiR example 2 of SEQ ID NO: 51 | — |
| 397 | isomiR example 1 of SEQ ID NO: 52 | — |
| 398 | isomiR example 2 of SEQ ID NO: 52 | — |
| 399 | isomiR example 1 of SEQ ID NO: 53 | — |
| 400 | isomiR example 2 of SEQ ID NO: 53 | — |
| 401 | isomiR example 1 of SEQ ID NO: 56 | — |
| 402 | isomiR example 2 of SEQ ID NO: 56 | — |
| 403 | isomiR example 1 of SEQ ID NO: 58 | — |
| 404 | isomiR example 2 of SEQ ID NO: 58 | — |
| 405 | isomiR example 1 of SEQ ID NO: 59 | — |
| 406 | isomiR example 2 of SEQ ID NO: 59 | — |
| 407 | isomiR example 1 of SEQ ID NO: 60 | — |
| 408 | isomiR example 2 of SEQ ID NO: 60 | — |
| 409 | isomiR example 1 of SEQ ID NO: 61 | — |
| 410 | isomiR example 2 of SEQ ID NO: 61 | — |
| 411 | isomiR example 1 of SEQ ID NO: 63 | — |
| 412 | isomiR example 2 of SEQ ID NO: 63 | — |
| 413 | isomiR example 1 of SEQ ID NO: 64 | — |
| 414 | isomiR example 2 of SEQ ID NO: 64 | — |
| 415 | isomiR example 1 of SEQ ID NO: 65 | — |
| 416 | isomiR example 2 of SEQ ID NO: 65 | — |
| 417 | isomiR example 1 of SEQ ID NO: 66 | — |
| 418 | isomiR example 2 of SEQ ID NO: 66 | — |
| 419 | isomiR example 1 of SEQ ID NO: 67 | — |
| 420 | isomiR example 2 of SEQ ID NO: 67 | — |
| 421 | isomiR example 1 of SEQ ID NO: 69 | — |
| 422 | isomiR example 2 of SEQ ID NO: 69 | — |
| 423 | isomiR example 1 of SEQ ID NO: 72 | — |
| 424 | isomiR example 2 of SEQ ID NO: 72 | — |
| 425 | isomiR example 1 of SEQ ID NO: 73 | — |
| 426 | isomiR example 2 of SEQ ID NO: 73 | — |
| 427 | isomiR example 1 of SEQ ID NO: 75 | — |
| 428 | isomiR example 2 of SEQ ID NO: 75 | — |
| 429 | isomiR example 1 of SEQ ID NO: 78 | — |
| 430 | isomiR example 2 of SEQ ID NO: 78 | — |
| 431 | isomiR example 1 of SEQ ID NO: 79 | — |
| 432 | isomiR example 2 of SEQ ID NO: 79 | — |
| 433 | isomiR example 1 of SEQ ID NO: 80 | — |
| 434 | isomiR example 2 of SEQ ID NO: 80 | — |
| 435 | isomiR example 1 of SEQ ID NO: 81 | — |
| 436 | isomiR example 2 of SEQ ID NO: 81 | — |
| 437 | isomiR example 1 of SEQ ID NO: 82 | — |
| 438 | isomiR example 2 of SEQ ID NO: 82 | — |
| 439 | isomiR example 1 of SEQ ID NO: 85 | — |
| 440 | isomiR example 2 of SEQ ID NO: 85 | — |
| 441 | isomiR example 1 of SEQ ID NO: 88 | — |
| 442 | isomiR example 2 of SEQ ID NO: 88 | — |
| 443 | isomiR example 1 of SEQ ID NO: 89 | — |
| 444 | isomiR example 2 of SEQ ID NO: 89 | — |
| 445 | isomiR example 1 of SEQ ID NO: 91 | — |
| 446 | isomiR example 2 of SEQ ID NO: 91 | — |
| 447 | isomiR example 1 of SEQ ID NO: 92 | — |
| 448 | isomiR example 2 of SEQ ID NO: 92 | — |
| 449 | isomiR example 1 of SEQ ID NO: 95 | — |
| 450 | isomiR example 2 of SEQ ID NO: 95 | — |
| 451 | isomiR example 1 of SEQ ID NO: 96 | — |
| 452 | isomiR example 2 of SEQ ID NO: 96 | — |
| 453 | isomiR example 1 of SEQ ID NO: 103 | — |
| 454 | isomiR example 2 of SEQ ID NO: 103 | — |
| 455 | isomiR example 1 of SEQ ID NO: 104 | — |
| 456 | isomiR example 2 of SEQ ID NO: 104 | — |
| 457 | isomiR example 1 of SEQ ID NO: 105 | — |
| 458 | isomiR example 2 of SEQ ID NO: 105 | — |
| 459 | isomiR example 1 of SEQ ID NO: 106 | — |
| 460 | isomiR example 2 of SEQ ID NO: 106 | — |
| 461 | isomiR example 1 of SEQ ID NO: 107 | — |
| 462 | isomiR example 2 of SEQ ID NO: 107 | — |

TABLE 1-continued

| SEQ ID NO: | Gene name | miRBase registration No. |
|---|---|---|
| 463 | isomiR example 1 of SEQ ID NO: 108 | — |
| 464 | isomiR example 2 of SEQ ID NO: 108 | — |
| 465 | isomiR example 1 of SEQ ID NO: 109 | — |
| 466 | isomiR example 2 of SEQ ID NO: 109 | — |
| 467 | isomiR example 1 of SEQ ID NO: 110 | — |
| 468 | isomiR example 2 of SEQ ID NO: 110 | — |
| 469 | isomiR example 1 of SEQ ID NO: 112 | — |
| 470 | isomiR example 2 of SEQ ID NO: 112 | — |
| 471 | isomiR example 1 of SEQ ID NO: 113 | — |
| 472 | isomiR example 2 of SEQ ID NO: 113 | — |
| 473 | isomiR example 1 of SEQ ID NO: 114 | — |
| 474 | isomiR example 2 of SEQ ID NO: 114 | — |
| 475 | isomiR example 1 of SEQ ID NO: 117 | — |
| 476 | isomiR example 2 of SEQ ID NO: 117 | — |
| 477 | isomiR example 1 of SEQ ID NO: 118 | — |
| 478 | isomiR example 2 of SEQ ID NO: 118 | — |
| 479 | isomiR example 1 of SEQ ID NO: 120 | — |
| 480 | isomiR example 2 of SEQ ID NO: 120 | — |
| 481 | isomiR example 1 of SEQ ID NO: 123 | — |
| 482 | isomiR example 2 of SEQ ID NO: 123 | — |
| 483 | isomiR example 1 of SEQ ID NO: 124 | — |
| 484 | isomiR example 2 of SEQ ID NO: 124 | — |
| 485 | isomiR example 1 of SEQ ID NO: 125 | — |
| 486 | isomiR example 2 of SEQ ID NO: 125 | — |
| 487 | isomiR example 1 of SEQ ID NO: 126 | — |
| 488 | isomiR example 2 of SEQ ID NO: 126 | — |
| 489 | isomiR example 1 of SEQ ID NO: 128 | — |
| 490 | isomiR example 2 of SEQ ID NO: 128 | — |
| 491 | isomiR example 1 of SEQ ID NO: 129 | — |
| 492 | isomiR example 2 of SEQ ID NO: 129 | — |
| 493 | isomiR example 1 of SEQ ID NO: 130 | — |
| 494 | isomiR example 2 of SEQ ID NO: 130 | — |
| 495 | isomiR example 1 of SEQ ID NO: 131 | — |
| 496 | isomiR example 2 of SEQ ID NO: 131 | — |
| 497 | isomiR example 1 of SEQ ID NO: 132 | — |
| 498 | isomiR example 2 of SEQ ID NO: 132 | — |
| 499 | isomiR example 1 of SEQ ID NO: 133 | — |
| 500 | isomiR example 2 of SEQ ID NO: 133 | — |
| 501 | isomiR example 1 of SEQ ID NO: 134 | — |
| 502 | isomiR example 2 of SEQ ID NO: 134 | — |
| 503 | isomiR example 1 of SEQ ID NO: 135 | — |
| 504 | isomiR example 2 of SEQ ID NO: 135 | — |
| 505 | isomiR example 1 of SEQ ID NO: 136 | — |
| 506 | isomiR example 2 of SEQ ID NO: 136 | — |
| 507 | isomiR example 1 of SEQ ID NO: 138 | — |
| 508 | isomiR example 2 of SEQ ID NO: 138 | — |
| 509 | isomiR example 1 of SEQ ID NO: 139 | — |
| 510 | isomiR example 2 of SEQ ID NO: 139 | — |
| 511 | isomiR example 1 of SEQ ID NO: 142 | — |
| 512 | isomiR example 2 of SEQ ID NO: 142 | — |
| 513 | isomiR example 1 of SEQ ID NO: 143 | — |
| 514 | isomiR example 2 of SEQ ID NO: 143 | — |
| 515 | isomiR example 1 of SEQ ID NO: 144 | — |
| 516 | isomiR example 2 of SEQ ID NO: 144 | — |
| 517 | isomiR example 1 of SEQ ID NO: 145 | — |
| 518 | isomiR example 2 of SEQ ID NO: 145 | — |
| 519 | isomiR example 1 of SEQ ID NO: 146 | — |
| 520 | isomiR example 2 of SEQ ID NO: 146 | — |
| 521 | isomiR example 1 of SEQ ID NO: 147 | — |
| 522 | isomiR example 2 of SEQ ID NO: 147 | — |
| 523 | isomiR example 1 of SEQ ID NO: 149 | — |
| 524 | isomiR example 2 of SEQ ID NO: 149 | — |
| 525 | isomiR example 1 of SEQ ID NO: 151 | — |
| 526 | isomiR example 2 of SEQ ID NO: 151 | — |
| 527 | isomiR example 1 of SEQ ID NO: 152 | — |
| 528 | isomiR example 2 of SEQ ID NO: 152 | — |
| 529 | isomiR example 1 of SEQ ID NO: 153 | — |
| 530 | isomiR example 2 of SEQ ID NO: 153 | — |
| 531 | isomiR example 1 of SEQ ID NO: 154 | — |
| 532 | isomiR example 2 of SEQ ID NO: 154 | — |
| 533 | isomiR example 1 of SEQ ID NO: 156 | — |
| 534 | isomiR example 2 of SEQ ID NO: 156 | — |
| 535 | isomiR example 1 of SEQ ID NO: 157 | — |
| 536 | isomiR example 2 of SEQ ID NO: 157 | — |
| 537 | isomiR example 1 of SEQ ID NO: 158 | — |
| 538 | isomiR example 2 of SEQ ID NO: 158 | — |
| 539 | isomiR example 1 of SEQ ID NO: 160 | — |
| 540 | isomiR example 2 of SEQ ID NO: 160 | — |
| 541 | isomiR example 1 of SEQ ID NO: 161 | — |
| 542 | isomiR example 2 of SEQ ID NO: 161 | — |
| 543 | isomiR example 1 of SEQ ID NO: 162 | — |
| 544 | isomiR example 2 of SEQ ID NO: 162 | — |
| 545 | isomiR example 1 of SEQ ID NO: 163 | — |
| 546 | isomiR example 2 of SEQ ID NO: 163 | — |
| 547 | isomiR example 1 of SEQ ID NO: 166 | — |
| 548 | isomiR example 2 of SEQ ID NO: 166 | — |
| 549 | isomiR example 1 of SEQ ID NO: 167 | — |
| 550 | isomiR example 2 of SEQ ID NO: 167 | — |
| 551 | isomiR example 1 of SEQ ID NO: 168 | — |
| 552 | isomiR example 2 of SEQ ID NO: 168 | — |
| 553 | isomiR example 1 of SEQ ID NO: 169 | — |
| 554 | isomiR example 2 of SEQ ID NO: 169 | — |
| 555 | isomiR example 1 of SEQ ID NO: 172 | — |
| 556 | isomiR example 2 of SEQ ID NO: 172 | — |
| 557 | isomiR example 1 of SEQ ID NO: 173 | — |
| 558 | isomiR example 2 of SEQ ID NO: 173 | — |
| 559 | isomiR example 1 of SEQ ID NO: 174 | — |
| 560 | isomiR example 2 of SEQ ID NO: 174 | — |
| 561 | hsa-miR-6073 | MIMAT0023698 |
| 562 | hsa-miR-6845-5p | MIMAT0027590 |
| 563 | hsa-miR-6769b-5p | MIMAT0027620 |
| 564 | hsa-miR-4665-3p | MIMAT0019740 |
| 565 | hsa-miR-1913 | MIMAT0007888 |
| 566 | hsa-miR-1228-3p | MIMAT0005583 |
| 567 | hsa-miR-940 | MIMAT0004983 |
| 568 | hsa-miR-296-3p | MIMAT0004679 |
| 569 | hsa-miR-4690-5p | MIMAT0019779 |
| 570 | hsa-miR-548q | MIMAT0011163 |
| 571 | hsa-miR-663a | MIMAT0003326 |
| 572 | hsa-miR-1249 | MIMAT0005901 |
| 573 | hsa-miR-1202 | MIMAT0005865 |
| 574 | hsa-miR-7113-3p | MIMAT0028124 |
| 575 | hsa-miR-1225-3p | MIMAT0005573 |
| 576 | hsa-miR-4783-3p | MIMAT0019947 |
| 577 | hsa-miR-4448 | MIMAT0018967 |
| 578 | hsa-miR-4534 | MIMAT0019073 |
| 579 | hsa-miR-1307-3p | MIMAT0005951 |
| 580 | hsa-mir-6073 | MI0020350 |
| 581 | hsa-mir-6845 | MI0022691 |
| 582 | hsa-mir-6769b | MI0022706 |
| 583 | hsa-mir-4665 | MI0017295 |
| 584 | hsa-mir-1913 | MI0008334 |
| 585 | hsa-mir-940 | MI0005762 |
| 586 | hsa-mir-296 | MI0000747 |
| 587 | hsa-mir-4690 | MI0017323 |
| 588 | hsa-mir-548q | MI0010637 |
| 589 | hsa-mir-663a | MI0003672 |
| 590 | hsa-mir-1249 | MI0006384 |
| 591 | hsa-mir-1202 | MI0006334 |
| 592 | hsa-mir-7113 | MI0022964 |
| 593 | hsa-mir-4783 | MI0017428 |
| 594 | hsa-mir-4448 | MI0016791 |
| 595 | hsa-mir-4534 | MI0016901 |
| 596 | hsa-mir-1307 | MI0006444 |
| 597 | isomiR example 1 of SEQ ID NO: 565 | — |
| 598 | isomiR example 2 of SEQ ID NO: 565 | — |
| 599 | isomiR example 1 of SEQ ID NO: 566 | — |
| 600 | isomiR example 2 of SEQ ID NO: 566 | — |
| 601 | isomiR example 1 of SEQ ID NO: 567 | — |
| 602 | isomiR example 2 of SEQ ID NO: 567 | — |
| 603 | isomiR example 1 of SEQ ID NO: 568 | — |
| 604 | isomiR example 2 of SEQ ID NO: 568 | — |
| 605 | isomiR example 1 of SEQ ID NO: 569 | — |
| 606 | isomiR example 2 of SEQ ID NO: 569 | — |
| 607 | isomiR example 1 of SEQ ID NO: 571 | — |
| 608 | isomiR example 2 of SEQ ID NO: 571 | — |
| 609 | isomiR example 1 of SEQ ID NO: 572 | — |
| 610 | isomiR example 2 of SEQ ID NO: 572 | — |
| 611 | isomiR example 1 of SEQ ID NO: 573 | — |
| 612 | isomiR example 2 of SEQ ID NO: 573 | — |
| 613 | isomiR example 1 of SEQ ID NO: 576 | — |
| 614 | isomiR example 2 of SEQ ID NO: 576 | — |
| 615 | isomiR example 1 of SEQ ID NO: 577 | — |
| 616 | isomiR example 2 of SEQ ID NO: 577 | — |

TABLE 1-continued

| SEQ ID NO: | Gene name | miRBase registration No. |
|---|---|---|
| 617 | isomiR example 1 of SEQ ID NO: 579 | — |
| 618 | isomiR example 2 of SEQ ID NO: 579 | — |

The present specification encompasses the contents described in the specification and/or drawings of Japanese Patent Application No. 2014-125561 on which the priority of the present application is based.

Advantageous Effects of Invention

According to the present invention, lung cancer can be detected easily and in high accuracy.

For example, the presence or absence of lung cancer in a patient can be easily detected by using, as an index, the expression level measurement values of several miRNAs in blood, serum, and/or plasma of the patient, which can be collected with limited invasiveness.

DESCRIPTION OF EMBODIMENTS

Figure 1:
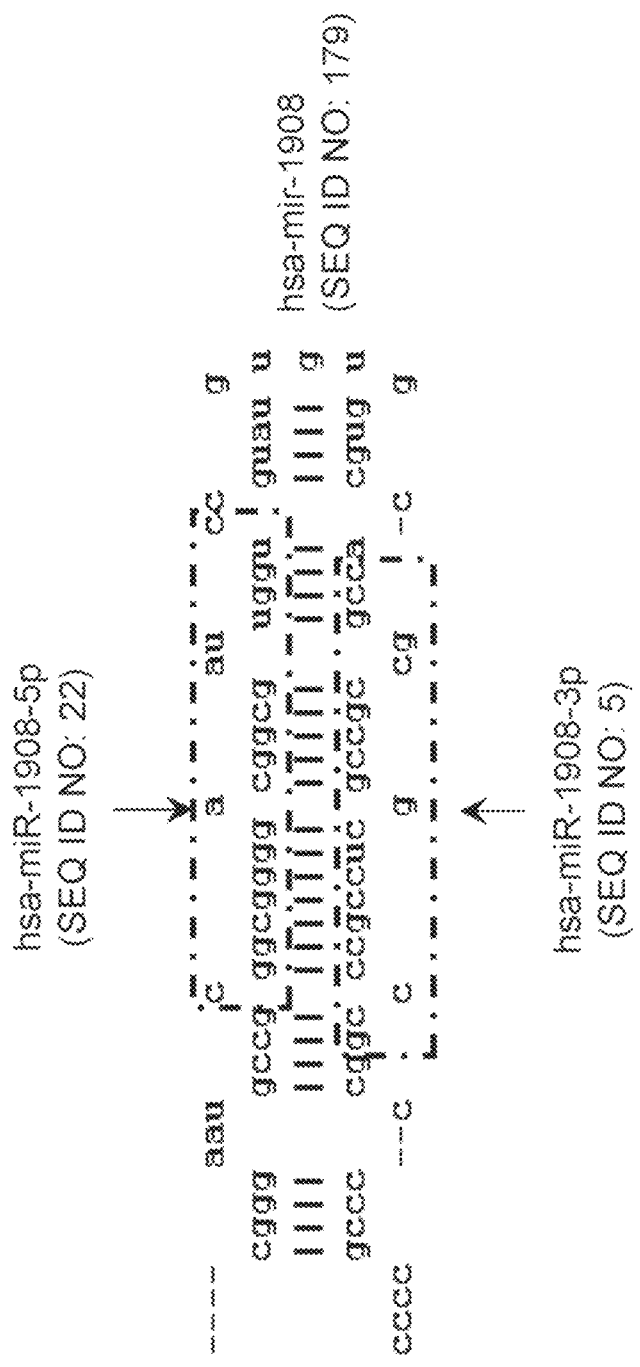
FIG. 1 This figure shows the relationship between the nucleotide sequences of hsa-miR-1908-5p represented by SEQ ID NO: 22 and hsa-miR-1908-3p represented by SEQ ID NO: 5, which are produced from a precursor hsa-mir-1908 represented by SEQ ID NO: 179.

Hereinafter, the present invention will be described further specifically.

1. Target Nucleic Acid for Lung Cancer

A primary target nucleic acid used as a lung cancer marker for detecting the presence and/or absence of lung cancer or lung cancer cells using the nucleic acid probe or the primer for the detection of lung cancer defined above according to the present invention can be at least one or more miRNA(s) selected from the group consisting of hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534. Furthermore, at least one or more miRNA(s) selected from the group consisting of other lung cancer markers that can be combined with these miRNAs, i.e., hsa-miR-19b-3p, hsa-miR-1228-5p, and hsa-miR-1307-3p, can also be preferably used as a target nucleic acid. Moreover, at least one or more miRNA(s) selected from the group consisting of other lung cancer markers that can be combined with these miRNAs, i.e., hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p can also be preferably used as a target nucleic acid.

These miRNAs include, for example, a human gene comprising a nucleotide sequence represented by any of SEQ ID NOs: 1 to 174 and 561 to 579 (i.e., hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6726-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-451a, hsa-miR-939-5p, hsa-miR-223-3p, hsa-miR-1228-5p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, hsa-miR-1307-3p, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 618 or a transcript thereof, more preferably the transcript, i.e., a miRNA or its precursor RNA (pri-miRNA or pre-miRNA).

The first target gene is the hsa-miR-6768-5p gene, a congener thereof, a transcript thereof, or a variant or a derivative thereof. None of the previously known reports show that change in the expression of the gene or the transcript thereof can serve as a marker for lung cancer.

The second target gene is the hsa-miR-6836-3p gene, a congener thereof, a transcript thereof, or a variant or a derivative thereof. None of the previously known reports show that change in the expression of the gene or the transcript thereof can serve as a marker for lung cancer.

The third target gene is the hsa-miR-6782-5p gene, a congener thereof, a transcript thereof, or a variant or a derivative thereof. None of the previously known reports show that change in the expression of the gene or the transcript thereof can serve as a marker for lung cancer.

The fourth target gene is the hsa-miR-3663-3p gene, a congener thereof, a transcript thereof, or a variant or a derivative thereof. None of the previously known reports show that change in the expression of the gene or the transcript thereof can serve as a marker for lung cancer.

The fifth target gene is the hsa-miR-1908-3p gene, a congener thereof, a transcript thereof, or a variant or a derivative thereof. None of the previously known reports show that change in the expression of the gene or the transcript thereof can serve as a marker for lung cancer.

The sixth target gene is the hsa-miR-6726-5p gene, a congener thereof, a transcript thereof, or a variant or a derivative thereof. None of the previously known reports show that change in the expression of the gene or the transcript thereof can serve as a marker for lung cancer.

The seventh target gene is the hsa-miR-4258 gene, a congener thereof, a transcript thereof, or a variant or a derivative thereof. None of the previously known reports show that change in the expression of the gene or the transcript thereof can serve as a marker for lung cancer.

The eighth target gene is the hsa-miR-1343-3p gene, a congener thereof, a transcript thereof, or a variant or a derivative thereof. None of the previously known reports show that change in the expression of the gene or the transcript thereof can serve as a marker for lung cancer.

The ninth target gene is the hsa-miR-4516 gene, a congener thereof, a transcript thereof, or a variant or a derivative thereof. None of the previously known reports show that change in the expression of the gene or the transcript thereof can serve as a marker for lung cancer.

The 10th target gene is the hsa-miR-6875-5p gene, a congener thereof, a transcript thereof, or a variant or a derivative thereof. None of the previously known reports show that change in the expression of the gene or the transcript thereof can serve as a marker for lung cancer.

The 11th target gene is the hsa-miR-4651 gene, a congener thereof, a transcript thereof, or a variant or a derivative thereof. None of the previously known reports show that change in the expression of the gene or the transcript thereof can serve as a marker for lung cancer.

The 12th target gene is the hsa-miR-6825-5p gene, a congener thereof, a transcript thereof, or a variant or a derivative thereof. None of the previously known reports show that change in the expression of the gene or the transcript thereof can serve as a marker for lung cancer.

The 13th target gene is the hsa-miR-6840-3p gene, a congener thereof, a transcript thereof, or a variant or a derivative thereof. None of the previously known reports show that change in the expression of the gene or the transcript thereof can serve as a marker for lung cancer.

The 14th target gene is the hsa-miR-6780b-5p gene, a congener thereof, a transcript thereof, or a variant or a derivative thereof. None of the previously known reports show that change in the expression of the gene or the transcript thereof can serve as a marker for lung cancer.

The 15th target gene is the hsa-miR-6749-5p gene, a congener thereof, a transcript thereof, or a variant or a derivative thereof. None of the previously known reports show that change in the expression of the gene or the transcript thereof can serve as a marker for lung cancer.

The 16th target gene is the hsa-miR-8063 gene, a congener thereof, a transcript thereof, or a variant or a derivative thereof. None of the previously known reports show that change in the expression of the gene or the transcript thereof can serve as a marker for lung cancer.

The 17th target gene is the hsa-miR-6784-5p gene, a congener thereof, a transcript thereof, or a variant or a derivative thereof. None of the previously known reports show that change in the expression of the gene or the transcript thereof can serve as a marker for lung cancer.

The 18th target gene is the hsa-miR-3679-5p gene, a congener thereof, a transcript thereof, or a variant or a derivative thereof. None of the previously known reports show that change in the expression of the gene or the transcript thereof can serve as a marker for lung cancer.

The 19th target gene is the hsa-miR-3184-5p gene, a congener thereof, a transcript thereof, or a variant or a derivative thereof. None of the previously known reports show that change in the expression of the gene or the transcript thereof can serve as a marker for lung cancer.

The 20th target gene is the hsa-miR-663b gene, a congener thereof, a transcript thereof, or a variant or a derivative thereof. None of the previously known reports show that change in the expression of the gene or the transcript thereof can serve as a marker for lung cancer.

The 21st target gene is the hsa-miR-6880-5p gene, a congener thereof, a transcript thereof, or a variant or a derivative thereof. None of the previously known reports show that change in the expression of the gene or the transcript thereof can serve as a marker for lung cancer.

The 22nd target gene is the hsa-miR-1908-5p gene, a congener thereof, a transcript thereof, or a variant or a derivative thereof. None of the previously known reports show that change in the expression of the gene or the transcript thereof can serve as a marker for lung cancer.

The 23rd target gene is the hsa-miR-92a-2-5p gene, a congener thereof, a transcript thereof, or a variant or a derivative thereof. None of the previously known reports show that change in the expression of the gene or the transcript thereof can serve as a marker for lung cancer.

The 24th target gene is the hsa-miR-7975 gene, a congener thereof, a transcript thereof, or a variant or a derivative thereof. None of the previously known reports show that change in the expression of the gene or the transcript thereof can serve as a marker for lung cancer.

The 25th target gene is the hsa-miR-7110-5p gene, a congener thereof, a transcript thereof, or a variant or a derivative thereof. None of the previously known reports show that change in the expression of the gene or the transcript thereof can serve as a marker for lung cancer.

The 26th target gene is the hsa-miR-6842-5p gene, a congener thereof, a transcript thereof, or a variant or a derivative thereof. None of the previously known reports show that change in the expression of the gene or the transcript thereof can serve as a marker for lung cancer.

The 27th target gene is the hsa-miR-6857-5p gene, a congener thereof, a transcript thereof, or a variant or a derivative thereof. None of the previously known reports show that change in the expression of the gene or the transcript thereof can serve as a marker for lung cancer.

The 28th target gene is the hsa-miR-5572 gene, a congener thereof, a transcript thereof, or a variant or a derivative thereof. None of the previously known reports show that change in the expression of the gene or the transcript thereof can serve as a marker for lung cancer.

The 29th target gene is the hsa-miR-3197 gene, a congener thereof, a transcript thereof, or a variant or a derivative thereof. None of the previously known reports show that change in the expression of the gene or the transcript thereof can serve as a marker for lung cancer.

The 30th target gene is the hsa-miR-6131 gene, a congener thereof, a transcript thereof, or a variant or a derivative thereof. None of the previously known reports show that change in the expression of the gene or the transcript thereof can serve as a marker for lung cancer.

The 31st target gene is the hsa-miR-6889-5p gene, a congener thereof, a transcript thereof, or a variant or a derivative thereof. None of the previously known reports show that change in the expression of the gene or the transcript thereof can serve as a marker for lung cancer.

The 32nd target gene is the hsa-miR-4454 gene, a congener thereof, a transcript thereof, or a variant or a derivative thereof. None of the previously known reports show that change in the expression of the gene or the transcript thereof can serve as a marker for lung cancer.

The 33rd target gene is the hsa-miR-1199-5p gene, a congener thereof, a transcript thereof, or a variant or a derivative thereof. None of the previously known reports show that change in the expression of the gene or the transcript thereof can serve as a marker for lung cancer.

The 34th target gene is the hsa-miR-1247-3p gene, a congener thereof, a transcript thereof, or a variant or a derivative thereof. None of the previously known reports show that change in the expression of the gene or the transcript thereof can serve as a marker for lung cancer.

The 35th target gene is the hsa-miR-6800-5p gene, a congener thereof, a transcript thereof, or a variant or a derivative thereof. None of the previously known reports show that change in the expression of the gene or the transcript thereof can serve as a marker for lung cancer.

The 36th target gene is the hsa-miR-6872-3p gene, a congener thereof, a transcript thereof, or a variant or a derivative thereof. None of the previously known reports show that change in the expression of the gene or the transcript thereof can serve as a marker for lung cancer.

The 37th target gene is the hsa-miR-4649-5p gene, a congener thereof, a transcript thereof, or a variant or a derivative thereof. None of the previously known reports show that change in the expression of the gene or the transcript thereof can serve as a marker for lung cancer.

The 38th target gene is the hsa-miR-6791-5p gene, a congener thereof, a transcript thereof, or a variant or a derivative thereof. None of the previously known reports show that change in the expression of the gene or the transcript thereof can serve as a marker for lung cancer.

The 39th target gene is the hsa-miR-4433b-3p gene, a congener thereof, a transcript thereof, or a variant or a derivative thereof. None of the previously known reports show that change in the expression of the gene or the transcript thereof can serve as a marker for lung cancer.

The 40th target gene is the hsa-miR-3135b gene, a congener thereof, a transcript thereof, or a variant or a derivative thereof. None of the previously known reports show that change in the expression of the gene or the transcript thereof can serve as a marker for lung cancer.

The 41st target gene is the hsa-miR-128-2-5p gene, a congener thereof, a transcript thereof, or a variant or a derivative thereof. None of the previously known reports show that change in the expression of the gene or the transcript thereof can serve as a marker for lung cancer.

The 42nd target gene is the hsa-miR-4675 gene, a congener thereof, a transcript thereof, or a variant or a derivative thereof. None of the previously known reports show that change in the expression of the gene or the transcript thereof can serve as a marker for lung cancer.

The 43rd target gene is the hsa-miR-4472 gene, a congener thereof, a transcript thereof, or a variant or a derivative thereof. None of the previously known reports show that change in the expression of the gene or the transcript thereof can serve as a marker for lung cancer.

The 44th target gene is the hsa-miR-6785-5p gene, a congener thereof, a transcript thereof, or a variant or a derivative thereof. None of the previously known reports show that change in the expression of the gene or the transcript thereof can serve as a marker for lung cancer.

The 45th target gene is the hsa-miR-6741-5p gene, a congener thereof, a transcript thereof, or a variant or a derivative thereof. None of the previously known reports show that change in the expression of the gene or the transcript thereof can serve as a marker for lung cancer.

The 46th target gene is the hsa-miR-7977 gene, a congener thereof, a transcript thereof, or a variant or a derivative thereof. None of the previously known reports show that change in the expression of the gene or the transcript thereof can serve as a marker for lung cancer.

The 47th target gene is the hsa-miR-3665 gene, a congener thereof, a transcript thereof, or a variant or a derivative thereof. None of the previously known reports show that change in the expression of the gene or the transcript thereof can serve as a marker for lung cancer.

The 48th target gene is the hsa-miR-128-1-5p gene, a congener thereof, a transcript thereof, or a variant or a derivative thereof. None of the previously known reports show that change in the expression of the gene or the transcript thereof can serve as a marker for lung cancer.

The 49th target gene is the hsa-miR-4286 gene, a congener thereof, a transcript thereof, or a variant or a derivative thereof. None of the previously known reports show that change in the expression of the gene or the transcript thereof can serve as a marker for lung cancer.

The 50th target gene is the hsa-miR-6765-3p gene, a congener thereof, a transcript thereof, or a variant or a derivative thereof. None of the previously known reports show that change in the expression of the gene or the transcript thereof can serve as a marker for lung cancer.

The 51st target gene is the hsa-miR-4632-5p gene, a congener thereof, a transcript thereof, or a variant or a derivative thereof. None of the previously known reports show that change in the expression of the gene or the transcript thereof can serve as a marker for lung cancer.

The 52nd target gene is the hsa-miR-365a-5p gene, a congener thereof, a transcript thereof, or a variant or a derivative thereof. None of the previously known reports show that change in the expression of the gene or the transcript thereof can serve as a marker for lung cancer.

The 53rd target gene is the hsa-miR-6088 gene, a congener thereof, a transcript thereof, or a variant or a derivative thereof. None of the previously known reports show that change in the expression of the gene or the transcript thereof can serve as a marker for lung cancer.

The 54th target gene is the hsa-miR-6816-5p gene, a congener thereof, a transcript thereof, or a variant or a derivative thereof. None of the previously known reports show that change in the expression of the gene or the transcript thereof can serve as a marker for lung cancer.

The 55th target gene is the hsa-miR-6885-5p gene, a congener thereof, a transcript thereof, or a variant or a derivative thereof. None of the previously known reports show that change in the expression of the gene or the transcript thereof can serve as a marker for lung cancer.

The 56th target gene is the hsa-miR-711 gene, a congener thereof, a transcript thereof, or a variant or a derivative thereof. None of the previously known reports show that change in the expression of the gene or the transcript thereof can serve as a marker for lung cancer.

The 57th target gene is the hsa-miR-6765-5p gene, a congener thereof, a transcript thereof, or a variant or a derivative thereof. None of the previously known reports show that change in the expression of the gene or the transcript thereof can serve as a marker for lung cancer.

The 58th target gene is the hsa-miR-3180 gene, a congener thereof, a transcript thereof, or a variant or a derivative thereof. None of the previously known reports show that change in the expression of the gene or the transcript thereof can serve as a marker for lung cancer.

The 59th target gene is the hsa-miR-4442 gene, a congener thereof, a transcript thereof, or a variant or a derivative thereof. None of the previously known reports show that change in the expression of the gene or the transcript thereof can serve as a marker for lung cancer.

The 60th target gene is the hsa-miR-4792 gene, a congener thereof, a transcript thereof, or a variant or a derivative thereof. None of the previously known reports show that change in the expression of the gene or the transcript thereof can serve as a marker for lung cancer.

The 61st target gene is the hsa-miR-6721-5p gene, a congener thereof, a transcript thereof, or a variant or a derivative thereof. None of the previously known reports show that change in the expression of the gene or the transcript thereof can serve as a marker for lung cancer.

The 62nd target gene is the hsa-miR-6798-5p gene, a congener thereof, a transcript thereof, or a variant or a derivative thereof. None of the previously known reports show that change in the expression of the gene or the transcript thereof can serve as a marker for lung cancer.

The 63rd target gene is the hsa-miR-3162-5p gene, a congener thereof, a transcript thereof, or a variant or a derivative thereof. None of the previously known reports show that change in the expression of the gene or the transcript thereof can serve as a marker for lung cancer.

The 64th target gene is the hsa-miR-6126 gene, a congener thereof, a transcript thereof, or a variant or a derivative thereof. None of the previously known reports show that change in the expression of the gene or the transcript thereof can serve as a marker for lung cancer.

The 65th target gene is the hsa-miR-4758-5p gene, a congener thereof, a transcript thereof, or a variant or a derivative thereof. None of the previously known reports show that change in the expression of the gene or the transcript thereof can serve as a marker for lung cancer.

The 66th target gene is the hsa-miR-2392 gene, a congener thereof, a transcript thereof, or a variant or a derivative thereof. None of the previously known reports show that change in the expression of the gene or the transcript thereof can serve as a marker for lung cancer.

The 67th target gene is the hsa-miR-486-3p gene, a congener thereof, a transcript thereof, or a variant or a derivative thereof. None of the previously known reports show that change in the expression of the gene or the transcript thereof can serve as a marker for lung cancer.

The 68th target gene is the hsa-miR-6727-5p gene, a congener thereof, a transcript thereof, or a variant or a derivative thereof. None of the previously known reports show that change in the expression of the gene or the transcript thereof can serve as a marker for lung cancer.

The 69th target gene is the hsa-miR-4728-5p gene, a congener thereof, a transcript thereof, or a variant or a derivative thereof. None of the previously known reports show that change in the expression of the gene or the transcript thereof can serve as a marker for lung cancer.

The 70th target gene is the hsa-miR-6746-5p gene, a congener thereof, a transcript thereof, or a variant or a derivative thereof. None of the previously known reports show that change in the expression of the gene or the transcript thereof can serve as a marker for lung cancer.

The 71st target gene is the hsa-miR-4270 gene, a congener thereof, a transcript thereof, or a variant or a derivative thereof. None of the previously known reports show that change in the expression of the gene or the transcript thereof can serve as a marker for lung cancer.

The 72nd target gene is the hsa-miR-3940-5p gene, a congener thereof, a transcript thereof, or a variant or a derivative thereof. None of the previously known reports show that change in the expression of the gene or the transcript thereof can serve as a marker for lung cancer.

The 73rd target gene is the hsa-miR-4725-3p gene, a congener thereof, a transcript thereof, or a variant or a derivative thereof. None of the previously known reports show that change in the expression of the gene or the transcript thereof can serve as a marker for lung cancer.

The 74th target gene is the hsa-miR-7108-5p gene, a congener thereof, a transcript thereof, or a variant or a derivative thereof. None of the previously known reports show that change in the expression of the gene or the transcript thereof can serve as a marker for lung cancer.

The 75th target gene is the hsa-miR-3656 gene, a congener thereof, a transcript thereof, or a variant or a derivative thereof. None of the previously known reports show that change in the expression of the gene or the transcript thereof can serve as a marker for lung cancer.

The 76th target gene is the hsa-miR-6879-5p gene, a congener thereof, a transcript thereof, or a variant or a derivative thereof. None of the previously known reports show that change in the expression of the gene or the transcript thereof can serve as a marker for lung cancer.

The 77th target gene is the hsa-miR-6738-5p gene, a congener thereof, a transcript thereof, or a variant or a derivative thereof. None of the previously known reports show that change in the expression of the gene or the transcript thereof can serve as a marker for lung cancer.

The 78th target gene is the hsa-miR-1260a gene, a congener thereof, a transcript thereof, or a variant or a derivative thereof. None of the previously known reports show that change in the expression of the gene or the transcript thereof can serve as a marker for lung cancer.

The 79th target gene is the hsa-miR-4446-3p gene, a congener thereof, a transcript thereof, or a variant or a derivative thereof. None of the previously known reports show that change in the expression of the gene or the transcript thereof can serve as a marker for lung cancer.

The 80th target gene is the hsa-miR-3131 gene, a congener thereof, a transcript thereof, or a variant or a derivative thereof. None of the previously known reports show that change in the expression of the gene or the transcript thereof can serve as a marker for lung cancer.

The 81st target gene is the hsa-miR-4463 gene, a congener thereof, a transcript thereof, or a variant or a derivative thereof. None of the previously known reports show that change in the expression of the gene or the transcript thereof can serve as a marker for lung cancer.

The 82nd target gene is the hsa-miR-3185 gene, a congener thereof, a transcript thereof, or a variant or a derivative thereof. None of the previously known reports show that change in the expression of the gene or the transcript thereof can serve as a marker for lung cancer.

The 83rd target gene is the hsa-miR-6870-5p gene, a congener thereof, a transcript thereof, or a variant or a derivative thereof. None of the previously known reports show that change in the expression of the gene or the transcript thereof can serve as a marker for lung cancer.

The 84th target gene is the hsa-miR-6779-5p gene, a congener thereof, a transcript thereof, or a variant or a derivative thereof. None of the previously known reports show that change in the expression of the gene or the transcript thereof can serve as a marker for lung cancer.

The 85th target gene is the hsa-miR-1273g-3p gene, a congener thereof, a transcript thereof, or a variant or a derivative thereof. None of the previously known reports show that change in the expression of the gene or the transcript thereof can serve as a marker for lung cancer.

The 86th target gene is the hsa-miR-8059 gene, a congener thereof, a transcript thereof, or a variant or a derivative thereof. None of the previously known reports show that change in the expression of the gene or the transcript thereof can serve as a marker for lung cancer.

The 87th target gene is the hsa-miR-4697-5p gene, a congener thereof, a transcript thereof, or a variant or a derivative thereof. None of the previously known reports show that change in the expression of the gene or the transcript thereof can serve as a marker for lung cancer.

The 88th target gene is the hsa-miR-4674 gene, a congener thereof, a transcript thereof, or a variant or a derivative thereof. None of the previously known reports show that change in the expression of the gene or the transcript thereof can serve as a marker for lung cancer.

The 89th target gene is the hsa-miR-4433-3p gene, a congener thereof, a transcript thereof, or a variant or a derivative thereof. None of the previously known reports show that change in the expression of the gene or the transcript thereof can serve as a marker for lung cancer.

The 90th target gene is the hsa-miR-4257 gene, a congener thereof, a transcript thereof, or a variant or a derivative thereof. None of the previously known reports show that change in the expression of the gene or the transcript thereof can serve as a marker for lung cancer.

The 91st target gene is the hsa-miR-1915-5p gene, a congener thereof, a transcript thereof, or a variant or a derivative thereof. None of the previously known reports show that change in the expression of the gene or the transcript thereof can serve as a marker for lung cancer.

The 92nd target gene is the hsa-miR-4417 gene, a congener thereof, a transcript thereof, or a variant or a derivative thereof. None of the previously known reports show that change in the expression of the gene or the transcript thereof can serve as a marker for lung cancer.

The 93rd target gene is the hsa-miR-1343-5p gene, a congener thereof, a transcript thereof, or a variant or a derivative thereof. None of the previously known reports show that change in the expression of the gene or the transcript thereof can serve as a marker for lung cancer.

The 94th target gene is the hsa-miR-6781-5p gene, a congener thereof, a transcript thereof, or a variant or a derivative thereof. None of the previously known reports show that change in the expression of the gene or the transcript thereof can serve as a marker for lung cancer.

The 95th target gene is the hsa-miR-4695-5p gene, a congener thereof, a transcript thereof, or a variant or a derivative thereof. None of the previously known reports show that change in the expression of the gene or the transcript thereof can serve as a marker for lung cancer.

The 96th target gene is the hsa-miR-1237-5p gene, a congener thereof, a transcript thereof, or a variant or a derivative thereof. None of the previously known reports show that change in the expression of the gene or the transcript thereof can serve as a marker for lung cancer.

The 97th target gene is the hsa-miR-6775-5p gene, a congener thereof, a transcript thereof, or a variant or a derivative thereof. None of the previously known reports show that change in the expression of the gene or the transcript thereof can serve as a marker for lung cancer.

The 98th target gene is the hsa-miR-7845-5p gene, a congener thereof, a transcript thereof, or a variant or a derivative thereof. None of the previously known reports show that change in the expression of the gene or the transcript thereof can serve as a marker for lung cancer.

The 99th target gene is the hsa-miR-4746-3p gene, a congener thereof, a transcript thereof, or a variant or a derivative thereof. None of the previously known reports show that change in the expression of the gene or the transcript thereof can serve as a marker for lung cancer.

The 100th target gene is the hsa-miR-7641 gene, a congener thereof, a transcript thereof, or a variant or a derivative thereof. None of the previously known reports show that change in the expression of the gene or the transcript thereof can serve as a marker for lung cancer.

The 101st target gene is the hsa-miR-7847-3p gene, a congener thereof, a transcript thereof, or a variant or a derivative thereof. None of the previously known reports show that change in the expression of the gene or the transcript thereof can serve as a marker for lung cancer.

The 102nd target gene is the hsa-miR-6806-5p gene, a congener thereof, a transcript thereof, or a variant or a derivative thereof. None of the previously known reports show that change in the expression of the gene or the transcript thereof can serve as a marker for lung cancer.

The 103rd target gene is the hsa-miR-4467 gene, a congener thereof, a transcript thereof, or a variant or a derivative thereof. None of the previously known reports show that change in the expression of the gene or the transcript thereof can serve as a marker for lung cancer.

The 104th target gene is the hsa-miR-4726-5p gene, a congener thereof, a transcript thereof, or a variant or a derivative thereof. None of the previously known reports show that change in the expression of the gene or the transcript thereof can serve as a marker for lung cancer.

The 105th target gene is the hsa-miR-4648 gene, a congener thereof, a transcript thereof, or a variant or a derivative thereof. None of the previously known reports show that change in the expression of the gene or the transcript thereof can serve as a marker for lung cancer.

The 106th target gene is the hsa-miR-6089 gene, a congener thereof, a transcript thereof, or a variant or a derivative thereof. None of the previously known reports show that change in the expression of the gene or the transcript thereof can serve as a marker for lung cancer.

The 107th target gene is the hsa-miR-1260b gene, a congener thereof, a transcript thereof, or a variant or a derivative thereof. None of the previously known reports show that change in the expression of the gene or the transcript thereof can serve as a marker for lung cancer.

The 108th target gene is the hsa-miR-4532 gene, a congener thereof, a transcript thereof, or a variant or a derivative thereof. None of the previously known reports show that change in the expression of the gene or the transcript thereof can serve as a marker for lung cancer.

The 109th target gene is the hsa-miR-5195-3p gene, a congener thereof, a transcript thereof, or a variant or a derivative thereof. None of the previously known reports show that change in the expression of the gene or the transcript thereof can serve as a marker for lung cancer.

The 110th target gene is the hsa-miR-3188 gene, a congener thereof, a transcript thereof, or a variant or a derivative thereof. None of the previously known reports show that change in the expression of the gene or the transcript thereof can serve as a marker for lung cancer.

The 111st target gene is the hsa-miR-6848-5p gene, a congener thereof, a transcript thereof, or a variant or a derivative thereof. None of the previously known reports show that change in the expression of the gene or the transcript thereof can serve as a marker for lung cancer.

The 112nd target gene is the hsa-miR-1233-5p gene, a congener thereof, a transcript thereof, or a variant or a derivative thereof. None of the previously known reports show that change in the expression of the gene or the transcript thereof can serve as a marker for lung cancer.

The 113rd target gene is the hsa-miR-6717-5p gene, a congener thereof, a transcript thereof, or a variant or a derivative thereof. None of the previously known reports show that change in the expression of the gene or the transcript thereof can serve as a marker for lung cancer.

The 114th target gene is the hsa-miR-3195 gene, a congener thereof, a transcript thereof, or a variant or a derivative thereof. None of the previously known reports show that change in the expression of the gene or the transcript thereof can serve as a marker for lung cancer.

The 115th target gene is the hsa-miR-6757-5p gene, a congener thereof, a transcript thereof, or a variant or a derivative thereof. None of the previously known reports show that change in the expression of the gene or the transcript thereof can serve as a marker for lung cancer.

The 116th target gene is the hsa-miR-8072 gene, a congener thereof, a transcript thereof, or a variant or a derivative thereof. None of the previously known reports show that change in the expression of the gene or the transcript thereof can serve as a marker for lung cancer.

The 117th target gene is the hsa-miR-4745-5p gene, a congener thereof, a transcript thereof, or a variant or a derivative thereof. None of the previously known reports show that change in the expression of the gene or the transcript thereof can serve as a marker for lung cancer.

The 118th target gene is the hsa-miR-6511a-5p gene, a congener thereof, a transcript thereof, or a variant or a derivative thereof. None of the previously known reports show that change in the expression of the gene or the transcript thereof can serve as a marker for lung cancer.

The 119th target gene is the hsa-miR-6776-5p gene, a congener thereof, a transcript thereof, or a variant or a derivative thereof. None of the previously known reports show that change in the expression of the gene or the transcript thereof can serve as a marker for lung cancer.

The 120th target gene is the hsa-miR-371a-5p gene, a congener thereof, a transcript thereof, or a variant or a derivative thereof. None of the previously known reports show that change in the expression of the gene or the transcript thereof can serve as a marker for lung cancer.

The 121st target gene is the hsa-miR-1227-5p gene, a congener thereof, a transcript thereof, or a variant or a derivative thereof. None of the previously known reports show that change in the expression of the gene or the transcript thereof can serve as a marker for lung cancer.

The 122nd target gene is the hsa-miR-7150 gene, a congener thereof, a transcript thereof, or a variant or a derivative thereof. None of the previously known reports show that change in the expression of the gene or the transcript thereof can serve as a marker for lung cancer.

The 123rd target gene is the hsa-miR-1915-3p gene, a congener thereof, a transcript thereof, or a variant or a derivative thereof. None of the previously known reports show that change in the expression of the gene or the transcript thereof can serve as a marker for lung cancer.

The 124th target gene is the hsa-miR-187-5p gene, a congener thereof, a transcript thereof, or a variant or a derivative thereof. None of the previously known reports show that change in the expression of the gene or the transcript thereof can serve as a marker for lung cancer.

The 125th target gene is the hsa-miR-614 gene, a congener thereof, a transcript thereof, or a variant or a derivative thereof. None of the previously known reports show that change in the expression of the gene or the transcript thereof can serve as a marker for lung cancer.

The 126th target gene is the hsa-miR-19b-3p gene, a congener thereof, a transcript thereof, or a variant or a derivative thereof. The previously known report shows that change in the expression of the gene or the transcript thereof can serve as a marker for lung cancer (Patent Literature 1).

The 127th target gene is the hsa-miR-1225-5p gene, a congener thereof, a transcript thereof, or a variant or a derivative thereof. None of the previously known reports show that change in the expression of the gene or the transcript thereof can serve as a marker for lung cancer.

The 128th target gene is the hsa-miR-451a gene, a congener thereof, a transcript thereof, or a variant or a derivative thereof. None of the previously known reports show that change in the expression of the gene or the transcript thereof can serve as a marker for lung cancer.

The 129th target gene is the hsa-miR-939-5p gene, a congener thereof, a transcript thereof, or a variant or a derivative thereof. None of the previously known reports show that change in the expression of the gene or the transcript thereof can serve as a marker for lung cancer.

The 130th target gene is the hsa-miR-223-3p gene, a congener thereof, a transcript thereof, or a variant or a derivative thereof. None of the previously known reports show that change in the expression of the gene or the transcript thereof can serve as a marker for lung cancer.

The 131st target gene is the hsa-miR-1228-5p gene, a congener thereof, a transcript thereof, or a variant or a derivative thereof. The previously known report shows that change in the expression of the gene or the transcript thereof can serve as a marker for lung cancer (Patent Literature 2).

The 132nd target gene is the hsa-miR-125a-3p gene, a congener thereof, a transcript thereof, or a variant or a derivative thereof. None of the previously known reports show that change in the expression of the gene or the transcript thereof can serve as a marker for lung cancer.

The 133rd target gene is the hsa-miR-92b-5p gene, a congener thereof, a transcript thereof, or a variant or a derivative thereof. None of the previously known reports show that change in the expression of the gene or the transcript thereof can serve as a marker for lung cancer.

The 134th target gene is the hsa-miR-22-3p gene, a congener thereof, a transcript thereof, or a variant or a derivative thereof. None of the previously known reports show that change in the expression of the gene or the transcript thereof can serve as a marker for lung cancer.

The 135th target gene is the hsa-miR-4271 gene, a congener thereof, a transcript thereof, or a variant or a derivative thereof. None of the previously known reports show that change in the expression of the gene or the transcript thereof can serve as a marker for lung cancer.

The 136th target gene is the hsa-miR-642b-3p gene, a congener thereof, a transcript thereof, or a variant or a derivative thereof. None of the previously known reports show that change in the expression of the gene or the transcript thereof can serve as a marker for lung cancer.

The 137th target gene is the hsa-miR-6075 gene, a congener thereof, a transcript thereof, or a variant or a derivative thereof. None of the previously known reports show that change in the expression of the gene or the transcript thereof can serve as a marker for lung cancer.

The 138th target gene is the hsa-miR-6125 gene, a congener thereof, a transcript thereof, or a variant or a derivative thereof. None of the previously known reports show that change in the expression of the gene or the transcript thereof can serve as a marker for lung cancer.

The 139th target gene is the hsa-miR-887-3p gene, a congener thereof, a transcript thereof, or a variant or a derivative thereof. None of the previously known reports show that change in the expression of the gene or the transcript thereof can serve as a marker for lung cancer.

The 140th target gene is the hsa-miR-6851-5p gene, a congener thereof, a transcript thereof, or a variant or a derivative thereof. None of the previously known reports show that change in the expression of the gene or the transcript thereof can serve as a marker for lung cancer.

The 141st target gene is the hsa-miR-6763-5p gene, a congener thereof, a transcript thereof, or a variant or a derivative thereof. None of the previously known reports show that change in the expression of the gene or the transcript thereof can serve as a marker for lung cancer.

The 142nd target gene is the hsa-miR-3928-3p gene, a congener thereof, a transcript thereof, or a variant or a derivative thereof. None of the previously known reports show that change in the expression of the gene or the transcript thereof can serve as a marker for lung cancer.

The 143rd target gene is the hsa-miR-4443 gene, a congener thereof, a transcript thereof, or a variant or a derivative thereof. None of the previously known reports show that change in the expression of the gene or the transcript thereof can serve as a marker for lung cancer.

The 144th target gene is the hsa-miR-3648 gene, a congener thereof, a transcript thereof, or a variant or a derivative thereof. None of the previously known reports show that change in the expression of the gene or the transcript thereof can serve as a marker for lung cancer.

The 145th target gene is the hsa-miR-149-3p gene, a congener thereof, a transcript thereof, or a variant or a derivative thereof. None of the previously known reports show that change in the expression of the gene or the transcript thereof can serve as a marker for lung cancer.

The 146th target gene is the hsa-miR-4689 gene, a congener thereof, a transcript thereof, or a variant or a derivative thereof. None of the previously known reports show that change in the expression of the gene or the transcript thereof can serve as a marker for lung cancer.

The 147th target gene is the hsa-miR-4763-3p gene, a congener thereof, a transcript thereof, or a variant or a derivative thereof. None of the previously known reports show that change in the expression of the gene or the transcript thereof can serve as a marker for lung cancer.

The 148th target gene is the hsa-miR-6729-5p gene, a congener thereof, a transcript thereof, or a variant or a derivative thereof. None of the previously known reports show that change in the expression of the gene or the transcript thereof can serve as a marker for lung cancer.

The 149th target gene is the hsa-miR-3196 gene, a congener thereof, a transcript thereof, or a variant or a derivative thereof. None of the previously known reports show that change in the expression of the gene or the transcript thereof can serve as a marker for lung cancer.

The 150th target gene is the hsa-miR-8069 gene, a congener thereof, a transcript thereof, or a variant or a derivative thereof. None of the previously known reports show that change in the expression of the gene or the transcript thereof can serve as a marker for lung cancer.

The 151st target gene is the hsa-miR-1268a gene, a congener thereof, a transcript thereof, or a variant or a derivative thereof. None of the previously known reports show that change in the expression of the gene or the transcript thereof can serve as a marker for lung cancer (Patent Literature 2).

The 152nd target gene is the hsa-miR-4739 gene, a congener thereof, a transcript thereof, or a variant or a derivative thereof. None of the previously known reports show that change in the expression of the gene or the transcript thereof can serve as a marker for lung cancer.

The 153rd target gene is the hsa-miR-1268b gene, a congener thereof, a transcript thereof, or a variant or a derivative thereof. None of the previously known reports show that change in the expression of the gene or the transcript thereof can serve as a marker for lung cancer.

The 154th target gene is the hsa-miR-5698 gene, a congener thereof, a transcript thereof, or a variant or a derivative thereof. None of the previously known reports show that change in the expression of the gene or the transcript thereof can serve as a marker for lung cancer.

The 155th target gene is the hsa-miR-6752-5p gene, a congener thereof, a transcript thereof, or a variant or a derivative thereof. None of the previously known reports show that change in the expression of the gene or the transcript thereof can serve as a marker for lung cancer.

The 156th target gene is the hsa-miR-4507 gene, a congener thereof, a transcript thereof, or a variant or a derivative thereof. None of the previously known reports show that change in the expression of the gene or the transcript thereof can serve as a marker for lung cancer.

The 157th target gene is the hsa-miR-564 gene, a congener thereof, a transcript thereof, or a variant or a derivative thereof. None of the previously known reports show that change in the expression of the gene or the transcript thereof can serve as a marker for lung cancer.

The 158th target gene is the hsa-miR-4497 gene, a congener thereof, a transcript thereof, or a variant or a derivative thereof. None of the previously known reports show that change in the expression of the gene or the transcript thereof can serve as a marker for lung cancer.

The 159th target gene is the hsa-miR-6877-5p gene, a congener thereof, a transcript thereof, or a variant or a derivative thereof. None of the previously known reports show that change in the expression of the gene or the transcript thereof can serve as a marker for lung cancer.

The 160th target gene is the hsa-miR-6087 gene, a congener thereof, a transcript thereof, or a variant or a derivative thereof. None of the previously known reports show that change in the expression of the gene or the transcript thereof can serve as a marker for lung cancer.

The 161st target gene is the hsa-miR-4731-5p gene, a congener thereof, a transcript thereof, or a variant or a derivative thereof. None of the previously known reports show that change in the expression of the gene or the transcript thereof can serve as a marker for lung cancer.

The 162nd target gene is the hsa-miR-615-5p gene, a congener thereof, a transcript thereof, or a variant or a derivative thereof. None of the previously known reports show that change in the expression of the gene or the transcript thereof can serve as a marker for lung cancer.

The 163rd target gene is the hsa-miR-760 gene, a congener thereof, a transcript thereof, or a variant or a derivative thereof. None of the previously known reports show that change in the expression of the gene or the transcript thereof can serve as a marker for lung cancer.

The 164th target gene is the hsa-miR-6891-5p gene, a congener thereof, a transcript thereof, or a variant or a derivative thereof. None of the previously known reports show that change in the expression of the gene or the transcript thereof can serve as a marker for lung cancer.

The 165th target gene is the hsa-miR-6887-5p gene, a congener thereof, a transcript thereof, or a variant or a derivative thereof. None of the previously known reports show that change in the expression of the gene or the transcript thereof can serve as a marker for lung cancer.

The 166th target gene is the hsa-miR-4525 gene, a congener thereof, a transcript thereof, or a variant or a derivative thereof. None of the previously known reports show that change in the expression of the gene or the transcript thereof can serve as a marker for lung cancer.

The 167th target gene is the hsa-miR-1914-3p gene, a congener thereof, a transcript thereof, or a variant or a derivative thereof. None of the previously known reports show that change in the expression of the gene or the transcript thereof can serve as a marker for lung cancer.

The 168th target gene is the hsa-miR-619-5p gene, a congener thereof, a transcript thereof, or a variant or a derivative thereof. None of the previously known reports show that change in the expression of the gene or the transcript thereof can serve as a marker for lung cancer.

The 169th target gene is the hsa-miR-5001-5p gene, a congener thereof, a transcript thereof, or a variant or a derivative thereof. None of the previously known reports show that change in the expression of the gene or the transcript thereof can serve as a marker for lung cancer.

The 170th target gene is the hsa-miR-6722-3p gene, a congener thereof, a transcript thereof, or a variant or a derivative thereof. None of the previously known reports show that change in the expression of the gene or the transcript thereof can serve as a marker for lung cancer.

The 171st target gene is the hsa-miR-3621 gene, a congener thereof, a transcript thereof, or a variant or a derivative thereof. None of the previously known reports show that change in the expression of the gene or the transcript thereof can serve as a marker for lung cancer.

The 172nd target gene is the hsa-miR-4298 gene, a congener thereof, a transcript thereof, or a variant or a derivative thereof. None of the previously known reports show that change in the expression of the gene or the transcript thereof can serve as a marker for lung cancer.

The 173rd target gene is the hsa-miR-675-5p gene, a congener thereof, a transcript thereof, or a variant or a derivative thereof. None of the previously known reports show that change in the expression of the gene or the transcript thereof can serve as a marker for lung cancer.

The 174th target gene is the hsa-miR-4655-5p gene, a congener thereof, a transcript thereof, or a variant or a derivative thereof. None of the previously known reports show that change in the expression of the gene or the transcript thereof can serve as a marker for lung cancer.

The 175th target gene is the hsa-miR-6073 gene, a congener thereof, a transcript thereof, or a variant or a derivative thereof. None of the previously known reports show that change in the expression of the gene or the transcript thereof can serve as a marker for lung cancer.

The 176th target gene is the hsa-miR-6845-5p gene, a congener thereof, a transcript thereof, or a variant or a derivative thereof. None of the previously known reports show that change in the expression of the gene or the transcript thereof can serve as a marker for lung cancer.

The 177th target gene is the hsa-miR-6769b-5p gene, a congener thereof, a transcript thereof, or a variant or a derivative thereof. None of the previously known reports show that change in the expression of the gene or the transcript thereof can serve as a marker for lung cancer.

The 178th target gene is the hsa-miR-4665-3p gene, a congener thereof, a transcript thereof, or a variant or a derivative thereof. None of the previously known reports show that change in the expression of the gene or the transcript thereof can serve as a marker for lung cancer.

The 179th target gene is the hsa-miR-1913 gene, a congener thereof, a transcript thereof, or a variant or a derivative thereof. None of the previously known reports show that change in the expression of the gene or the transcript thereof can serve as a marker for lung cancer.

The 180th target gene is the hsa-miR-1228-3p gene, a congener thereof, a transcript thereof, or a variant or a derivative thereof. None of the previously known reports show that change in the expression of the gene or the transcript thereof can serve as a marker for lung cancer.

The 181st target gene is the hsa-miR-940 gene, a congener thereof, a transcript thereof, or a variant or a derivative thereof. None of the previously known reports show that change in the expression of the gene or the transcript thereof can serve as a marker for lung cancer.

The 182nd target gene is the hsa-miR-296-3p gene, a congener thereof, a transcript thereof, or a variant or a derivative thereof. None of the previously known reports show that change in the expression of the gene or the transcript thereof can serve as a marker for lung cancer.

The 183rd target gene is the hsa-miR-4690-5p gene, a congener thereof, a transcript thereof, or a variant or a derivative thereof. None of the previously known reports show that change in the expression of the gene or the transcript thereof can serve as a marker for lung cancer.

The 184th target gene is the hsa-miR-548q gene, a congener thereof, a transcript thereof, or a variant or a derivative thereof. None of the previously known reports show that change in the expression of the gene or the transcript thereof can serve as a marker for lung cancer.

The 185th target gene is the hsa-miR-663a gene, a congener thereof, a transcript thereof, or a variant or a derivative thereof. None of the previously known reports show that change in the expression of the gene or the transcript thereof can serve as a marker for lung cancer.

The 186th target gene is the hsa-miR-1249 gene, a congener thereof, a transcript thereof, or a variant or a derivative thereof. None of the previously known reports show that change in the expression of the gene or the transcript thereof can serve as a marker for lung cancer.

The 187th target gene is the hsa-miR-1202 gene, a congener thereof, a transcript thereof, or a variant or a derivative thereof. None of the previously known reports show that change in the expression of the gene or the transcript thereof can serve as a marker for lung cancer.

The 188th target gene is the hsa-miR-7113-3p gene, a congener thereof, a transcript thereof, or a variant or a derivative thereof. None of the previously known reports show that change in the expression of the gene or the transcript thereof can serve as a marker for lung cancer.

The 189th target gene is the hsa-miR-1225-3p gene, a congener thereof, a transcript thereof, or a variant or a derivative thereof. None of the previously known reports show that change in the expression of the gene or the transcript thereof can serve as a marker for lung cancer.

The 190th target gene is the hsa-miR-4783-3p gene, a congener thereof, a transcript thereof, or a variant or a derivative thereof. None of the previously known reports show that change in the expression of the gene or the transcript thereof can serve as a marker for lung cancer.

The 191st target gene is the hsa-miR-4448 gene, a congener thereof, a transcript thereof, or a variant or a derivative thereof. None of the previously known reports show that change in the expression of the gene or the transcript thereof can serve as a marker for lung cancer.

The 192nd target gene is the hsa-miR-4534 gene, a congener thereof, a transcript thereof, or a variant or a derivative thereof. None of the previously known reports show that change in the expression of the gene or the transcript thereof can serve as a marker for lung cancer.

The 193rd target gene is the hsa-miR-1307-3p gene, a congener thereof, a transcript thereof, or a variant or a derivative thereof. The previously known report shows that change in the expression of the gene or the transcript thereof can serve as a marker for lung cancer (Patent Literature 3).

2. Nucleic Acid Probe or Primer for Detection of Lung Cancer

In the present invention, a nucleic acid capable of specifically binding to any of the target nucleic acids as the lung cancer markers described above can be used as a nucleic acid, for example, a nucleic acid probe or a primer, for the detection or diagnosis of lung cancer.

In the present invention, the nucleic acid probe or the primer that can be used for detecting lung cancer or for diagnosing lung cancer permits qualitative and/or quantitative measurement of the presence, expression level, or abundance of any of the target nucleic acids as the lung cancer markers described above, for example, human-derived hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448, and hsa-miR-4534 or a combination thereof, congeners thereof, transcripts thereof, or variants or derivatives thereof, optionally in combination therewith, hsa-miR-19b-3p, hsa-miR-1228-5p, and hsa-miR-1307-3p or a combination thereof, congeners thereof, transcripts thereof, or variants or derivatives thereof, and, optionally in combination therewith, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p or a combination thereof, congeners thereof, transcripts thereof, or variants or derivatives thereof.

The expression level of each target nucleic acid described above is increased or decreased (hereinafter, referred to as "increased/decreased") according to the type of the target nucleic acid in a subject who has lung cancer as compared with a healthy subject. Hence, the nucleic acid of the present invention can be effectively used for measuring the expression level of the target nucleic acid in a body fluid derived from a subject (e.g., a human) who is suspected of having lung cancer and a body fluid derived from a healthy subject, and detecting lung cancer by the comparison thereof.

The nucleic acid probe or the primer that can be used in the present invention is a nucleic acid probe capable of specifically binding to a polynucleotide consisting of a nucleotide sequence represented by at least one of SEQ ID NOs: 1 to 125, 127 to 130, 132 to 134, and 561 to 578, or a primer for amplifying a polynucleotide consisting of a nucleotide sequence represented by at least one of SEQ ID NOs: 1 to 125, 127 to 130, 132 to 134, and 561 to 578.

The nucleic acid probe or the primer that can be further used in the present invention can comprise a nucleic acid probe capable of specifically binding to a polynucleotide consisting of a nucleotide sequence represented by at least one of SEQ ID NOs: 126, 131, and 579, or a primer for amplifying a polynucleotide consisting of a nucleotide sequence represented by at least one of SEQ ID NOs: 126, 131, and 579.

The nucleic acid probe or the primer that can be further used in the present invention can comprise a nucleic acid probe capable of specifically binding to a polynucleotide consisting of a nucleotide sequence represented by at least one of SEQ ID NOs: 135 to 174, or a primer for amplifying a polynucleotide consisting of a nucleotide sequence represented by at least one of SEQ ID NOs: 135 to 174.

Specifically, these nucleic acid probes or primers comprise a combination of one or more polynucleotides selected from a polynucleotide group comprising nucleotide sequences represented by any of SEQ ID NOs: 1 to 618, or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the lung cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 125, 127 to 130, 132 to 134, and 561 to 578, (c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise the polynucleotides selected from the group consisting of the following polynucleotides (f) to (j):

(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 126, 131, and 579, (h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise the polynucleotides selected from the group consisting of the following polynucleotides (k) to (o):

(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 135 to 174, (m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 135 to 174 or a nucleotide sequence derived from the nucleotide sequence by the replacement of u with t, and (o) a polynucleotide hybridizing under stringent conditions to any of the polynucleotides (k) to (n).

For these polynucleotides, the "fragment thereof comprising 15 or more consecutive nucleotides" can contain the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR- 6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1133-p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-4511a, hsa-miR-939-5p, hsa-miR-223-3p, hsa-miR-1228-5p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-13p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, hsa-miR-1307-3p, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p represented by SEQ ID NOs: 1 to 174, and 561 to 579 are known in the art, and their acquisition methods are also known as mentioned above. Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 nucleotides can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 174, and 561 to 579 do not exist as miRNAs or precursors thereof in vivo. For example, the nucleotide sequences represented by SEQ ID NO: 5 and SEQ ID NO: 22 are produced from the precursor represented by SEQ ID NO: 179. This precursor has a hairpin-like structure as shown in FIG. 1, and the nucleotide sequences represented by SEQ ID NO: 5 and SEQ ID NO: 22 have mismatch sequences with each other. Likewise, a nucleotide sequence completely complementary to the nucleotide sequence represented by SEQ ID NO: 5 or SEQ ID NO: 22 is not naturally produced in vivo. Therefore, the nucleic acid probe and the primer for detecting the nucleotide sequence represented by any of SEQ ID NOs: 1 to 174, and 561 to 579 each have an artificial nucleotide sequence that does not exist in vivo.

3. Kit or Device for Detection of Lung Cancer

The present invention also provides a kit or a device for the detection of lung cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a lung cancer marker.

The target nucleic acid as a lung cancer marker according to the present invention is preferably selected from the following group 1: hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534.

An additional target nucleic acid that can be optionally used in the measurement is selected from the following group 2: hsa-miR-19b-3p, hsa-miR-1228-5p and hsa-miR-1307-3p.

An additional target nucleic acid that can be optionally further used in the measurement is selected from the following group 3: hsa-miR-4271, hsa-miR-642b-3p, hsa-miR- 6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p.

The kit or the device of the present invention comprises a nucleic acid capable of specifically binding to any of the target nucleic acids as the lung cancer markers described above, preferably one or more polynucleotide(s) selected from the nucleic acid probes or the primers described in the preceding Section 2, specifically, the polynucleotides described in the preceding paragraph 2, or variant(s) thereof.

Specifically, the kit or the device of the present invention can comprise at least one or more polynucleotide(s) comprising (or consisting of) a nucleotide sequence represented by any of SEQ ID NOs: 1 to 125, 127 to 130, 132 to 134, and 561 to 578 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 126 and 131 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 135 to 174 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):
(1) a polynucleotide comprising 15 or more consecutive nucleotides in a nucleotide sequence derived from a nucleotide sequence represented by any of SEQ ID NOs: 1 to 125, 127 to 130, 132 to 134, and 561 to 578 by the replacement of u with t, or a complementary sequence thereof;
(2) a polynucleotide comprising 15 or more consecutive nucleotides in a nucleotide sequence derived from a nucleotide sequence represented by any of SEQ ID NOs: 126, 131 and 579 by the replacement of u with t, or a complementary sequence thereof; and
(3) a polynucleotide comprising 15 or more consecutive nucleotides in a nucleotide sequence derived from a nucleotide sequence represented by any of SEQ ID NOs: 135 to 174 by the replacement of u with t, or a complementary sequence thereof.

In a preferred embodiment, the polynucleotide is a polynucleotide consisting of a nucleotide sequence represented by any of SEQ ID NOs: 1 to 125, 127 to 130, 132 to 134, and 561 to 578, or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 126, 134 and 579 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 135 to 174 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range from, for example, 15 consecutive nucleotides to less than the total number of bases of the sequence, from 17 consecutive nucleotides to less than the total number of bases of the sequence, or from 19 consecutive nucleotides to less than the total number of nucleotides of the sequence, in the nucleotide sequence of each polynucleotide.

Specific examples of the aforementioned combination of the polynucleotides constituting the kit or the device of the present invention can include the polynucleotides as to combinations of SEQ ID NOs shown in Table 1 (SEQ ID NOs: 1 to 174, and 561 to 579 corresponding to the miRNA markers in Table 1). However, these are given merely for illustrative purposes, and various other possible combinations are included in the present invention.

The aforementioned combination constituting the kit or the device for discriminating a lung cancer patient from a healthy subject according to the present invention is desirably, for example, a combination of two or more of the aforementioned polynucleotides consisting of nucleotide sequences represented by SEQ ID NOs shown in Table 1. Usually, a combination of two of these polynucleotides can produce adequate performance.

The combination of two polynucleotides consisting of the nucleotide sequences or the complementary sequences thereof for specifically discriminating a lung cancer patient from a healthy subject is preferably a combination comprising at least one or more of newly found polynucleotides consisting of the nucleotide sequences represented by SEQ ID NOs: 1 to 125, 127 to 130, 132 to 174, and 561 to 578, among the combinations constituted by two of the polynucleotides consisting of the nucleotide sequences represented by SEQ ID NOs: 1 to 174, and 561 to 579.

The combination of polynucleotides with cancer type specificity capable of discriminating a lung cancer patient not only from a healthy subject but also from other cancer patients is preferably, for example, a combination of multiple polynucleotides comprising at least one polynucleotide selected from the group consisting of polynucleotides of SEQ ID NOs: 1, 2, 3, 4, 5, 7, 9, 10, 11, 19, 21, 26, 29, 31, 52, 53, 63, 65, 69, 72, 87, 90, 113, 124, 125, 126, 128, 130, 143, 148, 160, 162, 561, 562, 563, 564, 565, 566, 567, 568, 569, 570, 571, 572, 573, 574, 575, 576, 577, 578 and 579 (hereinafter, this group is referred to as "cancer type-specific polynucleotide group 1"), with any of the polynucleotides of the other SEQ ID NOs.

The combination of polynucleotides with cancer type specificity capable of discriminating a lung cancer patient not only from a healthy subject but also from other cancer patients is more preferably a combination of multiple polynucleotides selected from the cancer type-specific polynucleotide group 1.

The combination of polynucleotides with cancer type specificity capable of discriminating a lung cancer patient not only from a healthy subject but also from other cancer patients is more preferably a combination comprising at least one or more polynucleotide(s) selected from the group consisting of polynucleotides of SEQ ID NOs: 1, 2, 3, 10, 63, 113, 124, 125, 126, 128, 130, 143, 160, 561, 568, 573 and 578 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the polynucleotides with cancer type specificity in the aforementioned combination can be 1, 2, 3, 4, 5, 6, 7, 8, 9, 10 or more for the combination and is more preferably 4 or more for the combination. Usually, the combination of 4 of these polynucleotides can produce adequate performance.

Non-limiting examples of the combination of the polynucleotide consisting of the nucleotide sequence represented by SEQ ID NO: 1 or a complementary sequence thereof with polynucleotides consisting of nucleotide sequences represented by SEQ ID NOs of five polynucleotides selected from the cancer type-specific polynucleotide group 1 or complementary sequences thereof will be listed below.

(1) a combination of SEQ ID NOs: 1, 53, 113, and 125 (markers: hsa-miR-6768-5p, hsa-miR-6088, hsa-miR-6717-5p, and hsa-miR-614);

(2) a combination of SEQ ID NOs: 1, 10, 63, and 113 (markers: hsa-miR-6768-5p, hsa-miR-6875-5p, hsa-miR-3162-5p, and hsa-miR-6717-5p);

(3) a combination of SEQ ID NOs: 1, 19, 113, and 143 (markers: hsa-miR-6768-5p, hsa-miR-3184-5p, hsa-miR-6717-5p, and hsa-miR-4443);

(4) a combination of SEQ ID NOs: 1, 10, 113, and 126 (markers: hsa-miR-6768-5p, hsa-miR-6875-5p, hsa-miR-6717-5p, and hsa-miR-19b-3p); and (5) a combination of SEQ ID NOs: 1, 2, 10, and 113 (markers: hsa-miR-6768-5p, hsa-miR-6836-3p, hsa-miR-6875-5p, and hsa-miR-6717-5p).

Non-limiting examples of the combination of the polynucleotide consisting of the nucleotide sequence represented by SEQ ID NO: 2 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 2, 19, 53, and 113 (markers: hsa-miR-6836-3p, hsa-miR-3184-5p, hsa-miR-6088, and hsa-miR-6717-5p);

(2) a combination of SEQ ID NOs: 2, 72, 113, and 125 (markers: hsa-miR-6836-3p, hsa-miR-3940-5p, hsa-miR-6717-5p, and hsa-miR-614);

(3) a combination of SEQ ID NOs: 2, 19, 72, and 113 (markers: hsa-miR-6836-3p, hsa-miR-3184-5p, hsa-miR-3940-5p, and hsa-miR-6717-5p);

(4) a combination of SEQ ID NOs: 2, 19, 113, and 579 (markers: hsa-miR-6836-3p, hsa-miR-3184-5p, hsa-miR-6717-5p, and hsa-miR-1307-3p); and (5) a combination of SEQ ID NOs: 1, 2, 19, and 113 (markers: hsa-miR-6768-5p, hsa-miR-6836-3p, hsa-miR-3184-5p, and hsa-miR-6717-5p).

Non-limiting examples of the combination of the polynucleotide consisting of the nucleotide sequence represented by SEQ ID NO: 3 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 3, 125, 128, and 568 (markers: hsa-miR-6782-5p, hsa-miR-614, hsa-miR-451a, and hsa-miR-296-3p);

(2) a combination of SEQ ID NOs: 1, 3, 10, and 113 (markers: hsa-miR-6768-5p, hsa-miR-6782-5p, hsa-miR-6875-5p, and hsa-miR-6717-5p);

(3) a combination of SEQ ID NOs: 3, 113, 125, and 126 (markers: hsa-miR-6782-5p, hsa-miR-6717-5p, hsa-miR-614, and hsa-miR-19b-3p);

(4) a combination of SEQ ID NOs: 1, 3, 126, and 573 (markers: hsa-miR-6768-5p, hsa-miR-6782-5p, hsa-miR-19b-3p, and hsa-miR-1202); and (5) a combination of SEQ ID NOs: 3, 126, 130, and 561 (markers: hsa-miR-6782-5p, hsa-miR-19b-3p, hsa-miR-223-3p, and hsa-miR-6073).

Non-limiting examples of the combination of the polynucleotide consisting of the nucleotide sequence represented by SEQ ID NO: 10 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 143 (markers: hsa-miR-6768-5p, hsa-miR-6875-5p, hsa-miR-6717-5p, and hsa-miR-4443);

(2) a combination of SEQ ID NOs: 1, 10, 113, and 569 (markers: hsa-miR-6768-5p, hsa-miR-6875-5p, hsa-miR-6717-5p, and hsa-miR-4690-5p);

(3) a combination of SEQ ID NOs: 1, 10, 113, and 562 (markers: hsa-miR-6768-5p, hsa-miR-6875-5p, hsa-miR-6717-5p, and hsa-miR-6845-5p);

(4) a combination of SEQ ID NOs: 1, 10, 113, and 578 (markers: hsa-miR-6768-5p, hsa-miR-6875-5p, hsa-miR-6717-5p, hsa-miR-4534); and (5) a combination of SEQ ID NOs: 1, 7, 10, and 113 (markers: hsa-miR-6768-5p, hsa-miR-4258, hsa-miR-6875-5p, and hsa-miR-6717-5p).

Non-limiting examples of the combination of the polynucleotide consisting of the nucleotide sequence represented by SEQ ID NO: 63 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 63, 567, and 578 (markers: hsa-miR-6768-5p, hsa-miR-3162-5p, hsa-miR-940, and hsa-miR-4534);

(2) a combination of SEQ ID NOs: 1, 53, 63, and 578 (markers: hsa-miR-6768-5p, hsa-miR-6088, hsa-miR-3162-5p, and hsa-miR-4534);

(3) a combination of SEQ ID NOs: 1, 63, 162, and 573 (markers: hsa-miR-6768-5p, hsa-miR-3162-5p, hsa-miR-615-5p, and hsa-miR-1202);

(4) a combination of SEQ ID NOs: 1, 63, 162, and 578 (markers: hsa-miR-6768-5p, hsa-miR-3162-5p, hsa-miR-615-5p, and hsa-miR-4534); and (5) a combination of SEQ ID NOs: 1, 63, 576, and 578 (markers: hsa-miR-6768-5p, hsa-miR-3162-5p, hsa-miR-4783-3p, and hsa-miR-4534).

Non-limiting examples of the combination of the polynucleotide consisting of the nucleotide sequence represented by SEQ ID NO: 113 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 567 (markers: hsa-miR-6768-5p, hsa-miR-6875-5p, hsa-miR-6717-5p, and hsa-miR-940);

(2) a combination of SEQ ID NOs: 1, 53, 63, and 113 (markers: hsa-miR-6768-5p, hsa-miR-6088, hsa-miR-3162-5p, and hsa-miR-6717-5p);

(3) a combination of SEQ ID NOs: 1, 53, 113, and 143 (markers: hsa-miR-6768-5p, hsa-miR-6088, hsa-miR-6717-5p, and hsa-miR-4443);

(4) a combination of SEQ ID NOs: 2, 19, 113, and 125 (markers: hsa-miR-6836-3p, hsa-miR-3184-5p, hsa-miR-6717-5p, and hsa-miR-614); and (5) a combination of SEQ ID NOs: 2, 10, 113, and 130 (markers: hsa-miR-6836-3p, hsa-miR-6875-5p, hsa-miR-6717-5p, and hsa-miR-223-3p).

Non-limiting examples of the combination of the polynucleotide consisting of the nucleotide sequence represented by SEQ ID NO: 124 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 124, 125, and 126 (markers: hsa-miR-6717-5p, hsa-miR-187-5p, hsa-miR-614, and hsa-miR-19b-3p);

(2) a combination of SEQ ID NOs: 124, 125, 128, and 568 (markers: hsa-miR-187-5p, hsa-miR-614, hsa-miR-451a, and hsa-miR-296-3p);

(3) a combination of SEQ ID NOs: 113, 124, 125, and 162 (markers: hsa-miR-6717-5p, hsa-miR-187-5p, hsa-miR-614, and hsa-miR-615-5p);

(4) a combination of SEQ ID NOs: 52, 124, 126, and 561 (markers: hsa-miR-365a-5p, hsa-miR-187-5p, hsa-miR-19b-3p, and hsa-miR-6073); and (5) a combination of SEQ ID NOs: 19, 113, 124, and 126 (markers: hsa-miR-3184-5p, hsa-miR-6717-5p, hsa-miR-187-5p, and hsa-miR-19b-3p).

Non-limiting examples of the combination of the polynucleotide consisting of the nucleotide sequence represented by SEQ ID NO: 125 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 113, 125, and 160 (markers: hsa-miR-6768-5p, hsa-miR-6717-5p, hsa-miR-614, and hsa-miR-6087);

(2) a combination of SEQ ID NOs: 31, 113, 125, and 568 (markers: hsa-miR-6889-5p, hsa-miR-6717-5p, hsa-miR-614, and hsa-miR-296-3p);

(3) a combination of SEQ ID NOs: 2, 53, 113, and 125 (markers: hsa-miR-6836-3p, hsa-miR-6088, hsa-miR-6717-5p, and hsa-miR-614);

(4) a combination of SEQ ID NOs: 1, 10, 113, and 125 (markers: hsa-miR-6768-5p, hsa-miR-6875-5p, hsa-miR-6717-5p, and hsa-miR-614); and (5) a combination of SEQ ID NOs: 1, 113, 125, and 143 (markers: hsa-miR-6768-5p, hsa-miR-6717-5p, hsa-miR-614, and hsa-miR-4443).

Non-limiting examples of the combination of the polynucleotide consisting of the nucleotide sequence represented by SEQ ID NO: 126 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 126, 561, and 573 (markers: hsa-miR-6768-5p, hsa-miR-19b-3p, hsa-miR-6073, and hsa-miR-1202);

(2) a combination of SEQ ID NOs: 113, 125, 126, and 568 (markers: hsa-miR-6717-5p, hsa-miR-614, hsa-miR-19b-3p, and hsa-miR-296-3p);

(3) a combination of SEQ ID NOs: 113, 125, 126, and 561 (markers: hsa-miR-6717-5p, hsa-miR-614, hsa-miR-19b-3p, and hsa-miR-6073);

(4) a combination of SEQ ID NOs: 1, 113, 125, and 126 (markers: hsa-miR-6768-5p, hsa-miR-6717-5p, hsa-miR-614, and hsa-miR-19b-3p); and (5) a combination of SEQ ID NOs: 1, 52, 126, and 561 (markers: hsa-miR-6768-5p, hsa-miR-365a-5p, hsa-miR-19b-3p, and hsa-miR-6073).

Non-limiting examples of the combination of the polynucleotide consisting of the nucleotide sequence represented by SEQ ID NO: 128 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 26, 113, 125, and 128 (markers: hsa-miR-6842-5p, hsa-miR-6717-5p, hsa-miR-614, and hsa-miR-451a);

(2) a combination of SEQ ID NOs: 1, 113, 125, and 128 (markers: hsa-miR-6768-5p, hsa-miR-6717-5p, hsa-miR-614, and hsa-miR-451a);

(3) a combination of SEQ ID NOs: 1, 10, 113, and 128 (markers: hsa-miR-6768-5p, hsa-miR-6875-5p, hsa-miR-6717-5p, and hsa-miR-451a);

(4) a combination of SEQ ID NOs: 31, 113, 125, and 128 (markers: hsa-miR-6889-5p, hsa-miR-6717-5p, hsa-miR-614, and hsa-miR-451a); and (5) a combination of SEQ ID NOs: 2, 19, 113, and 128 (markers: hsa-miR-6836-3p, hsa-miR-3184-5p, hsa-miR-6717-5p, and hsa-miR-451a).

Non-limiting examples of the combination of the polynucleotide consisting of the nucleotide sequence represented by SEQ ID NO: 130 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 3, 130, and 143 (markers: hsa-miR-6768-5p, hsa-miR-6782-5p, hsa-miR-223-3p, and hsa-miR-4443);

(2) a combination of SEQ ID NOs: 1, 10, 113, and 130 (markers: hsa-miR-6768-5p, hsa-miR-6875-5p, hsa-miR-6717-5p, and hsa-miR-223-3p);

(3) a combination of SEQ ID NOs: 1, 63, 130, and 578 (markers: hsa-miR-6768-5p, hsa-miR-3162-5p, hsa-miR-223-3p, and hsa-miR-4534);

(4) a combination of SEQ ID NOs: 124, 125, 130, and 568 (markers: hsa-miR-187-5p, hsa-miR-614, hsa-miR-223-3p, and hsa-miR-296-3p); and (5) a combination of SEQ ID NOs: 2, 19, 113, and 130 (markers: hsa-miR-6836-3p, hsa-miR-3184-5p, hsa-miR-6717-5p, and hsa-miR-223-3p).

Non-limiting examples of the combination of the polynucleotide consisting of the nucleotide sequence represented by SEQ ID NO: 143 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 3, 126, and 143 (markers: hsa-miR-6768-5p, hsa-miR-6782-5p, hsa-miR-19b-3p, and hsa-miR-4443);

(2) a combination of SEQ ID NOs: 1, 63, 130, and 143 (markers: hsa-miR-6768-5p, hsa-miR-3162-5p, hsa-miR-223-3p, and hsa-miR-4443);

(3) a combination of SEQ ID NOs: 1, 10, 52, and 143 (markers: hsa-miR-6768-5p, hsa-miR-6875-5p, hsa-miR-365a-5p, and hsa-miR-4443);

(4) a combination of SEQ ID NOs: 2, 19, 113, and 143 (markers: hsa-miR-6836-3p, hsa-miR-3184-5p, hsa-miR-6717-5p, and hsa-miR-4443); and (5) a combination of SEQ ID NOs: 63, 124, 130, and 143 (markers: hsa-miR-3162-5p, hsa-miR-187-5p, hsa-miR-223-3p, and hsa-miR-4443).

Non-limiting examples of the combination of the polynucleotide consisting of the nucleotide sequence represented by SEQ ID NO: 160 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 10, 113, and 160 (markers: hsa-miR-6768-5p, hsa-miR-6875-5p, hsa-miR-6717-5p, and hsa-miR-6087);

(2) a combination of SEQ ID NOs: 7, 113, 125, and 160 (markers: hsa-miR-4258, hsa-miR-6717-5p, hsa-miR-614, and hsa-miR-6087);

(3) a combination of SEQ ID NOs: 1, 113, 160, and 567 (markers: hsa-miR-6768-5p, hsa-miR-6717-5p, hsa-miR-6087, and hsa-miR-940);

(4) a combination of SEQ ID NOs: 1, 113, 160, and 578 (markers: hsa-miR-6768-5p, hsa-miR-6717-5p, hsa-miR-6087, and hsa-miR-4534); and (5) a combination of SEQ ID NOs: 2, 19, 113, and 160 (markers: hsa-miR-6836-3p, hsa-miR-3184-5p, hsa-miR-6717-5p, and hsa-miR-6087).

Non-limiting examples of the combination of the polynucleotide consisting of the nucleotide sequence represented by SEQ ID NO: 561 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 125, 130, and 561 (markers: hsa-miR-6717-5p, hsa-miR-614, hsa-miR-223-3p, and hsa-miR-6073);

(2) a combination of SEQ ID NOs: 7, 126, 143, and 561 (markers: hsa-miR-4258, hsa-miR-19b-3p, hsa-miR-4443, and hsa-miR-6073);

(3) a combination of SEQ ID NOs: 1, 113, and 126, 561 (markers: hsa-miR-6768-5p, hsa-miR-6717-5p, hsa-miR-19b-3p, and hsa-miR-6073);

(4) a combination of SEQ ID NOs: 1, 126, 561, and 568 (markers: hsa-miR-6768-5p, hsa-miR-19b-3p, hsa-miR-6073, and hsa-miR-296-3p); and (5) a combination of SEQ ID NOs: 7, 113, 126, and 561 (markers: hsa-miR-4258, hsa-miR-6717-5p, hsa-miR-19b-3p, and hsa-miR-6073).

Non-limiting examples of the combination of the polynucleotide consisting of the nucleotide sequence represented by SEQ ID NO: 568 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 7, 125, 126, and 568 (markers: hsa-miR-4258, hsa-miR-614, hsa-miR-19b-3p, and hsa-miR-296-3p);

(2) a combination of SEQ ID NOs: 124, 125, 126, and 568 (markers: hsa-miR-187-5p, hsa-miR-614, hsa-miR-19b-3p, and hsa-miR-296-3p);

(3) a combination of SEQ ID NOs: 7, 113, 125, and 568 (markers: hsa-miR-4258, hsa-miR-6717-5p, hsa-miR-614, and hsa-miR-296-3p);

(4) a combination of SEQ ID NOs: 1, 113, 125, and 568 (markers: hsa-miR-6768-5p, hsa-miR-6717-5p, hsa-miR-614, and hsa-miR-296-3p); and (5) a combination of SEQ ID NOs: 113, 125, 128, and 568 (markers: hsa-miR-6717-5p, hsa-miR-614, hsa-miR-451a, and hsa-miR-296-3p).

Non-limiting examples of the combination of the polynucleotide consisting of the nucleotide sequence represented by SEQ ID NO: 573 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 113, 125, 126, and 573 (markers: hsa-miR-6717-5p, hsa-miR-614, hsa-miR-19b-3p, and hsa-miR-1202);

(2) a combination of SEQ ID NOs: 1, 113, 125, and 573 (markers: hsa-miR-6768-5p, hsa-miR-6717-5p, hsa-miR-614, and hsa-miR-1202);

(3) a combination of SEQ ID NOs: 1, 53, 113, and 573 (markers: hsa-miR-6768-5p, hsa-miR-6088, hsa-miR-6717-5p, and hsa-miR-1202);

(4) a combination of SEQ ID NOs: 1, 124, 126, and 573 (markers: hsa-miR-6768-5p, hsa-miR-187-5p, hsa-miR-19b-3p, and hsa-miR-1202); and (5) a combination of SEQ ID NOs: 1, 63, 130, and 573 (markers: hsa-miR-6768-5p, hsa-miR-3162-5p, hsa-miR-223-3p, and hsa-miR-1202).

Non-limiting examples of the combination of the polynucleotide consisting of the nucleotide sequence represented by SEQ ID NO: 578 or a complementary sequence thereof with polynucleotides consisting of nucleotide sequences represented by SEQ ID NOs of five polynucleotides selected from the cancer type-specific polynucleotide group 1 or complementary sequences thereof will be further listed below.

(1) a combination of SEQ ID NOs: 1, 126, 567, and 578 (markers: hsa-miR-6768-5p, hsa-miR-19b-3p, hsa-miR-940, and hsa-miR-4534);

(2) a combination of SEQ ID NOs: 1, 19, 113, and 578 (markers: hsa-miR-6768-5p, hsa-miR-3184-5p, hsa-miR-6717-5p, and hsa-miR-4534);

(3) a combination of SEQ ID NOs: 31, 126, 561, and 578 (markers: hsa-miR-6889-5p, hsa-miR-19b-3p, hsa-miR-6073, and hsa-miR-4534);

(4) a combination of SEQ ID NOs: 1, 126, 160, and 578 (markers: hsa-miR-6768-5p, hsa-miR-19b-3p, hsa-miR-6087, and hsa-miR-4534); and (5) a combination of SEQ ID NOs: 1, 113, 125, 578 (markers: hsa-miR-6768-5p, hsa-miR-6717-5p, hsa-miR-614, and hsa-miR-4534).

The kit or the device of the present invention can also contain a polynucleotide that is already known or that will be found in the future, to enable detection of lung cancer, in addition to the polynucleotide(s) (which can include the variant(s), the fragment(s), and the derivative(s)) according to the present invention described above.

The kit of the present invention can also contain an antibody for measuring a marker for lung cancer examination known in the art, such as CEA, or CYFRA21-1, in addition to the polynucleotide(s) according to the present invention described above.

These polynucleotides contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the polynucleotides of at least one or more, preferably at least two or more, more preferably at least three or more, most preferably at least five or more to all of the lung cancer marker miRNAs, respectively, of the group 1 described above. The kit or the device of the present invention can optionally further comprise nucleic acids capable of specifically binding to the polynucleotides of at least one or more, preferably at least two or more, more preferably at least three or more, most preferably at least five or more to all of the lung cancer marker miRNAs, respectively, of the group 2 described above. The kit or the device of the present invention can optionally further comprise nucleic acids capable of specifically binding to the polynucleotides of at least one or more, preferably at least two or more, more preferably at least three or more, most preferably at least five or more to all of the lung cancer marker miRNAs, respectively, of the group 3 described above.

The kit or the device of the present invention can be used for detecting lung cancer as described in Section 4 below.

4. Method for Detecting Lung Cancer

The present invention further provides a method for detecting lung cancer, comprising using the kit or the device of the present invention (including the aforementioned nucleic acid(s) that can be used in the present invention) described in Section 3 above to measure an expression level(s) of one or more lung cancer-derived gene(s) represented by an expression level(s) of lung cancer-derived gene(s) selected from the following group A: hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-1225-5p, hsa-miR-451a, hsa-miR-939-5p, hsa-miR-223-3p, hsa-miR-125a-3p, hsa-miR-92b-5p, hsa-miR-22-3p, hsa-miR-6073, hsa-miR-6845-5p, hsa-miR-6769b-5p, hsa-miR-4665-3p, hsa-miR-1913, hsa-miR-1228-3p, hsa-miR-940, hsa-miR-296-3p, hsa-miR-4690-5p, hsa-miR-548q, hsa-miR-663a, hsa-miR-1249, hsa-miR-1202, hsa-miR-7113-3p, hsa-miR-1225-3p, hsa-miR-4783-3p, hsa-miR-4448 and hsa-miR-4534, optionally an expression level of lung cancer-derived gene(s) selected from the following group B: hsa-miR-19b-3p, hsa-miR-1228-5p, and hsa-miR-1307-3p, and optionally an expression level of lung cancer-derived gene(s) selected from the following group C: hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p and hsa-miR-4655-5p in a sample in vitro, further comparing, for example, the expression level(s) of the aforementioned gene(s) in the sample (e.g., blood, serum, or plasma) collected from a subject who is suspected of having lung cancer with a control expression level in the sample collected from a healthy subject (including a non-lung cancer patient), and evaluating the subject as having lung cancer when the expression level(s) of the target nucleic acid(s) is statistically significantly different between the samples.

This method of the present invention permits limitedly-invasive early diagnosis of cancer with high sensitivity and specificity, and thereby brings about early treatment and improved prognosis. In addition, exacerbation of the disease or the effectiveness of surgical, radiotherapeutic, and chemotherapeutic treatments can be monitored.

The method for extracting the lung cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The lung cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy™ Mini Kit (Qiagen N.V.) can be used, though the method is not limited thereto.

The present invention also provides use of the kit or the device of the present invention for detecting in vitro an expression product of a lung cancer-derived miRNA gene in a sample derived from a subject.

In the method of the present invention, a kit or a device comprising, each alone or in every possible composition, the polynucleotides that can be used in the present invention as described above is used as the kit or the device.

In the detection or (genetic) diagnosis of lung cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of lung cancer or the detection of the presence or absence of lung cancer. Specifically, the detection of lung cancer using the kit or the device can be performed by detecting in vitro an expression level of a gene using the nucleic acid probe or the primer contained in the kit or the device in a sample such as blood, serum, plasma, or urine from a subject suspected of having lung cancer. The subject suspected of having lung cancer can be evaluated as having lung cancer when the expression level of a target miRNA marker measured using polynucleotide(s) (including a variant(s), a fragment(s), and a derivative(s) thereof) consisting of a nucleotide sequence represented by at least one or more of SEQ ID NOs: 1 to 125, 127 to 130, 132 to 134 and 561 to 578 or a complementary sequence thereof, optionally a nucleotide sequence represented by one or more of SEQ ID NOs: 126 and 131 or a complementary sequence thereof, and optionally a nucleotide sequence represented by one or more of SEQ ID NOs: 135 to 174 or a complementary sequence thereof in the sample such as blood, serum, plasma, or urine of the subject is statistically significantly different from the expression level thereof in the sample such as blood, serum, or urine of a healthy subject.

The method of the present invention can be combined with chest X-ray examination as well as a diagnostic imaging method such as CT, MRI, or PET. The method of the present invention is capable of specifically detecting lung cancer and can substantially discriminate lung cancer from the other cancers.

The method for detecting the absence of an expression product of a lung cancer-derived gene or the presence of the expression product of a lung cancer-derived gene in a sample using the kit or the device of the present invention comprises collecting a body fluid such as blood, serum, plasma, or urine from a subject, and measuring the expression level of the target gene contained therein using one or more polynucleotide(s) (including a variant(s), a fragment(s), and a derivative(s)) selected from the polynucleotide group of the present invention, to evaluate the presence or absence of lung cancer or to detect lung cancer. Using the method for detecting lung cancer according to the present invention, for example, the presence or absence of amelioration of the disease or the degree of amelioration thereof in a lung cancer patient given a therapeutic drug for the amelioration of the disease can be also evaluated or diagnosed.

The method of the present invention can comprise, for example, the following steps (a), (b), and (c):

(a) a step of contacting a sample derived from a subject with a polynucleotide in the kit or the device of the present invention in vitro;

(b) a step of measuring an expression level of the target nucleic acid in the sample using the polynucleotide as a nucleic acid probe or a primer; and (c) a step of evaluating the presence or absence of lung cancer (cells) in the subject on the basis of the step (b).

Specifically, the present invention provides a method for detecting lung cancer, comprising measuring an expression level of a target nucleic acid in a sample of a subject using a nucleic acid capable of specifically binding to at least one or more (preferably at least two or more) polynucleotide(s) selected from the group consisting of miR-6768-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3679-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534, and evaluating in vitro whether or not the subject has lung cancer using the measured expression level and a control expression level of a healthy subject measured in the same way as above.

As used herein, the term "evaluation" is evaluation support based on results of in vitro examination, not physician's judgment.

As described above, as for the target nucleic acids in a preferred embodiment of the method of the present invention, specifically, miR-6768-5p is hsa-miR-6768-5p, miR-6836-3p is hsa-miR-6836-3p, miR-6782-5p is hsa-miR-6782-5p, miR-3663-3p is hsa-miR-3663-3p, miR-1908-3p is hsa-miR-1908-3p, miR-6726-5p is hsa-miR-6726-5p, miR-4258 is hsa-miR-4258, miR-1343-3p is hsa-miR-1343-3p, miR-4516 is hsa-miR-4516, miR-6875-5p is hsa-miR-6875-5p, miR-4651 is hsa-miR-4651, miR-6825-5p is hsa-miR-6825-5p, miR-6840-3p is hsa-miR-6840-3p, miR-6780b-5p is hsa-miR-6780b-5p, miR-6749-5p is hsa-miR-6749-5p, miR-8063 is hsa-miR-8063, miR-6784-5p is hsa-miR-6784-5p, miR-3679-5p is hsa-miR-3679-5p, miR-3184-5p is hsa-miR-3184-5p, miR-663b is hsa-miR-663b, miR-6880-5p is hsa-miR-6880-5p, miR-1908-5p is hsa-miR-1908-5p, miR-92a-2-5p is hsa-miR-92a-2-5p, miR-7975 is hsa-miR-7975, miR-7110-5p is hsa-miR-7110-5p, miR-6842-5p is hsa-miR-6842-5p, miR-6857-5p is hsa-miR-6857-5p, miR-5572 is hsa-miR-5572, miR-3197 is hsa-miR-3197, miR-6131 is hsa-miR-6131, miR-6889-5p is hsa-miR-6889-5p, miR-4454 is hsa-miR-4454, miR-1199-5p is hsa-miR-1199-5p, miR-1247-3p is hsa-miR-1247-3p, miR-6800-5p is hsa-miR-6800-5p, miR-6872-3p is hsa-miR-6872-3p, miR-4649-5p is hsa-miR-4649-5p, miR-6791-5p is hsa-miR-6791-5p, miR-4433b-3p is hsa-miR-4433b-3p, miR-3135b is hsa-miR-3135b, miR-128-2-5p is hsa-miR-128-2-5p, miR-4675 is hsa-miR-4675, miR-4472 is hsa-miR-4472, miR-6785-5p is hsa-miR-6785-5p, miR-6741-5p is hsa-miR-6741-5p, miR-7977 is hsa-miR-7977, miR-3665 is hsa-miR-3665, miR-128-1-5p is hsa-miR-128-1-5p, miR-4286 is hsa-miR-4286, miR-6765-3p is hsa-miR-6765-3p, miR-4632-5p is hsa-miR-4632-5p, miR-365a-5p is hsa-miR-365a-5p, miR-6088 is hsa-miR-6088, miR-6816-5p is hsa-miR-6816-5p, miR-6885-5p is hsa-miR-6885-5p, miR-711 is hsa-miR-711, miR-6765-5p is hsa-miR-6765-5p, miR-3180 is hsa-miR-3180, miR-4442 is hsa-miR-4442, miR-4792 is hsa-miR-4792, miR-6721-5p is hsa-miR-6721-5p, miR-6798-5p is hsa-miR-6798-5p, miR-3162-5p is hsa-miR-3162-5p, miR-6126 is hsa-miR-6126, miR-4758-5p is hsa-miR-4758-5p, miR-2392 is hsa-miR-2392, miR-486-3p is hsa-miR-486-3p, miR-6727-5p is hsa-miR-6727-5p, miR-4728-5p is hsa-miR-4728-5p, miR-6746-5p is hsa-miR-6746-5p, miR-4270 is hsa-miR-4270, miR-3940-5p is hsa-miR-3940-5p, miR-4725-3p is hsa-miR-4725-3p, miR-7108-5p is hsa-miR-7108-5p, miR-3656 is hsa-miR-3656, miR-6879-5p is hsa-miR-6879-5p, miR-6738-5p is hsa-miR-6738-5p, miR-1260a is hsa-miR-1260a, miR-4446-3p is hsa-miR-4446-3p, miR-3131 is hsa-miR-3131, miR-4463 is hsa-miR-4463, miR-3185 is hsa-miR-3185, miR-6870-5p is hsa-miR-6870-5p, miR-6779-5p is hsa-miR-6779-5p, miR-1273g-3p is hsa-miR-1273g-3p, miR-8059 is hsa-miR-8059, miR-4697-5p is hsa-miR-4697-5p, miR-4674 is hsa-miR-4674, miR-4433-3p is hsa-miR-4433-3p, miR-4257 is hsa-miR-4257, miR-1915-5p is hsa-miR-1915-5p, miR-4417 is hsa-miR-4417, miR-1343-5p is hsa-miR-1343-5p, miR-6781-5p is hsa-miR-6781-5p, miR-4695-5p is hsa-miR-4695-5p, miR-1237-5p is hsa-miR-1237-5p, miR-6775-5p is hsa-miR-6775-5p, miR-7845-5p is hsa-miR-7845-5p, miR-4746-3p is hsa-miR-4746-3p, miR-7641 is hsa-miR-7641, miR-7847-3p is hsa-miR-7847-3p, miR-6806-5p is hsa-miR-6806-5p, miR-4467 is hsa-miR-4467, miR-4726-5p is hsa-miR-4726-5p, miR-4648 is hsa-miR-4648, miR-6089 is hsa-miR-6089, miR-1260b is hsa-miR-1260b, miR-4532 is hsa-miR-4532, miR-5195-3p is hsa-miR-5195-3p, miR-3188 is hsa-miR-3188, miR-6848-5p is hsa-miR-6848-5p, miR-1233-5p is hsa-miR-1233-5p, miR-6717-5p is hsa-miR-6717-5p, miR-3195 is hsa-miR-3195, miR-6757-5p is hsa-miR-6757-5p, miR-8072 is hsa-miR-8072, miR-4745-5p is hsa-miR-4745-5p, miR-6511a-5p is hsa-miR-6511a-5p, miR-6776-5p is hsa-miR-6776-5p, miR- 371a-5p is hsa-miR-371a-5p, miR-1227-5p is hsa-miR-1227-5p, miR-7150 is hsa-miR-7150, miR-1915-3p is hsa-miR-1915-3p, miR-187-5p is hsa-miR-1187-5p, miR-614 is hsa-miR-614, miR-1225-5p is hsa-miR-1225-5p, miR-451a is hsa-miR-451a, miR-939-5p is hsa-miR-939-5p, miR-223-3p is hsa-miR-223-3p, miR-125a-3p is hsa-miR-125a-3p, miR-92b-5p is hsa-miR-92b-5p, miR-22-3p is hsa-miR-22-3p, miR-6073 is hsa-miR-6073, miR-6845-5p is hsa-miR-6845-5p, miR-6769b-5p is hsa-miR-6769b-5p, miR-4665-3p is hsa-miR-4665-3p, miR-1913 is hsa-miR-1913, miR-1228-3p is hsa-miR-1228-3p, miR-940 is hsa-miR-940, miR-296-3p is hsa-miR-296-3p, miR-4690-5p is hsa-miR-4690-5p, miR-548q is hsa-miR-548q, miR-663a is hsa-miR-663a, miR-1249 is hsa-miR-1249, miR-1202 is hsa-miR-1202, miR-7113-3p is hsa-miR-7113-3p, miR-1225-3p is hsa-miR-1225-3p, miR-4783-3p is hsa-miR-4783-3p, miR-4448 is hsa-miR-4448, and miR-4534 is hsa-miR-4534.

In a preferred embodiment of the method of the present invention, specifically, the nucleic acid (specifically, probe or primer) is selected from the group consisting of the following polynucleotides (a) to (e):
(a) a polynucleotide consisting of a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
(b) a polynucleotide comprising a nucleotide sequence represented by any of SEQ ID NOs: 1 to 125, 127 to 130, 132 to 134, and 561 to 578,
(c) a polynucleotide consisting of a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, a variant thereof, a derivative thereof, or a fragment thereof comprising 15 or more consecutive nucleotides,
(d) a polynucleotide comprising a nucleotide sequence complementary to a nucleotide sequence represented by any of SEQ ID NOs: 1 to 125, 127 to 130, 132 to 134, and 561 to 578 or a nucleotide sequence derived from the nucleotide sequence by the replacement of u with t, and
(e) a polynucleotide hybridizing under stringent conditions to any of the polynucleotides (a) to (d).

The method of the present invention can further employ a nucleic acid capable of specifically binding to at least one or more polynucleotide(s) selected from the group consisting of miR-19b-3p, miR-1228-5p, and miR-1307-3p.

As for such a nucleic acid, specifically, miR-19b-3p is hsa-miR-19b-3p, miR-1228-5p is hsa-miR-1228-5p, and miR-1307-3p is hsa-miR-1307-3p.

In a preferred embodiment, such a nucleic acid is specifically selected from the group consisting of the following polynucleotides (f) to (j):
(f) a polynucleotide consisting of a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides,
(g) a polynucleotide comprising a nucleotide sequence represented by any of SEQ ID NOs: 126, 131, and 579,
(h) a polynucleotide consisting of a nucleotide sequence complementary to a nucleotide sequence represented by any of SEQ ID NOs: 126, 131, and 579 or a nucleotide sequence derived from the nucleotide sequence by the replacement of u with t, a variant thereof, a derivative thereof, or a fragment thereof comprising 15 or more consecutive nucleotides,
(i) a polynucleotide comprising a nucleotide sequence complementary to a nucleotide sequence represented by any of SEQ ID NOs: 126, 131, and 579 or a nucleotide sequence derived from the nucleotide sequence by the replacement of u with t, and
(j) a polynucleotide hybridizing under stringent conditions to any of the polynucleotides (f) to (i).

The nucleic acid further used in the method of the present invention can comprise a nucleic acid capable of specifically binding to at least one or more polynucleotide(s) selected from the group consisting of miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p and miR-4655-5p.

As for such a nucleic acid, specifically, miR-4271 is hsa-miR-4271, miR-642b-3p is hsa-miR-642b-3p, miR-6075 is hsa-miR-6075, miR-6125 is hsa-miR-6125, miR-887-3p is hsa-miR-887-3p, miR-6851-5p is hsa-miR-6851-5p, miR-6763-5p is hsa-miR-6763-5p, miR-3928-3p is hsa-miR-3928-3p, miR-4443 is hsa-miR-4443, miR-3648 is hsa-miR-3648, miR-149-3p is hsa-miR-149-3p, miR-4689 is hsa-miR-4689, miR-4763-3p is hsa-miR-4763-3p, miR-6729-5p is hsa-miR-6729-5p, miR-3196 is hsa-miR-3196, miR-8069 is hsa-miR-8069, miR-1268a is hsa-miR-1268a, miR-4739 is hsa-miR-4739, miR-1268b is hsa-miR-1268b, miR-5698 is hsa-miR-5698, miR-6752-5p is hsa-miR-6752-5p, miR-4507 is hsa-miR-4507, miR-564 is hsa-miR-564, miR-4497 is hsa-miR-4497, miR-6877-5p is hsa-miR-6877-5p, miR-6087 is hsa-miR-6087, miR-4731-5p is hsa-miR-4731-5p, miR-615-5p is hsa-miR-615-5p, miR-760 is hsa-miR-760, miR-6891-5p is hsa-miR-6891-5p, miR-6887-5p is hsa-miR-6887-5p, miR-4525 is hsa-miR-4525, miR-1914-3p is hsa-miR-1914-3p, miR-619-5p is hsa-miR-619-5p, miR-5001-5p is hsa-miR-5001-5p, miR-6722-3p is hsa-miR-6722-3p, miR-3621 is hsa-miR-3621, miR-4298 is hsa-miR-4298, miR-675-5p is hsa-miR-675-5p, and miR-4655-5p is hsa-miR-4655-5p.

In a preferred embodiment, such a nucleic acid is specifically a polynucleotide selected from the group consisting of the following polynucleotides (k) to (o):
(k) a polynucleotide consisting of a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(l) a polynucleotide comprising a nucleotide sequence represented by any of SEQ ID NOs: 135 to 174,
(m) a polynucleotide consisting of a nucleotide sequence complementary to a nucleotide sequence represented by any of SEQ ID NOs: 135 to 174 or a nucleotide sequence derived from the nucleotide sequence by the replacement of u with t, a variant thereof, a derivative thereof, or a fragment thereof comprising 15 or more consecutive nucleotides,
(n) a polynucleotide comprising a nucleotide sequence complementary to a nucleotide sequence represented by any of SEQ ID NOs: 135 to 174 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a lung tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse and a rat, without any limitation, and is preferably a human.

The steps of the method of the present invention can be changed according to the type of the sample to be assayed.

In the case of using RNA as an analyte, the detection of lung cancer (cells) can comprise, for example, the following steps (a), (b), and (c):

(a) a step of binding RNA prepared from the sample of the subject or a complementary polynucleotide (cDNA) transcribed therefrom to a polynucleotide in the kit or the device of the present invention;

(b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) a step of evaluating the presence or absence of lung cancer (or lung cancer-derived gene expression) on the basis of the measurement results of the step (b).

For example, various hybridization methods can be used for detecting, examining, evaluating, or diagnosing lung cancer (or lung cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}$P, $^{33}$P, $^{35}$S, etc.), a fluorescent material, or the like, hybridizing the labeled product with the living tissue-derived RNA from a subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves preparing cDNA from the living tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions having the attached nucleic acid probes are referred to as probe spots, and regions having no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of them. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. The hybridization conditions are not limited and are conditions involving, for example, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions of the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer with composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™-based MicroRNA PCR (Exiqon), or Ncode™ miRNA qRT-PCT kit (Invitrogen Corp.) may be used.

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably $2^8$, more preferably $2^{10}$ or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a lung cancer patient and a sample derived from a healthy subject as supervising samples, and determining or evaluating the presence and/or absence of the lung cancer-derived gene in the sample.

Specifically, the present invention further provides the method comprising: a first step of measuring in vitro an expression level of a target gene in multiple samples that were known to be able to determine or evaluate the presence and/or absence of the lung cancer-derived gene in the samples, using the polynucleotide, the kit, or the device (e.g., chip) for detection of the present invention, or a combination thereof; a second step of constructing a discriminant with the measurement values of the expression level of the target gene (target nucleic acids) that was obtained in the first step as supervising samples; a third step of measuring in vitro an expression level of the target gene in a sample derived from a subject in the same way as in the first step; and a fourth step of assigning the measurement value of the expression level of the target gene obtained in the third step into the discriminant obtained in the second step, and determining or evaluating the presence and/or absence of the lung cancer-derived gene in the sample on the basis of the results obtained from the discriminant, wherein the target gene can be detected using a polynucleotide for the detection, that was contained in the polynucleotide, the kit or the device (e.g., chip). In this context, the discriminant can be prepared by use of Fisher's discriminant analysis, non-linear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of synthetic variables and minimizing the variance of data having the same label (Venables, W. N. et al., Modern Applied Statistics with S. Fourth edition. Springer., 2002). In the Fisher's linear discriminant analysis, direction w of projection is determined so as to maximize Formula 2. In this Formula, μ represents an average input, ng represents the number of data associate with class g, and μg represents an average input of the data associated with class g. The numerator and the denominator are the inter-classe variance and the intra-classe variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i: y_i = g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i: u_i = g}^{n} \frac{x_i}{n_g}$$

The Mahalanobis' distance is calculated according to Formula 3 in consideration of data correlation and can be used as nonlinear discriminant analysis for determining an associated cluster that shows a closer Mahalanobis' distance from each cluster. In this Formula 3, μ represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1}(x - \mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the results of the discriminant analysis may be classes, may be a probability of data to be classified into correct classes, or may be the distance from the hyperplane. In SVM, a method of nonlinearly converting a feature vector to a high dimension and performing linear discriminant in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a lung cancer patient group and a healthy subject group. For example, lung tissue examination can be used for a reference under which each subject is confirmed either as a lung cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using genes that were found to differ clearly in their gene expression levels between the two groups as explanatory variables, and using this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \qquad \text{Formula 4}$$

subject to $y^T a = 0, 0 \le a_i \le C, i = 1, \dots, l,$

Formula 5 is a finally obtained discriminant, and an associated group can be determined on the basis of the sign of a value obtained according to the discriminant. In this Formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \qquad \text{Formula 5}$$

For example, a RBF kernel defined by Formula 6 can be used as the kernel function. In this Formula, x represents a support vector, and y represents a kernel parameter for adjusting the complexity of the hyperplane.

$$K(x_i, x_j) = \exp(-r\|x_i - x_j\|^2), r < 0 \qquad \text{Formula 6}$$

In addition, an approach such as neural network, k-nearest neighbor algorithms, decision trees, or logistic regression analysis can be selected as a method for determining or evaluating the presence and/or absence of expression of a lung cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring an expression level of a target gene in tissues containing lung cancer-derived genes derived from lung cancer patients and/or samples that are already known to contain no lung cancer-derived gene derived from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level of the target gene in a sample derived from a subject using the polynucleotide, the kit, or the device (e.g., DNA chip) for detection according to the present invention, assigning the obtained measurement value to the discriminants prepared in the step (b), and determining or evaluating the presence and/or absence of expression of the lung cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described in Section 2 above, or a fragment thereof, etc. Specifically, the explanatory variable for discriminating a lung cancer patient from a healthy subject according to the present invention is a gene expression level selected from, for example, the following expression levels (1) to (3):

(1) a gene expression level in the serum of a lung cancer patient or a healthy subject measured by any DNA comprising 15 or more consecutive nucleotides in a nucleotide sequence represented by any of SEQ ID NOs: 1 to 125, 127 to 130, 132 to 134 and 561 to 578 or a complementary sequence thereof, (2) a gene expression level in the serum of a lung cancer patient or a healthy subject measured by any DNA comprising 15 or more consecutive nucleotides in a nucleotide sequence represented by any of SEQ ID NOs: 126, 131 and 579 or a complementary sequence thereof, and (3) a gene expression level in the serum of a lung cancer patient or a healthy subject measured by any DNA comprising 15 or more consecutive nucleotides in a nucleotide sequence represented by any of SEQ ID NOs: 135 to 174 or a complementary sequence thereof.

As described above, for the method for determining or evaluating the presence and/or absence of a lung cancer-derived gene in a sample derived from a subject, the preparation of a discriminant requires a discriminant prepared in a training cohort. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a lung cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a lung cancer patient group and gene expression levels of a healthy subject group may be calculated to select a gene that is used for an explanatory variable in a discriminant. Alternatively, ROC curves may be prepared using gene expression levels of a lung cancer patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discriminant accuracy include a method of constructing a discriminant in every combination of genes that satisfy the significance level of P value, and a method of repetitively evaluating a discriminant while increasing the number of genes for use one by one in a descending order of difference in gene expression level (Furey T S. et al., 2000, Bioinformatics., Vol. 16, p. 906-14). A gene expression level of another independent lung cancer patient or healthy subject is assigned as an explanatory variable to this discriminant to calculate discriminant results of the group to which this independent lung cancer patient or healthy subject associates. Specifically, the found gene set for diagnosis and the discriminant constructed using the gene set for diagnosis can be evaluated in an independent sample group to find a more universal gene set for diagnosis capable of detecting lung cancer and a more universal method for discriminating lung cancer.

Split-sample method is preferably used for evaluating the discriminant performance (generality) of the discriminant. Specifically, a data set is divided into a training cohort and a validation cohort, and gene selection by a statistical test and discriminant preparation are performed in the training cohort. Accuracy, sensitivity, and specificity are calculated using results of discriminating a validation cohort according to the discriminant and a true group to which the validation cohort associates, to evaluate the discriminant performance. On the other hand, instead of dividing a data set, gene selection by a statistical test and discriminant preparation may be performed using all of samples, and accuracy, sensitivity, and specificity can be calculated by the discriminant of newly prepared samples according to the discriminant to evaluate the discriminant performance.

The present invention provides a polynucleotide for detection and for disease diagnosis useful in the diagnosis and treatment of lung cancer, a method for detecting lung cancer using the polynucleotide, and a kit and a device for the detection of lung cancer, comprising the polynucleotide. Particularly, in order to select a gene for diagnosis and prepare a discriminant so as to exhibit accuracy beyond a lung cancer diagnosis method using existing tumor markers CEA, a gene set for diagnosis and a discriminant for the method of the present invention, that exhibit accuracy beyond CEA, can be constructed, for example, by comparing genes expressed in serum derived from a patient confirmed to be negative using CEA but finally found to have lung cancer by detailed examination such as computed tomography using a contrast medium, with genes expressed in serum derived from a patient having no lung cancer.

For example, the gene set for diagnosis is set to any combination selected from one or two or more of the polynucleotides based on a nucleotide sequence represented by any of SEQ ID NOs: 1 to 125, 127 to 130, 132 to 134, and 561 to 578, or a complementary sequence thereof as described above, optionally one or two or more of the polynucleotides based on a nucleotide sequence represented by any of SEQ ID NOs: 126, 131 and 579, or a complementary sequence thereof, and optionally one or two or more of the polynucleotides based on a nucleotide sequence represented by any of SEQ ID NOs: 135 to 174, or a complementary sequence thereof. Further, a discriminant is constructed using expression levels of the gene set for diagnosis in samples derived from class I lung cancer patients and samples derived from class II healthy subjects as a result of tissue diagnosis. As a result, the presence or absence of lung cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Lung Cancer Patients and Healthy Subjects>

Serum was collected using VENOJECT II vacuum blood collecting tube VP-AS109K60 (Terumo Corp.) from each of 100 healthy subjects and 17 lung cancer patients (8 lung adenocarcinoma cases involving 6 cases with T2N0M0, 1 case with T2N1M0, and 1 case with T2N2M0; and 8 squamous cell cancer cases involving 5 cases with T2N0M0, 1 case with T4N0M0, 1 case with T2N1M0, and 1 case with T4N2M0) confirmed to have no primary cancer other than lung cancer after acquisition of informed consent, and used as a training cohort. Likewise, serum was collected using VENOJECT II vacuum blood collecting tube VP-AS109K60 (Terumo Corp.) from each of 50 healthy subjects and 8 lung cancer patients (5 adenocarcinoma cases involving 3 cases with T2N0M0, 1 case with T3N0M0, and 1 case with T4N2M0; and 3 squamous cell cancer cases involving 1 case with T2N0M0, 1 case with T4N0M0, and 1 case with T2N1M0) confirmed to have no primary cancer other than lung cancer after acquisition of informed consent, and used as a validation cohort. The histological types and stages of these lung cancer samples are summarized in Tables 2-1 and 2-2.

<Extraction of Total RNA>

Total RNA was obtained from 300 μL of the serum sample obtained from each of 175 persons in total of 150 healthy subjects and 25 lung cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum sample of each of 175 persons in total of 150 healthy subjects and 25 lung cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miRBase Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 25 lung cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancers Other than Lung Cancer>

Serum was collected using VENOJECT II vacuum blood collecting tube VP-AS 109K60 (Terumo Corp.) from each of 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients confirmed to have no cancer in other organs after acquisition of informed consent, and used as a training cohort together with the samples of 17 lung cancer patients and 99 healthy subjects of Reference Example 1. Likewise, serum was collected using VENOJECT II vacuum blood collecting tube VP-AS109K60 (Terumo Corp.) from each of 28 pancreatic cancer patients, 38 biliary tract cancer patients, 18 colorectal cancer patients, 15 stomach cancer patients, 18 esophageal cancer patients, 19 liver cancer patients, and 8 benign pancreaticobiliary disease patients confirmed to have no cancer in other organs after acquisition of informed consent, and used as a validation cohort together with the samples of 8 lung cancer patients confirmed to have no cancer in organs except for lung cancer and 51 healthy subjects of Reference Example 1. Subsequent operations were conducted in the same way as in Reference Example 1.

TABLE 2-1

Training cohort

|  | Sample name | Cancer stage |
|---|---|---|
| Lung adenocarcinoma | LC01 | T2N0M0 |
|  | LC02 | T2N0M0 |
|  | LC03 | T2N0M0 |
|  | LC05 | T2N0M0 |
|  | LC07 | T2N0M0 |
|  | LC08 | T2N2M0 |
|  | LC11 | T2N0M0 |
|  | LC12 | T2N1M0 |
|  | LC14 | T2N0M0 |
| Squamous cell cancer | LC15 | T2N0M0 |
|  | LC18 | T2N0M0 |
|  | LC20 | T2N0M0 |
|  | LC21 | T2N0M0 |
|  | LC22 | T4N2M0 |
|  | LC23 | T2N1M0 |
|  | LC24 | T2N0M0 |
|  | LC25 | T4N0M0 |

TABLE 2-2

Validation cohort

|  | Sample name | Cancer stage |
|---|---|---|
| Lung adenocarcinoma | LC04 | T2N0M0 |
|  | LC06 | T2N0M0 |
|  | LC09 | T3N0M0 |
|  | LC10 | T4N2M0 |
|  | LC13 | T2N0M0 |

TABLE 2-2-continued

| | Validation cohort | |
|---|---|---|
| | Sample name | Cancer stage |
| Squamous cell cancer | LC16 | T2N1M0 |
| | LC17 | T2N0M0 |
| | LC19 | T4N0M0 |

Example 1

<Selection of Gene Marker Using Samples in the Training Cohort, and Method for Evaluating Lung Cancer Discriminant Performance of Single Gene Marker Using Samples in the Validation Cohort>

In this Example, a gene marker for discriminating a lung cancer patient from a healthy subject was selected from the training cohort and studied in samples of the validation cohort independent of the training cohort, for a method for evaluating the lung cancer discriminant performance of each selected gene marker alone.

Specifically, first, the miRNA expression levels in the training cohort and the validation cohort obtained in the preceding Reference Examples were combined and normalized by quantile normalization.

Next, genes for diagnosis were selected in the training cohort. Here, in order to acquire diagnostic markers with higher reliability, only genes having a gene expression level of $2^6$ or higher in 50% or more of the samples in either of the lung cancer patient group in the training cohort or the healthy subject group in the training cohort were selected. In order to further acquire statistically significant genes for discriminating a lung cancer patient group from a healthy subject group, the P value obtained by two-sample t-test assuming equal variance as to each gene expression level was corrected by the Bonferroni method, and genes that satisfied p<0.01 were acquired as gene markers for use in explanatory variables of a discriminant. The result is described in Table 3.

In this way, hsa-miR-6768-5p, hsa-miR-6836-3p, hsa-miR-6782-5p, hsa-miR-3663-3p, hsa-miR-1908-3p, hsa-miR-6726-5p, hsa-miR-4258, hsa-miR-1343-3p, hsa-miR-4516, hsa-miR-6875-5p, hsa-miR-4651, hsa-miR-6825-5p, hsa-miR-6840-3p, hsa-miR-6780b-5p, hsa-miR-6749-5p, hsa-miR-8063, hsa-miR-6784-5p, hsa-miR-3679-5p, hsa-miR-3184-5p, hsa-miR-663b, hsa-miR-6880-5p, hsa-miR-1908-5p, hsa-miR-92a-2-5p, hsa-miR-7975, hsa-miR-7110-5p, hsa-miR-6842-5p, hsa-miR-6857-5p, hsa-miR-5572, hsa-miR-3197, hsa-miR-6131, hsa-miR-6889-5p, hsa-miR-4454, hsa-miR-1199-5p, hsa-miR-1247-3p, hsa-miR-6800-5p, hsa-miR-6872-3p, hsa-miR-4649-5p, hsa-miR-6791-5p, hsa-miR-4433b-3p, hsa-miR-3135b, hsa-miR-128-2-5p, hsa-miR-4675, hsa-miR-4472, hsa-miR-6785-5p, hsa-miR-6741-5p, hsa-miR-7977, hsa-miR-3665, hsa-miR-128-1-5p, hsa-miR-4286, hsa-miR-6765-3p, hsa-miR-4632-5p, hsa-miR-365a-5p, hsa-miR-6088, hsa-miR-6816-5p, hsa-miR-6885-5p, hsa-miR-711, hsa-miR-6765-5p, hsa-miR-3180, hsa-miR-4442, hsa-miR-4792, hsa-miR-6721-5p, hsa-miR-6798-5p, hsa-miR-3162-5p, hsa-miR-6126, hsa-miR-4758-5p, hsa-miR-2392, hsa-miR-486-3p, hsa-miR-6727-5p, hsa-miR-4728-5p, hsa-miR-6746-5p, hsa-miR-4270, hsa-miR-3940-5p, hsa-miR-4725-3p, hsa-miR-7108-5p, hsa-miR-3656, hsa-miR-6879-5p, hsa-miR-6738-5p, hsa-miR-1260a, hsa-miR-4446-3p, hsa-miR-3131, hsa-miR-4463, hsa-miR-3185, hsa-miR-6870-5p, hsa-miR-6779-5p, hsa-miR-1273g-3p, hsa-miR-8059, hsa-miR-4697-5p, hsa-miR-4674, hsa-miR-4433-3p, hsa-miR-4257, hsa-miR-1915-5p, hsa-miR-4417, hsa-miR-1343-5p, hsa-miR-6781-5p, hsa-miR-4695-5p, hsa-miR-1237-5p, hsa-miR-6775-5p, hsa-miR-7845-5p, hsa-miR-4746-3p, hsa-miR-7641, hsa-miR-7847-3p, hsa-miR-6806-5p, hsa-miR-4467, hsa-miR-4726-5p, hsa-miR-4648, hsa-miR-6089, hsa-miR-1260b, hsa-miR-4532, hsa-miR-5195-3p, hsa-miR-3188, hsa-miR-6848-5p, hsa-miR-1233-5p, hsa-miR-6717-5p, hsa-miR-3195, hsa-miR-6757-5p, hsa-miR-8072, hsa-miR-4745-5p, hsa-miR-6511a-5p, hsa-miR-6776-5p, hsa-miR-371a-5p, hsa-miR-1227-5p, hsa-miR-7150, hsa-miR-1915-3p, hsa-miR-187-5p, hsa-miR-614, hsa-miR-19b-3p, hsa-miR-1225-5p, hsa-miR-451a, hsa-miR-939-5p, hsa-miR-223-3p, hsa-miR-1228-5p, hsa-miR-125a-3p, hsa-miR-92b-5p, and hsa-miR-22-3p genes, and polynucleotides consisting of the nucleotide sequences of SEQ ID NOs: 1 to 134 related thereto were found.

Among them, genes newly found as markers for examining the presence or absence of lung cancer are polynucleotides consisting of the nucleotide sequences represented by SEQ ID NOs: 1 to 125, 127 to 130, and 132 to 134.

A discriminant for determining the presence or absence of lung cancer was further prepared by Fisher's discriminant analysis with the expression levels of these genes as an index. Specifically, any newly found polynucleotide consisting of a nucleotide sequence represented by any of SEQ ID NOs: 1 to 134 in the training cohort was apply for Formula 2 above to construct a discriminant. Calculated accuracy, sensitivity, and specificity are shown in Table 4. In this respect, a discriminant coefficient and a constant term are shown in Table 5.

Figure 2:
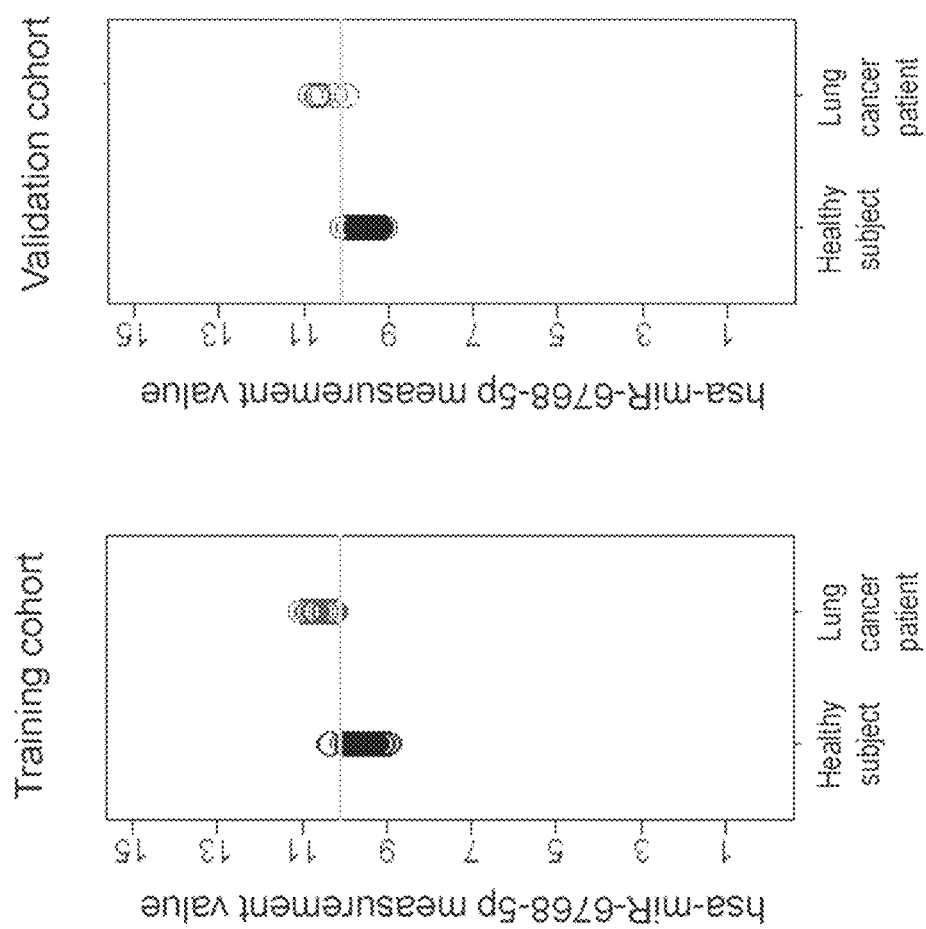
FIG. 2 Left diagram: the expression level measurement values of hsa-miR-6768-5p (SEQ ID NO: 1) in healthy subjects (100 persons) and lung cancer patients (17 persons) selected as a training cohort were each plotted on the ordinate. The horizontal line in the diagram depicts a threshold (10.08) that was optimized by Fisher's discriminant analysis and discriminated between the two groups. Right diagram: the expression level measurement values of hsa-miR-6768-5p (SEQ ID NO: 1) in healthy subjects (50 persons) and lung cancer patients (8 persons) selected as a validation cohort were each plotted on the ordinate. The horizontal line in the diagram depicts the threshold (10.08) that was set in the training cohort and discriminated between the two groups.

Accuracy, sensitivity, and specificity in the validation cohort were calculated using the discriminant thus prepared, and the discriminant performance of the selected polynucleotides was validated using independent samples (Table 4). For example, the expression level measurement value of the nucleotide sequence represented by SEQ ID NO: 1 was compared between the healthy subjects (100 persons) and the lung cancer patients (17 persons) in the training cohort. As a result, the gene expression level measurement values were found to be significantly lower in the lung cancer patient group than in the healthy subject group (see the left diagram of FIG. 2). These results were also reproducible for the healthy subjects (50 persons) and the lung cancer patients (8 persons) in the validation cohort (see the right diagram of FIG. 2). Likewise, the results obtained about the other polynucleotides shown in SEQ ID NOs: 2 to 134 showed that the gene expression level measurement values were significantly lower (−) or higher (+) in the lung cancer patient group than in the healthy subject group (Table 3). These results were able to be validated in the validation cohort. For example, as for this nucleotide sequence represented by SEQ ID NO: 1, the number of samples that were correctly identified in the detection of lung cancer was calculated using the threshold (10.08) that was set in the training cohort and discriminated between the two groups. As a result, 7 true positives, 50 true negatives, 0 false positives, and 1 false negative were obtained. From these values, 98.3% accuracy, 87.5% sensitivity, and 100% specificity were obtained as detection performance. In this way, the detection performance was calculated as to all of the polynucleotides shown in SEQ ID NOs: 1 to 134, and described in Table 4.

For example, 33 polynucleotides consisting of the nucleotide sequences represented by SEQ ID NOs: 1, 2, 3, 5, 7, 8, 9, 10, 11, 12, 13, 14, 15, 16, 17, 18, 19, 20, 22, 26, 27, 28, 29, 33, 34, 38, 41, 42, 44, 65, 124, 125, and 133 exhibited sensitivity of 87.5%, 100%, 100%, 75%, 75%, 75%, 87.5%, 87.5%, 87.5%, 87.5%, 87.5%, 87.5%, 87.5%, 87.5%, 87.5%, 100%, 75%, 87.5%, 87.5%, 87.5%, 87.5%, 87.5%, 87.5%, 87.5%, 75%, 87.5%, 75%, 75%, 75%, 75%, 75%, 75% and 75% respectively, in the validation cohort (Table 4). In this context, the tumor markers CEA and CYFRA21-1 in blood for lung cancer reportedly have general lung cancer detection sensitivity of 69% and 43%, respectively (Non Patent Literature 3). These results demonstrated that the 33 polynucleotides consisting of the nucleotide sequences represented by SEQ ID NOs: 1, 2, 3, 5, 7, 8, 9, 10, 11, 12, 13, 14, 15, 16, 17, 18, 19, 20, 22, 26, 27, 28, 29, 33, 34, 38, 41, 42, 44, 65, 124, 125, and 133 can discriminate, each alone, lung cancer in the validation cohort with sensitivity beyond the existing markers CEA and CYFRA21-1.

For example, 10 polynucleotides consisting of the nucleotide sequences represented by SEQ ID NOs: 2, 3, 11, 13, 20, 21, 22, 30, 31, and 37 were able to correctly determine lung cancer as to all of 4 samples from lung adenocarcinoma or squamous cell cancer having a tumor size of less than 7 cm and having no lymph node metastasis, contained in the validation cohort. Thus, these polynucleotides can detect even relatively early lung cancer and contributes to the early diagnosis of lung cancer.

TABLE 3

| SEQ ID NO: | Gene name | P value after Bonferroni correction | Expression level in lung cancer patient with respect to healthy subject |
|---|---|---|---|
| 1 | hsa-miR-6768-5p | 6.71E−24 | + |
| 2 | hsa-miR-6836-3p | 1.44E−20 | − |
| 3 | hsa-miR-6782-5p | 2.89E−20 | + |
| 4 | hsa-miR-3663-3p | 2.77E−18 | − |
| 5 | hsa-miR-1908-3p | 3.58E−18 | − |
| 6 | hsa-miR-6726-5p | 1.02E−17 | − |
| 7 | hsa-miR-4258 | 3.38E−17 | − |
| 8 | hsa-miR-1343-3p | 7.45E−17 | − |
| 9 | hsa-miR-4516 | 7.91E−17 | − |
| 10 | hsa-miR-6875-5p | 3.69E−16 | + |
| 11 | hsa-miR-4651 | 5.14E−16 | − |
| 12 | hsa-miR-6825-5p | 1.28E−14 | + |
| 13 | hsa-miR-6840-3p | 2.69E−14 | − |
| 14 | hsa-miR-6780b-5p | 3.47E−14 | + |
| 15 | hsa-miR-6749-5p | 3.82E−14 | − |
| 16 | hsa-miR-8063 | 3.58E−13 | − |
| 17 | hsa-miR-6784-5p | 7.06E−13 | + |
| 18 | hsa-miR-3679-5p | 7.64E−13 | + |
| 19 | hsa-miR-3184-5p | 1.78E−12 | + |
| 20 | hsa-miR-663b | 5.72E−12 | − |
| 21 | hsa-miR-6880-5p | 9.41E−12 | + |
| 22 | hsa-miR-1908-5p | 1.84E−11 | + |
| 23 | hsa-miR-92a-2-5p | 1.85E−11 | + |
| 24 | hsa-miR-7975 | 2.06E−11 | − |
| 25 | hsa-miR-7110-5p | 2.64E−11 | + |
| 26 | hsa-miR-6842-5p | 2.66E−11 | + |
| 27 | hsa-miR-6857-5p | 5.09E−11 | + |
| 28 | hsa-miR-5572 | 7.39E−11 | + |
| 29 | hsa-miR-3197 | 8.45E−11 | + |
| 30 | hsa-miR-6131 | 1.51E−10 | − |
| 31 | hsa-miR-6889-5p | 2.73E−10 | + |
| 32 | hsa-miR-4454 | 2.92E−10 | − |
| 33 | hsa-miR-1199-5p | 6.01E−10 | − |
| 34 | hsa-miR-1247-3p | 7.10E−10 | + |
| 35 | hsa-miR-6800-5p | 8.76E−10 | + |
| 36 | hsa-miR-6872-3p | 1.18E−09 | − |
| 37 | hsa-miR-4649-5p | 1.37E−09 | − |
| 38 | hsa-miR-6791-5p | 1.51E−09 | + |
| 39 | hsa-miR-4433b-3p | 1.57E−09 | + |
| 40 | hsa-miR-3135b | 1.78E−09 | − |
| 41 | hsa-miR-128-2-5p | 2.59E−09 | − |
| 42 | hsa-miR-4675 | 2.65E−09 | − |
| 43 | hsa-miR-4472 | 3.21E−09 | + |
| 44 | hsa-miR-6785-5p | 3.84E−09 | − |

TABLE 3-continued

| SEQ ID NO: | Gene name | P value after Bonferroni correction | Expression level in lung cancer patient with respect to healthy subject |
|---|---|---|---|
| 45 | hsa-miR-6741-5p | 6.85E−09 | − |
| 46 | hsa-miR-7977 | 8.90E−09 | − |
| 47 | hsa-miR-3665 | 2.49E−08 | − |
| 48 | hsa-miR-128-1-5p | 3.03E−08 | + |
| 49 | hsa-miR-4286 | 3.07E−08 | − |
| 50 | hsa-miR-6765-3p | 3.14E−08 | − |
| 51 | hsa-miR-4632-5p | 4.02E−08 | + |
| 52 | hsa-miR-365a-5p | 4.58E−08 | + |
| 53 | hsa-miR-6088 | 7.80E−08 | − |
| 54 | hsa-miR-6816-5p | 1.19E−07 | + |
| 55 | hsa-miR-6885-5p | 1.59E−07 | − |
| 56 | hsa-miR-711 | 1.93E−07 | + |
| 57 | hsa-miR-6765-5p | 2.99E−07 | + |
| 58 | hsa-miR-3180 | 3.65E−07 | + |
| 59 | hsa-miR-4442 | 3.89E−07 | − |
| 60 | hsa-miR-4792 | 3.97E−07 | + |
| 61 | hsa-miR-6721-5p | 6.66E−07 | + |
| 62 | hsa-miR-6798-5p | 8.81E−07 | + |
| 63 | hsa-miR-3162-5p | 1.07E−06 | + |
| 64 | hsa-miR-6126 | 1.26E−06 | + |
| 65 | hsa-miR-4758-5p | 1.35E−06 | − |
| 66 | hsa-miR-2392 | 1.58E−06 | + |
| 67 | hsa-miR-486-3p | 3.01E−06 | − |
| 68 | hsa-miR-6727-5p | 3.06E−06 | − |
| 69 | hsa-miR-4728-5p | 3.61E−06 | − |
| 70 | hsa-miR-6746-5p | 5.00E−06 | − |
| 71 | hsa-miR-4270 | 5.64E−06 | − |
| 72 | hsa-miR-3940-5p | 6.33E−06 | + |
| 73 | hsa-miR-4725-3p | 6.79E−06 | + |
| 74 | hsa-miR-7108-5p | 7.35E−06 | + |
| 75 | hsa-miR-3656 | 1.20E−05 | + |
| 76 | hsa-miR-6879-5p | 1.22E−05 | + |
| 77 | hsa-miR-6738-5p | 1.25E−05 | − |
| 78 | hsa-miR-1260a | 1.51E−05 | − |
| 79 | hsa-miR-4446-3p | 1.67E−05 | − |
| 80 | hsa-miR-3131 | 1.91E−05 | − |
| 81 | hsa-miR-4463 | 2.63E−05 | + |
| 82 | hsa-miR-3185 | 3.31E−05 | + |
| 83 | hsa-miR-6870-5p | 3.95E−05 | + |
| 84 | hsa-miR-6779-5p | 4.61E−05 | − |
| 85 | hsa-miR-1273g-3p | 4.73E−05 | − |
| 86 | hsa-miR-8059 | 5.08E−05 | − |
| 87 | hsa-miR-4697-5p | 5.16E−05 | − |
| 88 | hsa-miR-4674 | 7.31E−05 | − |
| 89 | hsa-miR-4433-3p | 8.12E−05 | + |
| 90 | hsa-miR-4257 | 9.79E−05 | − |
| 91 | hsa-miR-1915-5p | 1.18E−04 | − |
| 92 | hsa-miR-4417 | 1.36E−04 | + |
| 93 | hsa-miR-1343-5p | 1.45E−04 | − |
| 94 | hsa-miR-6781-5p | 1.54E−04 | + |
| 95 | hsa-miR-4695-5p | 1.57E−04 | + |
| 96 | hsa-miR-1237-5p | 1.80E−04 | + |
| 97 | hsa-miR-6775-5p | 2.34E−04 | − |
| 98 | hsa-miR-7845-5p | 2.40E−04 | + |
| 99 | hsa-miR-4746-3p | 2.62E−04 | + |
| 100 | hsa-miR-7641 | 4.57E−04 | − |
| 101 | hsa-miR-7847-3p | 5.01E−04 | − |
| 102 | hsa-miR-6806-5p | 5.86E−04 | − |
| 103 | hsa-miR-4467 | 6.28E−04 | + |
| 104 | hsa-miR-4726-5p | 6.35E−04 | − |
| 105 | hsa-miR-4648 | 6.87E−04 | + |
| 106 | hsa-miR-6089 | 8.08E−04 | + |
| 107 | hsa-miR-1260b | 8.29E−04 | − |
| 108 | hsa-miR-4532 | 8.69E−04 | − |
| 109 | hsa-miR-5195-3p | 1.02E−03 | − |
| 110 | hsa-miR-3188 | 1.12E−03 | + |
| 111 | hsa-miR-6848-5p | 1.36E−03 | + |
| 112 | hsa-miR-1233-5p | 1.41E−03 | − |
| 113 | hsa-miR-6717-5p | 1.63E−03 | + |
| 114 | hsa-miR-3195 | 1.95E−03 | + |
| 115 | hsa-miR-6757-5p | 2.65E−03 | − |
| 116 | hsa-miR-8072 | 3.49E−03 | + |
| 117 | hsa-miR-4745-5p | 4.17E−03 | − |
| 118 | hsa-miR-6511a-5p | 4.77E−03 | − |
| 119 | hsa-miR-6776-5p | 5.08E−03 | + |

TABLE 3-continued

| SEQ ID NO: | Gene name | P value after Bonferroni correction | Expression level in lung cancer patient with respect to healthy subject |
|---|---|---|---|
| 120 | hsa-miR-371a-5p | 6.92E−03 | − |
| 121 | hsa-miR-1227-5p | 7.47E−03 | + |
| 122 | hsa-miR-7150 | 8.50E−03 | + |
| 123 | hsa-miR-1915-3p | 9.50E−03 | + |
| 124 | hsa-miR-187-5p | 1.56E−18 | − |
| 125 | hsa-miR-614 | 2.22E−14 | − |
| 126 | hsa-miR-19b-3p | 1.77E−13 | + |
| 127 | hsa-miR-1225-5p | 2.30E−08 | + |
| 128 | hsa-miR-451a | 5.96E−08 | + |
| 129 | hsa-miR-939-5p | 1.29E−07 | + |
| 130 | hsa-miR-223-3p | 4.79E−06 | + |
| 131 | hsa-miR-1228-5p | 5.66E−06 | + |
| 132 | hsa-miR-125a-3p | 1.47E−04 | − |
| 133 | hsa-miR-92b-5p | 2.51E−04 | + |
| 134 | hsa-miR-22-3p | 6.49E−04 | + |

Example 2

<Method for Evaluating Lung Cancer Discriminant Performance by Combination of Multiple Gene Markers Using Samples in the Validation Cohort>

In this Example, a method for evaluating lung cancer discriminant performance by a combination of the gene markers selected in Example 1 was studied. Specifically, Fisher's discriminant analysis was conducted as to 8,910 combinations of two polynucleotides comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134 selected in Example 1, to construct a discriminant for determining the presence or absence of lung cancer. Next, accuracy, sensitivity, and specificity in the validation cohort were calculated using the discriminant thus prepared, and the discriminant performance of the selected polynucleotides was validated using the independent samples.

Figure 3:
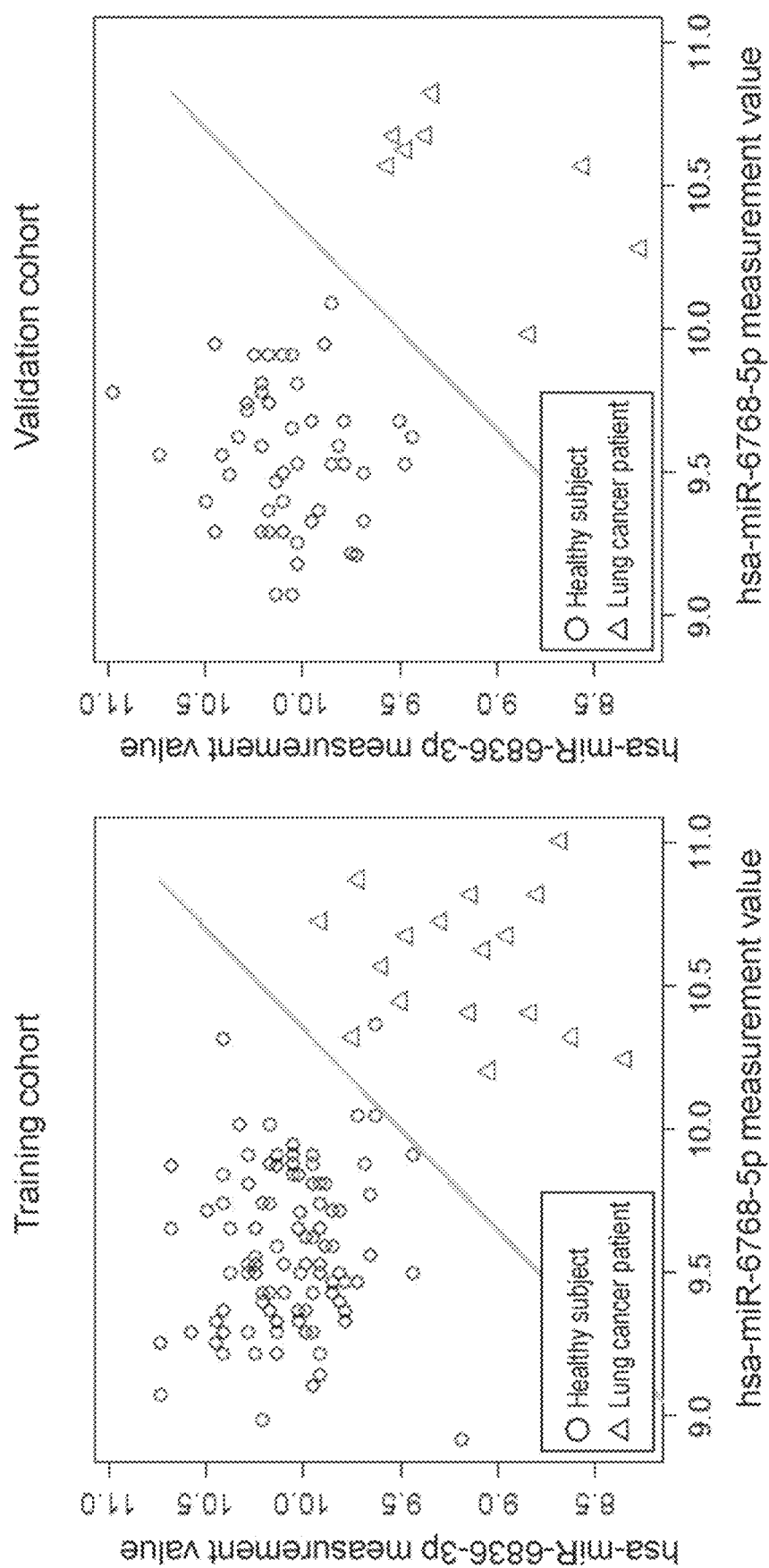
FIG. 3 Left diagram: the expression level measurement values of hsa-miR-6768-5p (SEQ ID NO: 1) in healthy subjects (100 persons, circles) and lung cancer patients (17 persons, triangles) selected as a training cohort were each plotted on the abscissa against their expression level measurement values of hsa-miR-6836-3p (SEQ ID NO: 2) on the ordinate. The line in the diagram depicts a discriminant function (0=−1.42x+y+4.7) that was optimized by Fisher's discriminant analysis and discriminated between the two groups. Right diagram: the expression level measurement values of hsa-miR-6768-5p (SEQ ID NO: 1) in healthy subjects (50 persons, circles) and lung cancer patients (8 persons, triangles) selected as a validation cohort were each plotted on the abscissa against their expression level measurement values of hsa-miR-6836-3p (SEQ ID NO: 2) on the ordinate. The line in the diagram depicts the threshold (0=−1.42x+y+4.7) that was set in the training cohort and discriminated between the two groups.

For example, the expression level measurement values of the nucleotide sequences represented by SEQ ID NO: 1 and SEQ ID NO: 2 were compared between the healthy subjects (100 persons) and the lung cancer patients (17 persons) in the training cohort. As a result, a scatter diagram that significantly separated the gene expression level measurement values of the lung cancer patient group from those of the healthy subject group was obtained (see the left diagram of FIG. 3). These results were also reproducible for the healthy subjects (50 persons) and the lung cancer patients (8 persons) in the validation cohort (see the right diagram of FIG. 3). Likewise, a scatter diagram that significantly separated the gene expression level measurement values of the lung cancer patient group from those of the healthy subject group was also obtained as to the other combinations of two expression level measurement values comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134. These results were able to be validated in the validation cohort. For example, as for these nucleotide sequences represented by SEQ ID NO: 1 and SEQ ID NO: 2, the number of samples that correctly identified in the detection of lung cancer was calculated using the function (0=−1.42x+y+4.7) that was set in the training cohort and discriminated between the two groups. As a result, 7 true positives, 50 true negatives, 0 false positives, and 1 false negative were obtained. From these values, 98.3% accuracy, 87.5% sensitivity, and 100% specificity were obtained as detection performance. In this way, the detection performance was calculated as to all of the combinations of two expression level measurement values comprising at least one or more of the expression level measurement values of any of the newly found polynucleotides consisting of the nucleotide sequences represented by SEQ ID NOs: 1 to 125, 127 to 130, and 132 to 134 among the polynucleotides consisting of the nucleotide sequences represented by SEQ ID NOs: 1 to 134. Among them, 133 combinations comprising the expression level measurement value of the polynucleotide consisting of the nucleotide sequence represented by SEQ ID NO: 1 and the detection performance thereof were described in Table 6 as an example. For example, all of 9 combinations of the expression level measurement values of the polynucleotides consisting of the nucleotide sequences represented by SEQ ID NOs: 1 and 6, SEQ ID NOs: 1 and 11, SEQ ID NOs: 1 and 19, SEQ ID NOs: 1 and 34, SEQ ID NOs: 1 and 38, SEQ ID NOs: 1 and 52, SEQ ID NOs: 1 and 53, SEQ ID NOs: 1 and 56, and SEQ ID NOs: 1 and 113 exhibited sensitivity of 100% in the validation cohort. Likewise, all of the 133 combinations of two polynucleotides consisting of the nucleotide sequence represented by SEQ ID NO: 1 and a nucleotide sequence represented by any of SEQ ID NOs: 2 to 134 exhibited sensitivity of 75% or higher. These values of sensitivity were higher than the sensitivity of the existing tumor markers CEA (69%) and CYFRA21-1 (43%) in blood (Non Patent Literature 3). Likewise, 5,742 combinations of the measurement values of the polynucleotides having sensitivity beyond the existing markers CEA and CYFRA21-1 were obtained in the validation cohort. All of the nucleotide sequences 1 to 134 described in Table 3 obtained in Example 1 were employed at least once in these combinations. Thus, the combinations of two of the polynucleotides that consist of the nucleotide sequences represented by SEQ ID NOs: 1 to 134 also produced excellent lung cancer detection sensitivity.

Markers for the detection of lung cancer with better sensitivity are obtained by further combining 3, 4, 5, 6, 7, 8, 9, 10 or more of the expression level measurement values of the polynucleotides consisting of the nucleotide sequences represented by SEQ ID NOs: 1 to 134. For example, the polynucleotides consisting of the nucleotide sequences represented by SEQ ID NOs: 1 to 134 selected in Example 1 were measured to obtain their expression levels between the healthy subject group and the lung cancer group in the validation cohort. All of the polynucleotides were ranked in the descending order of their P values based on the Student's t-test which indicates statistical significance of difference between groups (i.e., one having the lowest P value was ranked in the first place), and lung cancer detection sensitivity was evaluated using combinations of one or more polynucleotides to which the polynucleotides were added one by one from the top to the bottom according to the rank. In short, the order in which the polynucleotides were combined in this evaluation is in reverse in terms of SEQ ID NOs from SEQ ID NO: 134 to SEQ ID NOs: 133, 132, . . . shown in Table 3. As a result, the sensitivity in the validation cohort was 62.5% for 1 polynucleotide (SEQ ID NO: 134), 75% for 3 polynucleotides (SEQ ID NOs: 132 to 134), 87.5% for 5 polynucleotides (SEQ ID NOs: 130 to 134), 100% for 6 polynucleotides (SEQ ID NOs: 129 to 134), 100% for 10 polynucleotides (SEQ ID NOs: 125 to 134), 100% for 20 polynucleotides (SEQ ID NOs: 115 to 134), 100% for 30 polynucleotides (SEQ ID NOs: 105 to 134), 100% for 50 polynucleotides (SEQ ID NOs: 85 to 134), 100% for 80 polynucleotides (SEQ ID NOs: 55 to 134), 100% for 120 polynucleotides (SEQ ID NOs: 15 to 134), and 100% for 134 polynucleotides (SEQ ID NOs: 1 to 134).

These results demonstrated that a combination of multiple polynucleotides can produce higher lung cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of lung cancer.

From these results, it can be concluded that all of the polynucleotides consisting of the nucleotide sequences represented by SEQ ID NOs: 1 to 134 serve as excellent markers for the detection of lung cancer.

TABLE 4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 1 | 97.4 | 94.1 | 98 | 98.3 | 87.5 | 100 |
| 2 | 94.9 | 82.4 | 97 | 100 | 100 | 100 |
| 3 | 97.4 | 82.4 | 100 | 96.6 | 100 | 96 |
| 4 | 94 | 70.6 | 98 | 93.1 | 62.5 | 98 |
| 5 | 95.7 | 76.5 | 99 | 96.6 | 75 | 100 |
| 6 | 92.3 | 64.7 | 97 | 93.1 | 62.5 | 98 |
| 7 | 94.9 | 76.5 | 98 | 94.8 | 75 | 98 |
| 8 | 94.9 | 94.1 | 95 | 94.8 | 75 | 98 |
| 9 | 97.4 | 82.4 | 100 | 98.3 | 87.5 | 100 |
| 10 | 96.6 | 82.4 | 99 | 91.4 | 87.5 | 92 |
| 11 | 94.9 | 76.5 | 98 | 96.6 | 87.5 | 98 |
| 12 | 96.6 | 88.2 | 98 | 93.1 | 87.5 | 94 |
| 13 | 92.3 | 64.7 | 97 | 94.8 | 87.5 | 96 |
| 14 | 92.3 | 70.6 | 96 | 98.3 | 87.5 | 100 |
| 15 | 95.7 | 82.4 | 98 | 98.3 | 87.5 | 100 |
| 16 | 91.5 | 76.5 | 94 | 94.8 | 87.5 | 96 |
| 17 | 94 | 82.4 | 96 | 93.1 | 87.5 | 94 |
| 18 | 94.9 | 70.6 | 99 | 100 | 100 | 100 |
| 19 | 89.7 | 64.7 | 94 | 93.1 | 75 | 96 |
| 20 | 93.2 | 58.8 | 99 | 98.3 | 87.5 | 100 |
| 21 | 93.2 | 64.7 | 98 | 93.1 | 62.5 | 98 |
| 22 | 91.5 | 64.7 | 96 | 94.8 | 87.5 | 96 |
| 23 | 94 | 70.6 | 98 | 87.9 | 37.5 | 96 |
| 24 | 93.2 | 58.8 | 99 | 91.4 | 50 | 98 |
| 25 | 89.7 | 64.7 | 94 | 91.4 | 62.5 | 96 |
| 26 | 93.2 | 64.7 | 98 | 94.8 | 87.5 | 96 |
| 27 | 93.2 | 76.5 | 96 | 94.8 | 87.5 | 96 |
| 28 | 92.3 | 82.4 | 94 | 93.1 | 87.5 | 94 |
| 29 | 89.7 | 52.9 | 96 | 96.6 | 87.5 | 98 |
| 30 | 89.7 | 35.3 | 99 | 93.1 | 62.5 | 98 |
| 31 | 90.6 | 47.1 | 98 | 94.8 | 62.5 | 100 |
| 32 | 93.2 | 58.8 | 99 | 91.4 | 50 | 98 |
| 33 | 92.3 | 64.7 | 97 | 96.6 | 87.5 | 98 |
| 34 | 89.7 | 41.2 | 98 | 93.1 | 75 | 96 |
| 35 | 89.7 | 52.9 | 96 | 93.1 | 50 | 100 |
| 36 | 92.3 | 64.7 | 97 | 89.7 | 50 | 96 |
| 37 | 88.9 | 41.2 | 97 | 93.1 | 50 | 100 |
| 38 | 87.2 | 47.1 | 94 | 96.6 | 87.5 | 98 |
| 39 | 90.6 | 58.8 | 96 | 84.5 | 50 | 90 |
| 40 | 91.5 | 47.1 | 99 | 91.4 | 37.5 | 100 |
| 41 | 91.5 | 52.9 | 98 | 96.6 | 75 | 100 |
| 42 | 90.6 | 47.1 | 98 | 96.6 | 75 | 100 |
| 43 | 94 | 64.7 | 99 | 91.4 | 50 | 98 |
| 44 | 88 | 47.1 | 95 | 93.1 | 75 | 96 |
| 45 | 91.5 | 47.1 | 99 | 87.9 | 37.5 | 96 |
| 46 | 89.7 | 47.1 | 97 | 87.9 | 50 | 94 |
| 47 | 92.3 | 52.9 | 99 | 93.1 | 50 | 100 |
| 48 | 88 | 41.2 | 96 | 87.9 | 62.5 | 92 |

TABLE 4-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 49 | 87.2 | 41.2 | 95 | 89.7 | 62.5 | 94 |
| 50 | 88.9 | 47.1 | 96 | 87.9 | 37.5 | 96 |
| 51 | 92.3 | 47.1 | 100 | 94.8 | 62.5 | 100 |
| 52 | 91.5 | 47.1 | 99 | 94.8 | 62.5 | 100 |
| 53 | 91.5 | 47.1 | 99 | 91.4 | 62.5 | 96 |
| 54 | 86.3 | 41.2 | 94 | 94.8 | 62.5 | 100 |
| 55 | 90.6 | 41.2 | 99 | 94.8 | 62.5 | 100 |
| 56 | 90.6 | 58.8 | 96 | 94.8 | 62.5 | 100 |
| 57 | 91.5 | 52.9 | 98 | 93.1 | 62.5 | 98 |
| 58 | 88.9 | 35.3 | 98 | 93.1 | 62.5 | 98 |
| 59 | 86.3 | 41.2 | 94 | 87.9 | 50 | 94 |
| 60 | 89.7 | 47.1 | 97 | 89.7 | 37.5 | 98 |
| 61 | 90.6 | 52.9 | 97 | 86.2 | 37.5 | 94 |
| 62 | 87.2 | 29.4 | 97 | 87.9 | 62.5 | 92 |
| 63 | 88.9 | 41.2 | 97 | 82.8 | 0 | 96 |
| 64 | 89.7 | 35.3 | 99 | 93.1 | 50 | 100 |
| 65 | 89.7 | 41.2 | 98 | 94.8 | 75 | 98 |
| 66 | 89.7 | 29.4 | 100 | 91.4 | 37.5 | 100 |
| 67 | 90.6 | 41.2 | 99 | 94.8 | 62.5 | 100 |
| 68 | 88 | 47.1 | 95 | 87.9 | 25 | 98 |
| 69 | 88 | 35.3 | 97 | 91.4 | 50 | 98 |
| 70 | 87.2 | 41.2 | 95 | 86.2 | 25 | 96 |
| 71 | 88 | 35.3 | 97 | 84.5 | 25 | 94 |
| 72 | 88 | 23.5 | 99 | 89.7 | 37.5 | 98 |
| 73 | 88 | 35.3 | 97 | 86.2 | 12.5 | 98 |
| 74 | 89.7 | 35.3 | 99 | 87.9 | 37.5 | 96 |
| 75 | 88 | 41.2 | 96 | 93.1 | 62.5 | 98 |
| 76 | 89.7 | 35.3 | 99 | 94.8 | 62.5 | 100 |
| 77 | 88.9 | 35.3 | 98 | 87.9 | 37.5 | 96 |
| 78 | 88 | 35.3 | 97 | 87.9 | 50 | 94 |
| 79 | 88.9 | 29.4 | 99 | 93.1 | 50 | 100 |
| 80 | 88.9 | 29.4 | 99 | 87.9 | 25 | 98 |
| 81 | 88 | 23.5 | 99 | 87.9 | 12.5 | 100 |
| 82 | 83.8 | 11.8 | 96 | 87.9 | 37.5 | 96 |
| 83 | 88.9 | 23.5 | 100 | 87.9 | 12.5 | 100 |
| 84 | 87.2 | 23.5 | 98 | 87.9 | 12.5 | 100 |
| 85 | 89.7 | 47.1 | 97 | 94.8 | 62.5 | 100 |
| 86 | 87.2 | 29.4 | 97 | 86.2 | 12.5 | 98 |
| 87 | 88 | 23.5 | 99 | 86.2 | 37.5 | 94 |
| 88 | 85.5 | 29.4 | 95 | 91.4 | 37.5 | 100 |
| 89 | 87.2 | 29.4 | 97 | 86.2 | 25 | 96 |
| 90 | 88.9 | 35.3 | 98 | 87.9 | 50 | 94 |
| 91 | 89.7 | 41.2 | 98 | 91.4 | 62.5 | 96 |
| 92 | 86.3 | 23.5 | 97 | 84.5 | 12.5 | 96 |
| 93 | 89.7 | 41.2 | 98 | 94.8 | 62.5 | 100 |
| 94 | 87.2 | 17.6 | 99 | 81 | 0 | 94 |
| 95 | 89.7 | 41.2 | 98 | 94.8 | 62.5 | 100 |
| 96 | 87.2 | 29.4 | 97 | 89.7 | 37.5 | 98 |
| 97 | 86.3 | 17.6 | 98 | 81 | 0 | 94 |
| 98 | 89.7 | 35.3 | 99 | 87.9 | 37.5 | 96 |
| 99 | 87.2 | 17.6 | 99 | 94.8 | 62.5 | 100 |
| 100 | 84.5 | 18.8 | 95 | 86.2 | 25 | 96 |
| 101 | 83.8 | 11.8 | 96 | 84.5 | 0 | 98 |
| 102 | 86.3 | 5.9 | 100 | 91.4 | 37.5 | 100 |
| 103 | 83.8 | 11.8 | 96 | 86.2 | 12.5 | 98 |
| 104 | 84.6 | 17.6 | 96 | 86.2 | 25 | 96 |
| 105 | 85.5 | 11.8 | 98 | 89.7 | 25 | 100 |
| 106 | 89.7 | 41.2 | 98 | 89.7 | 37.5 | 98 |
| 107 | 87.2 | 23.5 | 98 | 91.4 | 50 | 98 |
| 108 | 88 | 23.5 | 99 | 91.4 | 37.5 | 100 |
| 109 | 87.2 | 17.6 | 99 | 87.9 | 25 | 98 |
| 110 | 86.3 | 23.5 | 97 | 89.7 | 25 | 100 |
| 111 | 85.5 | 11.8 | 98 | 86.2 | 25 | 96 |
| 112 | 86.3 | 17.6 | 98 | 86.2 | 0 | 100 |
| 113 | 84.6 | 23.5 | 95 | 89.7 | 25 | 100 |
| 114 | 86.3 | 23.5 | 97 | 84.5 | 25 | 94 |
| 115 | 82.9 | 0 | 97 | 89.7 | 25 | 100 |
| 116 | 88 | 23.5 | 99 | 89.7 | 25 | 100 |
| 117 | 88 | 17.6 | 100 | 89.7 | 25 | 100 |
| 118 | 84.6 | 11.8 | 97 | 86.2 | 0 | 100 |
| 119 | 85.5 | 5.9 | 99 | 89.7 | 25 | 100 |
| 120 | 84.6 | 0 | 99 | 84.5 | 0 | 98 |
| 121 | 88.9 | 23.5 | 100 | 87.9 | 12.5 | 100 |
| 122 | 88 | 17.6 | 100 | 89.7 | 25 | 100 |

TABLE 4-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 123 | 84.6 | 5.9 | 98 | 94.8 | 62.5 | 100 |
| 124 | 99.1 | 94.1 | 100 | 96.6 | 75 | 100 |
| 125 | 94 | 76.5 | 97 | 93.1 | 75 | 96 |
| 126 | 95.7 | 82.4 | 98 | 93.1 | 62.5 | 98 |
| 127 | 89.7 | 52.9 | 96 | 93.1 | 50 | 100 |
| 128 | 93.2 | 58.8 | 99 | 89.7 | 37.5 | 98 |
| 129 | 91.5 | 58.8 | 97 | 86.2 | 50 | 92 |
| 130 | 94 | 58.8 | 100 | 94.8 | 62.5 | 100 |
| 131 | 84.6 | 17.6 | 96 | 87.9 | 25 | 98 |
| 132 | 89.7 | 35.3 | 99 | 89.7 | 25 | 100 |
| 133 | 89.7 | 35.3 | 99 | 96.6 | 75 | 100 |
| 134 | 87.2 | 23.5 | 98 | 86.2 | 12.5 | 98 |

TABLE 5

| SEQ ID NO: | Discriminant coefficient | Constant term |
|---|---|---|
| 1 | 3.665 | 36.958 |
| 2 | 3.482 | 28.279 |
| 3 | 3.305 | 21.564 |
| 4 | 3.967 | 46.907 |
| 5 | 2.921 | 18.418 |
| 6 | 3.258 | 31.351 |
| 7 | 2.321 | 19.901 |
| 8 | 2.482 | 17.979 |
| 9 | 5.340 | 69.250 |
| 10 | 3.780 | 34.781 |
| 11 | 6.053 | 65.389 |
| 12 | 2.169 | 14.787 |
| 13 | 3.363 | 28.960 |
| 14 | 3.278 | 29.867 |
| 15 | 4.768 | 47.106 |
| 16 | 2.668 | 21.511 |
| 17 | 3.933 | 49.822 |
| 18 | 2.781 | 19.688 |
| 19 | 2.340 | 19.400 |
| 20 | 3.173 | 27.138 |
| 21 | 2.395 | 19.027 |
| 22 | 4.481 | 51.987 |
| 23 | 1.923 | 18.732 |
| 24 | 2.221 | 21.483 |
| 25 | 1.879 | 15.097 |
| 26 | 3.449 | 21.201 |
| 27 | 1.940 | 10.546 |
| 28 | 2.467 | 16.896 |
| 29 | 3.381 | 32.369 |
| 30 | 1.883 | 19.278 |
| 31 | 2.995 | 22.556 |
| 32 | 2.257 | 25.609 |
| 33 | 2.593 | 16.685 |
| 34 | 4.054 | 25.898 |
| 35 | 4.316 | 37.567 |
| 36 | 2.347 | 13.660 |
| 37 | 2.787 | 28.233 |
| 38 | 4.929 | 45.747 |
| 39 | 3.956 | 32.281 |
| 40 | 2.822 | 21.631 |
| 41 | 2.892 | 30.757 |
| 42 | 3.016 | 22.359 |
| 43 | 2.179 | 11.954 |
| 44 | 2.956 | 26.296 |
| 45 | 4.228 | 28.830 |
| 46 | 2.347 | 22.562 |
| 47 | 7.619 | 102.957 |
| 48 | 2.849 | 21.598 |
| 49 | 2.506 | 18.167 |
| 50 | 1.885 | 16.130 |
| 51 | 4.534 | 36.471 |
| 52 | 3.307 | 19.440 |
| 53 | 3.370 | 33.776 |

TABLE 5-continued

| SEQ ID NO: | Discriminant coefficient | Constant term |
|---|---|---|
| 54 | 4.473 | 45.416 |
| 55 | 3.058 | 33.429 |
| 56 | 4.044 | 33.691 |
| 57 | 4.924 | 52.340 |
| 58 | 4.740 | 41.821 |
| 59 | 3.556 | 33.458 |
| 60 | 2.051 | 13.913 |
| 61 | 4.118 | 31.479 |
| 62 | 2.848 | 30.006 |
| 63 | 2.967 | 23.118 |
| 64 | 3.094 | 33.898 |
| 65 | 6.747 | 57.639 |
| 66 | 3.115 | 18.546 |
| 67 | 2.952 | 23.150 |
| 68 | 6.267 | 79.386 |
| 69 | 5.244 | 36.656 |
| 70 | 3.634 | 23.502 |
| 71 | 5.682 | 45.289 |
| 72 | 4.756 | 58.458 |
| 73 | 3.941 | 38.866 |
| 74 | 4.639 | 42.673 |
| 75 | 4.686 | 54.180 |
| 76 | 3.379 | 28.223 |
| 77 | 3.897 | 27.668 |
| 78 | 2.497 | 17.033 |
| 79 | 2.622 | 18.728 |
| 80 | 2.639 | 18.344 |
| 81 | 4.764 | 52.837 |
| 82 | 2.582 | 18.301 |
| 83 | 3.517 | 26.318 |
| 84 | 6.525 | 46.333 |
| 85 | 2.880 | 21.133 |
| 86 | 3.254 | 24.541 |
| 87 | 4.996 | 39.036 |
| 88 | 3.508 | 36.118 |
| 89 | 3.944 | 29.161 |
| 90 | 3.193 | 21.619 |
| 91 | 1.406 | 8.631 |
| 92 | 5.754 | 47.280 |
| 93 | 3.850 | 40.213 |
| 94 | 5.850 | 61.192 |
| 95 | 4.464 | 33.686 |
| 96 | 4.601 | 58.630 |
| 97 | 6.817 | 56.624 |
| 98 | 3.273 | 21.990 |
| 99 | 2.934 | 19.283 |
| 100 | 1.405 | 10.220 |
| 101 | 3.974 | 25.352 |
| 102 | 3.294 | 21.365 |
| 103 | 2.273 | 22.405 |
| 104 | 4.014 | 26.327 |
| 105 | 1.371 | 8.370 |
| 106 | 5.947 | 79.958 |
| 107 | 2.441 | 20.646 |
| 108 | 3.287 | 38.733 |
| 109 | 3.026 | 20.705 |
| 110 | 3.417 | 20.796 |
| 111 | 5.205 | 38.779 |
| 112 | 2.897 | 32.216 |
| 113 | 2.584 | 17.226 |
| 114 | 3.934 | 32.685 |
| 115 | 3.076 | 22.309 |
| 116 | 5.228 | 64.304 |
| 117 | 2.180 | 25.963 |
| 118 | 2.566 | 14.847 |
| 119 | 3.282 | 19.125 |
| 120 | 3.663 | 26.980 |
| 121 | 6.563 | 62.775 |
| 122 | 4.018 | 31.312 |
| 123 | 4.220 | 46.687 |
| 124 | 2.174 | 20.711 |
| 125 | 1.889 | 11.995 |
| 126 | 1.102 | 5.734 |
| 127 | 3.626 | 27.002 |
| 128 | 0.979 | 9.798 |
| 129 | 2.534 | 19.444 |
| 130 | 1.051 | 6.668 |

TABLE 5-continued

| SEQ ID NO: | Discriminant coefficient | Constant term |
|---|---|---|
| 131 | 3.974 | 47.286 |
| 132 | 1.456 | 9.155 |
| 133 | 3.272 | 26.342 |
| 134 | 1.514 | 8.925 |

TABLE 6

| SEQ ID NO: | Training set | | | Validation set | | |
|---|---|---|---|---|---|---|
| | Accuracy (%) | Sensitivity (%) | Specificity (%) | Accuracy (%) | Sensitivity (%) | Specificity (%) |
| 1_2 | 98.3 | 94.1 | 99 | 98.3 | 87.5 | 100 |
| 1_3 | 100 | 100 | 100 | 98.3 | 87.5 | 100 |
| 1_4 | 97.4 | 88.2 | 99 | 98.3 | 87.5 | 100 |
| 1_5 | 99.1 | 100 | 99 | 98.3 | 87.5 | 100 |
| 1_6 | 99.1 | 100 | 99 | 100 | 100 | 100 |
| 1_7 | 99.1 | 100 | 99 | 98.3 | 87.5 | 100 |
| 1_8 | 98.3 | 94.1 | 99 | 98.3 | 87.5 | 100 |
| 1_9 | 99.1 | 100 | 99 | 98.3 | 87.5 | 100 |
| 1_10 | 100 | 100 | 100 | 98.3 | 87.5 | 100 |
| 1_11 | 98.3 | 100 | 98 | 100 | 100 | 100 |
| 1_12 | 98.3 | 100 | 98 | 98.3 | 87.5 | 100 |
| 1_13 | 98.3 | 100 | 98 | 98.3 | 87.5 | 100 |
| 1_14 | 100 | 100 | 100 | 98.3 | 87.5 | 100 |
| 1_15 | 98.3 | 100 | 98 | 98.3 | 87.5 | 100 |
| 1_16 | 99.1 | 100 | 99 | 98.3 | 87.5 | 100 |
| 1_17 | 98.3 | 100 | 98 | 98.3 | 87.5 | 100 |
| 1_18 | 99.1 | 100 | 99 | 98.3 | 87.5 | 100 |
| 1_19 | 99.1 | 100 | 99 | 100 | 100 | 100 |
| 1_20 | 98.3 | 94.1 | 99 | 98.3 | 87.5 | 100 |
| 1_21 | 98.3 | 94.1 | 99 | 96.6 | 87.5 | 98 |
| 1_22 | 98.3 | 100 | 98 | 98.3 | 87.5 | 100 |
| 1_23 | 97.4 | 94.1 | 98 | 98.3 | 87.5 | 100 |
| 1_24 | 97.4 | 94.1 | 98 | 98.3 | 87.5 | 100 |
| 1_25 | 98.3 | 100 | 98 | 98.3 | 87.5 | 100 |
| 1_26 | 99.1 | 100 | 99 | 96.6 | 87.5 | 98 |
| 1_27 | 98.3 | 100 | 98 | 98.3 | 87.5 | 100 |
| 1_28 | 98.3 | 100 | 98 | 98.3 | 87.5 | 100 |
| 1_29 | 98.3 | 94.1 | 99 | 98.3 | 87.5 | 100 |
| 1_30 | 97.4 | 94.1 | 98 | 98.3 | 87.5 | 100 |
| 1_31 | 98.3 | 100 | 98 | 98.3 | 87.5 | 100 |
| 1_32 | 97.4 | 94.1 | 98 | 96.6 | 75 | 100 |
| 1_33 | 98.3 | 94.1 | 99 | 98.3 | 87.5 | 100 |
| 1_34 | 99.1 | 100 | 99 | 100 | 100 | 100 |
| 1_35 | 98.3 | 100 | 98 | 98.3 | 87.5 | 100 |
| 1_36 | 97.4 | 94.1 | 98 | 96.6 | 75 | 100 |
| 1_37 | 98.3 | 100 | 98 | 98.3 | 87.5 | 100 |
| 1_38 | 98.3 | 100 | 98 | 100 | 100 | 100 |
| 1_39 | 97.4 | 94.1 | 98 | 98.3 | 87.5 | 100 |
| 1_40 | 98.3 | 100 | 98 | 96.6 | 75 | 100 |
| 1_41 | 98.3 | 100 | 98 | 98.3 | 87.5 | 100 |
| 1_42 | 98.3 | 100 | 98 | 98.3 | 87.5 | 100 |
| 1_43 | 97.4 | 94.1 | 98 | 98.3 | 87.5 | 100 |
| 1_44 | 97.4 | 94.1 | 98 | 98.3 | 87.5 | 100 |
| 1_45 | 97.4 | 94.1 | 98 | 98.3 | 87.5 | 100 |
| 1_46 | 96.6 | 88.2 | 98 | 96.6 | 75 | 100 |
| 1_47 | 98.3 | 100 | 98 | 98.3 | 87.5 | 100 |
| 1_48 | 99.1 | 100 | 99 | 98.3 | 87.5 | 100 |
| 1_49 | 97.4 | 94.1 | 98 | 96.6 | 75 | 100 |
| 1_50 | 97.4 | 94.1 | 98 | 96.6 | 75 | 100 |
| 1_51 | 99.1 | 100 | 99 | 98.3 | 87.5 | 100 |
| 1_52 | 99.1 | 100 | 99 | 100 | 100 | 100 |
| 1_53 | 99.1 | 100 | 99 | 100 | 100 | 100 |
| 1_54 | 98.3 | 100 | 98 | 98.3 | 87.5 | 100 |
| 1_55 | 98.3 | 100 | 98 | 98.3 | 87.5 | 100 |
| 1_56 | 100 | 100 | 100 | 100 | 100 | 100 |
| 1_57 | 98.3 | 100 | 98 | 98.3 | 87.5 | 100 |
| 1_58 | 98.3 | 100 | 98 | 98.3 | 87.5 | 100 |
| 1_59 | 98.3 | 100 | 98 | 98.3 | 87.5 | 100 |
| 1_60 | 97.4 | 94.1 | 98 | 98.3 | 87.5 | 100 |
| 1_61 | 98.3 | 100 | 98 | 98.3 | 87.5 | 100 |
| 1_62 | 97.4 | 94.1 | 98 | 98.3 | 87.5 | 100 |
| 1_63 | 98.3 | 100 | 98 | 98.3 | 87.5 | 100 |
| 1_64 | 98.3 | 100 | 98 | 98.3 | 87.5 | 100 |
| 1_65 | 97.4 | 94.1 | 98 | 98.3 | 87.5 | 100 |
| 1_66 | 98.3 | 100 | 98 | 98.3 | 87.5 | 100 |
| 1_67 | 98.3 | 100 | 98 | 98.3 | 87.5 | 100 |
| 1_68 | 98.3 | 100 | 98 | 98.3 | 87.5 | 100 |
| 1_69 | 97.4 | 94.1 | 98 | 98.3 | 87.5 | 100 |
| 1_70 | 97.4 | 94.1 | 98 | 98.3 | 87.5 | 100 |
| 1_71 | 97.4 | 94.1 | 98 | 98.3 | 87.5 | 100 |
| 1_72 | 97.4 | 94.1 | 98 | 98.3 | 87.5 | 100 |
| 1_73 | 98.3 | 94.1 | 99 | 98.3 | 87.5 | 100 |
| 1_74 | 98.3 | 100 | 98 | 98.3 | 87.5 | 100 |
| 1_75 | 97.4 | 100 | 97 | 98.3 | 87.5 | 100 |
| 1_76 | 99.1 | 94.1 | 100 | 98.3 | 87.5 | 100 |
| 1_77 | 97.4 | 94.1 | 98 | 98.3 | 87.5 | 100 |
| 1_78 | 97.4 | 94.1 | 98 | 98.3 | 87.5 | 100 |
| 1_79 | 97.4 | 94.1 | 98 | 98.3 | 87.5 | 100 |
| 1_80 | 98.3 | 94.1 | 99 | 98.3 | 87.5 | 100 |
| 1_81 | 97.4 | 94.1 | 98 | 98.3 | 87.5 | 100 |
| 1_82 | 99.1 | 100 | 99 | 98.3 | 87.5 | 100 |
| 1_83 | 98.3 | 100 | 98 | 98.3 | 87.5 | 100 |
| 1_84 | 98.3 | 100 | 98 | 98.3 | 87.5 | 100 |
| 1_85 | 97.4 | 88.2 | 99 | 98.3 | 87.5 | 100 |
| 1_86 | 97.4 | 94.1 | 98 | 98.3 | 87.5 | 100 |
| 1_87 | 98.3 | 100 | 98 | 98.3 | 87.5 | 100 |
| 1_88 | 98.3 | 100 | 98 | 98.3 | 87.5 | 100 |
| 1_89 | 97.4 | 94.1 | 98 | 98.3 | 87.5 | 100 |
| 1_90 | 97.4 | 94.1 | 98 | 98.3 | 87.5 | 100 |
| 1_91 | 98.3 | 94.1 | 99 | 98.3 | 87.5 | 100 |
| 1_92 | 97.4 | 94.1 | 98 | 98.3 | 87.5 | 100 |
| 1_93 | 98.3 | 100 | 98 | 98.3 | 87.5 | 100 |
| 1_94 | 98.3 | 100 | 98 | 98.3 | 87.5 | 100 |
| 1_95 | 98.3 | 94.1 | 99 | 98.3 | 87.5 | 100 |
| 1_96 | 98.3 | 100 | 98 | 98.3 | 87.5 | 100 |
| 1_97 | 97.4 | 94.1 | 98 | 98.3 | 87.5 | 100 |
| 1_98 | 98.3 | 94.1 | 99 | 98.3 | 87.5 | 100 |
| 1_99 | 98.3 | 100 | 98 | 98.3 | 87.5 | 100 |
| 1_100 | 99.1 | 100 | 99 | 98.3 | 87.5 | 100 |
| 1_101 | 97.4 | 94.1 | 98 | 98.3 | 87.5 | 100 |
| 1_102 | 97.4 | 94.1 | 98 | 98.3 | 87.5 | 100 |
| 1_103 | 99.1 | 100 | 99 | 98.3 | 87.5 | 100 |
| 1_104 | 97.4 | 94.1 | 98 | 98.3 | 87.5 | 100 |
| 1_105 | 97.4 | 94.1 | 98 | 98.3 | 87.5 | 100 |
| 1_106 | 98.3 | 94.1 | 99 | 98.3 | 87.5 | 100 |
| 1_107 | 96.6 | 88.2 | 98 | 96.6 | 75 | 100 |
| 1_108 | 98.3 | 100 | 98 | 98.3 | 87.5 | 100 |
| 1_109 | 99.1 | 100 | 99 | 98.3 | 87.5 | 100 |
| 1_110 | 97.4 | 94.1 | 98 | 98.3 | 87.5 | 100 |
| 1_111 | 97.4 | 94.1 | 98 | 98.3 | 87.5 | 100 |
| 1_112 | 97.4 | 94.1 | 98 | 98.3 | 87.5 | 100 |
| 1_113 | 99.1 | 100 | 99 | 100 | 100 | 100 |
| 1_114 | 98.3 | 100 | 98 | 98.3 | 87.5 | 100 |
| 1_115 | 97.4 | 94.1 | 98 | 98.3 | 87.5 | 100 |
| 1_116 | 98.3 | 100 | 98 | 98.3 | 87.5 | 100 |
| 1_117 | 97.4 | 94.1 | 98 | 98.3 | 87.5 | 100 |
| 1_118 | 97.4 | 94.1 | 98 | 98.3 | 87.5 | 100 |
| 1_119 | 97.4 | 94.1 | 98 | 98.3 | 87.5 | 100 |
| 1_120 | 98.3 | 100 | 98 | 98.3 | 87.5 | 100 |
| 1_121 | 98.3 | 94.1 | 99 | 98.3 | 87.5 | 100 |
| 1_122 | 98.3 | 100 | 98 | 98.3 | 87.5 | 100 |
| 1_123 | 98.3 | 100 | 98 | 98.3 | 87.5 | 100 |
| 1_124 | 98.3 | 100 | 98 | 98.3 | 87.5 | 100 |
| 1_125 | 97.4 | 94.1 | 98 | 98.3 | 87.5 | 100 |
| 1_126 | 99.1 | 100 | 99 | 98.3 | 87.5 | 100 |
| 1_127 | 98.3 | 100 | 98 | 98.3 | 87.5 | 100 |
| 1_128 | 98.3 | 100 | 98 | 98.3 | 87.5 | 100 |
| 1_129 | 98.3 | 100 | 98 | 98.3 | 87.5 | 100 |
| 1_130 | 98.3 | 100 | 98 | 98.3 | 87.5 | 100 |
| 1_131 | 97.4 | 94.1 | 98 | 98.3 | 87.5 | 100 |
| 1_132 | 98.3 | 88.2 | 100 | 98.3 | 87.5 | 100 |
| 1_133 | 97.4 | 94.1 | 98 | 98.3 | 87.5 | 100 |
| 1_134 | 98.3 | 100 | 98 | 98.3 | 87.5 | 100 |

Example 3

<Selection of Gene Marker Using all Samples and Method for Evaluating Lung Cancer Discriminant Performance of Acquired Gene Marker>

In this Example, the samples in the training cohort and the validation cohort used in Examples 1 and 2 were integrated, and selection of a gene marker and evaluation of its lung cancer discriminant performance were conducted using all of the samples.

Specifically, the miRNA expression levels in the serum of the 25 lung cancer patients and the 150 healthy subjects obtained in the preceding Reference Examples were normalized by quantile normalization. In order to acquire diagnostic markers with higher reliability, only genes having a gene expression level of $2^6$ or higher in 50% or more of the samples in either of the lung cancer patient group or the healthy subject group were selected in the gene marker selection. In order to further acquire statistical significance for discriminating a lung cancer patient group from a healthy subject group, the P value obtained by two-sample t-test assuming equal variance as to each gene expression level was corrected by the Bonferroni method, and genes that satisfied p<0.01 were selected as gene markers for use in explanatory variables of a discriminant. The acquired genes are described in Table 7. In this way, hsa-miR-4271, hsa-miR-642b-3p, hsa-miR-6075, hsa-miR-6125, hsa-miR-887-3p, hsa-miR-6851-5p, hsa-miR-6763-5p, hsa-miR-3928-3p, hsa-miR-4443, hsa-miR-3648, hsa-miR-149-3p, hsa-miR-4689, hsa-miR-4763-3p, hsa-miR-6729-5p, hsa-miR-3196, hsa-miR-8069, hsa-miR-1268a, hsa-miR-4739, hsa-miR-1268b, hsa-miR-5698, hsa-miR-6752-5p, hsa-miR-4507, hsa-miR-564, hsa-miR-4497, hsa-miR-6877-5p, hsa-miR-6087, hsa-miR-4731-5p, hsa-miR-615-5p, hsa-miR-760, hsa-miR-6891-5p, hsa-miR-6887-5p, hsa-miR-4525, hsa-miR-1914-3p, hsa-miR-619-5p, hsa-miR-5001-5p, hsa-miR-6722-3p, hsa-miR-3621, hsa-miR-4298, hsa-miR-675-5p, and hsa-miR-4655-5p genes, and the nucleotide sequences of SEQ ID NOs: 135 to 174 related thereto were found in addition to the genes described in Table 3. As with the nucleotide sequences of SEQ ID NOs: 1 to 134, the results obtained about the polynucleotides shown in SEQ ID NOs: 135 to 174 also showed that the measurement values were significantly lower (−) or higher (+) in the lung cancer patient group than in the healthy subject group (Table 7). These results were able to be validated in the validation cohort. Thus, the presence or absence of lung cancer in the newly obtained samples can be determined by the methods described in Examples 1 and 2 by using the gene expression level measurement values described in Table 7 either alone or in combination with the gene expression level measurement values described in Table 3.

TABLE 7

| SEQ ID NO: | Gene name | P value after Bonferroni correction | Expression level in lung cancer patient with respect to healthy subject |
|---|---|---|---|
| 1 | hsa-miR-6768-5p | 6.12E−37 | + |
| 2 | hsa-miR-6836-3p | 4.68E−36 | − |
| 3 | hsa-miR-6782-5p | 7.67E−29 | − |
| 4 | hsa-miR-3663-3p | 4.91E−29 | − |
| 5 | hsa-miR-1908-3p | 2.76E−30 | − |
| 6 | hsa-miR-6726-5p | 1.23E−26 | + |
| 7 | hsa-miR-4258 | 6.12E−28 | − |
| 8 | hsa-miR-1343-3p | 7.70E−26 | − |
| 9 | hsa-miR-4516 | 1.71E−29 | − |
| 10 | hsa-miR-6875-5p | 1.59E−18 | − |
| 11 | hsa-miR-4651 | 6.58E−26 | + |
| 12 | hsa-miR-6825-5p | 230E−22 | − |
| 13 | hsa-miR-6840-3p | 4.47E−24 | + |
| 14 | hsa-miR-6780b-5p | 7.12E−26 | − |
| 15 | hsa-miR-6749-5p | 3.83E−25 | − |
| 16 | hsa-miR-8063 | 7.83E−21 | − |
| 17 | hsa-miR-6784-5p | 1.37E−17 | + |
| 18 | hsa-miR-3679-5p | 2.70E−25 | − |
| 19 | hsa-miR-3184-5p | 5.58E−19 | + |
| 20 | hsa-miR-663b | 2.07E−22 | − |
| 21 | hsa-miR-6880-5p | 4.49E−19 | + |
| 22 | hsa-miR-1908-5p | 7.91E−21 | + |
| 23 | hsa-miR-92a-2-5p | 6.69E−15 | + |
| 24 | hsa-miR-7975 | 3.32E−17 | + |
| 25 | hsa-miR-7110-5p | 2.07E−16 | + |
| 26 | hsa-miR-6842-5p | 3.25E−19 | − |
| 27 | hsa-miR-6857-5p | 7.70E−16 | + |
| 28 | hsa-miR-5572 | 1.14E−17 | + |
| 29 | hsa-miR-3197 | 7.43E−21 | + |
| 30 | hsa-miR-6131 | 8.81E−19 | + |
| 31 | hsa-miR-6889-5p | 7.76E−18 | + |
| 32 | hsa-miR-4454 | 6.20E−15 | − |
| 33 | hsa-miR-1199-5p | 1.10E−16 | − |
| 34 | hsa-miR-1247-3p | 2.61E−15 | − |
| 35 | hsa-miR-6800-5p | 1.65E−14 | − |
| 36 | hsa-miR-6872-3p | 3.40E−13 | + |
| 37 | hsa-miR-4649-5p | 2.50E−16 | − |
| 38 | hsa-miR-6791-5p | 2.29E−18 | − |
| 39 | hsa-miR-4433b-3p | 1.12E−12 | + |
| 40 | hsa-miR-3135b | 7.14E−09 | + |
| 41 | hsa-miR-128-2-5p | 3.95E−17 | + |
| 42 | hsa-miR-4675 | 3.41E−17 | − |
| 43 | hsa-miR-4472 | 1.34E−15 | − |
| 44 | hsa-miR-6785-5p | 7.27E−16 | + |
| 45 | hsa-miR-6741-5p | 1.57E−11 | + |
| 46 | hsa-miR-7977 | 4.98E−13 | + |
| 47 | hsa-miR-3665 | 1.23E−11 | + |
| 48 | hsa-miR-128-1-5p | 6.12E−11 | + |
| 49 | hsa-miR-4286 | 8.20E−12 | + |
| 50 | hsa-miR-6765-3p | 3.54E−12 | + |
| 51 | hsa-miR-4632-5p | 1.23E−14 | − |
| 52 | hsa-miR-365a-5p | 3.37E−12 | − |
| 53 | hsa-miR-6088 | 2.65E−13 | − |
| 54 | hsa-miR-6816-5p | 3.35E−14 | + |
| 55 | hsa-miR-6885-5p | 1.83E−13 | − |
| 56 | hsa-miR-711 | 2.81E−14 | + |
| 57 | hsa-miR-6765-5p | 1.37E−11 | + |
| 58 | hsa-miR-3180 | 1.69E−14 | + |
| 59 | hsa-miR-4442 | 2.64E−12 | − |
| 60 | hsa-miR-4792 | 2.35E−11 | + |
| 61 | hsa-miR-6721-5p | 1.63E−09 | + |
| 62 | hsa-miR-6798-5p | 9.64E−11 | − |
| 63 | hsa-miR-3162-5p | 1.05E−08 | − |
| 64 | hsa-miR-6126 | 3.64E−14 | + |
| 65 | hsa-miR-4758-5p | 3.51E−15 | + |
| 66 | hsa-miR-2392 | 2.75E−12 | + |
| 67 | hsa-miR-486-3p | 2.02E−11 | − |
| 68 | hsa-miR-6727-5p | 3.30E−09 | + |
| 69 | hsa-miR-4728-5p | 9.06E−11 | − |
| 70 | hsa-miR-6746-5p | 1.45E−08 | + |
| 71 | hsa-miR-4270 | 1.52E−08 | + |
| 72 | hsa-miR-3940-5p | 3.98E−09 | + |
| 73 | hsa-miR-4725-3p | 2.40E−08 | − |
| 74 | hsa-miR-7108-5p | 5.64E−10 | + |
| 75 | hsa-miR-3656 | 6.69E−13 | + |
| 76 | hsa-miR-6879-5p | 3.97E−13 | + |
| 77 | hsa-miR-6738-5p | 1.60E−09 | + |
| 78 | hsa-miR-1260a | 1.22E−08 | + |
| 79 | hsa-miR-4446-3p | 3.23E−10 | − |
| 80 | hsa-miR-3131 | 2.40E−09 | + |
| 81 | hsa-miR-4463 | 1.54E−08 | − |
| 82 | hsa-miR-3185 | 5.62E−10 | − |
| 83 | hsa-miR-6870-5p | 3.81E−08 | + |
| 84 | hsa-miR-6779-5p | 3.02E−07 | + |

TABLE 7-continued

| SEQ ID NO: | Gene name | P value after Bonferroni correction | Expression level in lung cancer patient with respect to healthy subject |
|---|---|---|---|
| 85 | hsa-miR-1273g-3p | 2.06E−09 | + |
| 86 | hsa-miR-8059 | 2.01E−06 | − |
| 87 | hsa-miR-4697-5p | 1.86E−08 | + |
| 88 | hsa-miR-4674 | 4.38E−10 | − |
| 89 | hsa-miR-4433-3p | 2.20E−07 | − |
| 90 | hsa-miR-4257 | 1.87E−08 | + |
| 91 | hsa-miR-1915-5p | 4.76E−10 | − |
| 92 | hsa-miR-4417 | 2.14E−07 | − |
| 93 | hsa-miR-1343-5p | 1.06E−10 | + |
| 94 | hsa-miR-6781-5p | 4.10E−05 | − |
| 95 | hsa-miR-4695-5p | 3.31E−11 | − |
| 96 | hsa-miR-1237-5p | 3.95E−10 | + |
| 97 | hsa-miR-6775-5p | 4.09E−05 | + |
| 98 | hsa-miR-7845-5p | 2.84E−07 | − |
| 99 | hsa-miR-4746-3p | 9.11E−11 | − |
| 100 | hsa-miR-7641 | 1.14E−06 | − |
| 101 | hsa-miR-7847-3p | 5.71E−05 | + |
| 102 | hsa-miR-6806-5p | 1.87E−09 | − |
| 103 | hsa-miR-4467 | 2.48E−08 | − |
| 104 | hsa-miR-4726-5p | 8.08E−07 | + |
| 105 | hsa-miR-4648 | 1.15E−08 | + |
| 106 | hsa-miR-6089 | 1.19E−07 | + |
| 107 | hsa-miR-1260b | 1.62E−05 | + |
| 108 | hsa-miR-4532 | 8.30E−09 | + |
| 109 | hsa-miR-5195-3p | 2.03E−07 | + |
| 110 | hsa-miR-3188 | 4.84E−08 | − |
| 111 | hsa-miR-6848-5p | 6.01E−07 | + |
| 112 | hsa-miR-1233-5p | 3.76E−06 | + |
| 113 | hsa-miR-6717-5p | 2.38E−05 | + |
| 114 | hsa-miR-3195 | 7.67E−06 | − |
| 115 | hsa-miR-6757-5p | 1.58E−06 | − |
| 116 | hsa-miR-8072 | 1.17E−05 | − |
| 117 | hsa-miR-4745-5p | 5.89E−07 | + |
| 119 | hsa-miR-6776-5p | 1.26E−07 | − |
| 120 | hsa-miR-371a-5p | 9.22E−05 | + |
| 121 | hsa-miR-1227-5p | 9.64E−05 | − |
| 122 | hsa-miR-7150 | 0.000252 | − |
| 123 | hsa-miR-1915-3p | 2.18E−09 | − |
| 124 | hsa-miR-187-5p | 2.81E−27 | − |
| 125 | hsa-miR-614 | 1.65E−21 | − |
| 126 | hsa-miR-19b-3p | 1.33E−19 | + |
| 127 | hsa-miR-1225-5p | 6.67E−13 | − |
| 128 | hsa-miR-451a | 2.23E−10 | − |
| 129 | hsa-miR-939-5p | 1.89E−11 | + |
| 130 | hsa-miR-223-3p | 9.32E−11 | − |
| 131 | hsa-miR-1228-5p | 1.49E−09 | + |
| 132 | hsa-miR-125a-3p | 1.07E−05 | + |
| 133 | hsa-miR-92b-5p | 1.09E−11 | + |
| 134 | hsa-miR-22-3p | 9.71E−07 | + |
| 135 | hsa-miR-4271 | 5.64E−07 | + |
| 136 | hsa-miR-642b-3p | 6.99E−06 | − |
| 137 | hsa-miR-6075 | 1.17E−05 | + |
| 138 | hsa-miR-6125 | 1.63E−05 | + |
| 139 | hsa-miR-887-3p | 1.68E−05 | + |
| 140 | hsa-miR-6851-5p | 1.97E−05 | − |
| 141 | hsa-miR-6763-5p | 3.54E−05 | − |
| 142 | hsa-miR-3928-3p | 4.67E−05 | − |
| 143 | hsa-miR-4443 | 5.36E−05 | + |
| 144 | hsa-miR-3648 | 6.01E−05 | + |
| 145 | hsa-miR-149-3p | 9.80E−05 | − |
| 146 | hsa-miR-4689 | 1.01E−04 | + |
| 147 | hsa-miR-4763-3p | 1.20E−04 | + |
| 148 | hsa-miR-6729-5p | 1.28E−04 | + |
| 149 | hsa-miR-3196 | 1.31E−04 | + |
| 150 | hsa-miR-8069 | 1.84E−04 | + |
| 151 | hsa-miR-1268a | 2.58E−04 | + |
| 152 | hsa-miR-4739 | 2.68E−04 | + |
| 153 | hsa-miR-1268b | 3.37E−04 | + |
| 154 | hsa-miR-5698 | 4.34E−04 | − |
| 155 | hsa-miR-6752-5p | 5.63E−04 | + |
| 156 | hsa-miR-4507 | 6.34E−04 | + |
| 157 | hsa-miR-564 | 6.68E−04 | − |
| 158 | hsa-miR-4497 | 8.11E−04 | − |
| 159 | hsa-miR-6877-5p | 8.21E−04 | − |
| 160 | hsa-miR-6087 | 8.91E−04 | − |
| 161 | hsa-miR-4731-5p | 1.15E−03 | − |
| 162 | hsa-miR-615-5p | 1.25E−03 | − |
| 163 | hsa-miR-760 | 1.42E−03 | − |
| 164 | hsa-miR-6891-5p | 1.71E−03 | + |
| 165 | hsa-miR-6887-5p | 1.82E−03 | − |
| 166 | hsa-miR-4525 | 2.09E−03 | − |
| 167 | hsa-miR-1914-3p | 2.11E−03 | − |
| 168 | hsa-miR-619-5p | 2.61E−03 | − |
| 169 | hsa-miR-5001-5p | 3.01E−03 | − |
| 170 | hsa-miR-6722-3p | 3.88E−03 | + |
| 171 | hsa-miR-3621 | 4.02E−03 | − |
| 172 | hsa-miR-4298 | 7.88E−03 | − |
| 173 | hsa-miR-675-5p | 8.33E−03 | − |
| 174 | hsa-miR-4655-5p | 9.06E−03 | + |

Example 4

<Method for Evaluating Lung Cancer-Specific Discriminant Performance by Combination of Multiple Gene Markers Using Samples in the Validation Cohort>

In this Example, gene markers for diagnosis were selected by comparing gene expression levels of miRNAs in serum of lung cancer patients with that of a control group consisting of healthy subjects, pancreatic cancer patients, biliary tract cancer patients, colorectal cancer patients, stomach cancer patients, liver cancer patients, and benign pancreaticobiliary disease patients, in the same way as the method described in Example 1, using the gene markers selected in Example 1, and targeting the training cohort as the sample group described in Reference Example 2. The polynucleotides consisting of the nucleotide sequences represented by SEQ ID NOs: 561 to 579 thus selected were further combined therewith to study a method for evaluating lung cancer-specific discriminant performance.

Specifically, first, the miRNA expression levels in the training cohort and the validation cohort obtained in Reference Example 2 mentioned above were combined and normalized by quantile normalization. Next, Fisher's discriminant analysis was conducted as to combinations of 1 to 4 expression level measurement values comprising at least one or more of the expression level measurement values of the polynucleotides consisting of the nucleotide sequences represented by SEQ ID NOs: 1 to 174, and 561 to 579, to construct a discriminant for determining the presence or absence of lung cancer. Next, accuracy, sensitivity, and specificity in the validation cohort were calculated using the discriminant thus prepared, with the lung cancer patient group as a positive sample group and, on the other hand, the healthy subject group, the pancreatic cancer patient group, the biliary tract cancer patient group, the colorectal cancer patient group, the stomach cancer patient group, the liver cancer patient group, and the benign pancreaticobiliary disease patient group as a negative sample group. The discriminant performance of the selected polynucleotides was validated using the independent samples.

Most of polynucleotides consisting of the nucleotide sequences represented by these SEQ ID NOs (SEQ ID NOs: 1 to 174, and 561 to 579 corresponding to the miRNA markers of Table 1) or complementary sequences thereof mentioned above were able to provide relatively high accuracy, sensitivity, and specificity in the determination of the presence or absence of lung cancer, and furthermore, were able to specifically discriminate lung cancer from the other cancers. For example, among the combinations of multiple polynucleotides selected from the group consisting of polynucleotides consisting of the nucleotide sequences represented by SEQ ID NOs: 1, 2, 3, 4, 5, 7, 9, 10, 11, 19, 21, 26, 29, 31, 52, 53, 63, 65, 69, 72, 87, 90, 113, 124, 125, 126, 128, 130, 143, 148, 160, 162, 561, 562, 563, 564, 565, 566, 567, 568, 569, 570, 571, 572, 573, 574, 575, 576, 577, 578 and 579 or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 1, 2, 3, 10, 63, 113, 124, 125, 126, 128, 130, 143, 160, 561, 568, 573 and 578 or complementary sequences thereof (the cancer type-specific polynucleotide group 2) included in the cancer type-specific polynucleotide group 1 were able to specifically discriminate lung cancer from the other cancers with high accuracy.

The number of the polynucleotides with cancer type specificity in the combination can be 1, 2, 3, 4, 5, 6, 7, 8, 9, 10 or more for the combination. The combinations of 4 or more of these polynucleotides were able to exhibit discriminant accuracy of 90% or higher.

Specifically, the discriminant accuracy of the measurement using the polynucleotide consisting of the nucleotide sequence represented by SEQ ID NO: 1 or a complementary sequence thereof is shown in Table 8-1. For example, the measurement using the combination of one polynucleotide comprising at least one polynucleotide consisting of the nucleotide sequence represented by SEQ ID NO: 1 or a complementary sequence thereof exhibited accuracy of 94.2% in the training cohort and accuracy of 91.4% in the validation cohort. Also, for example, the measurement using the combinations of two polynucleotides comprising at least one polynucleotide consisting of the nucleotide sequence represented by SEQ ID NO: 1 or a complementary sequence thereof exhibited accuracy of 98.7% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 1 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 1 or a complementary sequence thereof exhibited accuracy of 99.7% in the training cohort and accuracy of 99.0% in the validation cohort.

Specifically, the discriminant accuracy of the measurement using the polynucleotide consisting of the nucleotide sequence represented by SEQ ID NO: 2 or a complementary sequence thereof is shown in Table 8-2. For example, the measurement using the combination of one polynucleotide comprising at least one polynucleotide consisting of the nucleotide sequence represented by SEQ ID NO: 2 or a complementary sequence thereof exhibited accuracy of 94.0% in the training cohort and accuracy of 92.4% in the validation cohort. Also, for example, the measurement using the combinations of two polynucleotides comprising at least one polynucleotide consisting of the nucleotide sequence represented by SEQ ID NO: 2 or a complementary sequence thereof exhibited accuracy of 97.2% in the training cohort and accuracy of 96.0% in the validation cohort. Furthermore, for example, the measurement using the combinations of three polynucleotides comprising at least one polynucleotide consisting of the nucleotide sequence represented by SEQ ID NO: 2 or a complementary sequence thereof exhibited accuracy of 99.5% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 2 or a complementary sequence thereof exhibited accuracy of 100% in the training cohort and accuracy of 98.0% in the validation cohort.

Specifically, the discriminant accuracy of the measurement using the polynucleotide consisting of the nucleotide sequence represented by SEQ ID NO: 3 or a complementary sequence thereof is shown in Table 8-3. For example, the measurement using the combination of one polynucleotide comprising at least one polynucleotide consisting of the nucleotide sequence represented by SEQ ID NO: 3 or a complementary sequence thereof exhibited accuracy of 85.7% in the training cohort and accuracy of 84.3% in the validation cohort. Also, for example, the measurement using the combinations of two polynucleotides comprising at least one polynucleotide consisting of the nucleotide sequence represented by SEQ ID NO: 3 or a complementary sequence thereof exhibited accuracy of 97.0% in the training cohort and accuracy of 97.0% in the validation cohort. Furthermore, for example, the measurement using the combinations of three polynucleotides comprising at least one polynucleotide consisting of the nucleotide sequence represented by SEQ ID NO: 3 or a complementary sequence thereof exhibited accuracy of 99.0% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 3 or a complementary sequence thereof exhibited accuracy of 99.5% in the training cohort and accuracy of 100% in the validation cohort.

Specifically, the discriminant accuracy of the measurement using the polynucleotide consisting of the nucleotide sequence represented by SEQ ID NO: 10 or a complementary sequence thereof is shown in Table 8-4. For example, the measurement using the combination of one polynucleotide comprising at least one polynucleotide consisting of the nucleotide sequence represented by SEQ ID NO: 10 or a complementary sequence thereof exhibited accuracy of 64.0% in the training cohort and accuracy of 61.6% in the validation cohort. Also, for example, the measurement using the combinations of two polynucleotides comprising at least one polynucleotide consisting of the nucleotide sequence represented by SEQ ID NO: 10 or a complementary sequence thereof exhibited accuracy of 94.0% in the training cohort and accuracy of 92.4% in the validation cohort. Furthermore, for example, the measurement using the combinations of three polynucleotides comprising at least one polynucleotide consisting of the nucleotide sequence represented by SEQ ID NO: 10 or a complementary sequence thereof exhibited accuracy of 99.2% in the training cohort and accuracy of 99.0% in the validation cohort. Furthermore, for example, the measurement using the combinations of four polynucleotides comprising at least one polynucleotide consisting of the nucleotide sequence represented by SEQ ID NO: 10 or a complementary sequence thereof exhibited accuracy of 99.2% in the training cohort and accuracy of 99.5% in the validation cohort.

Specifically, the discriminant accuracy of the measurement using the polynucleotide consisting of the nucleotide sequence represented by SEQ ID NO: 63 or a complementary sequence thereof is shown in Table 8-5. For example, the measurement using the combination of one polynucleotide comprising at least one polynucleotide consisting of the nucleotide sequence represented by SEQ ID NO: 63 or a complementary sequence thereof exhibited accuracy of 79.4% in the training cohort and accuracy of 80.8% in the validation cohort. Also, for example, the measurement using the combinations of two polynucleotides comprising at least one polynucleotide consisting of the nucleotide sequence represented by SEQ ID NO: 63 or a complementary sequence thereof exhibited accuracy of 95.7% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 63 or a complementary sequence thereof exhibited accuracy of 98.2% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 63 or a complementary sequence thereof exhibited accuracy of 99.5% in the training cohort and accuracy of 97.5% in the validation cohort.

Specifically, the discriminant accuracy of the measurement using the polynucleotide consisting of the nucleotide sequence represented by SEQ ID NO: 113 or a complementary sequence thereof is shown in Table 8-6. For example, the measurement using the combination of one polynucleotide comprising at least one polynucleotide consisting of the nucleotide sequence represented by SEQ ID NO: 113 or a complementary sequence thereof exhibited accuracy of 67.8% in the training cohort and accuracy of 69.2% in the validation cohort. Also, for example, the measurement using the combinations of two polynucleotides comprising at least one polynucleotide consisting of the nucleotide sequence represented by SEQ ID NO: 113 or a complementary sequence thereof exhibited accuracy of 97.7% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 113 or a complementary sequence thereof exhibited accuracy of 99.5% in the training cohort and accuracy of 99.0% in the validation cohort. Furthermore, for example, the measurement using the combinations of four polynucleotides comprising at least one polynucleotide consisting of the nucleotide sequence represented by SEQ ID NO: 113 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 124 or a complementary sequence thereof is shown in Table 8-7. For example, the measurement using the combination of one polynucleotide comprising at least one polynucleotide consisting of the nucleotide sequence represented by SEQ ID NO: 124 or a complementary sequence thereof exhibited accuracy of 79.6% in the training cohort and accuracy of 76.8% in the validation cohort. Also, for example, the measurement using the combinations of two polynucleotides comprising at least one polynucleotide consisting of the nucleotide sequence represented by SEQ ID NO: 124 or a complementary sequence thereof exhibited accuracy of 95.0% in the training cohort and accuracy of 91.4% in the validation cohort. Furthermore, for example, the measurement using the combinations of three polynucleotides comprising at least one polynucleotide consisting of the nucleotide sequence represented by SEQ ID NO: 124 or a complementary sequence thereof exhibited accuracy of 98.5% in the training cohort and accuracy of 97.5% in the validation cohort. Furthermore, for example, the measurement using the combinations of four polynucleotides comprising at least one polynucleotide consisting of the nucleotide sequence represented by SEQ ID NO: 124 or a complementary sequence thereof exhibited accuracy of 99.0% in the training cohort and accuracy of 99.0% in the validation cohort.

Specifically, the discriminant accuracy of the measurement using the polynucleotide consisting of the nucleotide sequence represented by SEQ ID NO: 125 or a complementary sequence thereof is shown in Table 8-8. For example, the measurement using the combination of one polynucleotide comprising at least one polynucleotide consisting of the nucleotide sequence represented by SEQ ID NO: 125 or a complementary sequence thereof exhibited accuracy of 77.6% in the training cohort and accuracy of 73.7% in the validation cohort. Also, for example, the measurement using the combinations of two polynucleotides comprising at least one polynucleotide consisting of the nucleotide sequence represented by SEQ ID NO: 125 or a complementary sequence thereof exhibited accuracy of 94.7% in the training cohort and accuracy of 93.4% in the validation cohort. Furthermore, for example, the measurement using the combinations of three polynucleotides comprising at least one polynucleotide consisting of the nucleotide sequence represented by SEQ ID NO: 125 or a complementary sequence thereof exhibited accuracy of 99.0% in the training cohort and accuracy of 96.5% in the validation cohort. Furthermore, for example, the measurement using the combinations of four polynucleotides comprising at least one polynucleotide consisting of the nucleotide sequence represented by SEQ ID NO:125 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 126 or a complementary sequence thereof is shown in Table 8-9. For example, the measurement using the combination of one polynucleotide comprising at least one polynucleotide consisting of the nucleotide sequence represented by SEQ ID NO: 126 or a complementary sequence thereof exhibited accuracy of 90.4% in the training cohort and accuracy of 92.4% in the validation cohort. Also, for example, the measurement using the combinations of two polynucleotides comprising at least one polynucleotide consisting of the nucleotide sequence represented by SEQ ID NO: 126 or a complementary sequence thereof exhibited accuracy of 96.7% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 126 or a complementary sequence thereof exhibited accuracy of 99.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 126 or a complementary sequence thereof exhibited accuracy of 99.7% in the training cohort and accuracy of 99.0% in the validation cohort.

Specifically, the discriminant accuracy of the measurement using the polynucleotide consisting of the nucleotide sequence represented by SEQ ID NO: 128 or a complementary sequence thereof is shown in Table 8-10. For example, the measurement using the combination of one polynucleotide comprising at least one polynucleotide consisting of the nucleotide sequence represented by SEQ ID NO: 128 or a complementary sequence thereof exhibited accuracy of 81.4% in the training cohort and accuracy of 81.3% in the validation cohort. Also, for example, the measurement using the combinations of two polynucleotides comprising at least one polynucleotide consisting of the nucleotide sequence represented by SEQ ID NO: 128 or a complementary sequence thereof exhibited accuracy of 96.2% in the training cohort and accuracy of 94.9% in the validation cohort. Furthermore, for example, the measurement using the combinations of three polynucleotides comprising at least one polynucleotide consisting of the nucleotide sequence represented by SEQ ID NO: 128 or a complementary sequence thereof exhibited accuracy of 98.7% in the training cohort and accuracy of 97.5% in the validation cohort. Furthermore, for example, the measurement using the combinations of four polynucleotides comprising at least one polynucleotide consisting of the nucleotide sequence represented by SEQ ID NO: 128 or a complementary sequence thereof exhibited accuracy of 99.2% in the training cohort and accuracy of 99.5% in the validation cohort.

Specifically, the discriminant accuracy of the measurement using the polynucleotide consisting of the nucleotide sequence represented by SEQ ID NO: 130 or a complementary sequence thereof is shown in Table 8-11. For example, the measurement using the combination of one polynucleotide comprising at least one polynucleotide consisting of the nucleotide sequence represented by SEQ ID NO: 130 or a complementary sequence thereof exhibited accuracy of 83.4% in the training cohort and accuracy of 87.4% in the validation cohort. Also, for example, the measurement using the combinations of two polynucleotides comprising at least one polynucleotide consisting of the nucleotide sequence represented by SEQ ID NO: 130 or a complementary sequence thereof exhibited accuracy of 96.2% in the training cohort and accuracy of 94.4% in the validation cohort. Furthermore, for example, the measurement using the combinations of three polynucleotides comprising at least one polynucleotide consisting of the nucleotide sequence represented by SEQ ID NO: 130 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 130 or a complementary sequence thereof exhibited accuracy of 99.5% in the training cohort and accuracy of 99.5% in the validation cohort.

Specifically, the discriminant accuracy of the measurement using the polynucleotide consisting of the nucleotide sequence represented by SEQ ID NO: 143 or a complementary sequence thereof is shown in Table 8-12. For example, the measurement using the combination of one polynucleotide comprising at least one polynucleotide consisting of the nucleotide sequence represented by SEQ ID NO: 143 or a complementary sequence thereof exhibited accuracy of 64.6% in the training cohort and accuracy of 66.2% in the validation cohort. Also, for example, the measurement using the combinations of two polynucleotides comprising at least one polynucleotide consisting of the nucleotide sequence represented by SEQ ID NO: 143 or a complementary sequence thereof exhibited accuracy of 96.0% in the training cohort and accuracy of 93.9% in the validation cohort. Furthermore, for example, the measurement using the combinations of three polynucleotides comprising at least one polynucleotide consisting of the nucleotide sequence represented by SEQ ID NO: 143 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 143 or a complementary sequence thereof exhibited accuracy of 99.0% in the training cohort and accuracy of 98.0% in the validation cohort.

Specifically, the discriminant accuracy of the measurement using the polynucleotide consisting of the nucleotide sequence represented by SEQ ID NO: 160 or a complementary sequence thereof is shown in Table 8-13. For example, the measurement using the combination of one polynucleotide comprising at least one polynucleotide consisting of the nucleotide sequence represented by SEQ ID NO: 160 or a complementary sequence thereof exhibited accuracy of 70.9% in the training cohort and accuracy of 67.2% in the validation cohort. Also, for example, the measurement using the combinations of two polynucleotides comprising at least one polynucleotide consisting of the nucleotide sequence represented by SEQ ID NO: 160 or a complementary sequence thereof exhibited accuracy of 96.0% in the training cohort and accuracy of 92.4% in the validation cohort. Furthermore, for example, the measurement using the combinations of three polynucleotides comprising at least one polynucleotide consisting of the nucleotide sequence represented by SEQ ID NO: 160 or a complementary sequence thereof exhibited accuracy of 99.2% in the training cohort and accuracy of 98.5% in the validation cohort. Furthermore, for example, the measurement using the combinations of four polynucleotides comprising at least one polynucleotide consisting of the nucleotide sequence represented by SEQ ID NO: 160 or a complementary sequence thereof exhibited accuracy of 99.5% in the training cohort and accuracy of 99.0% in the validation cohort.

Specifically, the discriminant accuracy of the measurement using the polynucleotide consisting of the nucleotide sequence represented by SEQ ID NO: 561 or a complementary sequence thereof is shown in Table 8-14. For example, the measurement using the combination of one polynucleotide comprising at least one polynucleotide consisting of the nucleotide sequence represented by SEQ ID NO: 561 or a complementary sequence thereof exhibited accuracy of 84.9% in the training cohort and accuracy of 81.8% in the validation cohort. Also, for example, the measurement using the combinations of two polynucleotides comprising at least one polynucleotide consisting of the nucleotide sequence represented by SEQ ID NO: 561 or a complementary sequence thereof exhibited accuracy of 96.5% in the training cohort and accuracy of 97.5% in the validation cohort. Furthermore, for example, the measurement using the combinations of three polynucleotides comprising at least one polynucleotide consisting of the nucleotide sequence represented by SEQ ID NO: 561 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 561 or a complementary sequence thereof exhibited accuracy of 100% in the training cohort and accuracy of 99.0% in the validation cohort.

Specifically, the discriminant accuracy of the measurement using the polynucleotide consisting of the nucleotide sequence represented by SEQ ID NO: 568 or a complementary sequence thereof is shown in Table 8-15. For example, the measurement using the combination of one polynucleotide comprising at least one polynucleotide consisting of the nucleotide sequence represented by SEQ ID NO: 568 or a complementary sequence thereof exhibited accuracy of 60.2% in the training cohort and accuracy of 67.2% in the validation cohort. Also, for example, the measurement using the combinations of two polynucleotides comprising at least one polynucleotide consisting of the nucleotide sequence represented by SEQ ID NO: 568 or a complementary sequence thereof exhibited accuracy of 97.0% in the training cohort and accuracy of 96.0% in the validation cohort. Furthermore, for example, the measurement using the combinations of three polynucleotides comprising at least one polynucleotide consisting of the nucleotide sequence represented by SEQ ID NO: 568 or a complementary sequence thereof exhibited accuracy of 99.0% in the training cohort and accuracy of 96.0% in the validation cohort. Furthermore, for example, the measurement using the combinations of four polynucleotides comprising at least one polynucleotide consisting of the nucleotide sequence represented by SEQ ID NO: 568 or a complementary sequence thereof exhibited accuracy of 99.5% in the training cohort and accuracy of 98.5% in the validation cohort.

Specifically, the discriminant accuracy of the measurement using the polynucleotide consisting of the nucleotide sequence represented by SEQ ID NO: 573 or a complementary sequence thereof is shown in Table 8-16. For example, the measurement using the combination of one polynucleotide comprising at least one polynucleotide consisting of the nucleotide sequence represented by SEQ ID NO: 573 or a complementary sequence thereof exhibited accuracy of 53.0% in the training cohort and accuracy of 53.5% in the validation cohort. Also, for example, the measurement using the combinations of two polynucleotides comprising at least one polynucleotide consisting of the nucleotide sequence represented by SEQ ID NO: 573 or a complementary sequence thereof exhibited accuracy of 96.5% in the training cohort and accuracy of 95.5% in the validation cohort. Furthermore, for example, the measurement using the combinations of three polynucleotides comprising at least one polynucleotide consisting of the nucleotide sequence represented by SEQ ID NO: 573 or a complementary sequence thereof exhibited accuracy of 98.7% in the training cohort and accuracy of 98.0% in the validation cohort. Furthermore, for example, the measurement using the combinations of four polynucleotides comprising at least one polynucleotide consisting of the nucleotide sequence represented by SEQ ID NO: 573 or a complementary sequence thereof exhibited accuracy of 99.2% in the training cohort and accuracy of 98.5% in the validation cohort.

Specifically, the discriminant accuracy of the measurement using the polynucleotide consisting of the nucleotide sequence represented by SEQ ID NO: 578 or a complementary sequence thereof is shown in Table 8-17. For example, the measurement using the combination of one polynucleotide comprising at least one polynucleotide consisting of the nucleotide sequence represented by SEQ ID NO: 578 or a complementary sequence thereof exhibited accuracy of 52.8% in the training cohort and accuracy of 53.5% in the validation cohort. Also, for example, the measurement using the combinations of two polynucleotides comprising at least one polynucleotide consisting of the nucleotide sequence represented by SEQ ID NO: 578 or a complementary sequence thereof exhibited accuracy of 96.2% in the training cohort and accuracy of 94.9% in the validation cohort. Furthermore, for example, the measurement using the combinations of three polynucleotides comprising at least one polynucleotide consisting of the nucleotide sequence represented by SEQ ID NO: 578 or a complementary sequence thereof exhibited accuracy of 98.5% in the training cohort and accuracy of 96.5% in the validation cohort. Furthermore, for example, the measurement using the combinations of four polynucleotides comprising at least one polynucleotide consisting of the nucleotide sequence represented by SEQ ID NO: 578 or a complementary sequence thereof exhibited accuracy of 99.2% in the training cohort and accuracy of 99.0% in the validation cohort.

Figure 4:
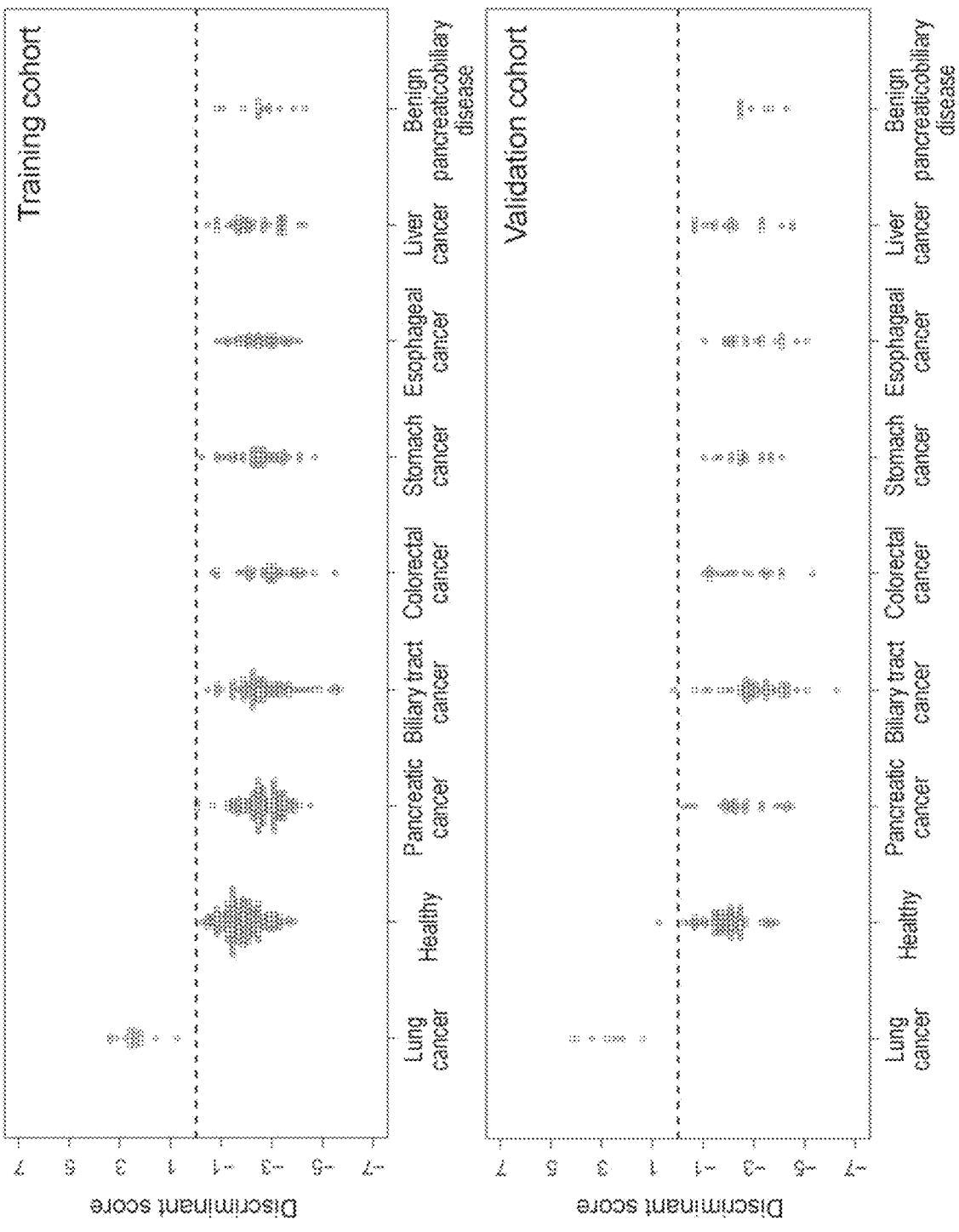
FIG. 4A: a discriminant (−1.86×hsa-miR-6768-5p−0.68×hsa-miR-19b-3p+0.43×hsa-miR-6073−0.87×hsa-miR-6717-5p+25.68) was prepared by use of Fisher's discriminant analysis from the expression level measurement values of hsa-miR-6768-5p (SEQ ID NO: 1), hsa-miR-6717-5p (SEQ ID NO: 113), hsa-miR-19b-3p (SEQ ID NO: 126), and hsa-miR-6073 (SEQ ID NO: 561) in 17 lung cancer patients, 99 healthy subjects, 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the two groups.
FIG. 4B: discriminant scores obtained from the discriminant prepared in the training cohort as to the expression level measurement values of hsa-miR-6768-5p (SEQ ID NO: 1), hsa-miR-6717-5p (SEQ ID NO: 113), hsa-miR-19b-3p (SEQ ID NO: 126), and hsa-miR-6073 (SEQ ID NO: 561) in 8 lung cancer patients, 51 healthy subjects, 23 pancreatic cancer patients, 38 biliary tract cancer patients, 18 colorectal cancer patients, 15 stomach cancer patients, 18 esophageal cancer patients, 19 liver cancer patients, and 8 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The measurement values of the nucleotide sequences represented by SEQ ID NOs: 1, 113, 126, and 561 were compared among 17 lung cancer patients, 99 healthy subjects, 75 pancreatic cancer patients, 62 biliary tract cancer patients, 32 colorectal cancer patients, 35 stomach cancer patients, 32 esophageal cancer patients, 33 liver cancer patients, and 13 benign pancreaticobiliary disease patients in the training cohort. As a result, a scatter diagram that significantly separated the discriminant score of the lung cancer patient group from the discriminant scores of the other groups was obtained in the training cohort (see FIG. 4A). These results were also reproducible for the validation cohort (see FIG. 4B).

TABLE 8-1

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 1 | 94.2 | 100 | 94.0 | 91.4 | 87.5 | 91.6 |
| 1_113 | 98.7 | 100 | 98.7 | 97.5 | 100 | 97.4 |
| 1_52_126 | 99.2 | 100 | 99.2 | 98.5 | 100 | 98.4 |
| 1_53_113_125 | 99.2 | 100 | 99.2 | 98.5 | 100 | 98.4 |
| 1_10_63_113 | 99.2 | 100 | 99.2 | 98.5 | 100 | 98.4 |
| 1_19_113_143 | 99.2 | 100 | 99.2 | 99.0 | 100 | 98.9 |
| 1_10_113_126 | 99.7 | 100 | 99.7 | 99.0 | 100 | 98.9 |
| 1_2_10_113 | 99.7 | 100 | 99.7 | 98.5 | 100 | 98.4 |

TABLE 8-2

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 2 | 94.0 | 94.1 | 94.0 | 92.4 | 100 | 92.1 |
| 2_126 | 97.2 | 100 | 97.1 | 96.0 | 100 | 95.8 |
| 1_2_113 | 99.5 | 100 | 99.5 | 98.0 | 100 | 97.9 |
| 2_19_53_113 | 99.2 | 100 | 99.2 | 97.5 | 100 | 97.4 |
| 2_72_113_125 | 99.0 | 100 | 99.0 | 96.5 | 100 | 96.3 |
| 2_19_72_113 | 99.0 | 100 | 99.0 | 97.0 | 100 | 96.8 |
| 2_19_113_579 | 98.5 | 100 | 98.4 | 96.5 | 100 | 96.3 |
| 1_2_19_113 | 100 | 100 | 100 | 98.0 | 100 | 97.9 |

TABLE 8-3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 3 | 85.7 | 94.1 | 85.3 | 84.3 | 100 | 83.7 |
| 3_126 | 97.0 | 94.1 | 97.1 | 97.0 | 100 | 96.8 |
| 1_3_113 | 99.0 | 100 | 99.0 | 98.5 | 100 | 98.4 |
| 3_125_128_568 | 98.5 | 100 | 98.4 | 97.0 | 100 | 96.8 |
| 1_3_10_113 | 99.2 | 100 | 99.2 | 99.0 | 100 | 98.9 |
| 3_113_125_126 | 99.5 | 94.1 | 99.7 | 100 | 100 | 100 |
| 1_3_126_573 | 98.5 | 100 | 98.4 | 98.0 | 100 | 97.9 |
| 3_126_130_561 | 98.2 | 94.1 | 98.4 | 98.0 | 100 | 97.9 |

TABLE 8-4

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 10 | 64.0 | 82.4 | 63.2 | 61.6 | 75.0 | 61.1 |
| 2_10 | 94.0 | 100 | 93.7 | 92.4 | 100 | 92.1 |
| 1_10_113 | 99.2 | 100 | 99.2 | 99.0 | 100 | 98.9 |
| 1_10_113_143 | 99.0 | 100 | 98.9 | 99.5 | 100 | 99.5 |
| 1_10_113_569 | 99.2 | 100 | 99.2 | 99.0 | 100 | 98.9 |
| 1_10_113_562 | 98.7 | 100 | 98.7 | 99.0 | 100 | 98.9 |
| 1_10_113_578 | 99.2 | 100 | 99.2 | 98.5 | 100 | 98.4 |
| 1_7_10_113 | 99.2 | 100 | 99.2 | 99.0 | 100 | 98.9 |

TABLE 8-5

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 63 | 79.4 | 94.1 | 78.7 | 80.8 | 75.0 | 81.1 |
| 63_126 | 95.7 | 94.1 | 95.8 | 97.5 | 100 | 97.4 |
| 1_63_113 | 98.2 | 100 | 98.2 | 98.0 | 100 | 97.9 |
| 1_63_567_578 | 99.5 | 100 | 99.5 | 97.5 | 100 | 97.4 |
| 1_53_63_578 | 98.2 | 100 | 98.2 | 98.0 | 100 | 97.9 |
| 1_63_162_573 | 98.0 | 100 | 97.9 | 97.5 | 87.5 | 97.9 |
| 1_63_162_578 | 98.5 | 100 | 98.4 | 98.0 | 100 | 97.9 |
| 1_63_576_578 | 98.7 | 100 | 98.7 | 98.0 | 100 | 97.9 |

TABLE 8-6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 113 | 67.8 | 76.5 | 67.5 | 69.2 | 100 | 67.9 |
| 2_113 | 97.7 | 100 | 97.6 | 95.5 | 100 | 95.3 |
| 1_19_113 | 99.5 | 100 | 99.5 | 99.0 | 100 | 98.9 |
| 1_10_113_567 | 99.5 | 100 | 99.5 | 99.0 | 100 | 98.9 |
| 1_53_63_113 | 99.0 | 100 | 99.0 | 98.0 | 100 | 97.9 |
| 1_53_113_143 | 99.0 | 100 | 99.0 | 98.0 | 100 | 97.9 |
| 2_19_113_125 | 99.0 | 100 | 99.0 | 98.0 | 100 | 97.9 |
| 2_10_113_130 | 99.2 | 100 | 99.2 | 99.5 | 100 | 99.5 |

TABLE 8-7

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 124 | 79.6 | 94.1 | 79.0 | 76.8 | 100 | 75.8 |
| 2_124 | 95.0 | 100 | 94.8 | 91.4 | 100 | 91.1 |
| 1_113_124 | 98.5 | 100 | 98.4 | 97.5 | 100 | 97.4 |
| 113_124_125_126 | 99.0 | 94.1 | 99.2 | 99.0 | 100 | 98.9 |
| 124_125_128_568 | 98.0 | 100 | 97.9 | 94.9 | 100 | 94.7 |
| 113_124_125_162 | 99.0 | 100 | 99.0 | 98.0 | 100 | 97.9 |
| 52_124_126_561 | 98.0 | 94.1 | 98.2 | 98.0 | 100 | 97.9 |
| 19_113_124_126 | 98.0 | 94.1 | 98.2 | 99.0 | 100 | 98.9 |

TABLE 8-8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (N | Specificity (%) |
| 125 | 77.6 | 82.4 | 77.4 | 73.7 | 87.5 | 73.2 |
| 113_125 | 94.7 | 100 | 94.5 | 93.4 | 100 | 93.2 |
| 2_113_125 | 99.0 | 100 | 99.0 | 96.5 | 100 | 96.3 |
| 1_113_125_160 | 99.5 | 100 | 99.5 | 98.5 | 100 | 98.4 |
| 31_113_125_568 | 99.0 | 100 | 98.9 | 98.0 | 100 | 97.9 |
| 2_53_113_125 | 99.2 | 100 | 99.2 | 98.0 | 100 | 97.9 |
| 1 10_113_125 | 99.5 | 100 | 99.5 | 99.0 | 100 | 98.9 |
| 1_113_125_143 | 99.2 | 100 | 99.2 | 99.0 | 100 | 98.9 |

TABLE 8-9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 126 | 90.4 | 94.1 | 90.3 | 92.4 | 100 | 92.1 |
| 1_126 | 96.7 | 100 | 96.6 | 95.5 | 100 | 95.3 |
| 1_113_126 | 99.7 | 100 | 99.7 | 98.0 | 100 | 97.9 |
| 1_126_561_573 | 98.5 | 100 | 98.4 | 97.5 | 100 | 97.4 |
| 113_125_126_568 | 98.5 | 100 | 98.4 | 98.5 | 100 | 98.4 |
| 113_125_126_561 | 99.0 | 94.1 | 99.2 | 98.5 | 100 | 98.4 |
| 1_113_125_126 | 99.7 | 100 | 99.7 | 99.0 | 100 | 98.9 |
| 1_52_126_561 | 99.5 | 100 | 99.5 | 98.0 | 100 | 97.9 |

TABLE 8-10

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 128 | 81.4 | 82.4 | 81.4 | 81.3 | 87.5 | 81.1 |
| 1_128 | 96.2 | 100 | 96.1 | 94.9 | 100 | 94.7 |
| 1_113_128 | 98.7 | 100 | 98.7 | 97.5 | 100 | 97.4 |
| 26_113_125_128 | 97.7 | 94.1 | 97.9 | 98.5 | 100 | 98.4 |
| 1_113_125_128 | 99.0 | 100 | 99.0 | 99.0 | 100 | 98.9 |
| 1_10_113_128 | 99.2 | 100 | 99.2 | 99.5 | 100 | 99.5 |
| 31_113_125_128 | 97.5 | 94.1 | 97.6 | 99.0 | 100 | 98.9 |
| 2_19_113_128 | 99.0 | 100 | 99.0 | 97.0 | 100 | 96.8 |

TABLE 8-11

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 130 | 83.4 | 88.2 | 83.2 | 87.4 | 100 | 86.8 |
| 1_130 | 96.2 | 100 | 96.1 | 94.4 | 100 | 94.2 |
| 1_113_130 | 99.2 | 100 | 99.2 | 98.5 | 100 | 98.4 |
| 1_3_130_143 | 97.7 | 100 | 97.6 | 99.0 | 100 | 98.9 |
| 1_10_113_130 | 99.5 | 100 | 99.5 | 99.5 | 100 | 99.5 |
| 1_63_130_578 | 98.7 | 100 | 98.7 | 98.5 | 100 | 98.4 |
| 124_125_130_568 | 98.5 | 100 | 98.4 | 96.5 | 100 | 96.3 |
| 2_19_113_130 | 99.0 | 100 | 99.0 | 98.0 | 100 | 97.9 |

TABLE 8-12

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 143 | 64.6 | 58.8 | 64.8 | 66.2 | 62.5 | 66.3 |
| 1_143 | 96.0 | 100 | 95.8 | 93.9 | 87.5 | 94.2 |
| 1_113_143 | 98.7 | 100 | 98.7 | 98.0 | 100 | 97.9 |
| 1_3_126_143 | 99.0 | 100 | 98.9 | 98.0 | 100 | 97.9 |
| 1_63_130_143 | 97.7 | 100 | 97.6 | 98.0 | 100 | 97.9 |
| 1_10_52_143 | 98.0 | 100 | 97.9 | 100 | 100 | 100 |
| 2_19_113_143 | 98.5 | 100 | 98.4 | 96.5 | 100 | 96.3 |
| 63_124_130_143 | 96.2 | 94.1 | 96.3 | 96.0 | 100 | 95.8 |

TABLE 8-13

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 160 | 70.9 | 70.6 | 70.9 | 67.2 | 37.5 | 68.4 |
| 2_160 | 96.0 | 100 | 95.8 | 92.4 | 100 | 92.1 |
| 1_113_160 | 99.2 | 100 | 99.2 | 98.5 | 100 | 98.4 |
| 1_10_113_160 | 99.2 | 100 | 99.2 | 99.0 | 100 | 98.9 |
| 7_113_125_160 | 99.0 | 100 | 99.0 | 97.5 | 100 | 97.4 |
| 1_113_160_567 | 99.5 | 100 | 99.5 | 98.0 | 100 | 97.9 |
| 1_113_160_578 | 98.7 | 100 | 98.7 | 98.0 | 100 | 97.9 |
| 2_19_113_160 | 99.5 | 100 | 99.5 | 98.0 | 100 | 97.9 |

TABLE 8-14

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 561 | 84.9 | 88.2 | 84.8 | 81.8 | 87.5 | 81.6 |
| 126_561 | 96.5 | 94.1 | 96.6 | 97.5 | 100 | 97.4 |
| 1_113_561 | 98.7 | 100 | 98.7 | 98.0 | 100 | 97.9 |
| 113_125_130_561 | 97.7 | 94.1 | 97.9 | 99.5 | 100 | 99.5 |
| 7_126_143_561 | 98.5 | 100 | 98.4 | 98.5 | 100 | 98.4 |
| 1_113_126_561 | 100 | 100 | 100 | 99.0 | 100 | 98.9 |
| 1_126_561_568 | 98.7 | 100 | 98.7 | 98.0 | 100 | 97.9 |
| 7_113_126_561 | 99.2 | 94.1 | 99.5 | 98.5 | 100 | 98.4 |

TABLE 8-15

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 568 | 60.2 | 58.8 | 60.3 | 67.2 | 100 | 65.8 |
| 1_568 | 97.0 | 100 | 96.8 | 96.0 | 100 | 95.8 |
| 1_2_568 | 99.0 | 100 | 98.9 | 96.0 | 100 | 95.8 |
| 7_125_126_568 | 99.2 | 100 | 99.2 | 98.0 | 100 | 97.9 |
| 124_125_126_568 | 98.5 | 100 | 98.4 | 98.0 | 100 | 97.9 |
| 7_113_125_568 | 98.5 | 100 | 98.4 | 98.0 | 100 | 97.9 |
| 1_113_125_568 | 99.5 | 100 | 99.5 | 98.0 | 100 | 97.9 |
| 113_125_128_568 | 97.5 | 100 | 97.4 | 98.5 | 100 | 98.4 |

TABLE 8-16

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 573 | 53.0 | 35.3 | 53.8 | 53.5 | 12.5 | 55.3 |
| 1_573 | 96.5 | 100 | 96.3 | 95.5 | 100 | 95.3 |
| 1_113_573 | 98.7 | 100 | 98.7 | 98.0 | 100 | 97.9 |
| 113_125_126_573 | 98.2 | 94.1 | 98.4 | 99.5 | 100 | 99.5 |
| 1_113_125_573 | 99.2 | 100 | 99.2 | 98.5 | 100 | 98.4 |
| 1_53_113_573 | 98.7 | 100 | 98.7 | 97.5 | 100 | 97.4 |
| 1_124_126_573 | 97.7 | 100 | 97.6 | 96.5 | 100 | 96.3 |
| 1_63_130_573 | 98.7 | 100 | 98.7 | 98.0 | 100 | 97.9 |

TABLE 8-17

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 578 | 52.8 | 52.9 | 52.8 | 53.5 | 50.0 | 53.7 |
| 1_578 | 96.2 | 100 | 96.1 | 94.9 | 100 | 94.7 |
| 1_113_578 | 98.5 | 100 | 98.4 | 96.5 | 100 | 96.3 |
| 1_126_567_578 | 98.5 | 100 | 98.4 | 97.5 | 100 | 97.4 |
| 1_19_113_578 | 99.2 | 100 | 99.2 | 99.0 | 100 | 98.9 |
| 31_126_561_578 | 97.5 | 94.1 | 97.6 | 97.5 | 100 | 97.4 |
| 1_126_160_578 | 98.7 | 100 | 98.7 | 97.0 | 100 | 96.8 |
| 1_113_125_578 | 98.7 | 100 | 98.7 | 98.5 | 100 | 98.4 |

INDUSTRIAL APPLICABILITY

According to the present invention, lung cancer can be effectively detected by a simple and inexpensive method. This permits early detection, diagnosis and treatment of lung cancer. The method of the present invention can detect lung cancer with limited invasiveness using the blood of a patient and therefore allows lung cancer to be detected conveniently and rapidly.

All publications, patents, and patent applications cited herein are incorporated herein by reference in their entirety.

The invention claimed is:

1. A method for detecting lung cancer in a human subject, comprising:
   measuring an expression level of hsa-miR-3679-5p in a blood, serum, or plasma sample from the subject;
   comparing the measured expression level of hsa-miR-3679-5p to a control expression level for a healthy subject;
   detecting an increased level of hsa-miR-3679-5p in the sample from the subject as compared to the control expression level;
   wherein the increased level of hsa-miR-3679-5p indicates that the subject has lung cancer; and
   wherein the method further comprises treating the subject for the lung cancer or performing a diagnostic procedure on the subject with the lung cancer;
   wherein the treating comprises surgery, radiotherapy, chemotherapy, or a combination thereof; and
   wherein the diagnostic procedure comprises chest X-ray examination or diagnostic imaging of the lung of the human subject.

2. The method according to claim 1, comprising performing the diagnostic procedure on the subject.

3. The method according to claim 1, wherein the expression level of hsa-miR-3679-5p in the sample is measured by using a device comprising a nucleic acid(s) that specifically binds to hsa-miR-3679-5p.

4. The method according to claim 3, wherein the device further comprises at least one nucleic acid capable of specifically binding to at least one polynucleotide selected from the group consisting of other lung cancer markers of miR-19b-3p, miR-1228-5p, and miR-1307-3p, miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p miR-4655-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

5. The method according to claim 1, wherein the expression level of hsa-miR-3679-5p in the sample is measured by using a kit comprising a nucleic acid(s) that specifically bind to hsa-miR-3679-5p.

6. The method according to claim 5, wherein the kit further comprises at least one nucleic acid capable of specifically binding to at least one polynucleotide selected from the group consisting of other lung cancer markers of miR-19b-3p, miR-1228-5p, and miR-1307-3p, miR-4271, miR-642b-3p, miR-6075, miR-6125, miR-887-3p, miR-6851-5p, miR-6763-5p, miR-3928-3p, miR-4443, miR-3648, miR-149-3p, miR-4689, miR-4763-3p, miR-6729-5p, miR-3196, miR-8069, miR-1268a, miR-4739, miR-1268b, miR-5698, miR-6752-5p, miR-4507, miR-564, miR-4497, miR-6877-5p, miR-6087, miR-4731-5p, miR-615-5p, miR-760, miR-6891-5p, miR-6887-5p, miR-4525, miR-1914-3p, miR-619-5p, miR-5001-5p, miR-6722-3p, miR-3621, miR-4298, miR-675-5p, miR-4655-5p, miR-6836-3p, miR-6782-5p, miR-3663-3p, miR-1908-3p, miR-6726-5p, miR-4258, miR-1343-3p, miR-4516, miR-6875-5p, miR-4651, miR-6825-5p, miR-6840-3p, miR-6780b-5p, miR-6749-5p, miR-8063, miR-6784-5p, miR-3184-5p, miR-663b, miR-6880-5p, miR-1908-5p, miR-92a-2-5p, miR-7975, miR-7110-5p, miR-6842-5p, miR-6857-5p, miR-5572, miR-3197, miR-6131, miR-6889-5p, miR-4454, miR-1199-5p, miR-1247-3p, miR-6800-5p, miR-6872-3p, miR-4649-5p, miR-6791-5p, miR-4433b-3p, miR-3135b, miR-128-2-5p, miR-4675, miR-4472, miR-6785-5p, miR-6741-5p, miR-7977, miR-3665, miR-128-1-5p, miR-4286, miR-6765-3p, miR-4632-5p, miR-365a-5p, miR-6088, miR-6816-5p, miR-6885-5p, miR-711, miR-6765-5p, miR-3180, miR-4442, miR-4792, miR-6721-5p, miR-6798-5p, miR-3162-5p, miR-6126, miR-4758-5p, miR-2392, miR-486-3p, miR-6727-5p, miR-4728-5p, miR-6746-5p, miR-4270, miR-3940-5p, miR-4725-3p, miR-7108-5p, miR-3656, miR-6879-5p, miR-6738-5p, miR-1260a, miR-4446-3p, miR-3131, miR-4463, miR-3185, miR-6870-5p, miR-6779-5p, miR-1273g-3p, miR-8059, miR-4697-5p, miR-4674, miR-4433-3p, miR-4257, miR-1915-5p, miR-4417, miR-1343-5p, miR-6781-5p, miR-4695-5p, miR-1237-5p, miR-6775-5p, miR-7845-5p, miR-4746-3p, miR-7641, miR-7847-3p, miR-6806-5p, miR-4467, miR-4726-5p, miR-4648, miR-6089, miR-1260b, miR-4532, miR-5195-3p, miR-3188, miR-6848-5p, miR-1233-5p, miR-6717-5p, miR-3195, miR-6757-5p, miR-8072, miR-4745-5p, miR-6511a-5p, miR-6776-5p, miR-371a-5p, miR-1227-5p, miR-7150, miR-1915-3p, miR-187-5p, miR-614, miR-1225-5p, miR-451a, miR-939-5p, miR-223-3p, miR-125a-3p, miR-92b-5p, miR-22-3p, miR-6073, miR-6845-5p, miR-6769b-5p, miR-4665-3p, miR-1913, miR-1228-3p, miR-940, miR-296-3p, miR-4690-5p, miR-548q, miR-663a, miR-1249, miR-1202, miR-7113-3p, miR-1225-3p, miR-4783-3p, miR-4448 and miR-4534.

* * * * *

SEQUENCE LISTING

```
<160> NUMBER OF SEQ ID NOS: 618

<210> SEQ ID NO 1
<211> LENGTH: 23
<212> TYPE: RNA
<213> ORGANISM: Homo sapiens

<400> SEQUENCE: 1
cacacaggaa aagcggggcc cug                                        23
```

```
<210> SEQ ID NO 2
<211> LENGTH: 21
<212> TYPE: RNA
<213> ORGANISM: Homo sapiens

<400> SEQUENCE: 2
augccucccc cggccccgca g                                              21

<210> SEQ ID NO 3
<211> LENGTH: 25
<212> TYPE: RNA
<213> ORGANISM: Homo sapiens

<400> SEQUENCE: 3 uaggggugggg ggaauucagg ggugu                                         25

<210> SEQ ID NO 4
<211> LENGTH: 23
<212> TYPE: RNA
<213> ORGANISM: Homo sapiens

<400> SEQUENCE: 4
ugagcaccac acaggccggg cgc                                            23

<210> SEQ ID NO 5
<211> LENGTH: 21
<212> TYPE: RNA
<213> ORGANISM: Homo sapiens

<400> SEQUENCE: 5
ccggccgccg gcuccgcccc g                                              21

<210> SEQ ID NO 6
<211> LENGTH: 21
<212> TYPE: RNA
<213> ORGANISM: Homo sapiens

<400> SEQUENCE: 6
cgggagcugg ggucugcagg u                                              21

<210> SEQ ID NO 7
<211> LENGTH: 17
<212> TYPE: RNA
<213> ORGANISM: Homo sapiens

<400> SEQUENCE: 7
ccccgccacc gccuugg                                                   17

<210> SEQ ID NO 8
<211> LENGTH: 22
<212> TYPE: RNA
<213> ORGANISM: Homo sapiens

<400> SEQUENCE: 8
cuccuggggc ccgcacucuc gc                                             22

<210> SEQ ID NO 9
<211> LENGTH: 17
<212> TYPE: RNA
<213> ORGANISM: Homo sapiens

<400> SEQUENCE: 9
gggagaaggg ucggggc                                                   17
```

```
<210> SEQ ID NO 10
<211> LENGTH: 21
<212> TYPE: RNA
<213> ORGANISM: Homo sapiens

<400> SEQUENCE: 10
ugagggaccc aggacaggag a                                              21

<210> SEQ ID NO 11
<211> LENGTH: 20
<212> TYPE: RNA
<213> ORGANISM: Homo sapiens

<400> SEQUENCE: 11
cggggugggu gaggucgggc                                                20

<210> SEQ ID NO 12
<211> LENGTH: 22
<212> TYPE: RNA
<213> ORGANISM: Homo sapiens

<400> SEQUENCE: 12
uggggaggug uggagucagc au                                             22

<210> SEQ ID NO 13
<211> LENGTH: 22
<212> TYPE: RNA
<213> ORGANISM: Homo sapiens

<400> SEQUENCE: 13
gcccaggacu uugugcgggg ug                                             22

<210> SEQ ID NO 14
<211> LENGTH: 23
<212> TYPE: RNA
<213> ORGANISM: Homo sapiens

<400> SEQUENCE: 14
uggggaaggc uuggcaggga aga                                            23

<210> SEQ ID NO 15
<211> LENGTH: 22
<212> TYPE: RNA
<213> ORGANISM: Homo sapiens

<400> SEQUENCE: 15
ucgggccugg gguuggggga gc                                             22

<210> SEQ ID NO 16
<211> LENGTH: 22
<212> TYPE: RNA
<213> ORGANISM: Homo sapiens

<400> SEQUENCE: 16
ucaaaaucag gagucgggc uu                                              22

<210> SEQ ID NO 17
<211> LENGTH: 20
<212> TYPE: RNA
<213> ORGANISM: Homo sapiens

<400> SEQUENCE: 17
```

```
gccgggcuu ugggugaggg                                                   20

<210> SEQ ID NO 18
<211> LENGTH: 23
<212> TYPE: RNA
<213> ORGANISM: Homo sapiens

<400> SEQUENCE: 18
ugaggauaug gcagggaagg gga                                              23

<210> SEQ ID NO 19
<211> LENGTH: 24
<212> TYPE: RNA
<213> ORGANISM: Homo sapiens

<400> SEQUENCE: 19 ugagggccu cagaccgagc uuuu                                              24

<210> SEQ ID NO 20
<211> LENGTH: 22
<212> TYPE: RNA
<213> ORGANISM: Homo sapiens

<400> SEQUENCE: 20
gguggcccgg ccgugccuga gg                                               22

<210> SEQ ID NO 21
<211> LENGTH: 22
<212> TYPE: RNA
<213> ORGANISM: Homo sapiens

<400> SEQUENCE: 21
ugguggagga agagggcagc uc                                               22

<210> SEQ ID NO 22
<211> LENGTH: 21
<212> TYPE: RNA
<213> ORGANISM: Homo sapiens

<400> SEQUENCE: 22
cggcggggac ggcgauuggu c                                                21

<210> SEQ ID NO 23
<211> LENGTH: 22
<212> TYPE: RNA
<213> ORGANISM: Homo sapiens

<400> SEQUENCE: 23 gggugggau uuguugcauu ac                                                22

<210> SEQ ID NO 24
<211> LENGTH: 18
<212> TYPE: RNA
<213> ORGANISM: Homo sapiens

<400> SEQUENCE: 24
auccuaguca cggcacca                                                    18

<210> SEQ ID NO 25
<211> LENGTH: 21
<212> TYPE: RNA
<213> ORGANISM: Homo sapiens

<400> SEQUENCE: 25
```

```
ugggggugug gggagagaga g                                          21

<210> SEQ ID NO 26
<211> LENGTH: 22
<212> TYPE: RNA
<213> ORGANISM: Homo sapiens

<400> SEQUENCE: 26
uggggguggu cucuagccaa gg                                         22

<210> SEQ ID NO 27
<211> LENGTH: 22
<212> TYPE: RNA
<213> ORGANISM: Homo sapiens

<400> SEQUENCE: 27
uuggggauug ggucaggcca gu                                         22

<210> SEQ ID NO 28
<211> LENGTH: 21
<212> TYPE: RNA
<213> ORGANISM: Homo sapiens

<400> SEQUENCE: 28
guuggggugc aggggucugc u                                          21

<210> SEQ ID NO 29
<211> LENGTH: 23
<212> TYPE: RNA
<213> ORGANISM: Homo sapiens

<400> SEQUENCE: 29
ggaggcgcag gcucggaaag gcg                                        23

<210> SEQ ID NO 30
<211> LENGTH: 19
<212> TYPE: RNA
<213> ORGANISM: Homo sapiens

<400> SEQUENCE: 30
ggcuggucag augggagug                                             19

<210> SEQ ID NO 31
<211> LENGTH: 23
<212> TYPE: RNA
<213> ORGANISM: Homo sapiens

<400> SEQUENCE: 31
ucggggaguc uggggccgg aau                                         23

<210> SEQ ID NO 32
<211> LENGTH: 20
<212> TYPE: RNA
<213> ORGANISM: Homo sapiens

<400> SEQUENCE: 32
ggauccgagu cacggcacca                                            20

<210> SEQ ID NO 33
<211> LENGTH: 20
<212> TYPE: RNA
<213> ORGANISM: Homo sapiens
```

```
<400> SEQUENCE: 33
ccugagcccg ggccgcgcag                                               20

<210> SEQ ID NO 34
<211> LENGTH: 24
<212> TYPE: RNA
<213> ORGANISM: Homo sapiens

<400> SEQUENCE: 34
ccccgggaac gucgagacug gagc                                          24

<210> SEQ ID NO 35
<211> LENGTH: 21
<212> TYPE: RNA
<213> ORGANISM: Homo sapiens

<400> SEQUENCE: 35
guaggugaca gucaggggcg g                                             21

<210> SEQ ID NO 36
<211> LENGTH: 21
<212> TYPE: RNA
<213> ORGANISM: Homo sapiens

<400> SEQUENCE: 36
cccaugccuc cugccgcggu c                                             21

<210> SEQ ID NO 37
<211> LENGTH: 24
<212> TYPE: RNA
<213> ORGANISM: Homo sapiens

<400> SEQUENCE: 37
ugggcgaggg gugggcucuc agag                                          24

<210> SEQ ID NO 38
<211> LENGTH: 22
<212> TYPE: RNA
<213> ORGANISM: Homo sapiens

<400> SEQUENCE: 38
ccccuggggc ugggcaggcg ga                                            22

<210> SEQ ID NO 39
<211> LENGTH: 21
<212> TYPE: RNA
<213> ORGANISM: Homo sapiens

<400> SEQUENCE: 39
caggaguggg ggugggacg u                                              21

<210> SEQ ID NO 40
<211> LENGTH: 22
<212> TYPE: RNA
<213> ORGANISM: Homo sapiens

<400> SEQUENCE: 40
ggcuggagcg agugcagugg ug                                            22

<210> SEQ ID NO 41
<211> LENGTH: 23
<212> TYPE: RNA
<213> ORGANISM: Homo sapiens
```

-continued

```
<400> SEQUENCE: 41
gggggccgau acacuguacg aga                                           23

<210> SEQ ID NO 42
<211> LENGTH: 22
<212> TYPE: RNA
<213> ORGANISM: Homo sapiens

<400> SEQUENCE: 42
ggggcuguga uugaccagca gg                                            22

<210> SEQ ID NO 43
<211> LENGTH: 18
<212> TYPE: RNA
<213> ORGANISM: Homo sapiens

<400> SEQUENCE: 43 ggugggggu guuguuuu                                                  18

<210> SEQ ID NO 44
<211> LENGTH: 22
<212> TYPE: RNA
<213> ORGANISM: Homo sapiens

<400> SEQUENCE: 44
ugggagggcg uggaugaugg ug                                            22

<210> SEQ ID NO 45
<211> LENGTH: 22
<212> TYPE: RNA
<213> ORGANISM: Homo sapiens

<400> SEQUENCE: 45
gugggugcug gugggagccg ug                                            22

<210> SEQ ID NO 46
<211> LENGTH: 18
<212> TYPE: RNA
<213> ORGANISM: Homo sapiens

<400> SEQUENCE: 46
uucccagcca acgcacca                                                 18

<210> SEQ ID NO 47
<211> LENGTH: 18
<212> TYPE: RNA
<213> ORGANISM: Homo sapiens

<400> SEQUENCE: 47
agcaggugcg gggcggcg                                                 18

<210> SEQ ID NO 48
<211> LENGTH: 23
<212> TYPE: RNA
<213> ORGANISM: Homo sapiens

<400> SEQUENCE: 48
cggggccgua gcacugucug aga                                           23

<210> SEQ ID NO 49
<211> LENGTH: 17
<212> TYPE: RNA
```

```
<213> ORGANISM: Homo sapiens

<400> SEQUENCE: 49
accccacucc ugguacc                                          17

<210> SEQ ID NO 50
<211> LENGTH: 21
<212> TYPE: RNA
<213> ORGANISM: Homo sapiens

<400> SEQUENCE: 50
ucaccuggcu ggcccgccca g                                     21

<210> SEQ ID NO 51
<211> LENGTH: 23
<212> TYPE: RNA
<213> ORGANISM: Homo sapiens

<400> SEQUENCE: 51
gagggcagcg ugggugiggc gga                                   23

<210> SEQ ID NO 52
<211> LENGTH: 23
<212> TYPE: RNA
<213> ORGANISM: Homo sapiens

<400> SEQUENCE: 52
agggacuuuu gggggcagau gug                                   23

<210> SEQ ID NO 53
<211> LENGTH: 20
<212> TYPE: RNA
<213> ORGANISM: Homo sapiens

<400> SEQUENCE: 53
agagaugaag cgggggggcg                                       20

<210> SEQ ID NO 54
<211> LENGTH: 21
<212> TYPE: RNA
<213> ORGANISM: Homo sapiens

<400> SEQUENCE: 54
uggggcgggg caggucccug c                                     21

<210> SEQ ID NO 55
<211> LENGTH: 25
<212> TYPE: RNA
<213> ORGANISM: Homo sapiens

<400> SEQUENCE: 55
aggggggcac ugcgcaagca aagcc                                 25

<210> SEQ ID NO 56
<211> LENGTH: 22
<212> TYPE: RNA
<213> ORGANISM: Homo sapiens

<400> SEQUENCE: 56
gggacccagg gagagacgua ag                                    22

<210> SEQ ID NO 57
<211> LENGTH: 25
```

<212> TYPE: RNA
<213> ORGANISM: Homo sapiens

<400> SEQUENCE: 57
gugaggcggg gccaggaggg ugugu					25

<210> SEQ ID NO 58
<211> LENGTH: 19
<212> TYPE: RNA
<213> ORGANISM: Homo sapiens

<400> SEQUENCE: 58
uggggcggag cuuccggag					19

<210> SEQ ID NO 59
<211> LENGTH: 17
<212> TYPE: RNA
<213> ORGANISM: Homo sapiens

<400> SEQUENCE: 59
gccggacaag agggagg					17

<210> SEQ ID NO 60
<211> LENGTH: 18
<212> TYPE: RNA
<213> ORGANISM: Homo sapiens

<400> SEQUENCE: 60
cggugagcgc ucgcuggc					18

<210> SEQ ID NO 61
<211> LENGTH: 23
<212> TYPE: RNA
<213> ORGANISM: Homo sapiens

<400> SEQUENCE: 61
ugggcagggg cuuauuguag gag					23

<210> SEQ ID NO 62
<211> LENGTH: 23
<212> TYPE: RNA
<213> ORGANISM: Homo sapiens

<400> SEQUENCE: 62 ccaggggau gggcgagcuu ggg					23

<210> SEQ ID NO 63
<211> LENGTH: 23
<212> TYPE: RNA
<213> ORGANISM: Homo sapiens

<400> SEQUENCE: 63
uuagggagua gaagguggg gag					23

<210> SEQ ID NO 64
<211> LENGTH: 18
<212> TYPE: RNA
<213> ORGANISM: Homo sapiens

<400> SEQUENCE: 64
gugaaggccc ggcggaga					18

<210> SEQ ID NO 65

-continued

```
<211> LENGTH: 23
<212> TYPE: RNA
<213> ORGANISM: Homo sapiens

<400> SEQUENCE: 65 gugagugggga gccgguggggg cug                                           23

<210> SEQ ID NO 66
<211> LENGTH: 20
<212> TYPE: RNA
<213> ORGANISM: Homo sapiens

<400> SEQUENCE: 66
uaggaugggg gugagaggug                                                 20

<210> SEQ ID NO 67
<211> LENGTH: 21
<212> TYPE: RNA
<213> ORGANISM: Homo sapiens

<400> SEQUENCE: 67
cggggcagcu caguacagga u                                               21

<210> SEQ ID NO 68
<211> LENGTH: 23
<212> TYPE: RNA
<213> ORGANISM: Homo sapiens

<400> SEQUENCE: 68
cucggggcag gcggcuggga gcg                                             23

<210> SEQ ID NO 69
<211> LENGTH: 23
<212> TYPE: RNA
<213> ORGANISM: Homo sapiens

<400> SEQUENCE: 69
ugggagggga gaggcagcaa gca                                             23

<210> SEQ ID NO 70
<211> LENGTH: 22
<212> TYPE: RNA
<213> ORGANISM: Homo sapiens

<400> SEQUENCE: 70
ccgggagaag gagguggccu gg                                              22

<210> SEQ ID NO 71
<211> LENGTH: 20
<212> TYPE: RNA
<213> ORGANISM: Homo sapiens

<400> SEQUENCE: 71
ucagggaguc aggggagggc                                                 20

<210> SEQ ID NO 72
<211> LENGTH: 20
<212> TYPE: RNA
<213> ORGANISM: Homo sapiens

<400> SEQUENCE: 72
guggguuggg gcgggcucug                                                 20
```

```
<210> SEQ ID NO 73
<211> LENGTH: 22
<212> TYPE: RNA
<213> ORGANISM: Homo sapiens

<400> SEQUENCE: 73 ugggggaaggc gucagugucg gg                                          22

<210> SEQ ID NO 74
<211> LENGTH: 21
<212> TYPE: RNA
<213> ORGANISM: Homo sapiens

<400> SEQUENCE: 74
guguggccgg caggcgggug g                                            21

<210> SEQ ID NO 75
<211> LENGTH: 17
<212> TYPE: RNA
<213> ORGANISM: Homo sapiens

<400> SEQUENCE: 75
ggcgggugcg gggugg                                                  17

<210> SEQ ID NO 76
<211> LENGTH: 22
<212> TYPE: RNA
<213> ORGANISM: Homo sapiens

<400> SEQUENCE: 76
cagggcaggg aaggugggag ag                                           22

<210> SEQ ID NO 77
<211> LENGTH: 23
<212> TYPE: RNA
<213> ORGANISM: Homo sapiens

<400> SEQUENCE: 77
cgagggguag aagagcacag ggg                                          23

<210> SEQ ID NO 78
<211> LENGTH: 18
<212> TYPE: RNA
<213> ORGANISM: Homo sapiens

<400> SEQUENCE: 78
aucccaccuc ugccacca                                                18

<210> SEQ ID NO 79
<211> LENGTH: 22
<212> TYPE: RNA
<213> ORGANISM: Homo sapiens

<400> SEQUENCE: 79
cagggcuggc agugacaugg gu                                           22

<210> SEQ ID NO 80
<211> LENGTH: 23
<212> TYPE: RNA
<213> ORGANISM: Homo sapiens

<400> SEQUENCE: 80
ucgaggacug guggaagggc cuu                                          23
```

```
<210> SEQ ID NO 81
<211> LENGTH: 17
<212> TYPE: RNA
<213> ORGANISM: Homo sapiens

<400> SEQUENCE: 81 gagacuggggg uggggcc                                                17

<210> SEQ ID NO 82
<211> LENGTH: 23
<212> TYPE: RNA
<213> ORGANISM: Homo sapiens

<400> SEQUENCE: 82
agaagaaggc ggucggucug cgg                                          23

<210> SEQ ID NO 83
<211> LENGTH: 19
<212> TYPE: RNA
<213> ORGANISM: Homo sapiens

<400> SEQUENCE: 83 uggggggagau ggggguuga                                              19

<210> SEQ ID NO 84
<211> LENGTH: 21
<212> TYPE: RNA
<213> ORGANISM: Homo sapiens

<400> SEQUENCE: 84 cugggaggggg cuggguuugg c                                           21

<210> SEQ ID NO 85
<211> LENGTH: 21
<212> TYPE: RNA
<213> ORGANISM: Homo sapiens

<400> SEQUENCE: 85
accacugcac uccagccuga g                                            21

<210> SEQ ID NO 86
<211> LENGTH: 22
<212> TYPE: RNA
<213> ORGANISM: Homo sapiens

<400> SEQUENCE: 86
ggggaacugu agaugaaaag gc                                           22

<210> SEQ ID NO 87
<211> LENGTH: 22
<212> TYPE: RNA
<213> ORGANISM: Homo sapiens

<400> SEQUENCE: 87 aggggggcgca gucacugacg ug                                          22

<210> SEQ ID NO 88
<211> LENGTH: 21
<212> TYPE: RNA
<213> ORGANISM: Homo sapiens

<400> SEQUENCE: 88
cugggcucgg gacgcgcggc u                                            21
```

```
<210> SEQ ID NO 89
<211> LENGTH: 21
<212> TYPE: RNA
<213> ORGANISM: Homo sapiens

<400> SEQUENCE: 89
acaggagugg ggugggaca u                                              21

<210> SEQ ID NO 90
<211> LENGTH: 18
<212> TYPE: RNA
<213> ORGANISM: Homo sapiens

<400> SEQUENCE: 90
ccagaggugg ggacugag                                                 18

<210> SEQ ID NO 91
<211> LENGTH: 22
<212> TYPE: RNA
<213> ORGANISM: Homo sapiens

<400> SEQUENCE: 91
accuugccuu gcugcccggg cc                                            22

<210> SEQ ID NO 92
<211> LENGTH: 18
<212> TYPE: RNA
<213> ORGANISM: Homo sapiens

<400> SEQUENCE: 92
ggugggcuuc ccggaggg                                                 18

<210> SEQ ID NO 93
<211> LENGTH: 22
<212> TYPE: RNA
<213> ORGANISM: Homo sapiens

<400> SEQUENCE: 93 ugggggagcgg cccccggguq gg                                           22

<210> SEQ ID NO 94
<211> LENGTH: 21
<212> TYPE: RNA
<213> ORGANISM: Homo sapiens

<400> SEQUENCE: 94
cgggccggag gucaagggcg u                                             21

<210> SEQ ID NO 95
<211> LENGTH: 22
<212> TYPE: RNA
<213> ORGANISM: Homo sapiens

<400> SEQUENCE: 95
caggaggcag ugggcgagca gg                                            22

<210> SEQ ID NO 96
<211> LENGTH: 21
<212> TYPE: RNA
<213> ORGANISM: Homo sapiens

<400> SEQUENCE: 96
``` cggggggcggg gccgaagcgc g                                        21

<210> SEQ ID NO 97
<211> LENGTH: 25
<212> TYPE: RNA
<213> ORGANISM: Homo sapiens

<400> SEQUENCE: 97
ucggggcaug ggggagggag gcugg                                     25

<210> SEQ ID NO 98
<211> LENGTH: 21
<212> TYPE: RNA
<213> ORGANISM: Homo sapiens

<400> SEQUENCE: 98
aagggacagg gagggucgug g                                         21

<210> SEQ ID NO 99
<211> LENGTH: 21
<212> TYPE: RNA
<213> ORGANISM: Homo sapiens

<400> SEQUENCE: 99
agcggugcuc cugcgggccg a                                         21

<210> SEQ ID NO 100
<211> LENGTH: 19
<212> TYPE: RNA
<213> ORGANISM: Homo sapiens

<400> SEQUENCE: 100
uugaucucgg aagcuaagc                                            19

<210> SEQ ID NO 101
<211> LENGTH: 21
<212> TYPE: RNA
<213> ORGANISM: Homo sapiens

<400> SEQUENCE: 101
cguggaggac gaggaggagg c                                         21

<210> SEQ ID NO 102
<211> LENGTH: 24
<212> TYPE: RNA
<213> ORGANISM: Homo sapiens

<400> SEQUENCE: 102
uguaggcaug aggcagggcc cagg                                      24

<210> SEQ ID NO 103
<211> LENGTH: 22
<212> TYPE: RNA
<213> ORGANISM: Homo sapiens

<400> SEQUENCE: 103
uggcggcggu aguuaugggc uu                                        22

<210> SEQ ID NO 104
<211> LENGTH: 23
<212> TYPE: RNA
<213> ORGANISM: Homo sapiens

<400> SEQUENCE: 104

```
agggccagag gagccuggag ugg                                      23

<210> SEQ ID NO 105
<211> LENGTH: 20
<212> TYPE: RNA
<213> ORGANISM: Homo sapiens

<400> SEQUENCE: 105
ugugggacug caaaugggag                                          20

<210> SEQ ID NO 106
<211> LENGTH: 24
<212> TYPE: RNA
<213> ORGANISM: Homo sapiens

<400> SEQUENCE: 106
ggaggccggg gugggcggg gcgg                                      24

<210> SEQ ID NO 107
<211> LENGTH: 19
<212> TYPE: RNA
<213> ORGANISM: Homo sapiens

<400> SEQUENCE: 107
aucccaccac ugccaccau                                           19

<210> SEQ ID NO 108
<211> LENGTH: 17
<212> TYPE: RNA
<213> ORGANISM: Homo sapiens

<400> SEQUENCE: 108
ccccggggag cccggcg                                             17

<210> SEQ ID NO 109
<211> LENGTH: 21
<212> TYPE: RNA
<213> ORGANISM: Homo sapiens

<400> SEQUENCE: 109
auccaguucu cugaggggc u                                         21

<210> SEQ ID NO 110
<211> LENGTH: 23
<212> TYPE: RNA
<213> ORGANISM: Homo sapiens

<400> SEQUENCE: 110
agaggcuuug ugcggauacg ggg                                      23

<210> SEQ ID NO 111
<211> LENGTH: 23
<212> TYPE: RNA
<213> ORGANISM: Homo sapiens

<400> SEQUENCE: 111 uggggcugg gaugggccau ggu                                       23

<210> SEQ ID NO 112
<211> LENGTH: 22
<212> TYPE: RNA
<213> ORGANISM: Homo sapiens
```

```
<400> SEQUENCE: 112
agugggaggc cagggcacgg ca                                                22

<210> SEQ ID NO 113
<211> LENGTH: 22
<212> TYPE: RNA
<213> ORGANISM: Homo sapiens

<400> SEQUENCE: 113
aggcgaugug gggauguaga ga                                                22

<210> SEQ ID NO 114
<211> LENGTH: 17
<212> TYPE: RNA
<213> ORGANISM: Homo sapiens

<400> SEQUENCE: 114
cgcgccgggc ccgggu u                                                     17

<210> SEQ ID NO 115
<211> LENGTH: 22
<212> TYPE: RNA
<213> ORGANISM: Homo sapiens

<400> SEQUENCE: 115
uagggauggg aggccaggau ga                                                22

<210> SEQ ID NO 116
<211> LENGTH: 20
<212> TYPE: RNA
<213> ORGANISM: Homo sapiens

<400> SEQUENCE: 116
ggcggcgggg agguaggcag                                                   20

<210> SEQ ID NO 117
<211> LENGTH: 23
<212> TYPE: RNA
<213> ORGANISM: Homo sapiens

<400> SEQUENCE: 117 ugagugggc ucccgggacg gcg                                                23

<210> SEQ ID NO 118
<211> LENGTH: 23
<212> TYPE: RNA
<213> ORGANISM: Homo sapiens

<400> SEQUENCE: 118
caggcagaag ugggggcugac agg                                              23

<210> SEQ ID NO 119
<211> LENGTH: 19
<212> TYPE: RNA
<213> ORGANISM: Homo sapiens

<400> SEQUENCE: 119
ucugggugca guggggguu                                                    19

<210> SEQ ID NO 120
<211> LENGTH: 20
<212> TYPE: RNA
<213> ORGANISM: Homo sapiens
```

```
<400> SEQUENCE: 120
acucaaacug uggggggcacu                                              20

<210> SEQ ID NO 121
<211> LENGTH: 17
<212> TYPE: RNA
<213> ORGANISM: Homo sapiens

<400> SEQUENCE: 121 gugggggccag gcggugg                                                 17

<210> SEQ ID NO 122
<211> LENGTH: 18
<212> TYPE: RNA
<213> ORGANISM: Homo sapiens

<400> SEQUENCE: 122
cuggcagggg gagaggua                                                 18

<210> SEQ ID NO 123
<211> LENGTH: 20
<212> TYPE: RNA
<213> ORGANISM: Homo sapiens

<400> SEQUENCE: 123
ccccagggcg acgcggcggg                                               20

<210> SEQ ID NO 124
<211> LENGTH: 22
<212> TYPE: RNA
<213> ORGANISM: Homo sapiens

<400> SEQUENCE: 124
ggcuacaaca caggacccgg gc                                            22

<210> SEQ ID NO 125
<211> LENGTH: 23
<212> TYPE: RNA
<213> ORGANISM: Homo sapiens

<400> SEQUENCE: 125
gaacgccugu ucuugccagg ugg                                           23

<210> SEQ ID NO 126
<211> LENGTH: 23
<212> TYPE: RNA
<213> ORGANISM: Homo sapiens

<400> SEQUENCE: 126
ugugcaaauc caugcaaaac uga                                           23

<210> SEQ ID NO 127
<211> LENGTH: 22
<212> TYPE: RNA
<213> ORGANISM: Homo sapiens

<400> SEQUENCE: 127
guggguacgg cccagugggg gg                                            22

<210> SEQ ID NO 128
<211> LENGTH: 22
<212> TYPE: RNA
```

```
<213> ORGANISM: Homo sapiens

<400> SEQUENCE: 128
aaaccguuac cauuacugag uu                                      22

<210> SEQ ID NO 129
<211> LENGTH: 24
<212> TYPE: RNA
<213> ORGANISM: Homo sapiens

<400> SEQUENCE: 129 ugggggagcug aggcucuggg ggug                                   24

<210> SEQ ID NO 130
<211> LENGTH: 22
<212> TYPE: RNA
<213> ORGANISM: Homo sapiens

<400> SEQUENCE: 130
ugucaguuug ucaaauaccc ca                                      22

<210> SEQ ID NO 131
<211> LENGTH: 21
<212> TYPE: RNA
<213> ORGANISM: Homo sapiens

<400> SEQUENCE: 131
gugggcgggg gcaggugugu g                                       21

<210> SEQ ID NO 132
<211> LENGTH: 22
<212> TYPE: RNA
<213> ORGANISM: Homo sapiens

<400> SEQUENCE: 132
acaggugagg uucuugggag cc                                      22

<210> SEQ ID NO 133
<211> LENGTH: 22
<212> TYPE: RNA
<213> ORGANISM: Homo sapiens

<400> SEQUENCE: 133
agggacggga cgcggugcag ug                                      22

<210> SEQ ID NO 134
<211> LENGTH: 22
<212> TYPE: RNA
<213> ORGANISM: Homo sapiens

<400> SEQUENCE: 134
aagcugccag uugaagaacu gu                                      22

<210> SEQ ID NO 135
<211> LENGTH: 19
<212> TYPE: RNA
<213> ORGANISM: Homo sapiens

<400> SEQUENCE: 135
gggggaagaa aaggugggg                                          19

<210> SEQ ID NO 136
<211> LENGTH: 22
```

```
<212> TYPE: RNA
<213> ORGANISM: Homo sapiens

<400> SEQUENCE: 136
agacacauuu ggagagggac cc                                              22

<210> SEQ ID NO 137
<211> LENGTH: 21
<212> TYPE: RNA
<213> ORGANISM: Homo sapiens

<400> SEQUENCE: 137
acggcccagg cggcauuggu g                                               21

<210> SEQ ID NO 138
<211> LENGTH: 20
<212> TYPE: RNA
<213> ORGANISM: Homo sapiens

<400> SEQUENCE: 138
gcggaaggcg gagcggcgga                                                 20

<210> SEQ ID NO 139
<211> LENGTH: 22
<212> TYPE: RNA
<213> ORGANISM: Homo sapiens

<400> SEQUENCE: 139
gugaacgggc gccaucccga gg                                              22

<210> SEQ ID NO 140
<211> LENGTH: 23
<212> TYPE: RNA
<213> ORGANISM: Homo sapiens

<400> SEQUENCE: 140
aggagguggu acuaggggcc agc                                             23

<210> SEQ ID NO 141
<211> LENGTH: 19
<212> TYPE: RNA
<213> ORGANISM: Homo sapiens

<400> SEQUENCE: 141
cuggggagug gcuggggag                                                  19

<210> SEQ ID NO 142
<211> LENGTH: 22
<212> TYPE: RNA
<213> ORGANISM: Homo sapiens

<400> SEQUENCE: 142
ggaggaaccu uggagcuucg gc                                              22

<210> SEQ ID NO 143
<211> LENGTH: 17
<212> TYPE: RNA
<213> ORGANISM: Homo sapiens

<400> SEQUENCE: 143
uuggaggcgu ggguuuu                                                    17

<210> SEQ ID NO 144
```

```
<211> LENGTH: 21
<212> TYPE: RNA
<213> ORGANISM: Homo sapiens

<400> SEQUENCE: 144
agccgcgggg aucgccgagg g                                                   21

<210> SEQ ID NO 145
<211> LENGTH: 21
<212> TYPE: RNA
<213> ORGANISM: Homo sapiens

<400> SEQUENCE: 145
agggagggac gggggcugug c                                                   21

<210> SEQ ID NO 146
<211> LENGTH: 22
<212> TYPE: RNA
<213> ORGANISM: Homo sapiens

<400> SEQUENCE: 146
uugaggagac auggugggggg cc                                                 22

<210> SEQ ID NO 147
<211> LENGTH: 24
<212> TYPE: RNA
<213> ORGANISM: Homo sapiens

<400> SEQUENCE: 147
aggcaggggc uggugcuggg cggg                                                24

<210> SEQ ID NO 148
<211> LENGTH: 22
<212> TYPE: RNA
<213> ORGANISM: Homo sapiens

<400> SEQUENCE: 148
ugggcgaggg cggcugagcg gc                                                  22

<210> SEQ ID NO 149
<211> LENGTH: 18
<212> TYPE: RNA
<213> ORGANISM: Homo sapiens

<400> SEQUENCE: 149
cggggcggca ggggccuc                                                       18

<210> SEQ ID NO 150
<211> LENGTH: 23
<212> TYPE: RNA
<213> ORGANISM: Homo sapiens

<400> SEQUENCE: 150
ggaugguugg gggcggucgg cgu                                                 23

<210> SEQ ID NO 151
<211> LENGTH: 18
<212> TYPE: RNA
<213> ORGANISM: Homo sapiens

<400> SEQUENCE: 151
cgggcguggu gguggggg                                                       18
```

```
<210> SEQ ID NO 152
<211> LENGTH: 25
<212> TYPE: RNA
<213> ORGANISM: Homo sapiens

<400> SEQUENCE: 152
aagggaggag gagcggaggg gcccu                                          25

<210> SEQ ID NO 153
<211> LENGTH: 20
<212> TYPE: RNA
<213> ORGANISM: Homo sapiens

<400> SEQUENCE: 153
cgggcguggu gguggggug                                                 20

<210> SEQ ID NO 154
<211> LENGTH: 22
<212> TYPE: RNA
<213> ORGANISM: Homo sapiens

<400> SEQUENCE: 154 uggggagug cagugauugu gg                                              22

<210> SEQ ID NO 155
<211> LENGTH: 22
<212> TYPE: RNA
<213> ORGANISM: Homo sapiens

<400> SEQUENCE: 155 gggggugug gagccagggg gc                                              22

<210> SEQ ID NO 156
<211> LENGTH: 20
<212> TYPE: RNA
<213> ORGANISM: Homo sapiens

<400> SEQUENCE: 156 cugguuggg cugggcuggg                                                 20

<210> SEQ ID NO 157
<211> LENGTH: 19
<212> TYPE: RNA
<213> ORGANISM: Homo sapiens

<400> SEQUENCE: 157
aggcacggug ucagcaggc                                                 19

<210> SEQ ID NO 158
<211> LENGTH: 17
<212> TYPE: RNA
<213> ORGANISM: Homo sapiens

<400> SEQUENCE: 158
cuccgggacg gcugggc                                                   17

<210> SEQ ID NO 159
<211> LENGTH: 22
<212> TYPE: RNA
<213> ORGANISM: Homo sapiens

<400> SEQUENCE: 159
agggccgaag gguggaagcu gc                                             22
```

```
<210> SEQ ID NO 160
<211> LENGTH: 18
<212> TYPE: RNA
<213> ORGANISM: Homo sapiens

<400> SEQUENCE: 160
ugaggcgggg gggcgagc                                                 18

<210> SEQ ID NO 161
<211> LENGTH: 22
<212> TYPE: RNA
<213> ORGANISM: Homo sapiens

<400> SEQUENCE: 161 ugcuggggc cacaugagug ug                                             22

<210> SEQ ID NO 162
<211> LENGTH: 22
<212> TYPE: RNA
<213> ORGANISM: Homo sapiens

<400> SEQUENCE: 162
gggggucccc ggugcucgga uc                                            22

<210> SEQ ID NO 163
<211> LENGTH: 20
<212> TYPE: RNA
<213> ORGANISM: Homo sapiens

<400> SEQUENCE: 163
cggcucuggg ucugugggga                                               20

<210> SEQ ID NO 164
<211> LENGTH: 19
<212> TYPE: RNA
<213> ORGANISM: Homo sapiens

<400> SEQUENCE: 164
uaaggagggg gaugagggg                                                19

<210> SEQ ID NO 165
<211> LENGTH: 23
<212> TYPE: RNA
<213> ORGANISM: Homo sapiens

<400> SEQUENCE: 165
uggggggaca gauggagagg aca                                           23

<210> SEQ ID NO 166
<211> LENGTH: 21
<212> TYPE: RNA
<213> ORGANISM: Homo sapiens

<400> SEQUENCE: 166 gggggaugu gcaugcuggu u                                              21

<210> SEQ ID NO 167
<211> LENGTH: 22
<212> TYPE: RNA
<213> ORGANISM: Homo sapiens

<400> SEQUENCE: 167
ggaggggucc cgcacuggga gg                                            22
```

<210> SEQ ID NO 168
<211> LENGTH: 22
<212> TYPE: RNA
<213> ORGANISM: Homo sapiens

<400> SEQUENCE: 168
gcugggauua caggcaugag cc                                              22

<210> SEQ ID NO 169
<211> LENGTH: 24
<212> TYPE: RNA
<213> ORGANISM: Homo sapiens

<400> SEQUENCE: 169
agggcuggac ucagcggcgg agcu                                            24

<210> SEQ ID NO 170
<211> LENGTH: 22
<212> TYPE: RNA
<213> ORGANISM: Homo sapiens

<400> SEQUENCE: 170
ugcagggguc gggugggcca gg                                              22

<210> SEQ ID NO 171
<211> LENGTH: 20
<212> TYPE: RNA
<213> ORGANISM: Homo sapiens

<400> SEQUENCE: 171
cgcgggucgg ggucugcagg                                                 20

<210> SEQ ID NO 172
<211> LENGTH: 22
<212> TYPE: RNA
<213> ORGANISM: Homo sapiens

<400> SEQUENCE: 172
cugggacagg aggaggaggc ag                                              22

<210> SEQ ID NO 173
<211> LENGTH: 23
<212> TYPE: RNA
<213> ORGANISM: Homo sapiens

<400> SEQUENCE: 173
uggugcggag agggcccaca gug                                             23

<210> SEQ ID NO 174
<211> LENGTH: 22
<212> TYPE: RNA
<213> ORGANISM: Homo sapiens

<400> SEQUENCE: 174
caccggggau ggcagagggu cg                                              22

<210> SEQ ID NO 175
<211> LENGTH: 72
<212> TYPE: RNA
<213> ORGANISM: Homo sapiens

<400> SEQUENCE: 175

```
ccaggcacac aggaaaagcg gggcccuggg uucggcugcu accccaaagg ccacauucuc    60
cugugcacac ag                                                       72

<210> SEQ ID NO 176
<211> LENGTH: 63
<212> TYPE: RNA
<213> ORGANISM: Homo sapiens

<400> SEQUENCE: 176
ggcuccgcag ggcccuggcg caggcaucca gacagcgggc gaaugccucc cccggccccg    60
cag                                                                 63

<210> SEQ ID NO 177
<211> LENGTH: 69
<212> TYPE: RNA
<213> ORGANISM: Homo sapiens

<400> SEQUENCE: 177 uggguaggg gugggggaau ucaggggugu cgaacucaug gcugccaccu uugucccc       60 auccugcag                                                           69

<210> SEQ ID NO 178
<211> LENGTH: 97
<212> TYPE: RNA
<213> ORGANISM: Homo sapiens

<400> SEQUENCE: 178
cccgggaccu ugguccaggc gcuggucugc guggugcucg gguggauaag ucgaucuga    60 gcaccacaca ggccgggcgc cgggaccaag ggggcuc                            97

<210> SEQ ID NO 179
<211> LENGTH: 80
<212> TYPE: RNA
<213> ORGANISM: Homo sapiens

<400> SEQUENCE: 179
cgggaaugcc gcggcgggga cggcgauugg uccguaugug uggugccacc ggccgccggc    60
uccgccccgg ccccgccccc                                               80

<210> SEQ ID NO 180
<211> LENGTH: 61
<212> TYPE: RNA
<213> ORGANISM: Homo sapiens

<400> SEQUENCE: 180
gggggcggga gcugggucu gcagguucgc acugaugccu gcucgcccug ucccgcua      60 g                                                                   61

<210> SEQ ID NO 181
<211> LENGTH: 91
<212> TYPE: RNA
<213> ORGANISM: Homo sapiens

<400> SEQUENCE: 181
acgccccccg ccccgccacc gccuuggagg cugaccucuu acuuucgguc ggucuucuuc    60
ccugggcuug guuuggggc gggggagugu c                                   91

<210> SEQ ID NO 182
<211> LENGTH: 84
```

```
<212> TYPE: RNA
<213> ORGANISM: Homo sapiens

<400> SEQUENCE: 182
gcuggcgucg gugcuggggga gcggcccccg ggugggccuc ugcucuggcc ccuccugggg    60
cccgcacucu cgcucugggc ccgc                                           84

<210> SEQ ID NO 183
<211> LENGTH: 86
<212> TYPE: RNA
<213> ORGANISM: Homo sapiens

<400> SEQUENCE: 183
agggagaagg gucgggcag ggagggcagg gcaggcucug ggugggggg ucugugaguc       60 agccacggcu cugcccacgu cucccc                                         86

<210> SEQ ID NO 184
<211> LENGTH: 72
<212> TYPE: RNA
<213> ORGANISM: Homo sapiens

<400> SEQUENCE: 184
gagucugagg gacccaggac aggagaaggc cuauggugau uugcauucuu ccugcccugg     60
cuccauccuc ag                                                        72

<210> SEQ ID NO 185
<211> LENGTH: 73
<212> TYPE: RNA
<213> ORGANISM: Homo sapiens

<400> SEQUENCE: 185
cggcgacggc gggugggug aggucgggcc ccaagacucg ggguugccg ggcgccucag       60 uucaccgcgg ccg                                                       73

<210> SEQ ID NO 186
<211> LENGTH: 66
<212> TYPE: RNA
<213> ORGANISM: Homo sapiens

<400> SEQUENCE: 186
gggcaugggg aguguggag ucagcauggg gcuaggaggc cccgcgcuga cccgccuucu      60
ccgcag                                                               66

<210> SEQ ID NO 187
<211> LENGTH: 71
<212> TYPE: RNA
<213> ORGANISM: Homo sapiens

<400> SEQUENCE: 187
ugaccacccc cggcaaaga ccugcagauc cccguuaga gacgggccca ggacuuugug       60
cggggugccc a                                                         71

<210> SEQ ID NO 188
<211> LENGTH: 79
<212> TYPE: RNA
<213> ORGANISM: Homo sapiens

<400> SEQUENCE: 188
cagccugggg aaggcuuggc agggaagaca caugagcagu gccuccacuu cacgccucuc     60
``` ccugucucc uuucccuag                                            79

<210> SEQ ID NO 189
<211> LENGTH: 69
<212> TYPE: RNA
<213> ORGANISM: Homo sapiens

<400> SEQUENCE: 189
ggcccucggg ccuggggung ggggagcucu guccugucuc acucauugcu ccuccccugc    60
cuggcccag                                                     69

<210> SEQ ID NO 190
<211> LENGTH: 81
<212> TYPE: RNA
<213> ORGANISM: Homo sapiens

<400> SEQUENCE: 190
uagaggcagu uucaacagau guguagacuu uugauaugag aaauugguuu caaaaucagg    60
agucggggcu uuacugcuuu u                                       81

<210> SEQ ID NO 191
<211> LENGTH: 67
<212> TYPE: RNA
<213> ORGANISM: Homo sapiens

<400> SEQUENCE: 191
uacaggccgg ggcuuugggu gagggacccc cggagucugu cacggucuca ccccaacucu    60
gccccag                                                       67

<210> SEQ ID NO 192
<211> LENGTH: 68
<212> TYPE: RNA
<213> ORGANISM: Homo sapiens

<400> SEQUENCE: 192
cguggugagg auauggcagg gaaggggagu uucccucuau uccuucccc ccaguaaucu     60 ucaucaug                                                      68

<210> SEQ ID NO 193
<211> LENGTH: 75
<212> TYPE: RNA
<213> ORGANISM: Homo sapiens

<400> SEQUENCE: 193
aagcaagacu gagggggccuc agaccgagcu uuuggaaaau agaaaagucu cgcucucugc    60
cccucagccu aacuu                                              75

<210> SEQ ID NO 194
<211> LENGTH: 115
<212> TYPE: RNA
<213> ORGANISM: Homo sapiens

<400> SEQUENCE: 194
ggugccgagg gccguccggc auccuaggcg ggucgcugcg guaccucccu ccugucugug    60 gcgguggau cccguggccg uguuuuccug guggcccggc cgugccugag guuuc         115

<210> SEQ ID NO 195
<211> LENGTH: 62
<212> TYPE: RNA
<213> ORGANISM: Homo sapiens

```
<400> SEQUENCE: 195 gagggugguug gaggaagagg gcagcuccca ugacugccug accgccuucu cuccuccccc    60
ag                                                                    62

<210> SEQ ID NO 196
<211> LENGTH: 75
<212> TYPE: RNA
<213> ORGANISM: Homo sapiens

<400> SEQUENCE: 196
ucaucccugg gugggauuuu guugcauuac uuguguucua auaaaguau ugcacuuguc      60 ccggccugug gaaga                                                      75

<210> SEQ ID NO 197
<211> LENGTH: 68
<212> TYPE: RNA
<213> ORGANISM: Homo sapiens

<400> SEQUENCE: 197
gugcaaagag caggaggaca ggggauuuau cucccaaggg aggucccug auccaguca       60 cggcacca                                                              68

<210> SEQ ID NO 198
<211> LENGTH: 86
<212> TYPE: RNA
<213> ORGANISM: Homo sapiens

<400> SEQUENCE: 198
ggggcugggg guguggggag agagagugca cagccagcuc agggauuaaa gcucuuucuc     60
ucucucucuc ucccacuucc cugcag                                          86

<210> SEQ ID NO 199
<211> LENGTH: 65
<212> TYPE: RNA
<213> ORGANISM: Homo sapiens

<400> SEQUENCE: 199
agcccugggg guggucucua gccaaggcuc uggggucuca cccuuggcug gucucugcuc     60
cgcag                                                                 65

<210> SEQ ID NO 200
<211> LENGTH: 93
<212> TYPE: RNA
<213> ORGANISM: Homo sapiens

<400> SEQUENCE: 200
gcuuguuggg gauuggguca ggccaguguu caagggcccc uccucuagua cucccuguuu     60
guguucugcc acugacugag cuucucccca cag                                  93

<210> SEQ ID NO 201
<211> LENGTH: 137
<212> TYPE: RNA
<213> ORGANISM: Homo sapiens

<400> SEQUENCE: 201
agccagacaa gagggucaug gggagucacu gucaacccag agcaggcacu gccccugcga     60
ccagccuggg gcaucgguug gggugcaggg gucugcuggu gaugcuuucc aucucuuugc    120
```

```
uuguccuga uuguagc                                                      137

<210> SEQ ID NO 202
<211> LENGTH: 73
<212> TYPE: RNA
<213> ORGANISM: Homo sapiens

<400> SEQUENCE: 202
ggcgagggga ggcgcaggcu cggaaaggcg cgcgaggcuc caggcuccuu cccgauccac      60
cgcucuccuc gcu                                                         73

<210> SEQ ID NO 203
<211> LENGTH: 109
<212> TYPE: RNA
<213> ORGANISM: Homo sapiens

<400> SEQUENCE: 203
ucccgcauuc ccucugcuuu ggucaggugg ugcccuccuu ccauggguag agccagagau      60
gguggguucu ggcuggucag augggagugg acagagaccc gggguccuc                 109

<210> SEQ ID NO 204
<211> LENGTH: 59
<212> TYPE: RNA
<213> ORGANISM: Homo sapiens

<400> SEQUENCE: 204
cugugucggg gagucugggg uccggaauuc uccagagccu cugugcccu acuucccag        59

<210> SEQ ID NO 205
<211> LENGTH: 55
<212> TYPE: RNA
<213> ORGANISM: Homo sapiens

<400> SEQUENCE: 205
ccggauccga gucacggcac caaauuucau gcguguccgu gugaagagac cacca           55

<210> SEQ ID NO 206
<211> LENGTH: 119
<212> TYPE: RNA
<213> ORGANISM: Homo sapiens

<400> SEQUENCE: 206
agccugcgcc ggagccgggg ccugagcccg ggccgcgcag gccgugaacu cgucgagcug      60
cgcgugcggc cggugcucaa ccugccgggu ccuggccccg cgucccgcg cgcccugga      119

<210> SEQ ID NO 207
<211> LENGTH: 136
<212> TYPE: RNA
<213> ORGANISM: Homo sapiens

<400> SEQUENCE: 207
ccgcuugccu cgcccagcgc agccccggcc gcugggcgca cccgucccgu ucgucccgg       60 acguugcucu cuaccccggg aacgucgaga cuggagcgcc cgaacugagc caccuucgcg    120
gaccccgaga gcggcg                                                    136

<210> SEQ ID NO 208
<211> LENGTH: 82
<212> TYPE: RNA
<213> ORGANISM: Homo sapiens

<400> SEQUENCE: 208
```

```
accuguaggu gacagucagg ggcggggugu gguggggcug ggcuggccc ccuccucaca    60 ccucccugg caucgccccc ag                                             82

<210> SEQ ID NO 209
<211> LENGTH: 62
<212> TYPE: RNA
<213> ORGANISM: Homo sapiens

<400> SEQUENCE: 209
gugggucucg caucaggagg caaggccagg acccgcugac ccaugccucc ugccgcgguc   60
ag                                                                  62

<210> SEQ ID NO 210
<211> LENGTH: 64
<212> TYPE: RNA
<213> ORGANISM: Homo sapiens

<400> SEQUENCE: 210
ucugggcgag gguggggcuc ucagagggc uggcaguacu gcucugaggc cugccucucc    60
ccag                                                                64

<210> SEQ ID NO 211
<211> LENGTH: 67
<212> TYPE: RNA
<213> ORGANISM: Homo sapiens

<400> SEQUENCE: 211
ccagaccccu ggggcugggc aggcggaaag aggucugaac ugccucugcc uccuuggucu   60
ccggcag                                                             67

<210> SEQ ID NO 212
<211> LENGTH: 102
<212> TYPE: RNA
<213> ORGANISM: Homo sapiens

<400> SEQUENCE: 212
uguguccccu auccuccuua uguccaccc ccacuccugu uugaauauuu caccagaaac    60 aggaguggg ggugggacgu aaggaggaug ggggaaagaa ca                      102

<210> SEQ ID NO 213
<211> LENGTH: 68
<212> TYPE: RNA
<213> ORGANISM: Homo sapiens

<400> SEQUENCE: 213
ugcccaggcu ggagcgagug cagguggca gucagucccua gcucacugca gccucgaacu   60
ccugggcu                                                            68

<210> SEQ ID NO 214
<211> LENGTH: 84
<212> TYPE: RNA
<213> ORGANISM: Homo sapiens

<400> SEQUENCE: 214
ugugcagugg gaaggggggc cgauacacug uacgagagug aguagcaggu cucacaguga   60
accggucucu uucccuacug uguc                                          84

<210> SEQ ID NO 215
```

```
<211> LENGTH: 77
<212> TYPE: RNA
<213> ORGANISM: Homo sapiens

<400> SEQUENCE: 215
caugagaaau ccugcugguc aaccauagcc cuggucagac ucuccggggc ugugauugac    60
cagcaggacu ucucaug                                                    77

<210> SEQ ID NO 216
<211> LENGTH: 80
<212> TYPE: RNA
<213> ORGANISM: Homo sapiens

<400> SEQUENCE: 216
uggcagaccc uugcucucuc acucucccua augggggcuga agacagcuca ggggcagggu   60
gggggguguu guuuuuguuu                                                80

<210> SEQ ID NO 217
<211> LENGTH: 67
<212> TYPE: RNA
<213> ORGANISM: Homo sapiens

<400> SEQUENCE: 217 ugguggggu gggggguguu guuuuuguuu uugagacaga gucuugcucc gucgcccagg     60
ccggagu                                                               67

<210> SEQ ID NO 218
<211> LENGTH: 81
<212> TYPE: RNA
<213> ORGANISM: Homo sapiens

<400> SEQUENCE: 218
cucccuggga gggcguggau gaugguggga gaggagcccc acuguggaag ucugaccccc    60
acaucgcccc accuuccccca g                                              81

<210> SEQ ID NO 219
<211> LENGTH: 63
<212> TYPE: RNA
<213> ORGANISM: Homo sapiens

<400> SEQUENCE: 219
aauggguggg ugcuggugggg agccgugccc uggccacuca uucggcucuc ucccucaccc    60
uag                                                                   63

<210> SEQ ID NO 220
<211> LENGTH: 49
<212> TYPE: RNA
<213> ORGANISM: Homo sapiens

<400> SEQUENCE: 220
uucccagcca acgcaccaaa aaugauaugg gucuguuguc uggagaaac                49

<210> SEQ ID NO 221
<211> LENGTH: 105
<212> TYPE: RNA
<213> ORGANISM: Homo sapiens

<400> SEQUENCE: 221
gcgggcggcg gcggcggcag cagcagcagg ugcggggcgg cggccgcgcu ggccgcucga    60
cuccgcagcu gcucguucug cuucuccagc uugcgcacca gcucc                   105
```

```
<210> SEQ ID NO 222
<211> LENGTH: 82
<212> TYPE: RNA
<213> ORGANISM: Homo sapiens

<400> SEQUENCE: 222
ugagcuguug gauucggggc cguagcacug ucugagaggu uuacauuucu cacagugaac    60
cggucucuuu uucagcugcu uc                                            82

<210> SEQ ID NO 223
<211> LENGTH: 93
<212> TYPE: RNA
<213> ORGANISM: Homo sapiens

<400> SEQUENCE: 223
uacuuauggc accccacucc ugguaccaua gucauaaguu aggagauguu agagcuguga    60
guaccaugac uuaagugugg uggcuuaaac aug                                93

<210> SEQ ID NO 224
<211> LENGTH: 87
<212> TYPE: RNA
<213> ORGANISM: Homo sapiens

<400> SEQUENCE: 224
gugaggcggg gccaggaggg uguguggcgu gggugcugcg gggccgucag ggugccugcg    60
ggacgcucac cuggcuggcc cgcccag                                       87

<210> SEQ ID NO 225
<211> LENGTH: 61
<212> TYPE: RNA
<213> ORGANISM: Homo sapiens

<400> SEQUENCE: 225
gagggcagcg ugggugugge ggaggcaggc gugaccguuu gccgcccucu cgcugcucua    60
g                                                                   61

<210> SEQ ID NO 226
<211> LENGTH: 87
<212> TYPE: RNA
<213> ORGANISM: Homo sapiens

<400> SEQUENCE: 226
accgcaggga aaaugaggga cuuuggggg cagaugguu ccauccac uaucauaaug       60 ccccuaaaaa uccuuauugc ucuugca                                       87

<210> SEQ ID NO 227
<211> LENGTH: 51
<212> TYPE: RNA
<213> ORGANISM: Homo sapiens

<400> SEQUENCE: 227
agagaugaag cgggggggcg gggucuugcu cuauugccua cgcugaucuc a            51

<210> SEQ ID NO 228
<211> LENGTH: 66
<212> TYPE: RNA
<213> ORGANISM: Homo sapiens

<400> SEQUENCE: 228
```

```
ccgagugggg cggggcaggu cccugcaggg acugugacac ugaaggaccu gcaccuucgc    60
ccacag                                                              66

<210> SEQ ID NO 229
<211> LENGTH: 66
<212> TYPE: RNA
<213> ORGANISM: Homo sapiens

<400> SEQUENCE: 229
ccuggagggg ggcacugcgc aagcaaagcc agggacccug agaggcuuug cuuccugcuc    60
cccuag                                                              66

<210> SEQ ID NO 230
<211> LENGTH: 76
<212> TYPE: RNA
<213> ORGANISM: Homo sapiens

<400> SEQUENCE: 230
acugacuuug agucucuccu cagggugcug caggcaaagc ugggacccca gggagagacg    60
uaagugaggg gagaug                                                   76

<210> SEQ ID NO 231
<211> LENGTH: 153
<212> TYPE: RNA
<213> ORGANISM: Homo sapiens

<400> SEQUENCE: 231
gcuccgcccc acgucgcaug cgccccggga acgcgugggg cggagcuucc ggaggccccg    60
cucugcugcc gacccugugg agcggagggu gaagccuccg gaugccaguc ccucaucgcu   120
ggccuggucg cgcuguggcg aaggggggcgg agc                               153

<210> SEQ ID NO 232
<211> LENGTH: 153
<212> TYPE: RNA
<213> ORGANISM: Homo sapiens

<400> SEQUENCE: 232
gcuccgcccc acgucgcaug cgccccggga acgcgugggg cggagcuucc ggaggccccg    60
cccugcugcc gacccugugg agcggagggu gaagccuccg gaugccaguc ccucaucgcu   120 gcccggucg cgcuguggcg aaggggggcgg agc                                153

<210> SEQ ID NO 233
<211> LENGTH: 67
<212> TYPE: RNA
<213> ORGANISM: Homo sapiens

<400> SEQUENCE: 233
gcgcccuccc ucucucccg gugugcaaau gugugugugc ggguguuaugc cggacaagag    60 ggaggug                                                             67

<210> SEQ ID NO 234
<211> LENGTH: 74
<212> TYPE: RNA
<213> ORGANISM: Homo sapiens

<400> SEQUENCE: 234
gcagcccggu gagcgcucgc uggccuggca gugcgucgga agaacagggc ggguggggcc    60
gcgcacaucu cugc                                                     74
```

<210> SEQ ID NO 235
<211> LENGTH: 87
<212> TYPE: RNA
<213> ORGANISM: Homo sapiens

<400> SEQUENCE: 235
cccucaucuc ugggcagggg cuuauuguag gagucucuga agagagcugu ggacugaccu    60
gcuuuacccc uucccaggu ucccauu                                          87

<210> SEQ ID NO 236
<211> LENGTH: 67
<212> TYPE: RNA
<213> ORGANISM: Homo sapiens

<400> SEQUENCE: 236
ggcagccagg gggaugggcg agcuugggcc cauuccuuuc cuuacccuac cccccauccc    60
ccuguag                                                               67

<210> SEQ ID NO 237
<211> LENGTH: 82
<212> TYPE: RNA
<213> ORGANISM: Homo sapiens

<400> SEQUENCE: 237
cugacuuuuu uagggaguag aagggugggg agcaugaaca auguuucuca cucccuaccc    60
cuccacuccc caaaaaaguc ag                                              82

<210> SEQ ID NO 238
<211> LENGTH: 89
<212> TYPE: RNA
<213> ORGANISM: Homo sapiens

<400> SEQUENCE: 238
agccuguggg aaagagaaga gcagggcagg gugaaggccc ggcggagaca cucugcccac    60
cccacacccu gccaugggc cacacagcu                                        89

<210> SEQ ID NO 239
<211> LENGTH: 71
<212> TYPE: RNA
<213> ORGANISM: Homo sapiens

<400> SEQUENCE: 239
ggugaguggg agccgguggg gcuggaguaa gggcacgccc ggggcugccc caccugcuga    60
ccacccuccc c                                                          71

<210> SEQ ID NO 240
<211> LENGTH: 84
<212> TYPE: RNA
<213> ORGANISM: Homo sapiens

<400> SEQUENCE: 240
auggucccuc ccaauccagc cauuccucag accagguggc ucccgagcca ccccaggcug    60 uaggauggg gugagaggug cuag                                             84

<210> SEQ ID NO 241
<211> LENGTH: 68
<212> TYPE: RNA
<213> ORGANISM: Homo sapiens

<400> SEQUENCE: 241
gcauccugua cugagcugcc ccgaggcccu ucaugcugcc cagcucgggg cagcucagua    60
caggauac                                                             68

<210> SEQ ID NO 242
<211> LENGTH: 64
<212> TYPE: RNA
<213> ORGANISM: Homo sapiens

<400> SEQUENCE: 242
uccuguacug agcugccccg agcugggcag caugaagggc cucggggcag cucaguacag    60
gaug                                                                 64

<210> SEQ ID NO 243
<211> LENGTH: 65
<212> TYPE: RNA
<213> ORGANISM: Homo sapiens

<400> SEQUENCE: 243
gggugcucgg ggcaggcggc ugggagcggc ccucacauug auggcccug ccaccuccuc    60 cgcag                                                                65

<210> SEQ ID NO 244
<211> LENGTH: 67
<212> TYPE: RNA
<213> ORGANISM: Homo sapiens

<400> SEQUENCE: 244
gugggagggg agaggcagca agcacacagg gccugggacu agcaugcuga ccucccuccu    60
gccccag                                                              67

<210> SEQ ID NO 245
<211> LENGTH: 63
<212> TYPE: RNA
<213> ORGANISM: Homo sapiens

<400> SEQUENCE: 245
cuugcccggg agaaggaggu ggccuggaga gcugcugucu ccagccgccg ccugucucca    60
cag                                                                  63

<210> SEQ ID NO 246
<211> LENGTH: 70
<212> TYPE: RNA
<213> ORGANISM: Homo sapiens

<400> SEQUENCE: 246
acaaauagcu ucagggaguc aggggagggc agaaauagau ggccuucccc ugcugggaag    60
aaaguggguc                                                           70

<210> SEQ ID NO 247
<211> LENGTH: 102
<212> TYPE: RNA
<213> ORGANISM: Homo sapiens

<400> SEQUENCE: 247
gcuuaucgag gaaaagaucg aggugggguug gggcgggcuc uggggauuug gucucacagc    60
ccggauccca gcccacuuac cuuggüuacu cuccuuccuu cu                       102

```
<210> SEQ ID NO 248
<211> LENGTH: 90
<212> TYPE: RNA
<213> ORGANISM: Homo sapiens

<400> SEQUENCE: 248
gugucucucu ggagacccug cagccuuccc acccaccagg gagcuuucca ugggcugugg    60
ggaaggcguc agugucgggu gagggaacac                                     90

<210> SEQ ID NO 249
<211> LENGTH: 87
<212> TYPE: RNA
<213> ORGANISM: Homo sapiens

<400> SEQUENCE: 249
guguggccgg caggcgggug ggcggggcg gccgguggga accccgcccc gccccgcgcc     60
cgcacucacc cgcccgucuc cccacag                                        87

<210> SEQ ID NO 250
<211> LENGTH: 69
<212> TYPE: RNA
<213> ORGANISM: Homo sapiens

<400> SEQUENCE: 250
cuuucggcca gcgggacggc auccgaggug ggcuaggcuc gggcccgugg cgggugcggg    60
ggugggagg                                                            69

<210> SEQ ID NO 251
<211> LENGTH: 66
<212> TYPE: RNA
<213> ORGANISM: Homo sapiens

<400> SEQUENCE: 251
cagagcaggg cagggaaggu gggagagggg cccagcugac ccuccuguca cccgcuccuu    60
gcccag                                                               66

<210> SEQ ID NO 252
<211> LENGTH: 64
<212> TYPE: RNA
<213> ORGANISM: Homo sapiens

<400> SEQUENCE: 252
gaaggcgagg gguagaagag cacagggguu cugauaaacc cuucugccug cauucuacuc    60
ccag                                                                 64

<210> SEQ ID NO 253
<211> LENGTH: 73
<212> TYPE: RNA
<213> ORGANISM: Homo sapiens

<400> SEQUENCE: 253
accuuuccag cucaucccac cucugccacc aaaacacuca ucgcggguc agagggagug     60 ccaaaaaagg uaa                                                       73

<210> SEQ ID NO 254
<211> LENGTH: 67
<212> TYPE: RNA
<213> ORGANISM: Homo sapiens

<400> SEQUENCE: 254
```

```
cugguccauu ucccugccau ucccuuggcu ucaauuuacu cccagggcug gcagugacau    60
gggucaa                                                              67

<210> SEQ ID NO 255
<211> LENGTH: 63
<212> TYPE: RNA
<213> ORGANISM: Homo sapiens

<400> SEQUENCE: 255
gagucgagga cuggugaag ggccuuuccc cucagaccaa ggcccuggcc ccagcuucuu     60
cuc                                                                  63

<210> SEQ ID NO 256
<211> LENGTH: 67
<212> TYPE: RNA
<213> ORGANISM: Homo sapiens

<400> SEQUENCE: 256
aauagauuau uggucaccac cuccaguuuc ugaauuugug agacuggggu ggggccugag    60
aauuugc                                                              67

<210> SEQ ID NO 257
<211> LENGTH: 68
<212> TYPE: RNA
<213> ORGANISM: Homo sapiens

<400> SEQUENCE: 257
gaauggaaga agaaggcggu cggucugcgg gagccaggcc gcagagccau ccgccuucug    60
uccauguc                                                             68

<210> SEQ ID NO 258
<211> LENGTH: 60
<212> TYPE: RNA
<213> ORGANISM: Homo sapiens

<400> SEQUENCE: 258
caaggugggg gagauggggg uugaacuuca uuucucaugc ucaucccau cuccuuucag     60

<210> SEQ ID NO 259
<211> LENGTH: 64
<212> TYPE: RNA
<213> ORGANISM: Homo sapiens

<400> SEQUENCE: 259
gagcucuggg aggggcuggg uuuggcagga caguuuccaa gcccugucuc cucccaucuu    60
ccag                                                                 64

<210> SEQ ID NO 260
<211> LENGTH: 100
<212> TYPE: RNA
<213> ORGANISM: Homo sapiens

<400> SEQUENCE: 260
gaggugggag gauugcuuga gucagggugg uugaggcugc aguaaguugu gaucauacca    60
cugcacucca gccugaguga cagagcaaga ccuugucuca                         100

<210> SEQ ID NO 261
<211> LENGTH: 81
<212> TYPE: RNA
<213> ORGANISM: Homo sapiens
```

<400> SEQUENCE: 261
uacaggugca ggggaacugu agaugaaaag gcuuggcacu ugagggaaag ccucaguuca    60
uucucauuuu gcucaccugu u    81

<210> SEQ ID NO 262
<211> LENGTH: 78
<212> TYPE: RNA
<213> ORGANISM: Homo sapiens

<400> SEQUENCE: 262
gggcccagaa gggggcgcag ucacugacgu gaagggacca caucccgcuu caugucagug    60
acuccugccc cuuggucu    78

<210> SEQ ID NO 263
<211> LENGTH: 87
<212> TYPE: RNA
<213> ORGANISM: Homo sapiens

<400> SEQUENCE: 263
cccaggcgcc cgcucccgac ccacgccgcg ccgccgdgguc ccuccucccc ggagaggcug    60
ggcucgggac gcgcggcuca gcucggg    87

<210> SEQ ID NO 264
<211> LENGTH: 81
<212> TYPE: RNA
<213> ORGANISM: Homo sapiens

<400> SEQUENCE: 264
cauccuccuu acgucccacc ccccacuccu guuucggug aaauauucaa acaggagugg    60 ggugggaca uaaggaggau a    81

<210> SEQ ID NO 265
<211> LENGTH: 86
<212> TYPE: RNA
<213> ORGANISM: Homo sapiens

<400> SEQUENCE: 265
ggcuuagaaa caguccccuag guaggauuug gggaggagcu aagaagcccc uacagggccc    60
agaggugggg acugagccuu aguugg    86

<210> SEQ ID NO 266
<211> LENGTH: 80
<212> TYPE: RNA
<213> ORGANISM: Homo sapiens

<400> SEQUENCE: 266
ugagaggccg caccuugccu ugcugcccgg gccgugcacc cgugggcccc agggcgacgc    60 ggcggggcg gcccuagcga    80

<210> SEQ ID NO 267
<211> LENGTH: 73
<212> TYPE: RNA
<213> ORGANISM: Homo sapiens

<400> SEQUENCE: 267
gaaaacaacc aggugggcuu cccggagggc ggaacaccca gccccagcau ccagggcuca    60
ccuaccacgu uug    73

<210> SEQ ID NO 268
<211> LENGTH: 64
<212> TYPE: RNA
<213> ORGANISM: Homo sapiens

<400> SEQUENCE: 268
aaccccgggc cggaggucaa gggcgucgcu ucucccuaau guugccucuu uuccacggcc    60
ucag                                                                64

<210> SEQ ID NO 269
<211> LENGTH: 74
<212> TYPE: RNA
<213> ORGANISM: Homo sapiens

<400> SEQUENCE: 269
ccugcaggag gcagugggcg agcaggcggg gcagcccaau gccaugggcc ugaucucacc    60
gcugccuccu uccc                                                     74

<210> SEQ ID NO 270
<211> LENGTH: 102
<212> TYPE: RNA
<213> ORGANISM: Homo sapiens

<400> SEQUENCE: 270
gugggagggc ccaggcgcgg gcaggggugg ggguggcaga gcgcuguccc gggggcgggg    60
ccgaagcgcg gcgaccguaa cuccuucugc uccgucccc ag                      102

<210> SEQ ID NO 271
<211> LENGTH: 69
<212> TYPE: RNA
<213> ORGANISM: Homo sapiens

<400> SEQUENCE: 271
gaaccucggg gcaugggga gggaggcugg acaggagagg gcucacccag gcccuguccu    60
cugccccag                                                          69

<210> SEQ ID NO 272
<211> LENGTH: 99
<212> TYPE: RNA
<213> ORGANISM: Homo sapiens

<400> SEQUENCE: 272
gcaagggaca gggagggucg uggcgacacu cgcgccagcu cccgggacgg cugggcucgg    60
gcuggucgcc gaccuccgac ccuccacuag augccuggc                         99

<210> SEQ ID NO 273
<211> LENGTH: 71
<212> TYPE: RNA
<213> ORGANISM: Homo sapiens

<400> SEQUENCE: 273
gugucugugc cggucccagg agaaccugca gaggcaucgg gucagcggug cuccugcggg    60
ccgacacuca c                                                       71

<210> SEQ ID NO 274
<211> LENGTH: 61
<212> TYPE: RNA
<213> ORGANISM: Homo sapiens

<400> SEQUENCE: 274
ucucguuuga ucucggaagc uaagcagggu ugggccuggu uaguacuugg augggaaacu      60
u                                                                     61

<210> SEQ ID NO 275
<211> LENGTH: 53
<212> TYPE: RNA
<213> ORGANISM: Homo sapiens

<400> SEQUENCE: 275
guuugaucuc ggaagcuaag cagggucggg ccugguuagu acuuggaugg gag            53

<210> SEQ ID NO 276
<211> LENGTH: 103
<212> TYPE: RNA
<213> ORGANISM: Homo sapiens

<400> SEQUENCE: 276
gugucggcug uggcgugacu gucccucugu gucccccacu aggcccacug cucaguggag     60
cguggaggac gaggaggagg ccguccacga gcaaugccag cau                      103

<210> SEQ ID NO 277
<211> LENGTH: 64
<212> TYPE: RNA
<213> ORGANISM: Homo sapiens

<400> SEQUENCE: 277
ugcucuguag gcaugaggca gggcccaggu uccaugugau gcugaagcuc ugacauuccu     60
gcag                                                                 64

<210> SEQ ID NO 278
<211> LENGTH: 63
<212> TYPE: RNA
<213> ORGANISM: Homo sapiens

<400> SEQUENCE: 278 uggugcggc gguaguuaug ggcuucucuu ucucaccagc agcccugggg ccgccgccuc      60
ccu                                                                  63

<210> SEQ ID NO 279
<211> LENGTH: 58
<212> TYPE: RNA
<213> ORGANISM: Homo sapiens

<400> SEQUENCE: 279
agggccagag gagccuggag uggucggguc gacugaaccc agguucccuc uggccgca      58

<210> SEQ ID NO 280
<211> LENGTH: 72
<212> TYPE: RNA
<213> ORGANISM: Homo sapiens

<400> SEQUENCE: 280
ugugggacug caaaugggag cucagcaccu gccugccacc cacgcagacc agcccugcu     60 cuguucccac ag                                                        72

<210> SEQ ID NO 281
<211> LENGTH: 64
<212> TYPE: RNA
<213> ORGANISM: Homo sapiens -continued

```
<400> SEQUENCE: 281
ccccgggccc ggcguucccu ccccuuccgu gcgccagugg aggccggggu ggggcggggc     60
gggg                                                                 64

<210> SEQ ID NO 282
<211> LENGTH: 64
<212> TYPE: RNA
<213> ORGANISM: Homo sapiens

<400> SEQUENCE: 282
ccccgggccc ggcguucccu ccccuuccgu gcgccagugg aggccggggu ggggcggggc     60
gggg                                                                 64

<210> SEQ ID NO 283
<211> LENGTH: 89
<212> TYPE: RNA
<213> ORGANISM: Homo sapiens

<400> SEQUENCE: 283
ucuccguuua ucccaccacu gccaccauua uugcuacugu ucagcaggug cugcuggugg     60
ugauggugau agucuggugg gggcggugg                                      89

<210> SEQ ID NO 284
<211> LENGTH: 51
<212> TYPE: RNA
<213> ORGANISM: Homo sapiens

<400> SEQUENCE: 284
acagaccccg gggagcccgg cggugaagcu ccugguaucc uggguguucug a             51

<210> SEQ ID NO 285
<211> LENGTH: 115
<212> TYPE: RNA
<213> ORGANISM: Homo sapiens

<400> SEQUENCE: 285
gagcaaaaac cagagaacaa caugggagcg uuccuaaccc cuaaggcaac uggaugggag     60
accugaccca uccaguucuc ugaggggcu cuugugguu cuacaagguu guuca           115

<210> SEQ ID NO 286
<211> LENGTH: 85
<212> TYPE: RNA
<213> ORGANISM: Homo sapiens

<400> SEQUENCE: 286
ggcgccuccu gcucugcugu gccgccaggg ccucccuag cgcgccuucu ggagaggcuu      60
ugugcggaua cggggcugga ggccu                                          85

<210> SEQ ID NO 287
<211> LENGTH: 70
<212> TYPE: RNA
<213> ORGANISM: Homo sapiens

<400> SEQUENCE: 287
gucccugggg gcugggaugg gccauggugu gcucugaucc cccugugguc ucuuggcccc     60
caggaacucc                                                           70

<210> SEQ ID NO 288
<211> LENGTH: 82
```

```
<212> TYPE: RNA
<213> ORGANISM: Homo sapiens

<400> SEQUENCE: 288
gugaguggga ggccagggca cggcaggggg agcugcaggg cuaugggagg ggccccagcg    60
ucugagcccu guccucccgc ag                                              82

<210> SEQ ID NO 289
<211> LENGTH: 82
<212> TYPE: RNA
<213> ORGANISM: Homo sapiens

<400> SEQUENCE: 289
gugaguggga ggccagggca cggcaggggg agcugcaggg cuaugggagg ggccccagcg    60
ucugagcccu guccucccgc ag                                              82

<210> SEQ ID NO 290
<211> LENGTH: 73
<212> TYPE: RNA
<213> ORGANISM: Homo sapiens

<400> SEQUENCE: 290
cugguguuug aggcgaugug gggauguaga gacaacuucc cagucucauu uccucauccu    60
gccaggccac cau                                                        73

<210> SEQ ID NO 291
<211> LENGTH: 84
<212> TYPE: RNA
<213> ORGANISM: Homo sapiens

<400> SEQUENCE: 291
ccgcagccgc cgcgccgggc ccggguuggc cgcugacccc cgcggggccc ccggcggccg    60
gggcgggggc gggggcugcc ccgg                                            84

<210> SEQ ID NO 292
<211> LENGTH: 69
<212> TYPE: RNA
<213> ORGANISM: Homo sapiens

<400> SEQUENCE: 292
gggcuuaggg augggaggcc aggaugaaga uuaaucccua auccccaaca cuggccuugc    60
uaucccag                                                              69

<210> SEQ ID NO 293
<211> LENGTH: 80
<212> TYPE: RNA
<213> ORGANISM: Homo sapiens

<400> SEQUENCE: 293
gcgucaagau ggcggcgggg agguaggcag agcaggacgc cgcugcugcc gccgccaccg    60
ccgccuccgc uccagucgcc                                                 80

<210> SEQ ID NO 294
<211> LENGTH: 62
<212> TYPE: RNA
<213> ORGANISM: Homo sapiens

<400> SEQUENCE: 294
gugagugggg cucccgggac ggcgcccgcc cuggcccugg cccggcgacg ucucacgguc    60
``` cc                                                                    62

<210> SEQ ID NO 295
<211> LENGTH: 67
<212> TYPE: RNA
<213> ORGANISM: Homo sapiens

<400> SEQUENCE: 295
ccugcaggca aagugggcc ugacagggca gaggguugcg ccccucacc aucccuucug        60 ccugcag                                                               67

<210> SEQ ID NO 296
<211> LENGTH: 67
<212> TYPE: RNA
<213> ORGANISM: Homo sapiens

<400> SEQUENCE: 296
ccugcaggca aagugggcc ugacagggca gaggguugcg ccccucacc aucccuucug        60 ccugcag                                                               67

<210> SEQ ID NO 297
<211> LENGTH: 67
<212> TYPE: RNA
<213> ORGANISM: Homo sapiens

<400> SEQUENCE: 297
ccugcaggca aagugggcc ugacagggca gaggguugcg ccccucacc aucccuucug        60 ccugcag                                                               67

<210> SEQ ID NO 298
<211> LENGTH: 67
<212> TYPE: RNA
<213> ORGANISM: Homo sapiens

<400> SEQUENCE: 298
ccugcaggca aagugggcc ugacagggca gaggguugcg ccccucacc aucccuucug        60 ccugcag                                                               67

<210> SEQ ID NO 299
<211> LENGTH: 59
<212> TYPE: RNA
<213> ORGANISM: Homo sapiens

<400> SEQUENCE: 299
cgggcucugg gugcaguggg gguucccacg ccgcggcaac caccacuguc ucuccccag       59

<210> SEQ ID NO 300
<211> LENGTH: 67
<212> TYPE: RNA
<213> ORGANISM: Homo sapiens

<400> SEQUENCE: 300
guggcacuca aacuguggg gcacuuucug cucucuggug aaagugccgc caucuuuga        60 guguuac                                                               67

<210> SEQ ID NO 301
<211> LENGTH: 88
<212> TYPE: RNA
<213> ORGANISM: Homo sapiens

<400> SEQUENCE: 301

```
gugggGccag gcggugGugG gcacugcugg gguGggcaca gcagccaugc agagcGGGca    60
uuugaccccg ugccacccuu uuccccag                                      88

<210> SEQ ID NO 302
<211> LENGTH: 94
<212> TYPE: RNA
<213> ORGANISM: Homo sapiens

<400> SEQUENCE: 302
cacgguGucc ccugguGgaa ccuGgcaGGG GGaGaGGuaa GGucuuucag ccucuccaaa    60
gcccauGGuc agGuacucag guGGGGGaGc ccug                               94

<210> SEQ ID NO 303
<211> LENGTH: 109
<212> TYPE: RNA
<213> ORGANISM: Homo sapiens

<400> SEQUENCE: 303
ggucgggcuc accaugacac aguGuGaGac ucgggcuac aacacaggac ccgggcgcug     60
cucugacccc ucguGucuug uguugcagcc ggagggacgc agGuccgca              109

<210> SEQ ID NO 304
<211> LENGTH: 90
<212> TYPE: RNA
<213> ORGANISM: Homo sapiens

<400> SEQUENCE: 304
ucuaagaaac gcaGuggucu cugaagccug cagGGGcagG ccagcccugc acgaacgcc    60 uguucuugcc aGGuGGcaga aGGuugcugc                                    90

<210> SEQ ID NO 305
<211> LENGTH: 87
<212> TYPE: RNA
<213> ORGANISM: Homo sapiens

<400> SEQUENCE: 305
cacuGuucua ugGuuaGuuu ugcagguuug cauccagcug uGuGauauuc ugcugugcaa    60
auccaugcaa aacugacugu gguagug                                       87

<210> SEQ ID NO 306
<211> LENGTH: 96
<212> TYPE: RNA
<213> ORGANISM: Homo sapiens

<400> SEQUENCE: 306
acauugcuac uuacaauuag uuuugcaggu uugcauuuca gcguauauau guauaugugg    60
cugugcaaau ccaugcaaaa cugauuguga uaaugu                             96

<210> SEQ ID NO 307
<211> LENGTH: 90
<212> TYPE: RNA
<213> ORGANISM: Homo sapiens

<400> SEQUENCE: 307
gugGGuacgg cccaguGGGG GGGaGaGGGa cacgcccugg gcucugccca GGugcagcc    60 ggacugacug agccccugug ccgcccccag                                    90

<210> SEQ ID NO 308
```

```
<211> LENGTH: 72
<212> TYPE: RNA
<213> ORGANISM: Homo sapiens

<400> SEQUENCE: 308
cuugggaaug gcaaggaaac cguuaccauu acugaguuua guaaugguaa ugguucucuu    60
gcuauaccca ga                                                        72

<210> SEQ ID NO 309
<211> LENGTH: 82
<212> TYPE: RNA
<213> ORGANISM: Homo sapiens

<400> SEQUENCE: 309 uguggggcagg gcccuggggga gcugaggcuc uggggguggc cggggcugac ccugggccuc   60 ugcucccccag ugucugaccg cg                                            82

<210> SEQ ID NO 310
<211> LENGTH: 110
<212> TYPE: RNA
<213> ORGANISM: Homo sapiens

<400> SEQUENCE: 310
ccuggccucc ugcagugcca cgcuccgugu auuugacaag cugaguugga cacuccaugu    60
gguagagugu caguuuguca aauaccccaa gugcggcaca ugcuuaccag              110

<210> SEQ ID NO 311
<211> LENGTH: 73
<212> TYPE: RNA
<213> ORGANISM: Homo sapiens

<400> SEQUENCE: 311
gugggcgggg gcaggugugu gguggguggu ggccugcggu gagcagggcc cucacaccug    60
ccucgccccc cag                                                       73

<210> SEQ ID NO 312
<211> LENGTH: 86
<212> TYPE: RNA
<213> ORGANISM: Homo sapiens

<400> SEQUENCE: 312
ugccagucuc uagguccccug agacccuuua accugugagg acauccaggg ucacagguga   60
gguucuuggg agccuggcgu cuggcc                                         86

<210> SEQ ID NO 313
<211> LENGTH: 96
<212> TYPE: RNA
<213> ORGANISM: Homo sapiens

<400> SEQUENCE: 313
cgggccccgg gcgggcggga gggacgggac gcggugcagu guuguuuuuu cccccgccaa    60
uauugcacuc gucccggccu ccggcccccc cggccc                              96

<210> SEQ ID NO 314
<211> LENGTH: 85
<212> TYPE: RNA
<213> ORGANISM: Homo sapiens

<400> SEQUENCE: 314
ggcugagccg caguaguucu ucaguggcaa gcuuuaugucc cugacccagc uaaagcugcc   60
```
aguugaagaa cuguugcccu cugcc 85

<210> SEQ ID NO 315
<211> LENGTH: 67
<212> TYPE: RNA
<213> ORGANISM: Homo sapiens

<400> SEQUENCE: 315
aaaucucucu ccauaucuuu ccugcagccc ccaggugggg gggaagaaaa ggugggaau 60 uagauuc 67

<210> SEQ ID NO 316
<211> LENGTH: 77
<212> TYPE: RNA
<213> ORGANISM: Homo sapiens

<400> SEQUENCE: 316
gaguugggag guucccucuc caaauguguc uugaucccc accccaagac acauuggag 60 agggacccuc ccaacuc 77

<210> SEQ ID NO 317
<211> LENGTH: 95
<212> TYPE: RNA
<213> ORGANISM: Homo sapiens

<400> SEQUENCE: 317
gacaccacau gcuccuccag gccugccugc ccuccagguc auguuccagu gucccacaga 60
ugcagcacca cggcccaggc ggcauuggug ucacc 95

<210> SEQ ID NO 318
<211> LENGTH: 96
<212> TYPE: RNA
<213> ORGANISM: Homo sapiens

<400> SEQUENCE: 318
gcucuggggc gugccgccgc cgucgcugcc accuccccua ccgcuagugg aagaagaugg 60
cggaaggcgg agcggcggau cuggacaccc agcggu 96

<210> SEQ ID NO 319
<211> LENGTH: 79
<212> TYPE: RNA
<213> ORGANISM: Homo sapiens

<400> SEQUENCE: 319
gugcagaucc uugggagccc uguuagacuc uggauuuuac acuggagug aacgggcgcc 60 aucccgaggc uuugcacag 79

<210> SEQ ID NO 320
<211> LENGTH: 67
<212> TYPE: RNA
<213> ORGANISM: Homo sapiens

<400> SEQUENCE: 320
cagggaggag guggu acuag gggccagcaa ccugauuacc ccucuuuggc ccuuuguacc 60
ccuccag 67

<210> SEQ ID NO 321
<211> LENGTH: 65
<212> TYPE: RNA

<213> ORGANISM: Homo sapiens

<400> SEQUENCE: 321
uucuccuggg gaguggcugg ggagcagaca gacccaaccu caugcucccc ggccucugcc    60
cccag                                                                65

<210> SEQ ID NO 322
<211> LENGTH: 58
<212> TYPE: RNA
<213> ORGANISM: Homo sapiens

<400> SEQUENCE: 322
gcugaagcuc uaagguuccg ccugcgggca ggaagcggag gaaccuugga gcuucggc     58

<210> SEQ ID NO 323
<211> LENGTH: 53
<212> TYPE: RNA
<213> ORGANISM: Homo sapiens

<400> SEQUENCE: 323 ggugggguu ggaggcgugg guuuuagaac cuaucccuuu cuagcccuga gca           53

<210> SEQ ID NO 324
<211> LENGTH: 180
<212> TYPE: RNA
<213> ORGANISM: Homo sapiens

<400> SEQUENCE: 324
cgcgacugcg gcggcggugg uggggggagc cgcggggauc gccgagggcc ggucggccgc    60
cccgggugcc gcgcggugcc gccggcggcg gugaggcccc gcgcgugugu cccggcugcg   120
gucggccgcg cucgaggggu ccccguggcg uccccuuccc cgccggccgc cuuucucgcg   180

<210> SEQ ID NO 325
<211> LENGTH: 89
<212> TYPE: RNA
<213> ORGANISM: Homo sapiens

<400> SEQUENCE: 325
gccggcgccc gagcucuggc uccgugucuu cacucccgug cuuguccgag gagggaggga    60
gggacggggg cugugcuggg gcagcugga                                       89

<210> SEQ ID NO 326
<211> LENGTH: 70
<212> TYPE: RNA
<213> ORGANISM: Homo sapiens

<400> SEQUENCE: 326
gguuucuccu ugaggagaca uggugggggc cggucaggca gcccaugcca ugugccuca    60 uggagaggcc                                                            70

<210> SEQ ID NO 327
<211> LENGTH: 92
<212> TYPE: RNA
<213> ORGANISM: Homo sapiens

<400> SEQUENCE: 327
ccugucccuc cugcccugcg ccugcccagc ccuccugcuc uggugacuga ggaccgccag    60
gcaggggcug gugcugggcg gggggcggcg gg                                   92

```
<210> SEQ ID NO 328
<211> LENGTH: 65
<212> TYPE: RNA
<213> ORGANISM: Homo sapiens

<400> SEQUENCE: 328
gagggugggc gagggcggcu gagcggcucc auccccggc cugcucaucc cccucgcccu    60
cucag                                                              65

<210> SEQ ID NO 329
<211> LENGTH: 64
<212> TYPE: RNA
<213> ORGANISM: Homo sapiens

<400> SEQUENCE: 329 ggguggggc gggcggcag gggccucccc cagugccagg ccccauucug cuucucuccc     60
agcu                                                               64

<210> SEQ ID NO 330
<211> LENGTH: 86
<212> TYPE: RNA
<213> ORGANISM: Homo sapiens

<400> SEQUENCE: 330
cgccugagcg ugcagcagga caucuuccug accugguaau aauuagguga gaaggauggu    60 uggggcggu cggcguaacu caggga                                         86

<210> SEQ ID NO 331
<211> LENGTH: 52
<212> TYPE: RNA
<213> ORGANISM: Homo sapiens

<400> SEQUENCE: 331
uagccgggcg uggugguggg ggccuguggu cccagcuacu uuggaggcug ag            52

<210> SEQ ID NO 332
<211> LENGTH: 74
<212> TYPE: RNA
<213> ORGANISM: Homo sapiens

<400> SEQUENCE: 332
gggaggaaga agggaggagg agcggagggg cccuugucuu cccagagccu cucccuuccu    60 ccccucccc uccc                                                     74

<210> SEQ ID NO 333
<211> LENGTH: 50
<212> TYPE: RNA
<213> ORGANISM: Homo sapiens

<400> SEQUENCE: 333
acccgggcgu gguggugggg gugggugccu guaauuccag cuaguuggga              50

<210> SEQ ID NO 334
<211> LENGTH: 72
<212> TYPE: RNA
<213> ORGANISM: Homo sapiens

<400> SEQUENCE: 334
cugugcaccu gggggagugc agugauugug gaaugcaaag ucccacaauc acuguacucc    60
ccaggugcac ag                                                      72
```

<210> SEQ ID NO 335
<211> LENGTH: 71
<212> TYPE: RNA
<213> ORGANISM: Homo sapiens

<400> SEQUENCE: 335
auggaggggg guguggagcc aggggggccca ggucuacagc uucucccgc ucccugcccc    60 cauacuccca g                                                        71

<210> SEQ ID NO 336
<211> LENGTH: 52
<212> TYPE: RNA
<213> ORGANISM: Homo sapiens

<400> SEQUENCE: 336
ucugggcuga gccgagcugg guuaagccga gcuggguugg gcugggcugg gu            52

<210> SEQ ID NO 337
<211> LENGTH: 94
<212> TYPE: RNA
<213> ORGANISM: Homo sapiens

<400> SEQUENCE: 337
cgggcagcgg gugccaggca cggugucagc aggcaacaug gccgagaggc cggggccucc    60
gggcggcgcc guguccgcga ccgcguaccc ugac                               94

<210> SEQ ID NO 338
<211> LENGTH: 89
<212> TYPE: RNA
<213> ORGANISM: Homo sapiens

<400> SEQUENCE: 338
accuccggga cggcugggcg ccggcggccg ggagauccgc gcuuccugaa ucccggccgg    60 cccgccggc gcccguccgc ccgcgggguc                                     89

<210> SEQ ID NO 339
<211> LENGTH: 64
<212> TYPE: RNA
<213> ORGANISM: Homo sapiens

<400> SEQUENCE: 339
aguucagggc cgaagggugg aagcugcugg ugcucaucuc agccucugcc cuuggccucc    60
ccag                                                                64

<210> SEQ ID NO 340
<211> LENGTH: 49
<212> TYPE: RNA
<213> ORGANISM: Homo sapiens

<400> SEQUENCE: 340
ggugaggcgg gggggcgagc ccugaggggc ucucgcuucu ggcgccaag                49

<210> SEQ ID NO 341
<211> LENGTH: 70
<212> TYPE: RNA
<213> ORGANISM: Homo sapiens

<400> SEQUENCE: 341
cccugccagu gcuggggggcc acaugagugu gcagucaucc acacacaagu ggcccccaac    60
acuggcaggg                                                          70

```
<210> SEQ ID NO 342
<211> LENGTH: 96
<212> TYPE: RNA
<213> ORGANISM: Homo sapiens

<400> SEQUENCE: 342
cucgggaggg gcgggagggg ggucccggu gcucggaucu cgagggugcu uauuguucgg      60
uccgagccug ggucucccuc uuccccccaa cccccc                              96

<210> SEQ ID NO 343
<211> LENGTH: 80
<212> TYPE: RNA
<213> ORGANISM: Homo sapiens

<400> SEQUENCE: 343
ggcgcgucgc cccccucagu ccaccagagc ccggauaccu cagaaauucg gcucggguc      60 ugugggagc gaaaugcaac                                                 80

<210> SEQ ID NO 344
<211> LENGTH: 93
<212> TYPE: RNA
<213> ORGANISM: Homo sapiens

<400> SEQUENCE: 344
guaaggaggg ggaugagggg ucauaucucu ucucagggaa agcaggagcc cuucagcagg     60
gucagggccc cucaucuucc ccuccuuucc cag                                 93

<210> SEQ ID NO 345
<211> LENGTH: 65
<212> TYPE: RNA
<213> ORGANISM: Homo sapiens

<400> SEQUENCE: 345
gagaaugggg ggacagaugg agaggacaca ggcuggcacu gaggucccu ccacuuuccu      60 ccuag                                                                65

<210> SEQ ID NO 346
<211> LENGTH: 75
<212> TYPE: RNA
<213> ORGANISM: Homo sapiens

<400> SEQUENCE: 346
gucagagggg ggaugugcau gcugguuggg gugggcugcc uguggaccaa ucagcgugca     60 cuucccccacc cugaa                                                    75

<210> SEQ ID NO 347
<211> LENGTH: 80
<212> TYPE: RNA
<213> ORGANISM: Homo sapiens

<400> SEQUENCE: 347
cgugugagcc cgcccugugc ccggcccacu ucugcuuccu cuuagcgcag gagggguccc     60 gcacuggag gggcccucac                                                 80

<210> SEQ ID NO 348
<211> LENGTH: 99
<212> TYPE: RNA
<213> ORGANISM: Homo sapiens
```

<400> SEQUENCE: 348
cgcccaccuc agccucccaa aaugcuggga uuacaggcau gagccacugc ggucgaccau    60
gaccuggaca uguuugugcc caguacuguc aguuugcag                          99

<210> SEQ ID NO 349
<211> LENGTH: 100
<212> TYPE: RNA
<213> ORGANISM: Homo sapiens

<400> SEQUENCE: 349
agcucagggc ggcugcgcag agggcuggac ucagcggcgg agcuggcugc uggccucagu    60
ucugccucug uccagguccu ugugacccgc ccgcucuccu                         100

<210> SEQ ID NO 350
<211> LENGTH: 78
<212> TYPE: RNA
<213> ORGANISM: Homo sapiens

<400> SEQUENCE: 350 ggcucaggc aggcgcaccc gaccacaugc auggcuggug gcggcgugca ggggucgggu     60
gggccaggcu gugggcg                                                  78

<210> SEQ ID NO 351
<211> LENGTH: 85
<212> TYPE: RNA
<213> ORGANISM: Homo sapiens

<400> SEQUENCE: 351
gugagcugcu ggggacgcgg gucgggucu gcagggcggu gcggcagccg ccaccugacg    60
ccgcgccuuu gucuguguucc cacag                                        85

<210> SEQ ID NO 352
<211> LENGTH: 73
<212> TYPE: RNA
<213> ORGANISM: Homo sapiens

<400> SEQUENCE: 352
ggggagguac cugggacagg aggaggaggc agccuugccu cagaaaccaa acugucaaaa   60
guguagguuc cac                                                       73

<210> SEQ ID NO 353
<211> LENGTH: 73
<212> TYPE: RNA
<213> ORGANISM: Homo sapiens

<400> SEQUENCE: 353
cccagggucu ggugcggaga gggcccacag uggacuuggu gacgcuguau gcccucaccg    60
cucagccccu ggg                                                       73

<210> SEQ ID NO 354
<211> LENGTH: 74
<212> TYPE: RNA
<213> ORGANISM: Homo sapiens

<400> SEQUENCE: 354
ccaagggcac accggggaug gcagagggguc gugggaaagu guugacccuc gucagguccc    60
cggggagccc cugg                                                      74

```
<210> SEQ ID NO 355
<211> LENGTH: 21
<212> TYPE: RNA
<213> ORGANISM: Homo sapiens

<400> SEQUENCE: 355
ccggccgccg gcuccgcccc g                                              21

<210> SEQ ID NO 356
<211> LENGTH: 17
<212> TYPE: RNA
<213> ORGANISM: Homo sapiens

<400> SEQUENCE: 356
ccggccgccg gcuccgc                                                   17

<210> SEQ ID NO 357
<211> LENGTH: 23
<212> TYPE: RNA
<213> ORGANISM: Homo sapiens

<400> SEQUENCE: 357
cuccuggggc ccgcacucuc gcu                                            23

<210> SEQ ID NO 358
<211> LENGTH: 18
<212> TYPE: RNA
<213> ORGANISM: Homo sapiens

<400> SEQUENCE: 358
cuccuggggc ccgcacuc                                                  18

<210> SEQ ID NO 359
<211> LENGTH: 23
<212> TYPE: RNA
<213> ORGANISM: Homo sapiens

<400> SEQUENCE: 359
agggucgggg cagggagggc agg                                            23

<210> SEQ ID NO 360
<211> LENGTH: 15
<212> TYPE: RNA
<213> ORGANISM: Homo sapiens

<400> SEQUENCE: 360
gggagaaggg ucggg                                                     15

<210> SEQ ID NO 361
<211> LENGTH: 23
<212> TYPE: RNA
<213> ORGANISM: Homo sapiens

<400> SEQUENCE: 361
ggugggugag gucgggcccc aag                                            23

<210> SEQ ID NO 362
<211> LENGTH: 20
<212> TYPE: RNA
<213> ORGANISM: Homo sapiens

<400> SEQUENCE: 362
cggggugggu gaggucgggc                                                20
```

```
<210> SEQ ID NO 363
<211> LENGTH: 23
<212> TYPE: RNA
<213> ORGANISM: Homo sapiens

<400> SEQUENCE: 363
ugaggauaug gcagggaagg gga                                              23

<210> SEQ ID NO 364
<211> LENGTH: 19
<212> TYPE: RNA
<213> ORGANISM: Homo sapiens

<400> SEQUENCE: 364
ugaggauaug gcagggaag                                                   19

<210> SEQ ID NO 365
<211> LENGTH: 23
<212> TYPE: RNA
<213> ORGANISM: Homo sapiens

<400> SEQUENCE: 365
ggcccggccg ugccugaggu uuc                                              23

<210> SEQ ID NO 366
<211> LENGTH: 15
<212> TYPE: RNA
<213> ORGANISM: Homo sapiens

<400> SEQUENCE: 366
ggcgguggga ucccg                                                       15

<210> SEQ ID NO 367
<211> LENGTH: 22
<212> TYPE: RNA
<213> ORGANISM: Homo sapiens

<400> SEQUENCE: 367
cgcggcgggg acggcgauug gu                                               22

<210> SEQ ID NO 368
<211> LENGTH: 17
<212> TYPE: RNA
<213> ORGANISM: Homo sapiens

<400> SEQUENCE: 368
cggcggggac ggcgauu                                                     17

<210> SEQ ID NO 369
<211> LENGTH: 25
<212> TYPE: RNA
<213> ORGANISM: Homo sapiens

<400> SEQUENCE: 369
ggguggggau uuguugcauu acuug                                            25

<210> SEQ ID NO 370
<211> LENGTH: 20
<212> TYPE: RNA
<213> ORGANISM: Homo sapiens

<400> SEQUENCE: 370
ggguggggau uuguugcauu                                                  20
```

<210> SEQ ID NO 371
<211> LENGTH: 17
<212> TYPE: RNA
<213> ORGANISM: Homo sapiens

<400> SEQUENCE: 371
uccuagucac ggcacca                                                      17

<210> SEQ ID NO 372
<211> LENGTH: 17
<212> TYPE: RNA
<213> ORGANISM: Homo sapiens

<400> SEQUENCE: 372
uccuagucac ggcacca                                                      17

<210> SEQ ID NO 373
<211> LENGTH: 16
<212> TYPE: RNA
<213> ORGANISM: Homo sapiens

<400> SEQUENCE: 373
ugcuggugau gcuuuc                                                       16

<210> SEQ ID NO 374
<211> LENGTH: 16
<212> TYPE: RNA
<213> ORGANISM: Homo sapiens

<400> SEQUENCE: 374
ugcuggugau gcuuuc                                                       16

<210> SEQ ID NO 375
<211> LENGTH: 23
<212> TYPE: RNA
<213> ORGANISM: Homo sapiens

<400> SEQUENCE: 375
ggaggcgcag gcucggaaag gcg                                               23

<210> SEQ ID NO 376
<211> LENGTH: 15
<212> TYPE: RNA
<213> ORGANISM: Homo sapiens

<400> SEQUENCE: 376
gcaggcucgg aaagg                                                        15

<210> SEQ ID NO 377
<211> LENGTH: 20
<212> TYPE: RNA
<213> ORGANISM: Homo sapiens

<400> SEQUENCE: 377
ggcuggucag augggagugg                                                   20

<210> SEQ ID NO 378
<211> LENGTH: 20
<212> TYPE: RNA
<213> ORGANISM: Homo sapiens

<400> SEQUENCE: 378
ggcuggucag augggagugg                                              20

<210> SEQ ID NO 379
<211> LENGTH: 21
<212> TYPE: RNA
<213> ORGANISM: Homo sapiens

<400> SEQUENCE: 379
cggauccgag ucacggcacc a                                            21

<210> SEQ ID NO 380
<211> LENGTH: 15
<212> TYPE: RNA
<213> ORGANISM: Homo sapiens

<400> SEQUENCE: 380
ggauccgagu cacgg                                                   15

<210> SEQ ID NO 381
<211> LENGTH: 22
<212> TYPE: RNA
<213> ORGANISM: Homo sapiens

<400> SEQUENCE: 381
ccgggaacgu cgagacugga gc                                           22

<210> SEQ ID NO 382
<211> LENGTH: 15
<212> TYPE: RNA
<213> ORGANISM: Homo sapiens

<400> SEQUENCE: 382
cgggaacguc gagac                                                   15

<210> SEQ ID NO 383
<211> LENGTH: 15
<212> TYPE: RNA
<213> ORGANISM: Homo sapiens

<400> SEQUENCE: 383
ucugggcgag gggug                                                   15

<210> SEQ ID NO 384
<211> LENGTH: 15
<212> TYPE: RNA
<213> ORGANISM: Homo sapiens

<400> SEQUENCE: 384
ucugggcgag gggug                                                   15

<210> SEQ ID NO 385
<211> LENGTH: 21
<212> TYPE: RNA
<213> ORGANISM: Homo sapiens

<400> SEQUENCE: 385
cccaggcugg agcgagugca g                                            21

<210> SEQ ID NO 386
<211> LENGTH: 15
<212> TYPE: RNA
<213> ORGANISM: Homo sapiens

<400> SEQUENCE: 386
agcucacugc agccu 15

<210> SEQ ID NO 387
<211> LENGTH: 23
<212> TYPE: RNA
<213> ORGANISM: Homo sapiens

<400> SEQUENCE: 387
gggggccgau acacuguacg aga 23

<210> SEQ ID NO 388
<211> LENGTH: 20
<212> TYPE: RNA
<213> ORGANISM: Homo sapiens

<400> SEQUENCE: 388
gggggccgau acacuguacg 20

<210> SEQ ID NO 389
<211> LENGTH: 18
<212> TYPE: RNA
<213> ORGANISM: Homo sapiens

<400> SEQUENCE: 389
gcggcggcgg cggcagca 18

<210> SEQ ID NO 390
<211> LENGTH: 15
<212> TYPE: RNA
<213> ORGANISM: Homo sapiens

<400> SEQUENCE: 390
gcgggcggcg gcggc 15

<210> SEQ ID NO 391
<211> LENGTH: 23
<212> TYPE: RNA
<213> ORGANISM: Homo sapiens

<400> SEQUENCE: 391
cggggccgua gcacugucug aga 23

<210> SEQ ID NO 392
<211> LENGTH: 20
<212> TYPE: RNA
<213> ORGANISM: Homo sapiens

<400> SEQUENCE: 392
cggggccgua gcacugucug 20

<210> SEQ ID NO 393
<211> LENGTH: 22
<212> TYPE: RNA
<213> ORGANISM: Homo sapiens

<400> SEQUENCE: 393
accccacucc ugguaccaua gu 22

<210> SEQ ID NO 394
<211> LENGTH: 15
<212> TYPE: RNA
<213> ORGANISM: Homo sapiens

```
<400> SEQUENCE: 394
accccacucc uggua                                              15

<210> SEQ ID NO 395
<211> LENGTH: 21
<212> TYPE: RNA
<213> ORGANISM: Homo sapiens

<400> SEQUENCE: 395
gagggcagcg ugguguggc g                                        21

<210> SEQ ID NO 396
<211> LENGTH: 21
<212> TYPE: RNA
<213> ORGANISM: Homo sapiens

<400> SEQUENCE: 396
gagggcagcg ugguguggc g                                        21

<210> SEQ ID NO 397
<211> LENGTH: 27
<212> TYPE: RNA
<213> ORGANISM: Homo sapiens

<400> SEQUENCE: 397
ugagggacuu uuggggcag auguguu                                  27

<210> SEQ ID NO 398
<211> LENGTH: 17
<212> TYPE: RNA
<213> ORGANISM: Homo sapiens

<400> SEQUENCE: 398
ggacuuuugg gggcaga                                            17

<210> SEQ ID NO 399
<211> LENGTH: 15
<212> TYPE: RNA
<213> ORGANISM: Homo sapiens

<400> SEQUENCE: 399
ugaagcgggg gggcg                                              15

<210> SEQ ID NO 400
<211> LENGTH: 15
<212> TYPE: RNA
<213> ORGANISM: Homo sapiens

<400> SEQUENCE: 400
ugaagcgggg gggcg                                              15

<210> SEQ ID NO 401
<211> LENGTH: 16
<212> TYPE: RNA
<213> ORGANISM: Homo sapiens

<400> SEQUENCE: 401
ggacccaggg agagac                                             16

<210> SEQ ID NO 402
<211> LENGTH: 16
<212> TYPE: RNA
<213> ORGANISM: Homo sapiens
```

```
-continued

<400> SEQUENCE: 402
ggacccaggg agagac                                                   16

<210> SEQ ID NO 403
<211> LENGTH: 23
<212> TYPE: RNA
<213> ORGANISM: Homo sapiens

<400> SEQUENCE: 403 ugggcggag cuccggagg ccc                                             23

<210> SEQ ID NO 404
<211> LENGTH: 16
<212> TYPE: RNA
<213> ORGANISM: Homo sapiens

<400> SEQUENCE: 404
aucgcuggcc uggucg                                                   16

<210> SEQ ID NO 405
<211> LENGTH: 20
<212> TYPE: RNA
<213> ORGANISM: Homo sapiens

<400> SEQUENCE: 405
cuccccggug ugcaaaugug                                               20

<210> SEQ ID NO 406
<211> LENGTH: 15
<212> TYPE: RNA
<213> ORGANISM: Homo sapiens

<400> SEQUENCE: 406
gugugcggug uuaug                                                    15

<210> SEQ ID NO 407
<211> LENGTH: 17
<212> TYPE: RNA
<213> ORGANISM: Homo sapiens

<400> SEQUENCE: 407
ggugagcgcu cgcuggc                                                  17

<210> SEQ ID NO 408
<211> LENGTH: 15
<212> TYPE: RNA
<213> ORGANISM: Homo sapiens

<400> SEQUENCE: 408
cggugagcgc ucgcu                                                    15

<210> SEQ ID NO 409
<211> LENGTH: 25
<212> TYPE: RNA
<213> ORGANISM: Homo sapiens

<400> SEQUENCE: 409
ugggcagggg cuuauuguag gaguc                                         25

<210> SEQ ID NO 410
<211> LENGTH: 19
<212> TYPE: RNA
```

<213> ORGANISM: Homo sapiens

<400> SEQUENCE: 410
ugggcagggg cuuauugua					19

<210> SEQ ID NO 411
<211> LENGTH: 23
<212> TYPE: RNA
<213> ORGANISM: Homo sapiens

<400> SEQUENCE: 411
agggaguaga aggugggga gca					23

<210> SEQ ID NO 412
<211> LENGTH: 16
<212> TYPE: RNA
<213> ORGANISM: Homo sapiens

<400> SEQUENCE: 412
uagggaguag aagggu					16

<210> SEQ ID NO 413
<211> LENGTH: 16
<212> TYPE: RNA
<213> ORGANISM: Homo sapiens

<400> SEQUENCE: 413
gugaaggccc ggcgga					16

<210> SEQ ID NO 414
<211> LENGTH: 15
<212> TYPE: RNA
<213> ORGANISM: Homo sapiens

<400> SEQUENCE: 414
gugaaggccc ggcgg					15

<210> SEQ ID NO 415
<211> LENGTH: 24
<212> TYPE: RNA
<213> ORGANISM: Homo sapiens

<400> SEQUENCE: 415
gugaguggga gccggugggg cugg					24

<210> SEQ ID NO 416
<211> LENGTH: 15
<212> TYPE: RNA
<213> ORGANISM: Homo sapiens

<400> SEQUENCE: 416
ggggcuggag uaagg					15

<210> SEQ ID NO 417
<211> LENGTH: 20
<212> TYPE: RNA
<213> ORGANISM: Homo sapiens

<400> SEQUENCE: 417
uaggaugggg gugagaggug					20

<210> SEQ ID NO 418
<211> LENGTH: 18

<212> TYPE: RNA
<213> ORGANISM: Homo sapiens

<400> SEQUENCE: 418
uaggaugggg gugagagg                                         18

<210> SEQ ID NO 419
<211> LENGTH: 23
<212> TYPE: RNA
<213> ORGANISM: Homo sapiens

<400> SEQUENCE: 419
cggggcagcu caguacagga uac                                   23

<210> SEQ ID NO 420
<211> LENGTH: 15
<212> TYPE: RNA
<213> ORGANISM: Homo sapiens

<400> SEQUENCE: 420
agcucaguac aggau                                            15

<210> SEQ ID NO 421
<211> LENGTH: 22
<212> TYPE: RNA
<213> ORGANISM: Homo sapiens

<400> SEQUENCE: 421
ugggagggga gaggcagcaa gc                                    22

<210> SEQ ID NO 422
<211> LENGTH: 22
<212> TYPE: RNA
<213> ORGANISM: Homo sapiens

<400> SEQUENCE: 422
ugggagggga gaggcagcaa gc                                    22

<210> SEQ ID NO 423
<211> LENGTH: 19
<212> TYPE: RNA
<213> ORGANISM: Homo sapiens

<400> SEQUENCE: 423
guggguuggg gcgggcucu                                        19

<210> SEQ ID NO 424
<211> LENGTH: 19
<212> TYPE: RNA
<213> ORGANISM: Homo sapiens

<400> SEQUENCE: 424
guggguuggg gcgggcucu                                        19

<210> SEQ ID NO 425
<211> LENGTH: 23
<212> TYPE: RNA
<213> ORGANISM: Homo sapiens

<400> SEQUENCE: 425
uggggaaggc gucagugucg ggu                                   23

<210> SEQ ID NO 426

```
<211> LENGTH: 16
<212> TYPE: RNA
<213> ORGANISM: Homo sapiens

<400> SEQUENCE: 426 ugggaaggc gucagu                                                        16

<210> SEQ ID NO 427
<211> LENGTH: 19
<212> TYPE: RNA
<213> ORGANISM: Homo sapiens

<400> SEQUENCE: 427
uggcgggugc ggggguggg                                                    19

<210> SEQ ID NO 428
<211> LENGTH: 15
<212> TYPE: RNA
<213> ORGANISM: Homo sapiens

<400> SEQUENCE: 428
uggcgggugc ggggg                                                        15

<210> SEQ ID NO 429
<211> LENGTH: 20
<212> TYPE: RNA
<213> ORGANISM: Homo sapiens

<400> SEQUENCE: 429
aucccaccuc ugccaccaaa                                                   20

<210> SEQ ID NO 430
<211> LENGTH: 15
<212> TYPE: RNA
<213> ORGANISM: Homo sapiens

<400> SEQUENCE: 430
aucccaccuc ugcca                                                        15

<210> SEQ ID NO 431
<211> LENGTH: 23
<212> TYPE: RNA
<213> ORGANISM: Homo sapiens

<400> SEQUENCE: 431
ccagggcugg cagugacaug ggu                                               23

<210> SEQ ID NO 432
<211> LENGTH: 19
<212> TYPE: RNA
<213> ORGANISM: Homo sapiens

<400> SEQUENCE: 432
cagggcuggc agugacaug                                                    19

<210> SEQ ID NO 433
<211> LENGTH: 24
<212> TYPE: RNA
<213> ORGANISM: Homo sapiens

<400> SEQUENCE: 433
ucgaggacug guggaagggc cuuu                                              24
```

```
<210> SEQ ID NO 434
<211> LENGTH: 16
<212> TYPE: RNA
<213> ORGANISM: Homo sapiens

<400> SEQUENCE: 434
ucgaggacug guggaa                                                    16

<210> SEQ ID NO 435
<211> LENGTH: 18
<212> TYPE: RNA
<213> ORGANISM: Homo sapiens

<400> SEQUENCE: 435
gagacugggg ugggccu                                                   18

<210> SEQ ID NO 436
<211> LENGTH: 16
<212> TYPE: RNA
<213> ORGANISM: Homo sapiens

<400> SEQUENCE: 436
agacuggggu ggggcc                                                    16

<210> SEQ ID NO 437
<211> LENGTH: 23
<212> TYPE: RNA
<213> ORGANISM: Homo sapiens

<400> SEQUENCE: 437
agaagaaggc ggucggucug cgg                                            23

<210> SEQ ID NO 438
<211> LENGTH: 21
<212> TYPE: RNA
<213> ORGANISM: Homo sapiens

<400> SEQUENCE: 438
aagaaggcgg ucggucugcg g                                              21

<210> SEQ ID NO 439
<211> LENGTH: 21
<212> TYPE: RNA
<213> ORGANISM: Homo sapiens

<400> SEQUENCE: 439
cagccugagu gacagagcaa g                                              21

<210> SEQ ID NO 440
<211> LENGTH: 15
<212> TYPE: RNA
<213> ORGANISM: Homo sapiens

<400> SEQUENCE: 440
acugcacucc agccu                                                     15

<210> SEQ ID NO 441
<211> LENGTH: 22
<212> TYPE: RNA
<213> ORGANISM: Homo sapiens

<400> SEQUENCE: 441
cugggcucgg gacgcgcggc uc                                             22
```

<210> SEQ ID NO 442
<211> LENGTH: 19
<212> TYPE: RNA
<213> ORGANISM: Homo sapiens

<400> SEQUENCE: 442
cugggcucgg gacgcgcgg                                            19

<210> SEQ ID NO 443
<211> LENGTH: 23
<212> TYPE: RNA
<213> ORGANISM: Homo sapiens

<400> SEQUENCE: 443
acaggagugg ggugggaca uaa                                        23

<210> SEQ ID NO 444
<211> LENGTH: 20
<212> TYPE: RNA
<213> ORGANISM: Homo sapiens

<400> SEQUENCE: 444
acaggagugg ggugggaca                                            20

<210> SEQ ID NO 445
<211> LENGTH: 23
<212> TYPE: RNA
<213> ORGANISM: Homo sapiens

<400> SEQUENCE: 445
caccuugccu ugcugcccgg gcc                                       23

<210> SEQ ID NO 446
<211> LENGTH: 22
<212> TYPE: RNA
<213> ORGANISM: Homo sapiens

<400> SEQUENCE: 446
caccuugccu ugcugcccgg gc                                        22

<210> SEQ ID NO 447
<211> LENGTH: 18
<212> TYPE: RNA
<213> ORGANISM: Homo sapiens

<400> SEQUENCE: 447
ggugggcuuc ccggaggg                                             18

<210> SEQ ID NO 448
<211> LENGTH: 15
<212> TYPE: RNA
<213> ORGANISM: Homo sapiens

<400> SEQUENCE: 448
ggugggcuuc ccgga                                                15

<210> SEQ ID NO 449
<211> LENGTH: 21
<212> TYPE: RNA
<213> ORGANISM: Homo sapiens

<400> SEQUENCE: 449
aggaggcagu gggcgagcag g                                         21

```
<210> SEQ ID NO 450
<211> LENGTH: 21
<212> TYPE: RNA
<213> ORGANISM: Homo sapiens

<400> SEQUENCE: 450
aggaggcagu gggcgagcag g                                              21

<210> SEQ ID NO 451
<211> LENGTH: 15
<212> TYPE: RNA
<213> ORGANISM: Homo sapiens

<400> SEQUENCE: 451
uggcagagcg cuguc                                                     15

<210> SEQ ID NO 452
<211> LENGTH: 15
<212> TYPE: RNA
<213> ORGANISM: Homo sapiens

<400> SEQUENCE: 452
uggcagagcg cuguc                                                     15

<210> SEQ ID NO 453
<211> LENGTH: 25
<212> TYPE: RNA
<213> ORGANISM: Homo sapiens

<400> SEQUENCE: 453
uggcggcggu aguaugggc uucuc                                           25

<210> SEQ ID NO 454
<211> LENGTH: 25
<212> TYPE: RNA
<213> ORGANISM: Homo sapiens

<400> SEQUENCE: 454
uggcggcggu aguaugggc uucuc                                           25

<210> SEQ ID NO 455
<211> LENGTH: 27
<212> TYPE: RNA
<213> ORGANISM: Homo sapiens

<400> SEQUENCE: 455
agggccagag gagccuggag uggucgg                                        27

<210> SEQ ID NO 456
<211> LENGTH: 23
<212> TYPE: RNA
<213> ORGANISM: Homo sapiens

<400> SEQUENCE: 456
agggccagag gagccuggag ugg                                            23

<210> SEQ ID NO 457
<211> LENGTH: 22
<212> TYPE: RNA
<213> ORGANISM: Homo sapiens

<400> SEQUENCE: 457
```

```
ugugggacug caaaugggag cu                                    22

<210> SEQ ID NO 458
<211> LENGTH: 22
<212> TYPE: RNA
<213> ORGANISM: Homo sapiens

<400> SEQUENCE: 458
ugugggacug caaaugggag cu                                    22

<210> SEQ ID NO 459
<211> LENGTH: 16
<212> TYPE: RNA
<213> ORGANISM: Homo sapiens

<400> SEQUENCE: 459
cgggcccggc guuccc                                           16

<210> SEQ ID NO 460
<211> LENGTH: 15
<212> TYPE: RNA
<213> ORGANISM: Homo sapiens

<400> SEQUENCE: 460
ccgggcccgg cguuc                                            15

<210> SEQ ID NO 461
<211> LENGTH: 20
<212> TYPE: RNA
<213> ORGANISM: Homo sapiens

<400> SEQUENCE: 461
aucccaccac ugccaccauu                                       20

<210> SEQ ID NO 462
<211> LENGTH: 15
<212> TYPE: RNA
<213> ORGANISM: Homo sapiens

<400> SEQUENCE: 462
aucccaccac ugcca                                            15

<210> SEQ ID NO 463
<211> LENGTH: 20
<212> TYPE: RNA
<213> ORGANISM: Homo sapiens

<400> SEQUENCE: 463
ccccggggag cccggcggug                                       20

<210> SEQ ID NO 464
<211> LENGTH: 15
<212> TYPE: RNA
<213> ORGANISM: Homo sapiens

<400> SEQUENCE: 464
accccgggga gcccg                                            15

<210> SEQ ID NO 465
<211> LENGTH: 21
<212> TYPE: RNA
<213> ORGANISM: Homo sapiens

<400> SEQUENCE: 465
```

```
auccaguucu cugagggggc u                                              21

<210> SEQ ID NO 466
<211> LENGTH: 21
<212> TYPE: RNA
<213> ORGANISM: Homo sapiens

<400> SEQUENCE: 466
auccaguucu cugagggggc u                                              21

<210> SEQ ID NO 467
<211> LENGTH: 26
<212> TYPE: RNA
<213> ORGANISM: Homo sapiens

<400> SEQUENCE: 467
ccuucuggag aggcuuugug cggaua                                         26

<210> SEQ ID NO 468
<211> LENGTH: 15
<212> TYPE: RNA
<213> ORGANISM: Homo sapiens

<400> SEQUENCE: 468
ccuucuggag aggcu                                                     15

<210> SEQ ID NO 469
<211> LENGTH: 19
<212> TYPE: RNA
<213> ORGANISM: Homo sapiens

<400> SEQUENCE: 469
agugggaggc cagggcacg                                                 19

<210> SEQ ID NO 470
<211> LENGTH: 15
<212> TYPE: RNA
<213> ORGANISM: Homo sapiens

<400> SEQUENCE: 470 aggggagcu gcagg                                                      15

<210> SEQ ID NO 471
<211> LENGTH: 21
<212> TYPE: RNA
<213> ORGANISM: Homo sapiens

<400> SEQUENCE: 471
gaggcgaugu ggggauguag a                                              21

<210> SEQ ID NO 472
<211> LENGTH: 20
<212> TYPE: RNA
<213> ORGANISM: Homo sapiens

<400> SEQUENCE: 472
cccagucuca uuuccucauc                                                20

<210> SEQ ID NO 473
<211> LENGTH: 17
<212> TYPE: RNA
<213> ORGANISM: Homo sapiens
```

```
<400> SEQUENCE: 473
ggggcggggg cgggggc                                                    17

<210> SEQ ID NO 474
<211> LENGTH: 15
<212> TYPE: RNA
<213> ORGANISM: Homo sapiens

<400> SEQUENCE: 474
cgcgccgggc ccggg                                                      15

<210> SEQ ID NO 475
<211> LENGTH: 20
<212> TYPE: RNA
<213> ORGANISM: Homo sapiens

<400> SEQUENCE: 475
ugaguggggc ucccgggacg                                                 20

<210> SEQ ID NO 476
<211> LENGTH: 20
<212> TYPE: RNA
<213> ORGANISM: Homo sapiens

<400> SEQUENCE: 476
ugaguggggc ucccgggacg                                                 20

<210> SEQ ID NO 477
<211> LENGTH: 25
<212> TYPE: RNA
<213> ORGANISM: Homo sapiens

<400> SEQUENCE: 477
ugcaggcaga agugggcug acagg                                            25

<210> SEQ ID NO 478
<211> LENGTH: 20
<212> TYPE: RNA
<213> ORGANISM: Homo sapiens

<400> SEQUENCE: 478
cugcaggcag aagugggcu                                                  20

<210> SEQ ID NO 479
<211> LENGTH: 22
<212> TYPE: RNA
<213> ORGANISM: Homo sapiens

<400> SEQUENCE: 479
acucaaacug uggggcacu uu                                               22

<210> SEQ ID NO 480
<211> LENGTH: 19
<212> TYPE: RNA
<213> ORGANISM: Homo sapiens

<400> SEQUENCE: 480
acucaaacug uggggcac                                                   19

<210> SEQ ID NO 481
<211> LENGTH: 20
<212> TYPE: RNA
<213> ORGANISM: Homo sapiens
```

<400> SEQUENCE: 481
ccccagggcg acgcggcggg                                              20

<210> SEQ ID NO 482
<211> LENGTH: 15
<212> TYPE: RNA
<213> ORGANISM: Homo sapiens

<400> SEQUENCE: 482
cgcggcgggg gcggc                                                   15

<210> SEQ ID NO 483
<211> LENGTH: 23
<212> TYPE: RNA
<213> ORGANISM: Homo sapiens

<400> SEQUENCE: 483
ggcuacaaca caggacccgg gcg                                          23

<210> SEQ ID NO 484
<211> LENGTH: 21
<212> TYPE: RNA
<213> ORGANISM: Homo sapiens

<400> SEQUENCE: 484
ggcuacaaca caggacccgg g                                            21

<210> SEQ ID NO 485
<211> LENGTH: 17
<212> TYPE: RNA
<213> ORGANISM: Homo sapiens

<400> SEQUENCE: 485
ugcaggggca ggccagc                                                 17

<210> SEQ ID NO 486
<211> LENGTH: 17
<212> TYPE: RNA
<213> ORGANISM: Homo sapiens

<400> SEQUENCE: 486
ugcaggggca ggccagc                                                 17

<210> SEQ ID NO 487
<211> LENGTH: 24
<212> TYPE: RNA
<213> ORGANISM: Homo sapiens

<400> SEQUENCE: 487
cugugcaaau ccaugcaaaa cuga                                         24

<210> SEQ ID NO 488
<211> LENGTH: 15
<212> TYPE: RNA
<213> ORGANISM: Homo sapiens

<400> SEQUENCE: 488
ugugcaaauc caugc                                                   15

<210> SEQ ID NO 489
<211> LENGTH: 27
<212> TYPE: RNA

```
<213> ORGANISM: Homo sapiens

<400> SEQUENCE: 489
aaaccguuac cauuacugag uuuagua                                    27

<210> SEQ ID NO 490
<211> LENGTH: 15
<212> TYPE: RNA
<213> ORGANISM: Homo sapiens

<400> SEQUENCE: 490
gaaaccguua ccauu                                                 15

<210> SEQ ID NO 491
<211> LENGTH: 24
<212> TYPE: RNA
<213> ORGANISM: Homo sapiens

<400> SEQUENCE: 491
uggggagcug aggcucuggg ggug                                       24

<210> SEQ ID NO 492
<211> LENGTH: 15
<212> TYPE: RNA
<213> ORGANISM: Homo sapiens

<400> SEQUENCE: 492
ggcccugggg agcug                                                 15

<210> SEQ ID NO 493
<211> LENGTH: 25
<212> TYPE: RNA
<213> ORGANISM: Homo sapiens

<400> SEQUENCE: 493
ugucaguuug ucaaauaccc caagu                                      25

<210> SEQ ID NO 494
<211> LENGTH: 15
<212> TYPE: RNA
<213> ORGANISM: Homo sapiens

<400> SEQUENCE: 494
uccauguggu agagu                                                 15

<210> SEQ ID NO 495
<211> LENGTH: 22
<212> TYPE: RNA
<213> ORGANISM: Homo sapiens

<400> SEQUENCE: 495
gugggcgggg gcaggugugu gg                                         22

<210> SEQ ID NO 496
<211> LENGTH: 15
<212> TYPE: RNA
<213> ORGANISM: Homo sapiens

<400> SEQUENCE: 496
cgggggcagg ugugu                                                 15

<210> SEQ ID NO 497
<211> LENGTH: 23
```

```
<212> TYPE: RNA
<213> ORGANISM: Homo sapiens

<400> SEQUENCE: 497
cacaggugag guucuuggga gcc                                          23

<210> SEQ ID NO 498
<211> LENGTH: 15
<212> TYPE: RNA
<213> ORGANISM: Homo sapiens

<400> SEQUENCE: 498
acaggugagg uucuu                                                   15

<210> SEQ ID NO 499
<211> LENGTH: 26
<212> TYPE: RNA
<213> ORGANISM: Homo sapiens

<400> SEQUENCE: 499
agggacggga cgcggugcag uguugu                                       26

<210> SEQ ID NO 500
<211> LENGTH: 15
<212> TYPE: RNA
<213> ORGANISM: Homo sapiens

<400> SEQUENCE: 500
ggcgggcggg aggga                                                   15

<210> SEQ ID NO 501
<211> LENGTH: 25
<212> TYPE: RNA
<213> ORGANISM: Homo sapiens

<400> SEQUENCE: 501
aagcugccag uugaagaacu guugc                                        25

<210> SEQ ID NO 502
<211> LENGTH: 15
<212> TYPE: RNA
<213> ORGANISM: Homo sapiens

<400> SEQUENCE: 502
aagcugccag uugaa                                                   15

<210> SEQ ID NO 503
<211> LENGTH: 16
<212> TYPE: RNA
<213> ORGANISM: Homo sapiens

<400> SEQUENCE: 503 uggggggaa gaaaag                                                   16

<210> SEQ ID NO 504
<211> LENGTH: 16
<212> TYPE: RNA
<213> ORGANISM: Homo sapiens

<400> SEQUENCE: 504 uggggggaa gaaaag                                                   16

<210> SEQ ID NO 505
```

```
<211> LENGTH: 20
<212> TYPE: RNA
<213> ORGANISM: Homo sapiens

<400> SEQUENCE: 505
aagacacauu uggagaggga                                                   20

<210> SEQ ID NO 506
<211> LENGTH: 16
<212> TYPE: RNA
<213> ORGANISM: Homo sapiens

<400> SEQUENCE: 506
agacacauuu ggagag                                                       16

<210> SEQ ID NO 507
<211> LENGTH: 23
<212> TYPE: RNA
<213> ORGANISM: Homo sapiens

<400> SEQUENCE: 507
cuaguggaag aagauggcgg aag                                               23

<210> SEQ ID NO 508
<211> LENGTH: 15
<212> TYPE: RNA
<213> ORGANISM: Homo sapiens

<400> SEQUENCE: 508
uaguggaaga agaug                                                        15

<210> SEQ ID NO 509
<211> LENGTH: 27
<212> TYPE: RNA
<213> ORGANISM: Homo sapiens

<400> SEQUENCE: 509
gugaacgggc gccaucccga ggcuuug                                           27

<210> SEQ ID NO 510
<211> LENGTH: 16
<212> TYPE: RNA
<213> ORGANISM: Homo sapiens

<400> SEQUENCE: 510
gugaacgggc gccauc                                                       16

<210> SEQ ID NO 511
<211> LENGTH: 22
<212> TYPE: RNA
<213> ORGANISM: Homo sapiens

<400> SEQUENCE: 511
ggcaggaagc ggaggaaccu ug                                                22

<210> SEQ ID NO 512
<211> LENGTH: 17
<212> TYPE: RNA
<213> ORGANISM: Homo sapiens

<400> SEQUENCE: 512
ggaggaaccu uggagcu                                                      17
```

```
<210> SEQ ID NO 513
<211> LENGTH: 21
<212> TYPE: RNA
<213> ORGANISM: Homo sapiens

<400> SEQUENCE: 513
guuggaggcg ugguuuuag a                                              21

<210> SEQ ID NO 514
<211> LENGTH: 15
<212> TYPE: RNA
<213> ORGANISM: Homo sapiens

<400> SEQUENCE: 514
guuggaggcg ugggu                                                    15

<210> SEQ ID NO 515
<211> LENGTH: 29
<212> TYPE: RNA
<213> ORGANISM: Homo sapiens

<400> SEQUENCE: 515
gggagccgcg gggaucgccg agggccggu                                     29

<210> SEQ ID NO 516
<211> LENGTH: 15
<212> TYPE: RNA
<213> ORGANISM: Homo sapiens

<400> SEQUENCE: 516
ggcggcggug guggg                                                    15

<210> SEQ ID NO 517
<211> LENGTH: 23
<212> TYPE: RNA
<213> ORGANISM: Homo sapiens

<400> SEQUENCE: 517
gagggaggga cggggcugu gcu                                            23

<210> SEQ ID NO 518
<211> LENGTH: 15
<212> TYPE: RNA
<213> ORGANISM: Homo sapiens

<400> SEQUENCE: 518
gaggagggag ggagg                                                    15

<210> SEQ ID NO 519
<211> LENGTH: 21
<212> TYPE: RNA
<213> ORGANISM: Homo sapiens

<400> SEQUENCE: 519
uugaggagac auggugggg c                                              21

<210> SEQ ID NO 520
<211> LENGTH: 15
<212> TYPE: RNA
<213> ORGANISM: Homo sapiens

<400> SEQUENCE: 520
uugaggagac auggu                                                    15
```

```
<210> SEQ ID NO 521
<211> LENGTH: 24
<212> TYPE: RNA
<213> ORGANISM: Homo sapiens

<400> SEQUENCE: 521
aggcaggggc uggugcuggg cggg                                          24

<210> SEQ ID NO 522
<211> LENGTH: 15
<212> TYPE: RNA
<213> ORGANISM: Homo sapiens

<400> SEQUENCE: 522 gggcggggggg cggcg                                                   15

<210> SEQ ID NO 523
<211> LENGTH: 17
<212> TYPE: RNA
<213> ORGANISM: Homo sapiens

<400> SEQUENCE: 523
gcggggcggc aggggcc                                                  17

<210> SEQ ID NO 524
<211> LENGTH: 15
<212> TYPE: RNA
<213> ORGANISM: Homo sapiens

<400> SEQUENCE: 524
gggggcgggg cggca                                                    15

<210> SEQ ID NO 525
<211> LENGTH: 21
<212> TYPE: RNA
<213> ORGANISM: Homo sapiens

<400> SEQUENCE: 525
gccgggcgug guggugggg c                                              21

<210> SEQ ID NO 526
<211> LENGTH: 15
<212> TYPE: RNA
<213> ORGANISM: Homo sapiens

<400> SEQUENCE: 526
uagccgggcg uggug                                                    15

<210> SEQ ID NO 527
<211> LENGTH: 23
<212> TYPE: RNA
<213> ORGANISM: Homo sapiens

<400> SEQUENCE: 527
aagggaggag gagcggaggg gcc                                           23

<210> SEQ ID NO 528
<211> LENGTH: 15
<212> TYPE: RNA
<213> ORGANISM: Homo sapiens

<400> SEQUENCE: 528
gggaggagga gcgga                                                    15
```

<210> SEQ ID NO 529
<211> LENGTH: 24
<212> TYPE: RNA
<213> ORGANISM: Homo sapiens

<400> SEQUENCE: 529
cgggcguggu gguggggug ggug                                    24

<210> SEQ ID NO 530
<211> LENGTH: 15
<212> TYPE: RNA
<213> ORGANISM: Homo sapiens

<400> SEQUENCE: 530
cgggcguggu ggugg                                             15

<210> SEQ ID NO 531
<211> LENGTH: 24
<212> TYPE: RNA
<213> ORGANISM: Homo sapiens

<400> SEQUENCE: 531 uggggagug cagugauugu ggaa                                    24

<210> SEQ ID NO 532
<211> LENGTH: 19
<212> TYPE: RNA
<213> ORGANISM: Homo sapiens

<400> SEQUENCE: 532 uggggagug cagugauug                                          19

<210> SEQ ID NO 533
<211> LENGTH: 29
<212> TYPE: RNA
<213> ORGANISM: Homo sapiens

<400> SEQUENCE: 533
gcuggguuaa gccgagcugg guugggcug                              29

<210> SEQ ID NO 534
<211> LENGTH: 19
<212> TYPE: RNA
<213> ORGANISM: Homo sapiens

<400> SEQUENCE: 534 cugguuggg cugggcugg                                          19

<210> SEQ ID NO 535
<211> LENGTH: 18
<212> TYPE: RNA
<213> ORGANISM: Homo sapiens

<400> SEQUENCE: 535
cuccgggcgg cgccgugu                                          18

<210> SEQ ID NO 536
<211> LENGTH: 18
<212> TYPE: RNA
<213> ORGANISM: Homo sapiens

<400> SEQUENCE: 536
cuccgggcgg cgccgugu                                                        18

<210> SEQ ID NO 537
<211> LENGTH: 17
<212> TYPE: RNA
<213> ORGANISM: Homo sapiens

<400> SEQUENCE: 537
ccuccgggac ggcuggg                                                         17

<210> SEQ ID NO 538
<211> LENGTH: 15
<212> TYPE: RNA
<213> ORGANISM: Homo sapiens

<400> SEQUENCE: 538
cuccgggacg gcugg                                                           15

<210> SEQ ID NO 539
<211> LENGTH: 26
<212> TYPE: RNA
<213> ORGANISM: Homo sapiens

<400> SEQUENCE: 539
gaggggcucu cgcuucuggc gccaag                                               26

<210> SEQ ID NO 540
<211> LENGTH: 15
<212> TYPE: RNA
<213> ORGANISM: Homo sapiens

<400> SEQUENCE: 540
ggugaggcgg ggggg                                                           15

<210> SEQ ID NO 541
<211> LENGTH: 21
<212> TYPE: RNA
<213> ORGANISM: Homo sapiens

<400> SEQUENCE: 541 ugcuggggc cacaugagug u                                                     21

<210> SEQ ID NO 542
<211> LENGTH: 20
<212> TYPE: RNA
<213> ORGANISM: Homo sapiens

<400> SEQUENCE: 542 gcuggggcc acaugagugu                                                       20

<210> SEQ ID NO 543
<211> LENGTH: 23
<212> TYPE: RNA
<213> ORGANISM: Homo sapiens

<400> SEQUENCE: 543 ggggguccc ggugcucgga ucu                                                   23

<210> SEQ ID NO 544
<211> LENGTH: 16
<212> TYPE: RNA
<213> ORGANISM: Homo sapiens

<400> SEQUENCE: 544
ucgggagggg cgggag 16

<210> SEQ ID NO 545
<211> LENGTH: 23
<212> TYPE: RNA
<213> ORGANISM: Homo sapiens

<400> SEQUENCE: 545
ucggcucugg gucuguggggg agc 23

<210> SEQ ID NO 546
<211> LENGTH: 15
<212> TYPE: RNA
<213> ORGANISM: Homo sapiens

<400> SEQUENCE: 546
gcccggauac cucag 15

<210> SEQ ID NO 547
<211> LENGTH: 23
<212> TYPE: RNA
<213> ORGANISM: Homo sapiens

<400> SEQUENCE: 547 gggggaugu gcaugcuggu ugg 23

<210> SEQ ID NO 548
<211> LENGTH: 15
<212> TYPE: RNA
<213> ORGANISM: Homo sapiens

<400> SEQUENCE: 548
aucagcgugc acuuc 15

<210> SEQ ID NO 549
<211> LENGTH: 23
<212> TYPE: RNA
<213> ORGANISM: Homo sapiens

<400> SEQUENCE: 549 aggaggggguc ccgcacuggg agg 23

<210> SEQ ID NO 550
<211> LENGTH: 15
<212> TYPE: RNA
<213> ORGANISM: Homo sapiens

<400> SEQUENCE: 550
ugggaggggc ccuca 15

<210> SEQ ID NO 551
<211> LENGTH: 24
<212> TYPE: RNA
<213> ORGANISM: Homo sapiens

<400> SEQUENCE: 551
cccaaaaugc ugggauuaca ggca 24

<210> SEQ ID NO 552
<211> LENGTH: 15
<212> TYPE: RNA
<213> ORGANISM: Homo sapiens

```
<400> SEQUENCE: 552
gcccaccuca gccuc                                                    15

<210> SEQ ID NO 553
<211> LENGTH: 26
<212> TYPE: RNA
<213> ORGANISM: Homo sapiens

<400> SEQUENCE: 553
agggcuggac ucagcggcgg agcugg                                        26

<210> SEQ ID NO 554
<211> LENGTH: 17
<212> TYPE: RNA
<213> ORGANISM: Homo sapiens

<400> SEQUENCE: 554
gcggcggagc uggcugc                                                  17

<210> SEQ ID NO 555
<211> LENGTH: 15
<212> TYPE: RNA
<213> ORGANISM: Homo sapiens

<400> SEQUENCE: 555
aggaggagga ggcag                                                    15

<210> SEQ ID NO 556
<211> LENGTH: 15
<212> TYPE: RNA
<213> ORGANISM: Homo sapiens

<400> SEQUENCE: 556
aggaggagga ggcag                                                    15

<210> SEQ ID NO 557
<211> LENGTH: 23
<212> TYPE: RNA
<213> ORGANISM: Homo sapiens

<400> SEQUENCE: 557
uggugcggag agggcccaca gug                                           23

<210> SEQ ID NO 558
<211> LENGTH: 15
<212> TYPE: RNA
<213> ORGANISM: Homo sapiens

<400> SEQUENCE: 558
gggucuggug cggag                                                    15

<210> SEQ ID NO 559
<211> LENGTH: 22
<212> TYPE: RNA
<213> ORGANISM: Homo sapiens

<400> SEQUENCE: 559
acaccgggga uggcagaggg uc                                            22

<210> SEQ ID NO 560
<211> LENGTH: 20
<212> TYPE: RNA
<213> ORGANISM: Homo sapiens
```

```
<400> SEQUENCE: 560
caccggggau ggcagagggu                                          20

<210> SEQ ID NO 561
<211> LENGTH: 20
<212> TYPE: RNA
<213> ORGANISM: Homo sapiens

<400> SEQUENCE: 561
gguagugagu uaucagcuac                                          20

<210> SEQ ID NO 562
<211> LENGTH: 19
<212> TYPE: RNA
<213> ORGANISM: Homo sapiens

<400> SEQUENCE: 562
cggggccaga gcagagagc                                           19

<210> SEQ ID NO 563
<211> LENGTH: 23
<212> TYPE: RNA
<213> ORGANISM: Homo sapiens

<400> SEQUENCE: 563
uggugggugg ggaggagaag ugc                                      23

<210> SEQ ID NO 564
<211> LENGTH: 26
<212> TYPE: RNA
<213> ORGANISM: Homo sapiens

<400> SEQUENCE: 564
cucggccgcg gcgcguagcc cccgcc                                   26

<210> SEQ ID NO 565
<211> LENGTH: 22
<212> TYPE: RNA
<213> ORGANISM: Homo sapiens

<400> SEQUENCE: 565
ucugcccccu ccgcugcugc ca                                       22

<210> SEQ ID NO 566
<211> LENGTH: 20
<212> TYPE: RNA
<213> ORGANISM: Homo sapiens

<400> SEQUENCE: 566
ucacaccugc cucgcccccc                                          20

<210> SEQ ID NO 567
<211> LENGTH: 21
<212> TYPE: RNA
<213> ORGANISM: Homo sapiens

<400> SEQUENCE: 567
aaggcagggc ccccgcuccc c                                        21

<210> SEQ ID NO 568
<211> LENGTH: 22
<212> TYPE: RNA
```

```
<213> ORGANISM: Homo sapiens

<400> SEQUENCE: 568
gaggguuggg uggaggcucu cc                                              22

<210> SEQ ID NO 569
<211> LENGTH: 22
<212> TYPE: RNA
<213> ORGANISM: Homo sapiens

<400> SEQUENCE: 569
gagcaggcga ggcugggcug aa                                              22

<210> SEQ ID NO 570
<211> LENGTH: 22
<212> TYPE: RNA
<213> ORGANISM: Homo sapiens

<400> SEQUENCE: 570
gcuggugcaa aaguaauggc gg                                              22

<210> SEQ ID NO 571
<211> LENGTH: 22
<212> TYPE: RNA
<213> ORGANISM: Homo sapiens

<400> SEQUENCE: 571
aggcggggcg ccgcgggacc gc                                              22

<210> SEQ ID NO 572
<211> LENGTH: 22
<212> TYPE: RNA
<213> ORGANISM: Homo sapiens

<400> SEQUENCE: 572
acgcccuucc cccccuucuu ca                                              22

<210> SEQ ID NO 573
<211> LENGTH: 21
<212> TYPE: RNA
<213> ORGANISM: Homo sapiens

<400> SEQUENCE: 573
gugccagcug caguggggga g                                               21

<210> SEQ ID NO 574
<211> LENGTH: 23
<212> TYPE: RNA
<213> ORGANISM: Homo sapiens

<400> SEQUENCE: 574
ccucccugcc cgccucucug cag                                             23

<210> SEQ ID NO 575
<211> LENGTH: 22
<212> TYPE: RNA
<213> ORGANISM: Homo sapiens

<400> SEQUENCE: 575
ugagccccug ugccgccccc ag                                              22

<210> SEQ ID NO 576
<211> LENGTH: 23
```

```
<212> TYPE: RNA
<213> ORGANISM: Homo sapiens

<400> SEQUENCE: 576
ccccgguguu ggggcgcguc ugc                                              23

<210> SEQ ID NO 577
<211> LENGTH: 20
<212> TYPE: RNA
<213> ORGANISM: Homo sapiens

<400> SEQUENCE: 577
ggcuccuugg ucuaggggua                                                  20

<210> SEQ ID NO 578
<211> LENGTH: 17
<212> TYPE: RNA
<213> ORGANISM: Homo sapiens

<400> SEQUENCE: 578
ggauggagga ggggucu                                                     17

<210> SEQ ID NO 579
<211> LENGTH: 22
<212> TYPE: RNA
<213> ORGANISM: Homo sapiens

<400> SEQUENCE: 579
acucggcgug gcgucggucg ug                                               22

<210> SEQ ID NO 580
<211> LENGTH: 89
<212> TYPE: RNA
<213> ORGANISM: Homo sapiens

<400> SEQUENCE: 580
uagauguugg uccaaacuga aaguugauga gucacugugc cucucggggu agugaguuau      60
cagcuacagu gagagagcag uguuuggcc                                        89

<210> SEQ ID NO 581
<211> LENGTH: 61
<212> TYPE: RNA
<213> ORGANISM: Homo sapiens

<400> SEQUENCE: 581
aacugcgggg ccagagcaga gagcccuugc acaccaccag ccucuccucc cugugcccca      60
g                                                                      61

<210> SEQ ID NO 582
<211> LENGTH: 62
<212> TYPE: RNA
<213> ORGANISM: Homo sapiens

<400> SEQUENCE: 582
cuuccuggug ggugggagg agaagugccg uccucaugag ccccucucug ucccacccau       60
ag                                                                     62

<210> SEQ ID NO 583
<211> LENGTH: 79
<212> TYPE: RNA
<213> ORGANISM: Homo sapiens
```

<400> SEQUENCE: 583
cucgaggugc uggggacgc gugagcgcga gccgcuuccu cacggcucgg ccgcggcgcg     60
uagcccccgc cacaucggg                                                79

<210> SEQ ID NO 584
<211> LENGTH: 80
<212> TYPE: RNA
<213> ORGANISM: Homo sapiens

<400> SEQUENCE: 584
accucuaccu cccggcagag gaggcugcag aggcuggcuu ccaaaacuc ugcccccucc     60 gcugcugcca aguggcuggu                                               80

<210> SEQ ID NO 585
<211> LENGTH: 94
<212> TYPE: RNA
<213> ORGANISM: Homo sapiens

<400> SEQUENCE: 585
gugaggugug ggcccggccc caggagcggg gccugggcag ccccgugugu ugaggaagga    60
aggcagggcc cccgcucccc gggccugacc ccac                               94

<210> SEQ ID NO 586
<211> LENGTH: 80
<212> TYPE: RNA
<213> ORGANISM: Homo sapiens

<400> SEQUENCE: 586
aggacccuuc cagagggccc ccccucaauc cuguugugcc uaauucagag gguugggugg    60
aggcucuccu gaagggcucu                                               80

<210> SEQ ID NO 587
<211> LENGTH: 60
<212> TYPE: RNA
<213> ORGANISM: Homo sapiens

<400> SEQUENCE: 587
gagcaggcga ggcugggcug aacccguggg ugaggagugc agcccagcug aggccucugc    60

<210> SEQ ID NO 588
<211> LENGTH: 100
<212> TYPE: RNA
<213> ORGANISM: Homo sapiens

<400> SEQUENCE: 588
auauuaggcu ggugcaaaag uaauggcggu uuuugccauu acuuucauu uuuaccauua     60 aaaguaaugg caaaaagcau gauuacuuuu ucaccaaccu                          100

<210> SEQ ID NO 589
<211> LENGTH: 93
<212> TYPE: RNA
<213> ORGANISM: Homo sapiens

<400> SEQUENCE: 589
ccuuccggcg ucccaggcgg ggcgccgcgg gaccgcccuc gugucugugg cgguggggauc    60 ccgcggccgu guuuccugg uggcccggcc aug                                 93

<210> SEQ ID NO 590
<211> LENGTH: 66

```
<212> TYPE: RNA
<213> ORGANISM: Homo sapiens

<400> SEQUENCE: 590
gggaggaggg aggagauggg ccaaguuccc ucuggcugga acgcccuucc cccccuucuu    60
caccug                                                              66

<210> SEQ ID NO 591
<211> LENGTH: 83
<212> TYPE: RNA
<213> ORGANISM: Homo sapiens

<400> SEQUENCE: 591
ccugcugcag aggugccagc ugcagugggg gaggcacugc cagggcugcc cacucugcuu    60
agccagcagg ugccaagaac agg                                           83

<210> SEQ ID NO 592
<211> LENGTH: 59
<212> TYPE: RNA
<213> ORGANISM: Homo sapiens

<400> SEQUENCE: 592
cuccagggag acagugugug aggccucuug ccauggccuc ccugcccgcc ucucugcag     59

<210> SEQ ID NO 593
<211> LENGTH: 82
<212> TYPE: RNA
<213> ORGANISM: Homo sapiens

<400> SEQUENCE: 593
gggaaagcgg agggcgcgcc cagcucccgg gcugauugcg cuaacagugg ccccgguguu    60
ggggcgcguc ugccgcugcc cc                                            82

<210> SEQ ID NO 594
<211> LENGTH: 86
<212> TYPE: RNA
<213> ORGANISM: Homo sapiens

<400> SEQUENCE: 594
aggagugacc aaaagacaag agugcgagcc uucuauuaug cccagacagg gccaccagag    60
ggcuccuugg ucuagggua augcca                                         86

<210> SEQ ID NO 595
<211> LENGTH: 60
<212> TYPE: RNA
<213> ORGANISM: Homo sapiens

<400> SEQUENCE: 595
ugugaaugac ccccuuccag agccaaaauc accagggaug gaggaggggu cuugggu acu   60

<210> SEQ ID NO 596
<211> LENGTH: 149
<212> TYPE: RNA
<213> ORGANISM: Homo sapiens

<400> SEQUENCE: 596
caucaagacc cagcugaguc acugucacug ccuaccaauc ucgaccggac cucgaccggc    60
ucgucugugu ugccaaucga cucggcgugg cgucggucgu gguagauagg cggucaugca   120
uacgaauuuu cagcucuugu ucuggugac                                    149
```

```
<210> SEQ ID NO 597
<211> LENGTH: 22
<212> TYPE: RNA
<213> ORGANISM: Homo sapiens

<400> SEQUENCE: 597
ccggcagagg aggcugcaga gg                                          22

<210> SEQ ID NO 598
<211> LENGTH: 19
<212> TYPE: RNA
<213> ORGANISM: Homo sapiens

<400> SEQUENCE: 598
ccggcagagg aggcugcag                                              19

<210> SEQ ID NO 599
<211> LENGTH: 22
<212> TYPE: RNA
<213> ORGANISM: Homo sapiens

<400> SEQUENCE: 599
ccucacaccu gccucgcccc cc                                          22

<210> SEQ ID NO 600
<211> LENGTH: 15
<212> TYPE: RNA
<213> ORGANISM: Homo sapiens

<400> SEQUENCE: 600
ucacaccugc cucgc                                                  15

<210> SEQ ID NO 601
<211> LENGTH: 25
<212> TYPE: RNA
<213> ORGANISM: Homo sapiens

<400> SEQUENCE: 601
aaggcagggc ccccgcuccc cgggc                                       25

<210> SEQ ID NO 602
<211> LENGTH: 15
<212> TYPE: RNA
<213> ORGANISM: Homo sapiens

<400> SEQUENCE: 602
guguguugag gaagg                                                  15

<210> SEQ ID NO 603
<211> LENGTH: 22
<212> TYPE: RNA
<213> ORGANISM: Homo sapiens

<400> SEQUENCE: 603
gaggguuggg uggaggcucu cc                                          22

<210> SEQ ID NO 604
<211> LENGTH: 15
<212> TYPE: RNA
<213> ORGANISM: Homo sapiens

<400> SEQUENCE: 604
gaggguuggg uggag                                                  15
```

```
<210> SEQ ID NO 605
<211> LENGTH: 19
<212> TYPE: RNA
<213> ORGANISM: Homo sapiens

<400> SEQUENCE: 605
gcaggcgagg cugggcuga                                              19

<210> SEQ ID NO 606
<211> LENGTH: 16
<212> TYPE: RNA
<213> ORGANISM: Homo sapiens

<400> SEQUENCE: 606
aggcgaggcu gggcug                                                 16

<210> SEQ ID NO 607
<211> LENGTH: 26
<212> TYPE: RNA
<213> ORGANISM: Homo sapiens

<400> SEQUENCE: 607 cgugggauc ccgcggccgu guuuuc                                       26

<210> SEQ ID NO 608
<211> LENGTH: 15
<212> TYPE: RNA
<213> ORGANISM: Homo sapiens

<400> SEQUENCE: 608
ggggcgccgc gggac                                                  15

<210> SEQ ID NO 609
<211> LENGTH: 26
<212> TYPE: RNA
<213> ORGANISM: Homo sapiens

<400> SEQUENCE: 609
aggagggagg agaugggcca aguucc                                      26

<210> SEQ ID NO 610
<211> LENGTH: 15
<212> TYPE: RNA
<213> ORGANISM: Homo sapiens

<400> SEQUENCE: 610
gggaggaggg aggag                                                  15

<210> SEQ ID NO 611
<211> LENGTH: 16
<212> TYPE: RNA
<213> ORGANISM: Homo sapiens

<400> SEQUENCE: 611
agcugcagug ggggag                                                 16

<210> SEQ ID NO 612
<211> LENGTH: 15
<212> TYPE: RNA
<213> ORGANISM: Homo sapiens

<400> SEQUENCE: 612
```

```
<210> SEQ ID NO 613
<211> LENGTH: 22
<212> TYPE: RNA
<213> ORGANISM: Homo sapiens

<400> SEQUENCE: 613
ccccguguuu ggggcgcguc ug                                              22

<210> SEQ ID NO 614
<211> LENGTH: 21
<212> TYPE: RNA
<213> ORGANISM: Homo sapiens

<400> SEQUENCE: 614
cccgguguug gggcgcgucu g                                               21

<210> SEQ ID NO 615
<211> LENGTH: 20
<212> TYPE: RNA
<213> ORGANISM: Homo sapiens

<400> SEQUENCE: 615
ggcuccuugg ucuaggggua                                                 20

<210> SEQ ID NO 616
<211> LENGTH: 15
<212> TYPE: RNA
<213> ORGANISM: Homo sapiens

<400> SEQUENCE: 616 cuugggucuag gggua                                                     15

<210> SEQ ID NO 617
<211> LENGTH: 25
<212> TYPE: RNA
<213> ORGANISM: Homo sapiens

<400> SEQUENCE: 617
acucggcgug gcgucggucg uggua                                           25

<210> SEQ ID NO 618
<211> LENGTH: 15
<212> TYPE: RNA
<213> ORGANISM: Homo sapiens

<400> SEQUENCE: 618
acucggcgug gcguc                                                      15
```